United States Patent
Baudouin et al.

(10) Patent No.: US 11,103,227 B2
(45) Date of Patent: Aug. 31, 2021

(54) SPINAL ACCESS RETRACTOR

(71) Applicant: DePuy Synthes Products, Inc., Raynham, MA (US)

(72) Inventors: Cyril Baudouin, Hegenhein (FR); Matthew Fenn, Rochester, NY (US); Markus Hunziker, Aarau (CH); Sean Saidha, Franklin, MA (US); Michael White, Liestal (CH); Khawar Siddique, Los Angeles, CA (US); Brian Perri, Los Angeles, CA (US); Philippe Lindenmann, Basel (CH)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 16/372,903

(22) Filed: Apr. 2, 2019

(65) Prior Publication Data
US 2019/0223854 A1 Jul. 25, 2019

Related U.S. Application Data

(60) Continuation of application No. 15/370,201, filed on Dec. 6, 2016, now Pat. No. 10,278,686, which is a (Continued)

(51) Int. Cl.
*A61B 17/02* (2006.01)
*A61B 17/80* (2006.01)
*A61B 17/00* (2006.01)

(52) U.S. Cl.
CPC ...... *A61B 17/0206* (2013.01); *A61B 17/0218* (2013.01); *A61B 17/0293* (2013.01);
(Continued)

(58) Field of Classification Search
CPC ............ A61B 17/0206; A61B 17/0218; A61B 17/0293; A61B 17/02; A61B 17/808;
(Continued)

(56) References Cited

U.S. PATENT DOCUMENTS

| 3,384,078 A | 5/1968 | Gauthier |
| 3,486,505 A | 12/1969 | Morrison |

(Continued)

FOREIGN PATENT DOCUMENTS

| AU | 2005225394 A1 | 10/2005 |
| BE | 873977 A1 | 5/1979 |

(Continued)

OTHER PUBLICATIONS

Nuvasive, Maximum Access Surgical Platform, MaXcess, XLIF Surgical Technique Guide, 2007, 30 pages.

*Primary Examiner* — Eduardo C Robert
*Assistant Examiner* — David C Comstock
(74) *Attorney, Agent, or Firm* — BakerHostetler

(57) ABSTRACT

A retractor includes a first arm, a second arm, and a translating member. The first arm comprises a proximal portion configured to retain a first retractor member and a distal portion configured to rotate relative to the proximal portion about a first axis. The second arm is configured to retain a second retractor member, such that rotation of the distal portion about the first axis causes the first retractor member to pivot toward or away from the second retractor member when the first retractor member and the second retractor member are coupled to the first arm and the second arm, respectively. The translating member is coupled between the proximal portion and the distal portion, and is configured to receive a drive force that causes the translating member to bias the distal portion to pivot relative to the proximal portion about the first axis.

20 Claims, 107 Drawing Sheets

Related U.S. Application Data division of application No. 13/237,710, filed on Sep. 20, 2011, now Pat. No. 9,615,818.

(60) Provisional application No. 61/420,918, filed on Dec. 8, 2010, provisional application No. 61/384,453, filed on Sep. 20, 2010.

(52) U.S. Cl.
CPC ............ *A61B 17/02* (2013.01); *A61B 17/808* (2013.01); *A61B 2017/00407* (2013.01); *A61B 2017/00902* (2013.01); *A61B 2017/0256* (2013.01); *A61B 2017/0262* (2013.01)

(58) Field of Classification Search
CPC ........... A61B 2017/00407; A61B 2017/00902; A61B 2017/0256; A61B 2017/0262
USPC .................... 600/214–216, 219, 222, 224
See application file for complete search history.

(56) References Cited

U.S. PATENT DOCUMENTS

| | | |
|---|---|---|
| 3,965,890 A | 6/1976 | Gauthier |
| 4,545,374 A | 10/1985 | Jacobson |
| 5,395,317 A | 3/1995 | Kambin |
| 5,431,658 A | 7/1995 | Moskovich |
| 5,437,672 A | 8/1995 | Alleyne |
| 5,474,558 A | 12/1995 | Neubardt |
| 5,484,437 A | 1/1996 | Michelson |
| 5,489,307 A | 2/1996 | Kuslich et al. |
| 5,653,761 A | 8/1997 | Pisharodi |
| 5,681,265 A | 10/1997 | Maeda et al. |
| 5,722,977 A | 3/1998 | Wilhelmy |
| 5,766,252 A | 6/1998 | Henry et al. |
| 5,772,661 A | 6/1998 | Michelson |
| 5,797,909 A | 8/1998 | Michelson |
| 5,868,745 A | 2/1999 | Alleyne |
| 5,899,901 A | 5/1999 | Middleton |
| 5,902,231 A | 5/1999 | Foley et al. |
| 5,928,139 A | 7/1999 | Koros et al. |
| 5,944,658 A | 8/1999 | Koros et al. |
| 5,954,635 A | 9/1999 | Foley et al. |
| 5,964,698 A | 10/1999 | Fowler |
| 5,976,146 A | 11/1999 | Ogawa et al. |
| 6,055,456 A | 4/2000 | Gerber |
| 6,063,088 A | 5/2000 | Winslow |
| 6,074,343 A | 6/2000 | Nathanson et al. |
| 6,080,155 A | 6/2000 | Michelson |
| 6,083,225 A | 7/2000 | Winslow et al. |
| 6,090,113 A | 7/2000 | Le et al. |
| 6,096,038 A | 8/2000 | Michelson |
| 6,139,493 A | 10/2000 | Koros et al. |
| 6,187,000 B1 | 2/2001 | Davison et al. |
| 6,200,324 B1 | 3/2001 | Regni, Jr. |
| 6,224,545 B1 | 5/2001 | Cocchia et al. |
| 6,261,295 B1 | 7/2001 | Nicholson et al. |
| 6,267,763 B1 | 7/2001 | Castro |
| 6,270,498 B1 | 8/2001 | Michelson |
| 6,283,966 B1 | 9/2001 | Houfburg |
| 6,322,500 B1 | 11/2001 | Sikora et al. |
| 6,454,767 B2 | 9/2002 | Alleyne |
| 6,466,817 B1 | 10/2002 | Kaula et al. |
| 6,500,128 B2 | 12/2002 | Marino |
| 6,564,078 B1 | 5/2003 | Marino et al. |
| 6,579,291 B1 | 6/2003 | Keith et al. |
| 6,626,905 B1 | 9/2003 | Schmiel et al. |
| 6,709,389 B2 | 3/2004 | Farascioni |
| 6,712,825 B2 | 3/2004 | Aebi et al. |
| 6,716,218 B2 | 4/2004 | Holmes et al. |
| 6,755,839 B2 | 6/2004 | Van et al. |
| 6,760,616 B2 | 7/2004 | Hoey et al. |
| 6,811,558 B2 | 11/2004 | Davison et al. |
| 6,896,680 B2 | 5/2005 | Michelson |
| 6,932,765 B2 | 8/2005 | Berg |
| 6,945,933 B2 | 9/2005 | Branch et al. |
| 7,008,432 B2 | 3/2006 | Schlaepfer et al. |
| 7,050,848 B2 | 5/2006 | Hoey et al. |
| 7,074,226 B2 | 7/2006 | Roehm et al. |
| 7,079,883 B2 | 7/2006 | Marino et al. |
| 7,081,118 B2 | 7/2006 | Weber et al. |
| 7,087,055 B2 | 8/2006 | Lim et al. |
| 7,097,647 B2 | 8/2006 | Segler |
| 7,108,698 B2 | 9/2006 | Robbins et al. |
| 7,156,805 B2 | 1/2007 | Thalgott et al. |
| 7,177,677 B2 | 2/2007 | Kaula et al. |
| 7,207,949 B2 | 4/2007 | Miles et al. |
| 7,207,991 B2 | 4/2007 | Michelson |
| 7,226,413 B2 | 6/2007 | McKinley |
| 7,261,688 B2 | 8/2007 | Smith et al. |
| 7,326,216 B2 | 2/2008 | Bertagnoli et al. |
| 7,435,219 B2 | 10/2008 | Kim |
| 7,470,236 B1 | 12/2008 | Kelleher et al. |
| 7,473,222 B2 | 1/2009 | Dewey et al. |
| 7,491,168 B2 | 2/2009 | Raymond et al. |
| 7,491,205 B1 | 2/2009 | Michelson |
| 7,513,869 B2 | 4/2009 | Branch et al. |
| 7,522,953 B2 | 4/2009 | Kaula et al. |
| 7,524,285 B2 | 4/2009 | Branch et al. |
| 7,556,600 B2 | 7/2009 | Landry et al. |
| 7,582,058 B1 | 9/2009 | Miles et al. |
| 7,691,057 B2 | 4/2010 | Miles et al. |
| 7,785,253 B1 | 8/2010 | Arambula et al. |
| 7,819,801 B2 | 10/2010 | Miles et al. |
| 7,892,173 B2 | 2/2011 | Miles et al. |
| 7,905,840 B2 | 3/2011 | Pimenta et al. |
| 7,920,922 B2 | 4/2011 | Gharib et al. |
| 7,922,658 B2 | 4/2011 | Cohen et al. |
| 7,935,051 B2 | 5/2011 | Miles et al. |
| 7,935,053 B2 | 5/2011 | Karpowicz et al. |
| 7,976,463 B2 | 7/2011 | Dewey et al. |
| 7,981,029 B2 | 7/2011 | Branch et al. |
| 8,000,782 B2 | 8/2011 | Gharib et al. |
| 8,005,535 B2 | 8/2011 | Gharib et al. |
| 8,016,767 B2 | 9/2011 | Miles et al. |
| 8,027,716 B2 | 9/2011 | Gharib et al. |
| 8,066,705 B2 | 11/2011 | Michelson |
| 8,068,912 B2 | 11/2011 | Kaula et al. |
| 8,114,019 B2 | 2/2012 | Miles et al. |
| 8,133,173 B2 | 3/2012 | Miles et al. |
| 8,137,284 B2 | 3/2012 | Miles et al. |
| 8,147,421 B2 | 4/2012 | Farquhar et al. |
| 8,165,653 B2 | 4/2012 | Marino et al. |
| 8,172,750 B2 | 5/2012 | Miles et al. |
| 8,182,423 B2 | 5/2012 | Miles et al. |
| 8,187,179 B2 | 5/2012 | Miles et al. |
| 8,192,356 B2 | 6/2012 | Miles et al. |
| 8,192,357 B2 | 6/2012 | Miles et al. |
| 8,206,312 B2 | 6/2012 | Farquhar |
| 8,244,343 B2 | 8/2012 | Gharib et al. |
| 8,251,997 B2 | 8/2012 | Michelson |
| 8,255,045 B2 | 8/2012 | Gharib et al. |
| 8,265,744 B2 | 9/2012 | Gharib et al. |
| 8,277,486 B2 | 10/2012 | Davison |
| 8,303,498 B2 | 11/2012 | Miles et al. |
| 8,303,515 B2 | 11/2012 | Miles et al. |
| 8,317,817 B2 | 11/2012 | Davison et al. |
| 8,337,410 B2 | 12/2012 | Kelleher et al. |
| 8,343,046 B2 | 1/2013 | Miles et al. |
| 8,353,826 B2 | 1/2013 | Weiman |
| 8,355,780 B2 | 1/2013 | Miles et al. |
| 8,357,184 B2 | 1/2013 | Woolley et al. |
| 8,388,527 B2 | 3/2013 | Miles et al. |
| 8,401,632 B1 | 3/2013 | Stone et al. |
| 8,403,841 B2 | 3/2013 | Miles et al. |
| 8,489,170 B2 | 7/2013 | Marino et al. |
| 8,500,634 B2 | 8/2013 | Miles et al. |
| 8,500,653 B2 | 8/2013 | Farquhar |
| 8,512,235 B2 | 8/2013 | Miles et al. |
| 8,523,768 B2 | 9/2013 | Miles et al. |
| 8,535,320 B2 | 9/2013 | Woolley et al. |
| 8,538,539 B2 | 9/2013 | Gharib et al. |
| 8,548,579 B2 | 10/2013 | Gharib et al. |
| 8,550,994 B2 | 10/2013 | Miles et al. |

(56) References Cited

U.S. PATENT DOCUMENTS

| | | |
|---|---|---|
| 8,556,808 B2 | 10/2013 | Miles et al. |
| 8,562,521 B2 | 10/2013 | Miles et al. |
| 8,562,539 B2 | 10/2013 | Marino |
| 8,568,317 B1 | 10/2013 | Gharib et al. |
| 8,591,432 B2 | 11/2013 | Pimenta et al. |
| 8,602,982 B2 | 12/2013 | Miles et al. |
| 8,628,469 B2 | 1/2014 | Miles et al. |
| 8,634,904 B2 | 1/2014 | Kaula et al. |
| 8,641,638 B2 | 2/2014 | Kelleher et al. |
| 8,652,177 B1 | 2/2014 | Cornwall et al. |
| 8,663,100 B2 | 3/2014 | Miles et al. |
| 8,672,840 B2 | 3/2014 | Miles et al. |
| 8,673,005 B1 | 3/2014 | Pimenta et al. |
| 8,679,006 B2 | 3/2014 | Miles et al. |
| 8,696,559 B2 | 4/2014 | Miles et al. |
| 8,708,899 B2 | 4/2014 | Miles et al. |
| 8,738,123 B2 | 5/2014 | Gharib et al. |
| 8,747,307 B2 | 6/2014 | Miles et al. |
| 8,753,270 B2 | 6/2014 | Miles et al. |
| 8,753,271 B1 | 6/2014 | Miles et al. |
| 8,758,344 B2 | 6/2014 | Michelson |
| 8,764,649 B2 | 7/2014 | Miles et al. |
| 8,768,450 B2 | 7/2014 | Gharib et al. |
| 8,812,116 B2 | 8/2014 | Kaula et al. |
| 8,821,396 B1 | 9/2014 | Miles et al. |
| 8,827,900 B1 | 9/2014 | Pimenta |
| 8,840,622 B1 | 9/2014 | Vellido et al. |
| 8,840,668 B1 | 9/2014 | Donahoe et al. |
| 8,876,851 B1 | 11/2014 | Woolley et al. |
| 8,876,904 B2 | 11/2014 | Pimenta et al. |
| 8,915,846 B2 | 12/2014 | Miles et al. |
| 8,920,500 B1 | 12/2014 | Pimenta et al. |
| 8,942,801 B2 | 1/2015 | Miles et al. |
| 8,945,004 B2 | 2/2015 | Miles et al. |
| 8,956,283 B2 | 2/2015 | Miles et al. |
| 8,958,869 B2 | 2/2015 | Kelleher et al. |
| 8,968,351 B2 | 3/2015 | Davison et al. |
| 8,968,363 B2 | 3/2015 | Weiman et al. |
| 8,977,352 B2 | 3/2015 | Gharib et al. |
| 8,983,567 B1 | 3/2015 | Miles et al. |
| 8,989,866 B2 | 3/2015 | Gharib et al. |
| 8,992,425 B2 | 3/2015 | Karpowicz et al. |
| 8,992,579 B1 | 3/2015 | Gustine et al. |
| 9,014,776 B2 | 4/2015 | Marino et al. |
| 9,037,250 B2 | 5/2015 | Kaula et al. |
| 9,050,146 B2 | 6/2015 | Woolley et al. |
| 9,066,701 B1 | 6/2015 | Finley et al. |
| 9,131,947 B2 | 9/2015 | Ferree |
| 9,180,021 B2 | 11/2015 | Curran et al. |
| 9,186,261 B2 | 11/2015 | Pimenta et al. |
| 9,192,415 B1 | 11/2015 | Arnold et al. |
| 9,192,482 B1 | 11/2015 | Pimenta et al. |
| 9,204,871 B2 | 12/2015 | Miles et al. |
| 9,259,144 B2 | 2/2016 | Smith et al. |
| 9,265,493 B2 | 2/2016 | Miles et al. |
| 9,295,396 B2 | 3/2016 | Gharib et al. |
| 9,301,743 B2 | 4/2016 | Miles et al. |
| 9,307,972 B2 | 4/2016 | Lovell et al. |
| 9,314,152 B2 | 4/2016 | Pimenta et al. |
| 9,351,718 B1 | 5/2016 | Arambula et al. |
| 9,351,845 B1 | 5/2016 | Pimenta et al. |
| D761,957 S | 7/2016 | Lee et al. |
| 9,392,953 B1 | 7/2016 | Gharib |
| 9,456,783 B2 | 10/2016 | Kaula et al. |
| 9,468,405 B2 | 10/2016 | Miles et al. |
| 9,468,536 B1 | 10/2016 | Pimenta |
| 9,474,627 B2 | 10/2016 | Curran et al. |
| 2001/0029377 A1 | 10/2001 | Aebi et al. |
| 2001/0031969 A1 | 10/2001 | Aebi et al. |
| 2002/0010466 A1 | 1/2002 | Alleyne |
| 2002/0091390 A1 | 7/2002 | Michelson |
| 2002/0123754 A1 | 9/2002 | Holmes et al. |
| 2002/0128659 A1 | 9/2002 | Michelson |
| 2003/0158553 A1 | 8/2003 | Michelson |
| 2003/0187453 A1 | 10/2003 | Schlapfer et al. |
| 2003/0191371 A1 | 10/2003 | Smith et al. |
| 2003/0220650 A1 | 11/2003 | Major et al. |
| 2004/0002629 A1 | 1/2004 | Branch et al. |
| 2004/0039397 A1 | 2/2004 | Weber et al. |
| 2004/0059339 A1 | 3/2004 | Roehm et al. |
| 2004/0097927 A1 | 5/2004 | Yeung et al. |
| 2004/0106999 A1 | 6/2004 | Mathews |
| 2004/0225196 A1 | 11/2004 | Ruane |
| 2005/0080320 A1 | 4/2005 | Lee et al. |
| 2005/0137461 A1 | 6/2005 | Marchek et al. |
| 2005/0149035 A1* | 7/2005 | Pimenta ................ A61B 17/02 606/86 R |
| 2005/0154395 A1 | 7/2005 | Robbins et al. |
| 2005/0192574 A1 | 9/2005 | Blain |
| 2006/0224044 A1 | 10/2006 | Marchek et al. |
| 2006/0247651 A1 | 11/2006 | Roehm et al. |
| 2007/0073111 A1 | 3/2007 | Bass |
| 2007/0100212 A1* | 5/2007 | Pimenta ................ A61B 5/742 600/210 |
| 2007/0156024 A1 | 7/2007 | Frasier et al. |
| 2007/0208227 A1 | 9/2007 | Smith et al. |
| 2007/0233065 A1 | 10/2007 | Donofrio et al. |
| 2007/0238932 A1 | 10/2007 | Jones et al. |
| 2007/0282171 A1 | 12/2007 | Karpowicz et al. |
| 2008/0097164 A1 | 4/2008 | Miles et al. |
| 2008/0114208 A1 | 5/2008 | Hutton et al. |
| 2008/0215081 A1 | 9/2008 | Hsueh et al. |
| 2008/0319290 A1 | 12/2008 | Mao et al. |
| 2009/0018399 A1 | 1/2009 | Martinelli et al. |
| 2009/0036746 A1 | 2/2009 | Blackwell et al. |
| 2009/0182203 A1 | 7/2009 | Hartnick et al. |
| 2009/0227845 A1 | 9/2009 | Lo et al. |
| 2009/0259107 A1 | 10/2009 | Crenshaw et al. |
| 2010/0022845 A1 | 1/2010 | Ott et al. |
| 2010/0069783 A1 | 3/2010 | Miles et al. |
| 2010/0152603 A1* | 6/2010 | Miles ................ A61B 5/04001 600/546 |
| 2010/0174148 A1 | 7/2010 | Miles et al. |
| 2010/0222644 A1 | 9/2010 | Sebastian et al. |
| 2010/0286486 A1 | 11/2010 | Parker et al. |
| 2010/0317989 A1 | 12/2010 | Gharib et al. |
| 2011/0208226 A1 | 8/2011 | Fatone et al. |
| 2011/0224497 A1* | 9/2011 | Weiman ............ A61B 17/0206 600/231 |
| 2011/0257487 A1 | 10/2011 | Thalgott et al. |

FOREIGN PATENT DOCUMENTS

| | | |
|---|---|---|
| CN | 100364483 C | 1/2008 |
| CN | 100488462 C | 5/2009 |
| EP | 0792620 A2 | 9/1997 |
| EP | 1192905 A1 | 4/2002 |
| EP | 1488755 A1 | 12/2004 |
| EP | 1515646 A2 | 3/2005 |
| EP | 1727477 A1 | 12/2006 |
| EP | 1994889 A2 | 11/2008 |
| EP | 2179695 A2 | 4/2010 |
| WO | 2004/091426 A2 | 10/2004 |
| WO | 2005/092206 A1 | 10/2005 |
| WO | 2005/094695 A2 | 10/2005 |
| WO | 2005/096735 A2 | 10/2005 |
| WO | 2006/031451 A1 | 3/2006 |
| WO | 2007/016368 A2 | 2/2007 |
| WO | 2007/087536 A2 | 8/2007 |
| WO | 2011/069036 A1 | 6/2011 |
| WO | 2011/112878 A1 | 9/2011 |

* cited by examiner

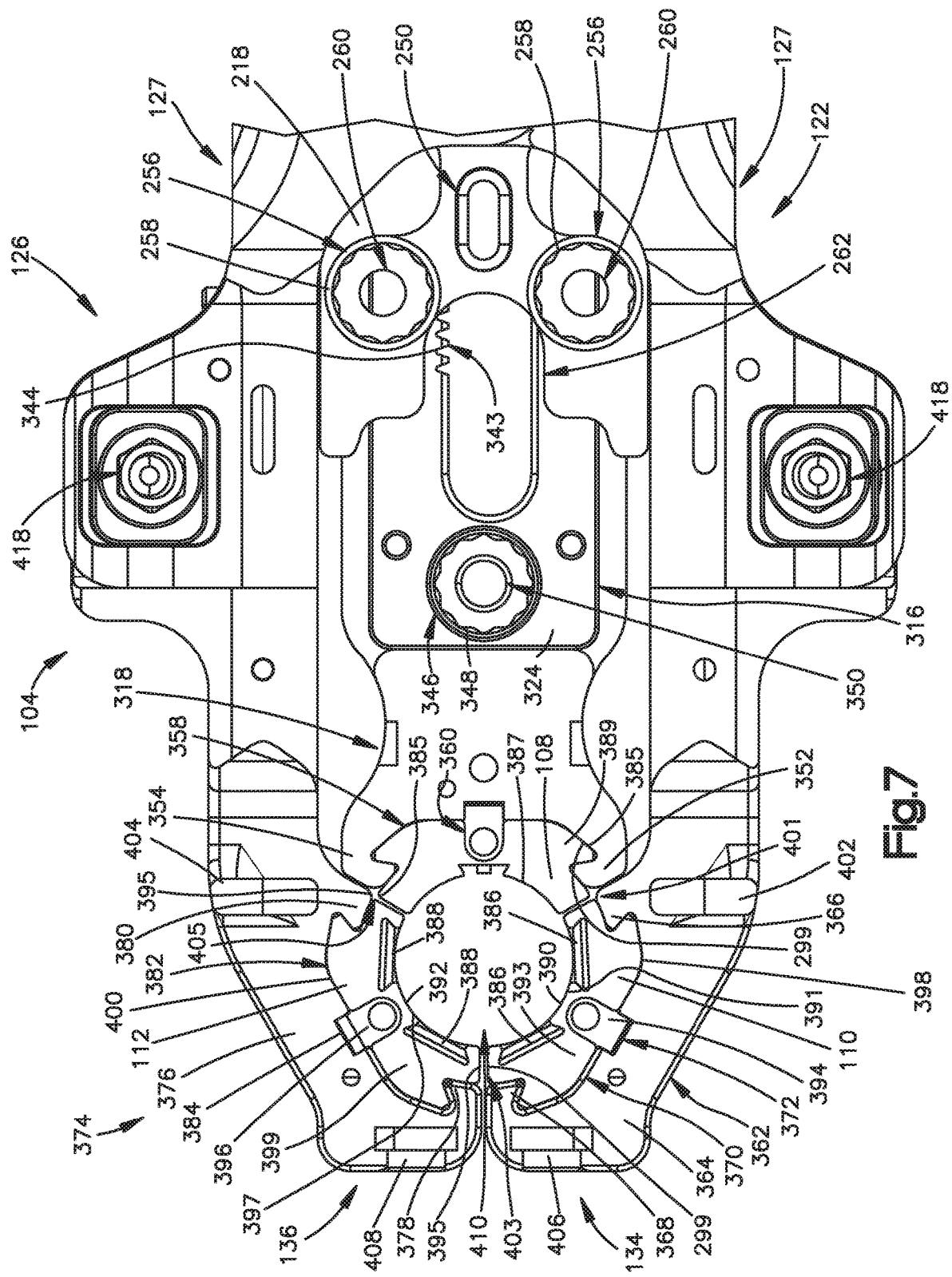

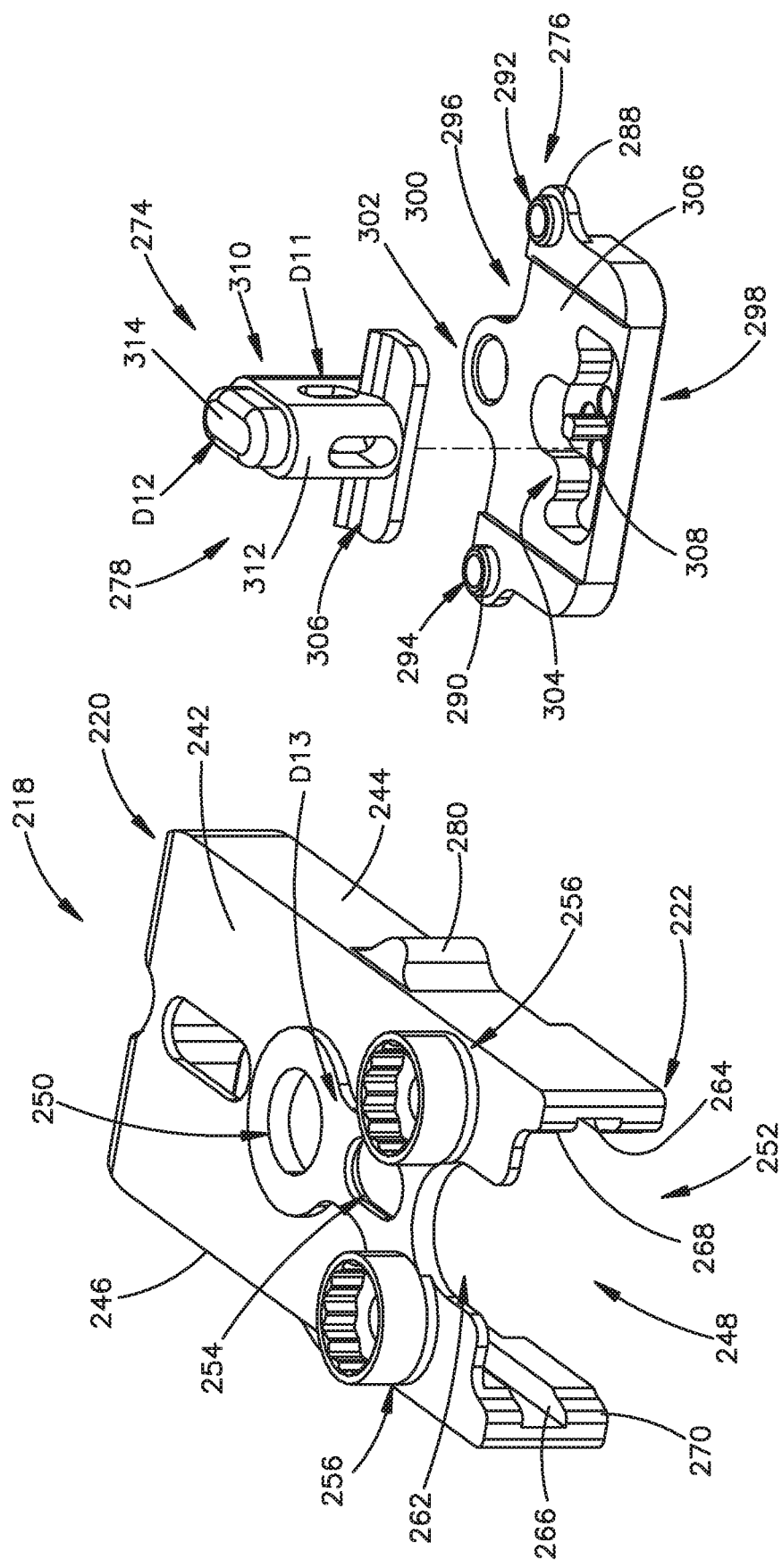

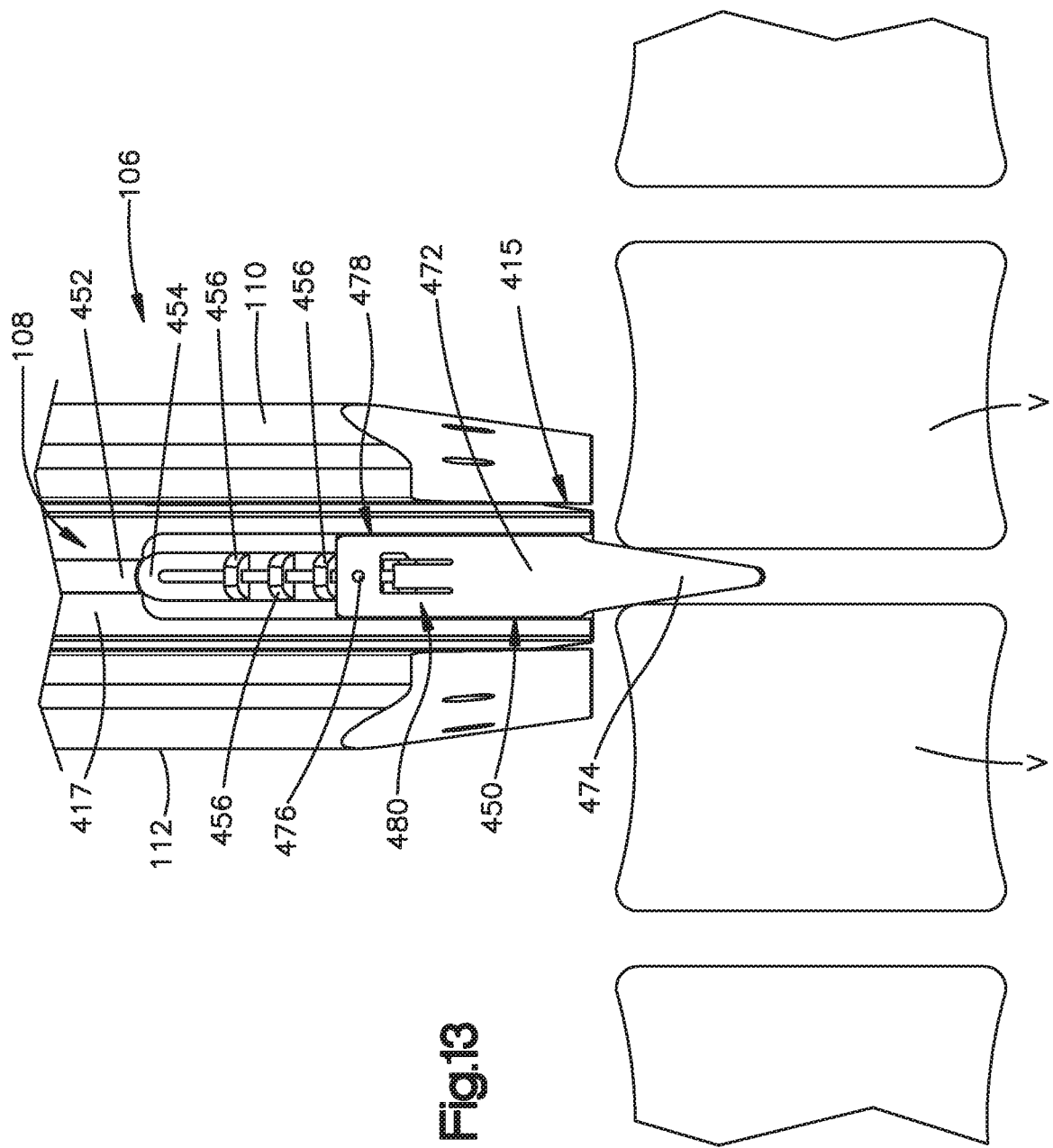

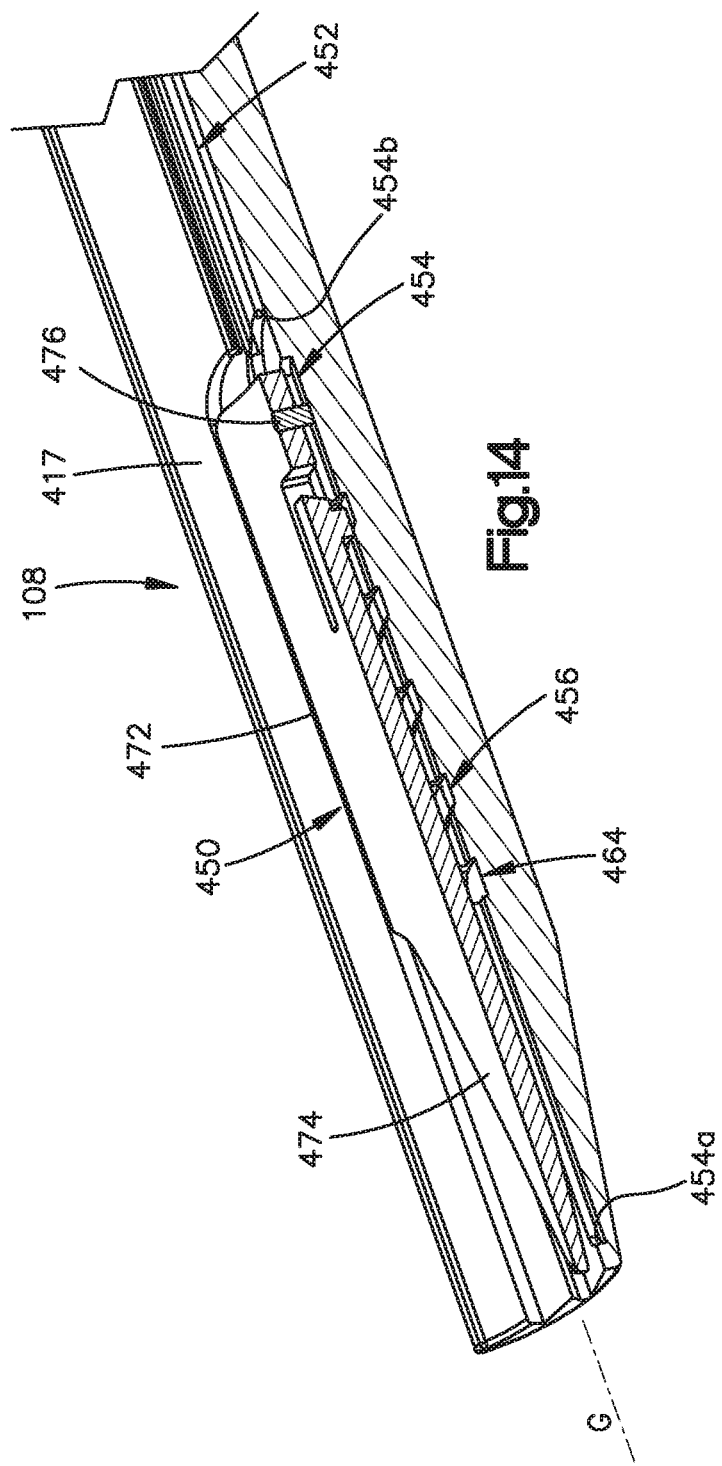

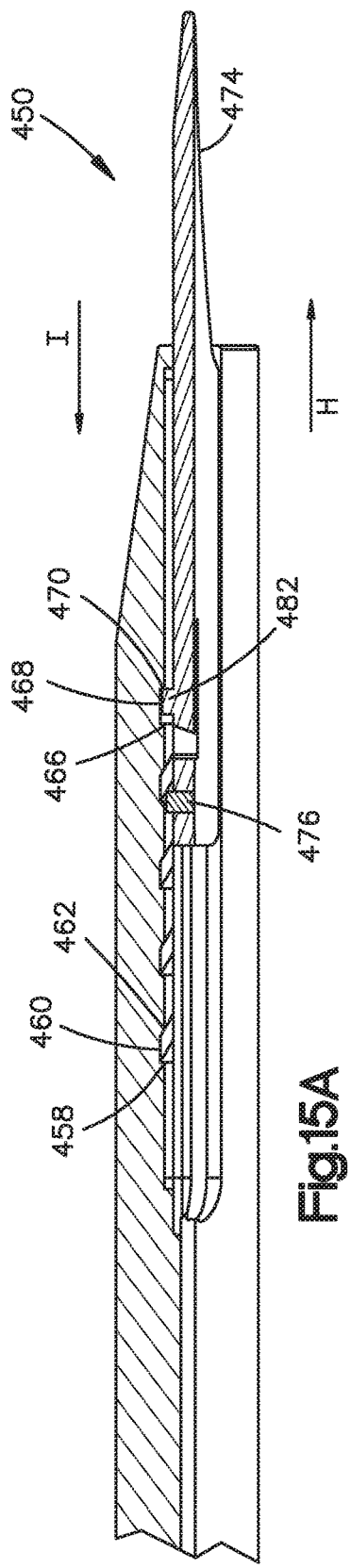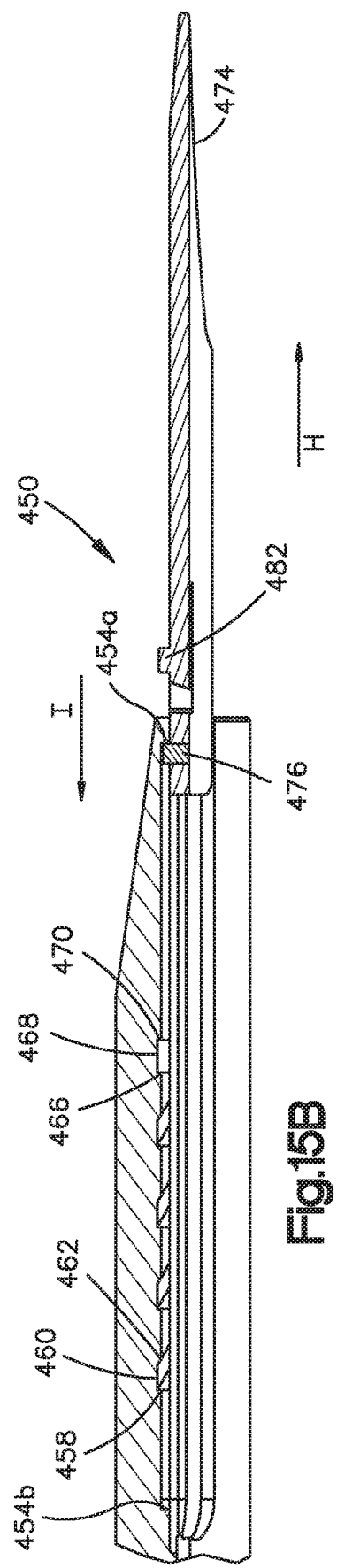

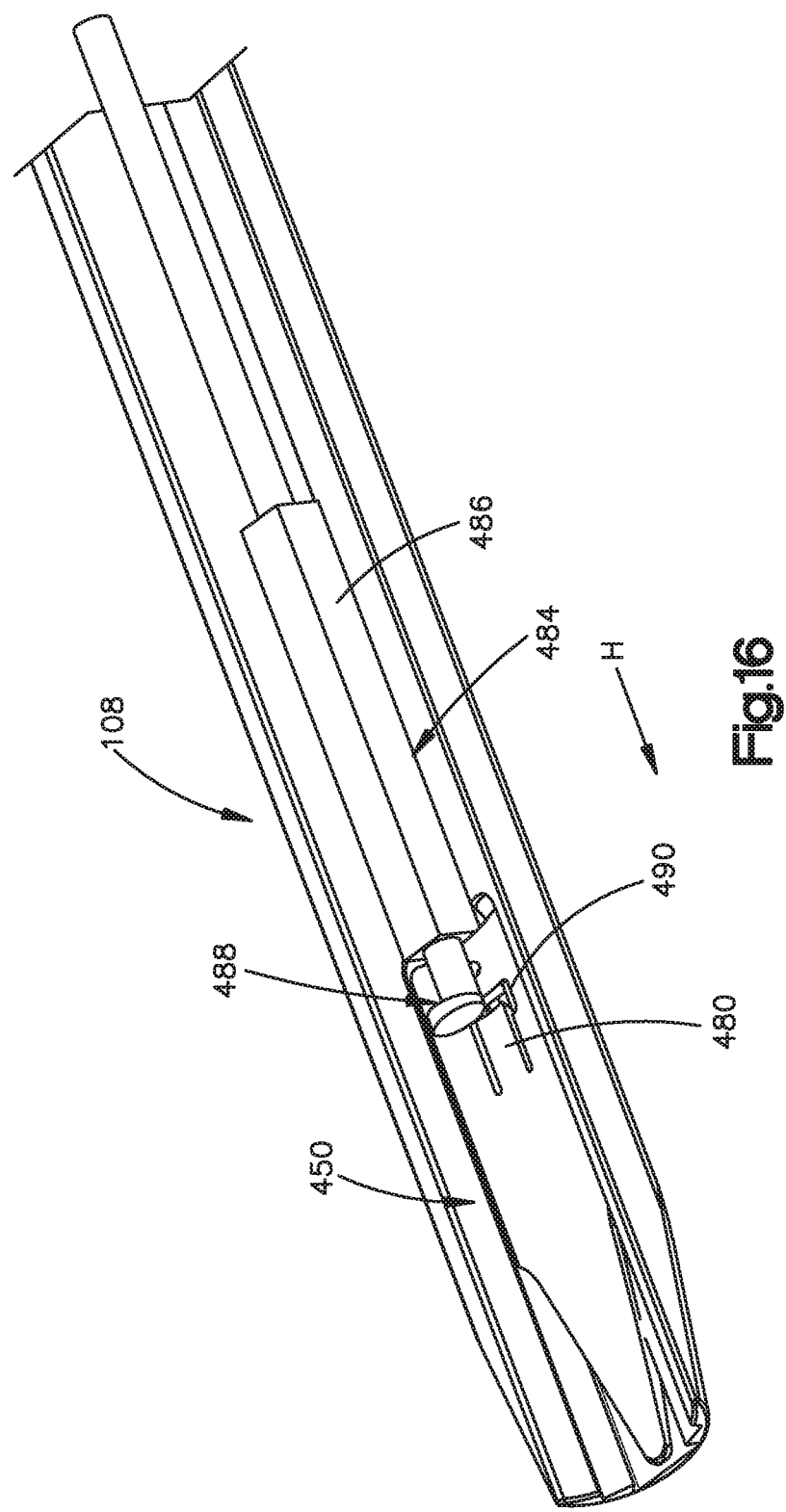

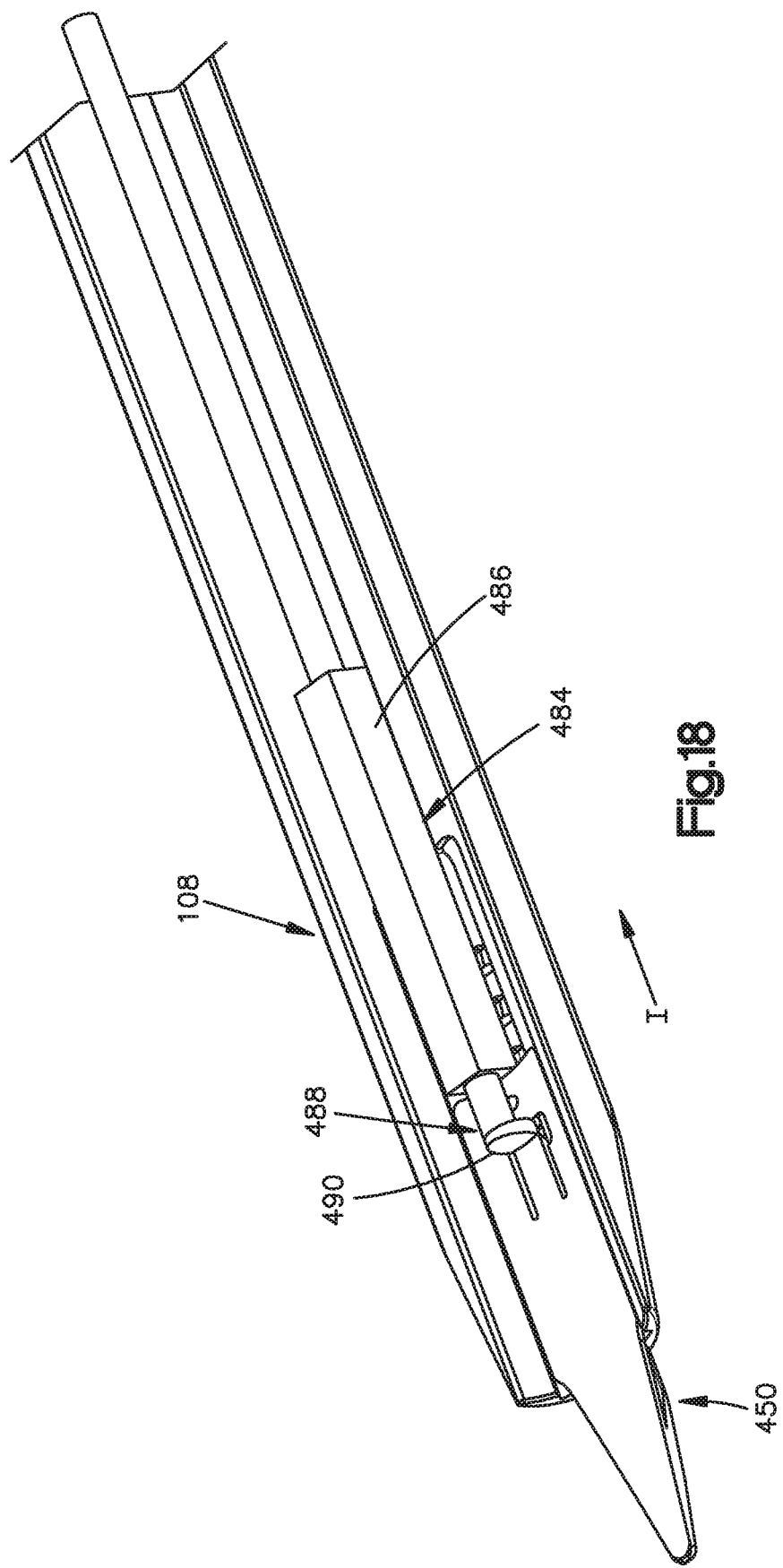

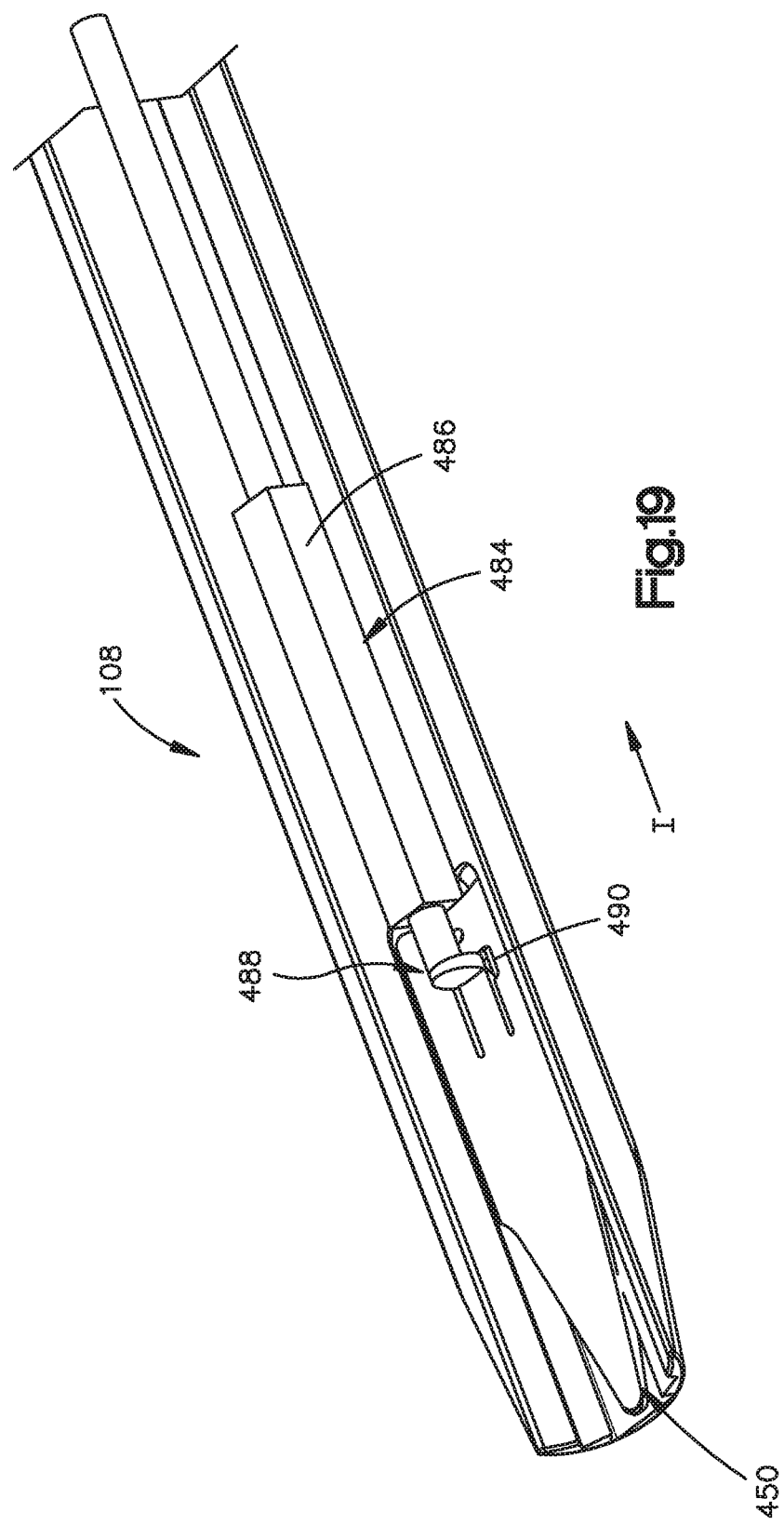

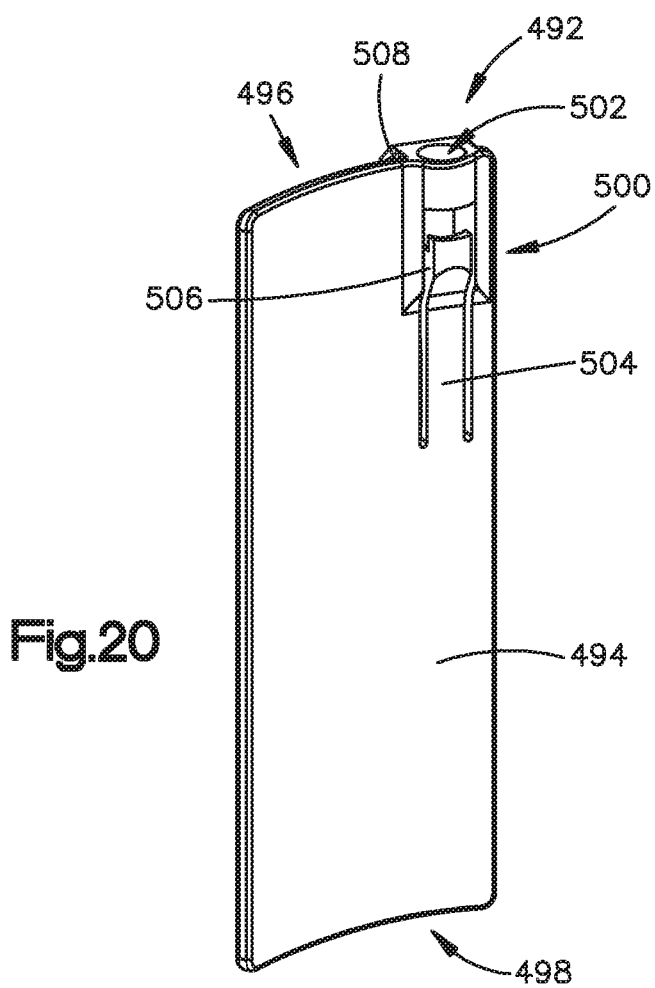
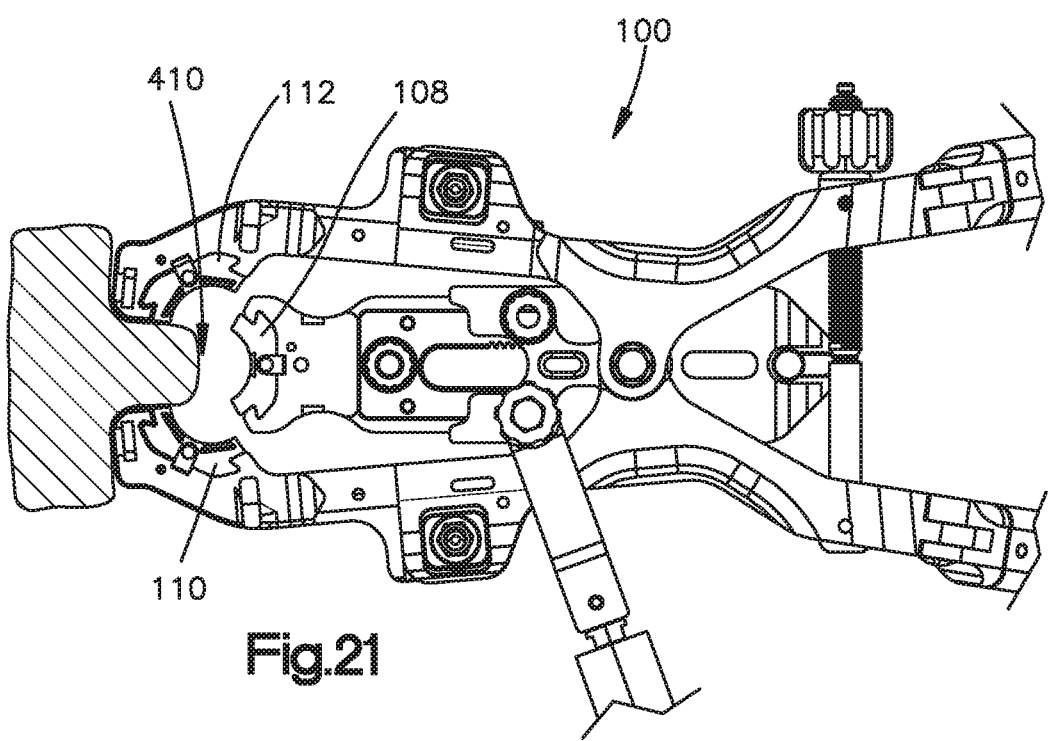

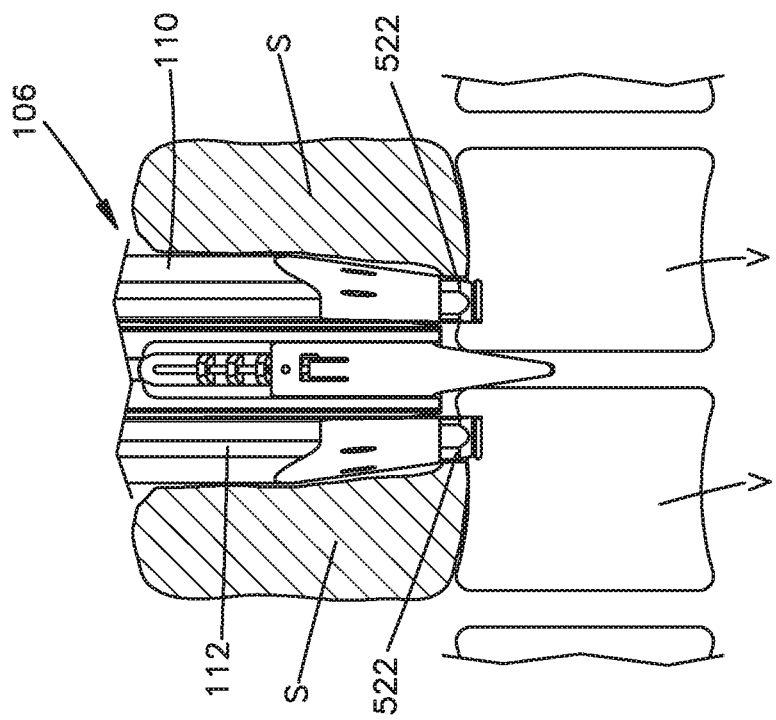
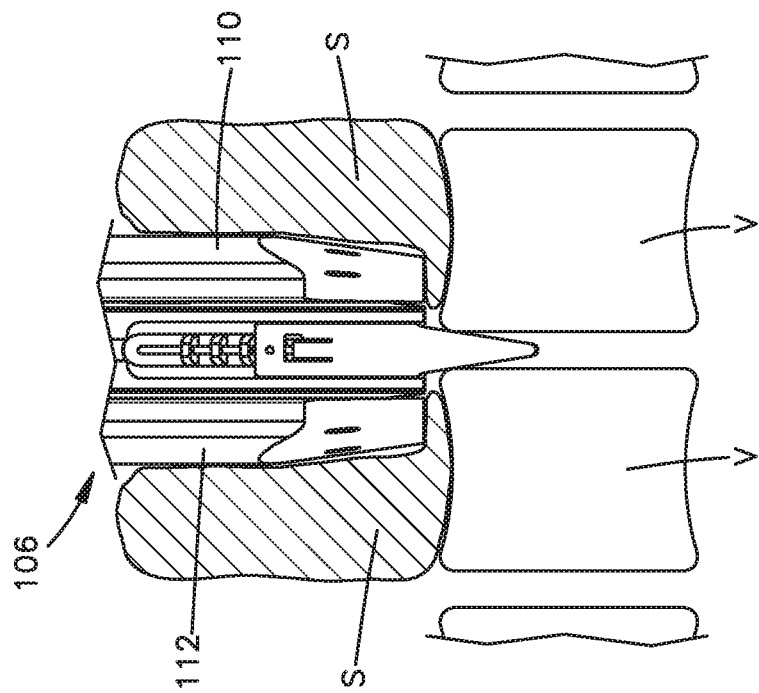

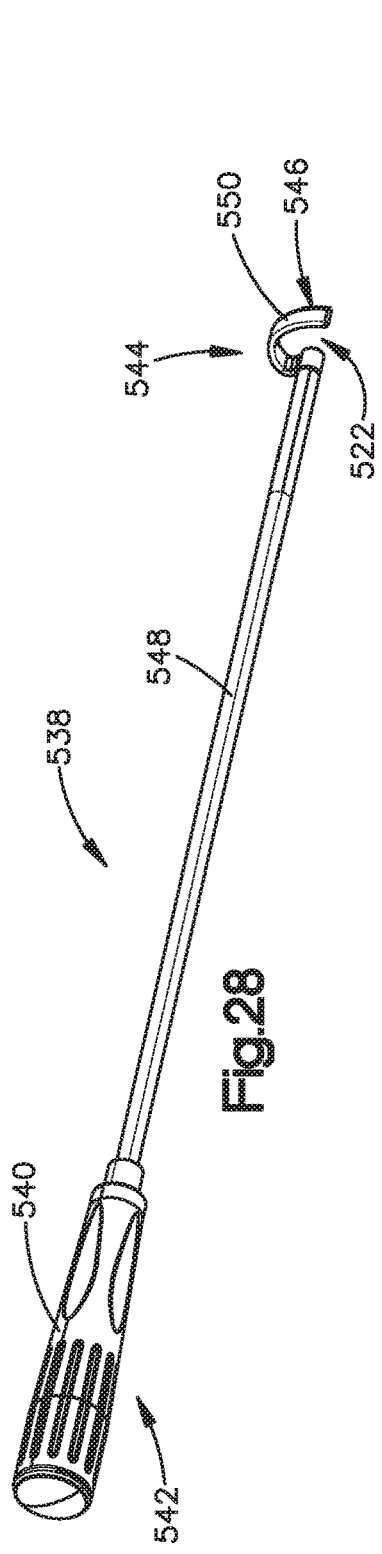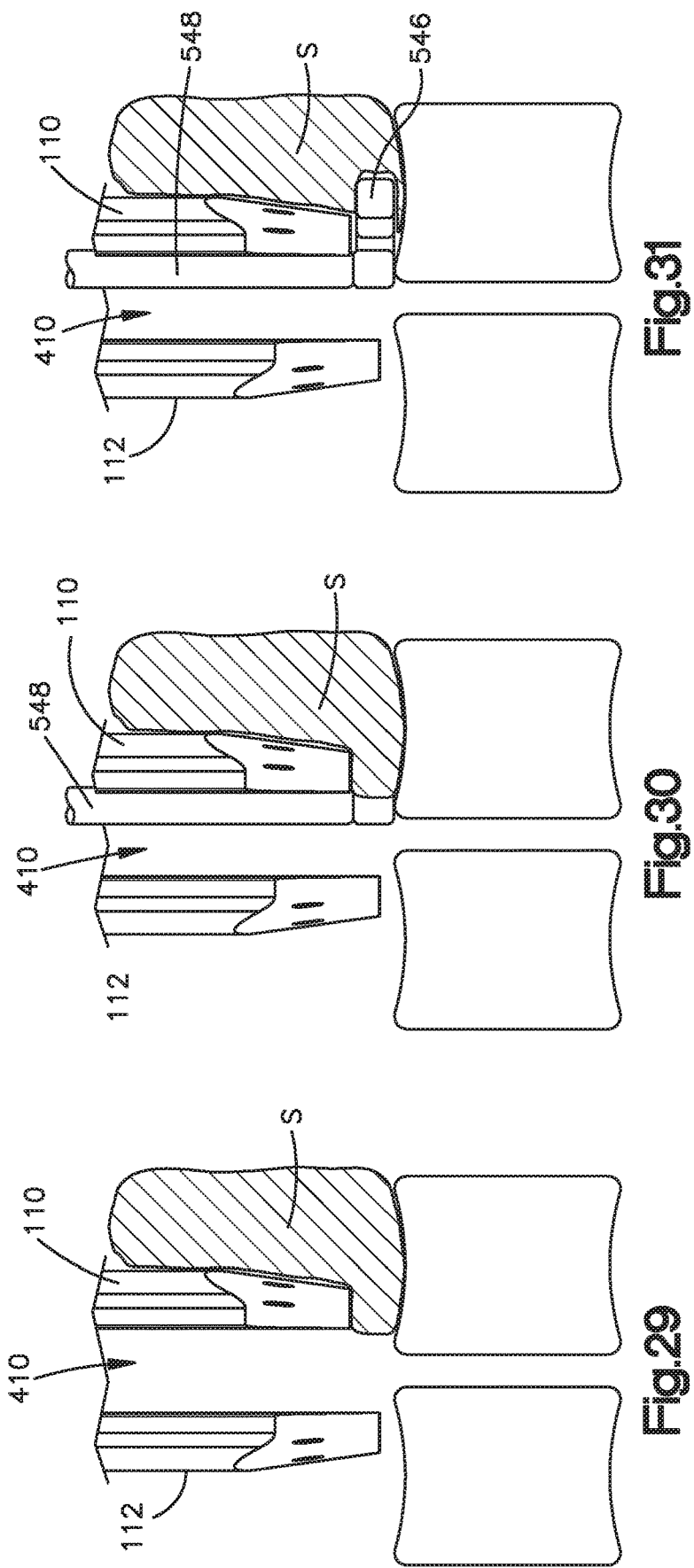

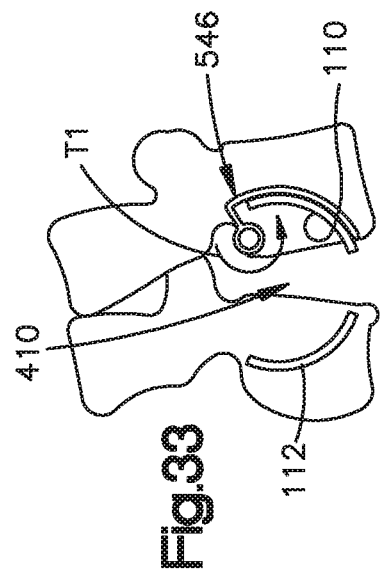
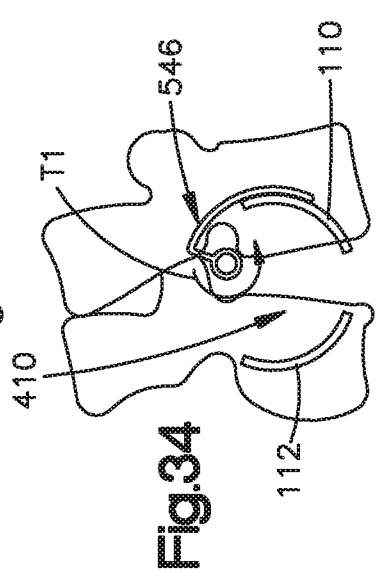
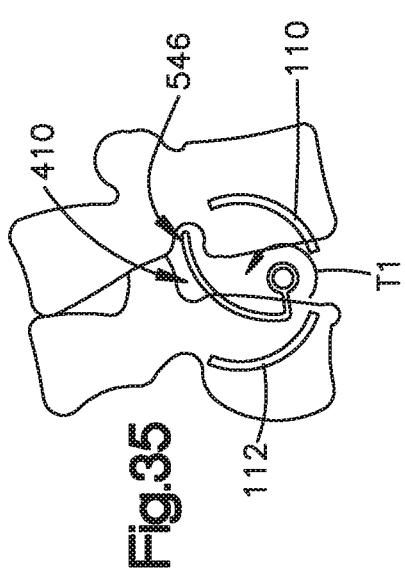
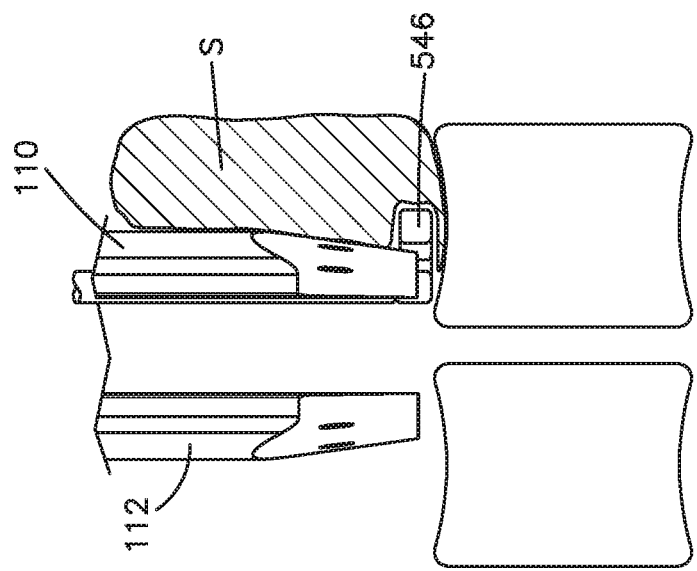

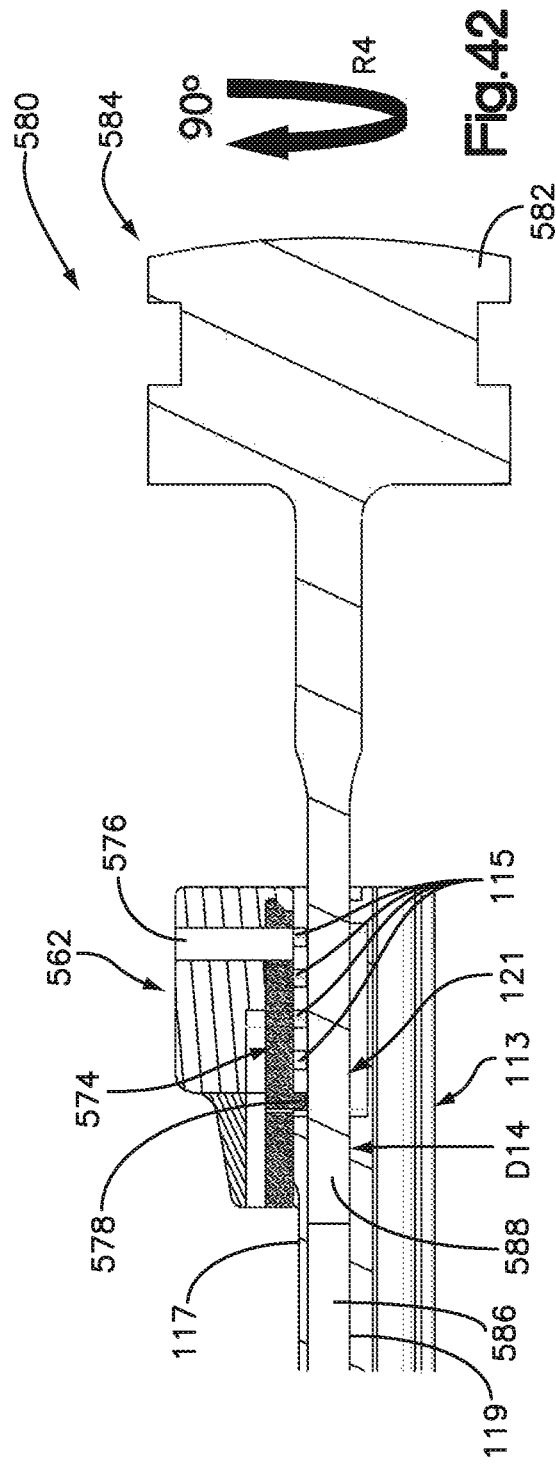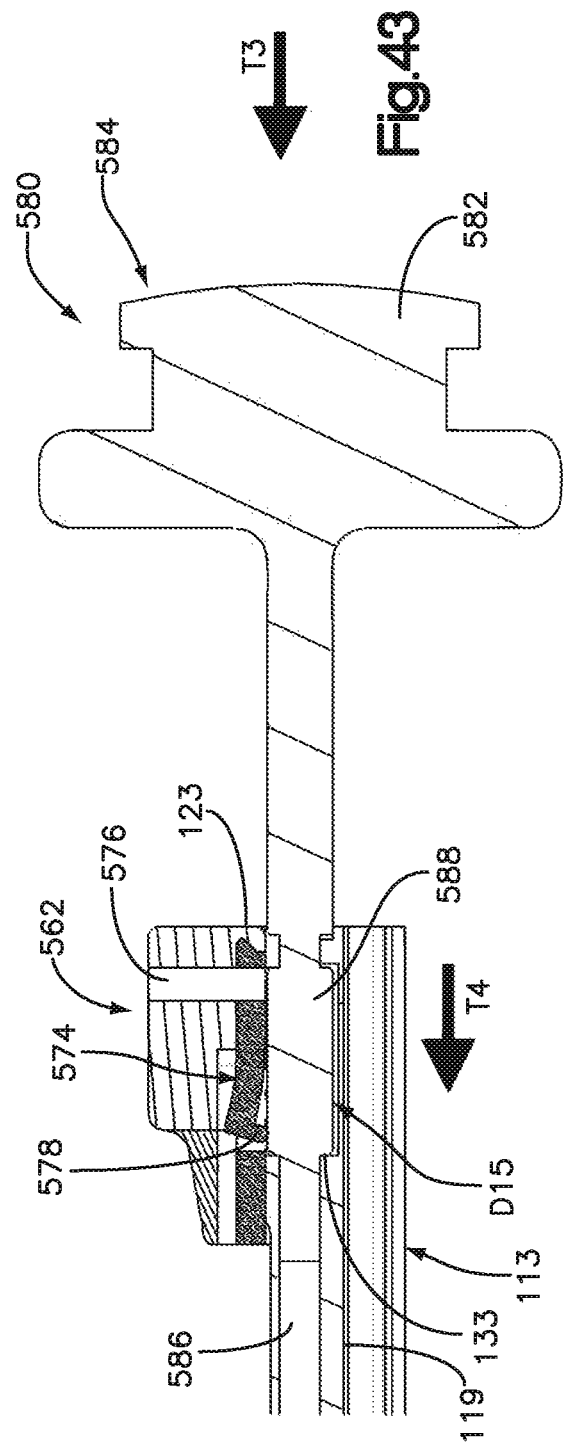

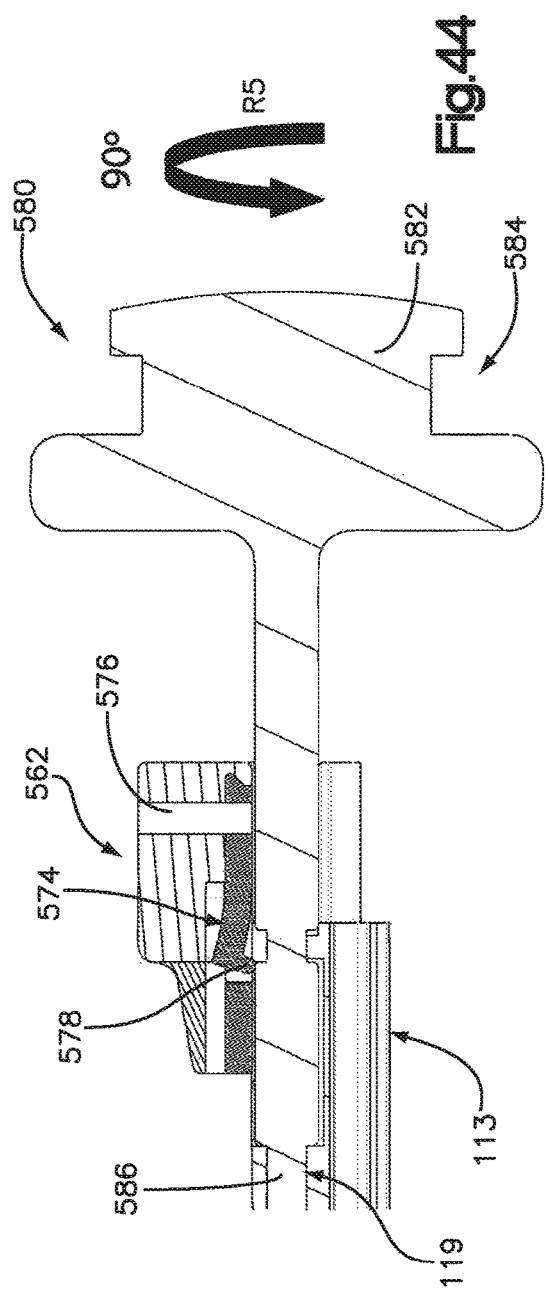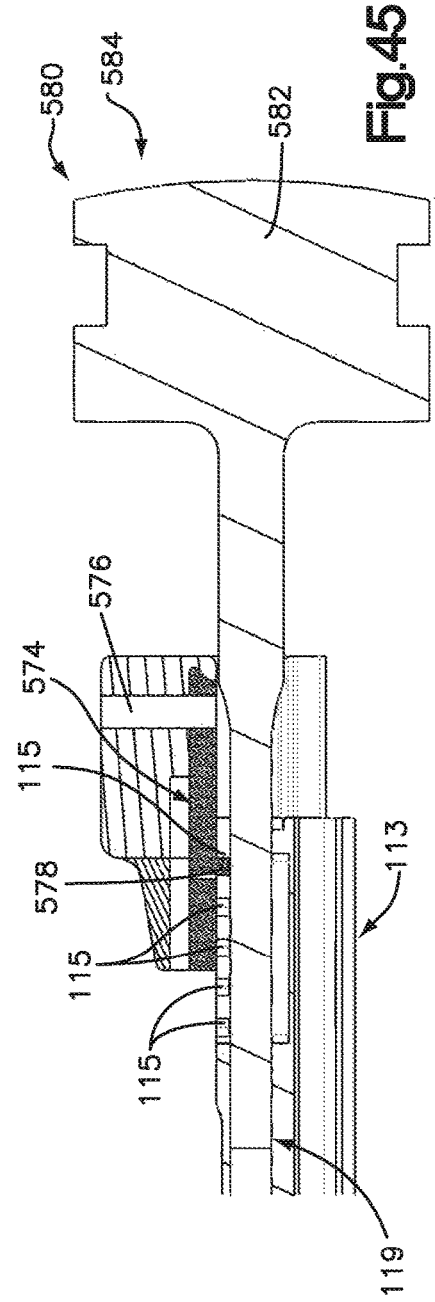

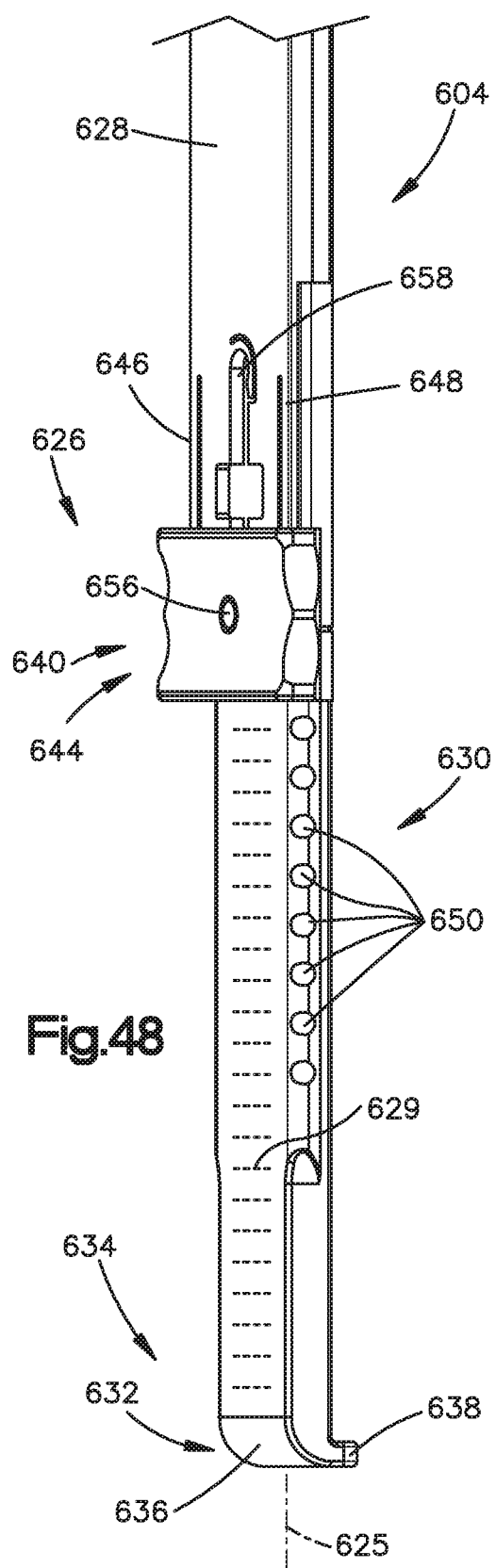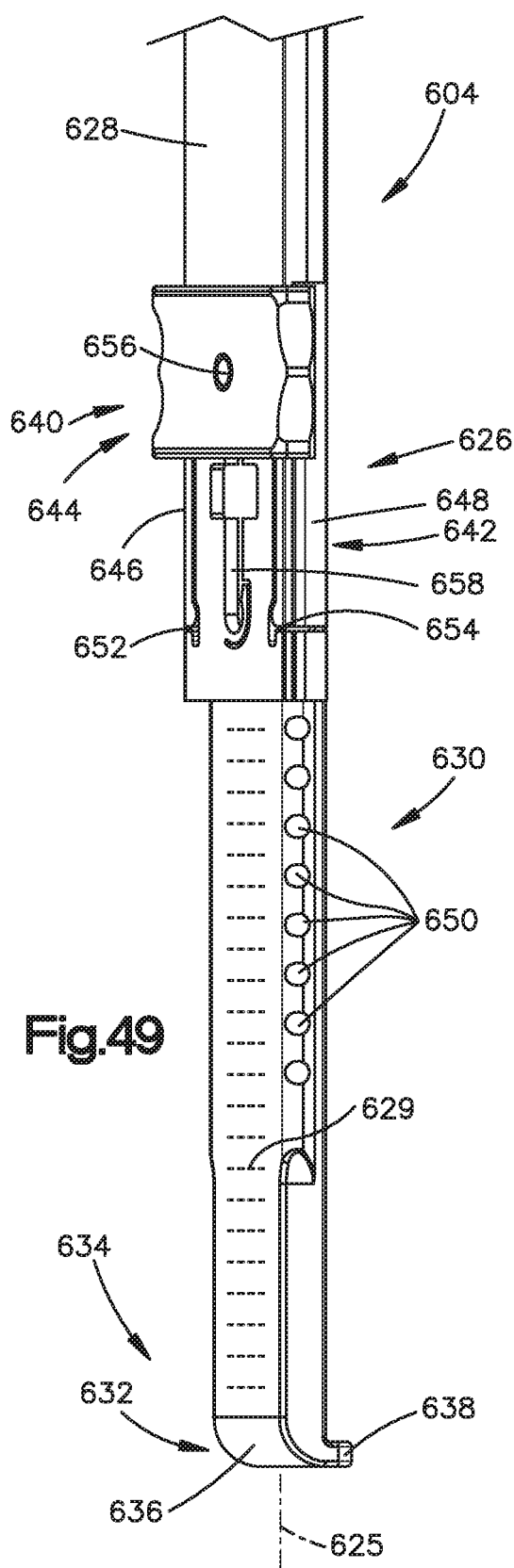

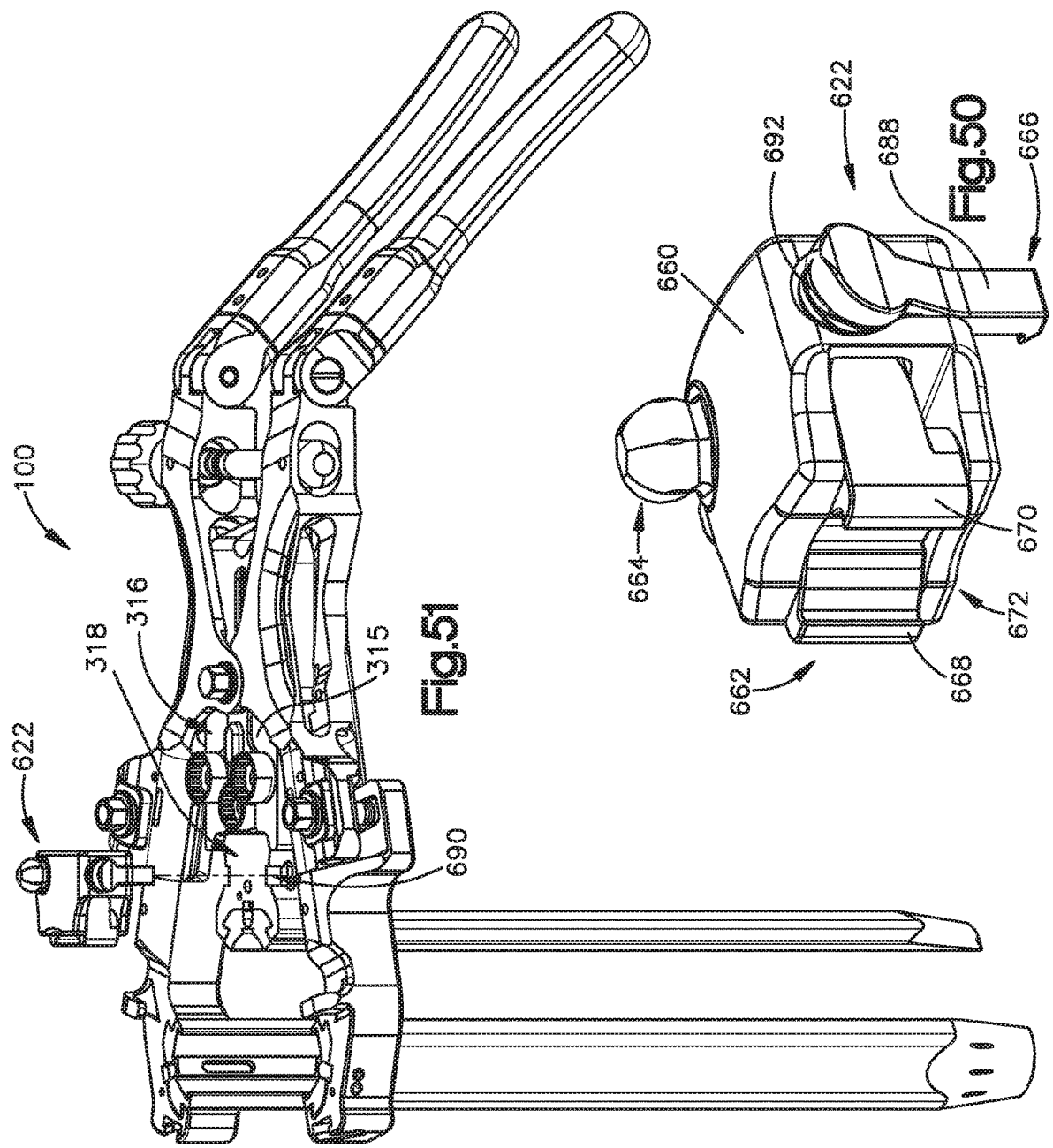

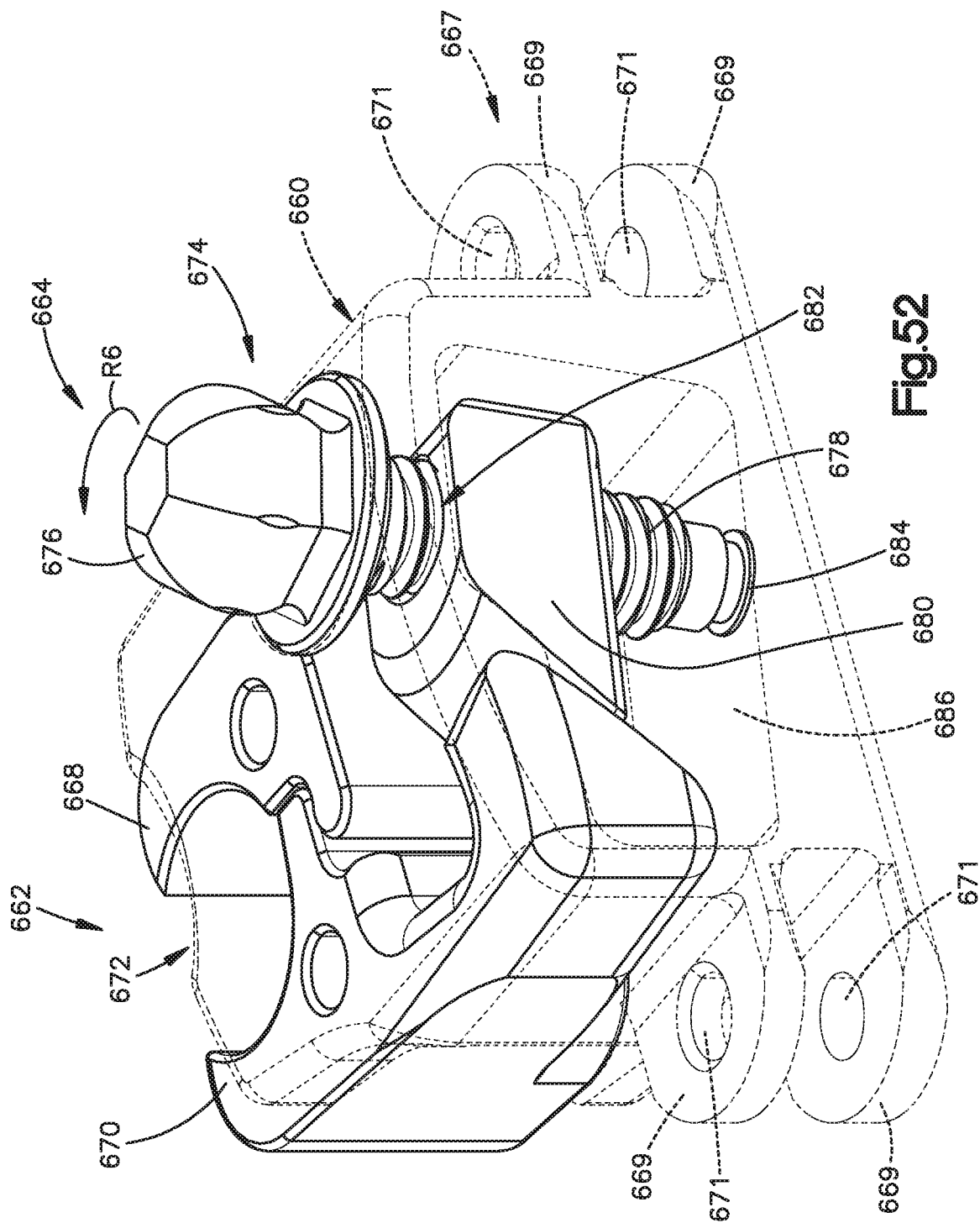

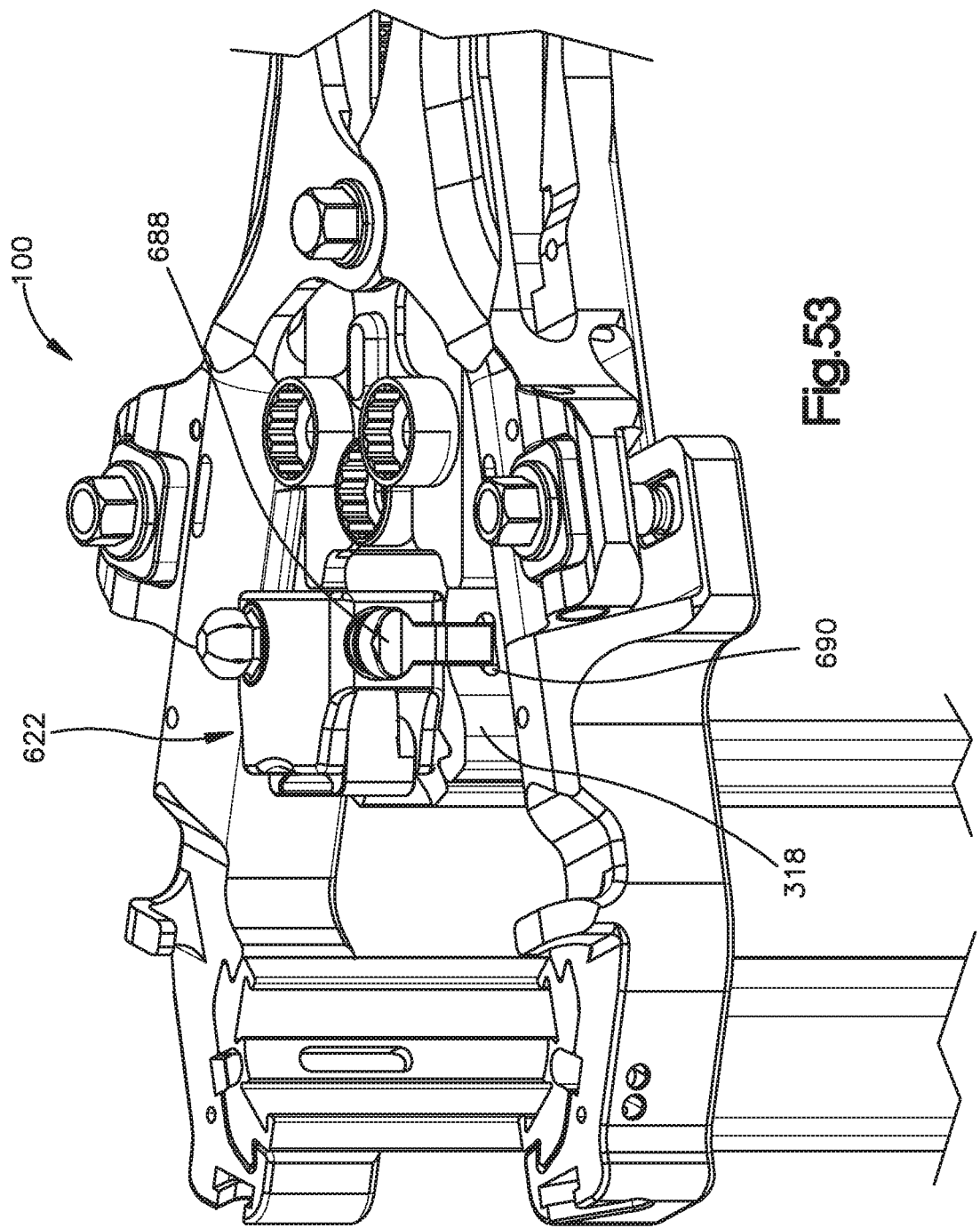

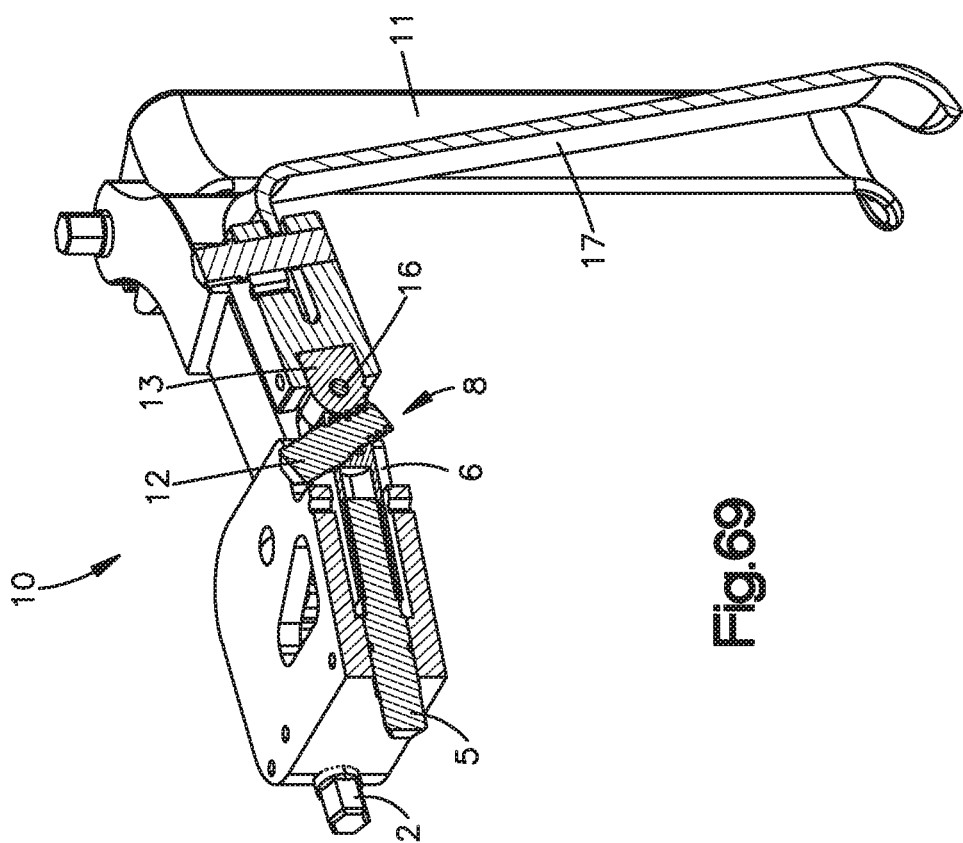
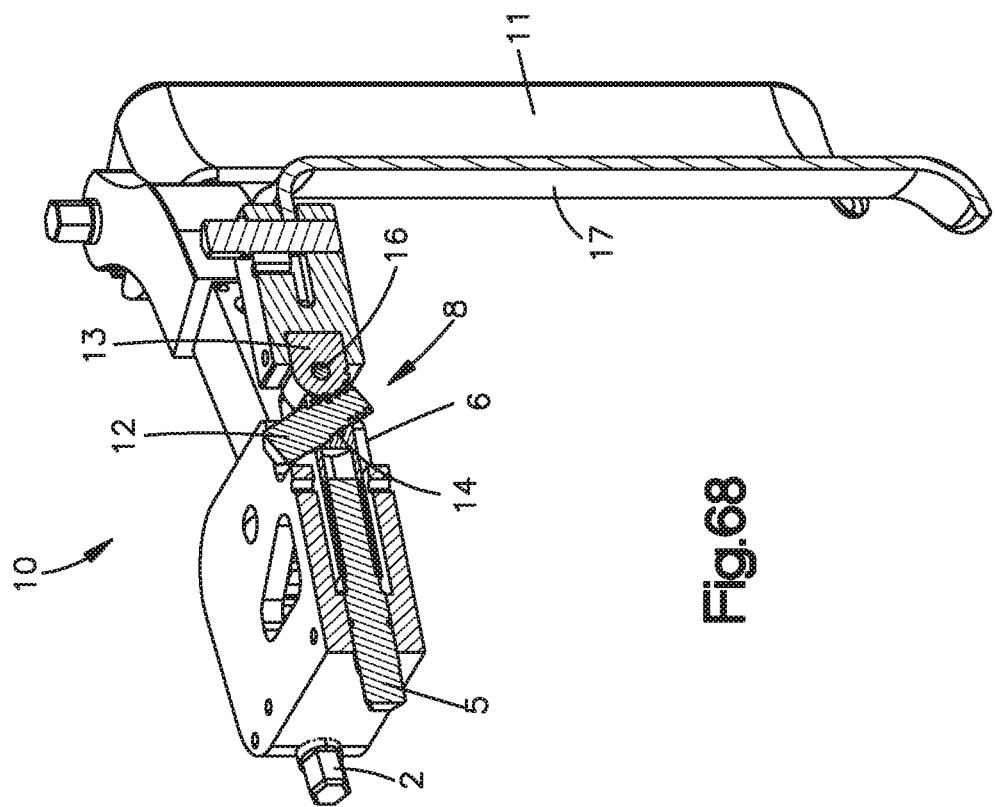

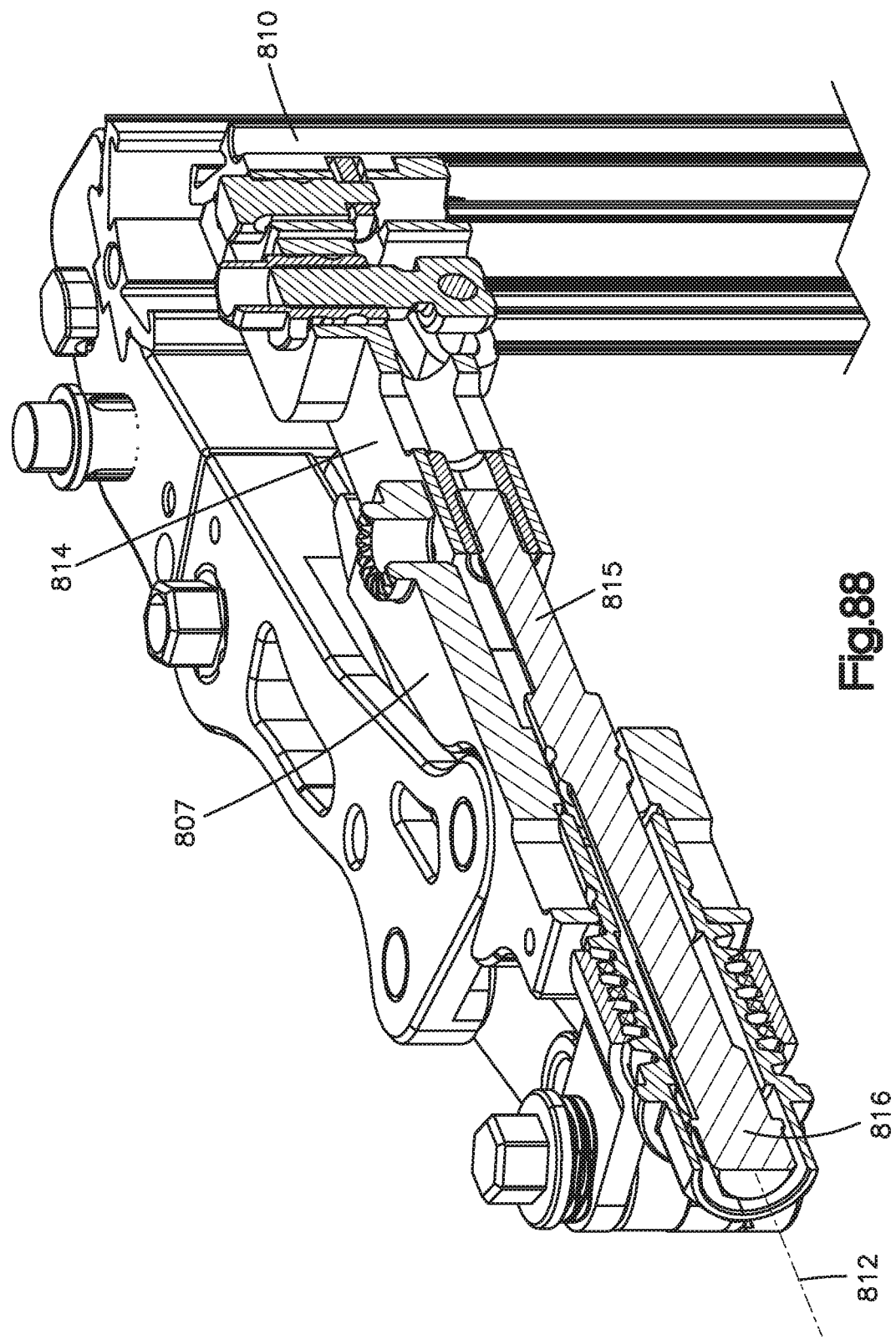

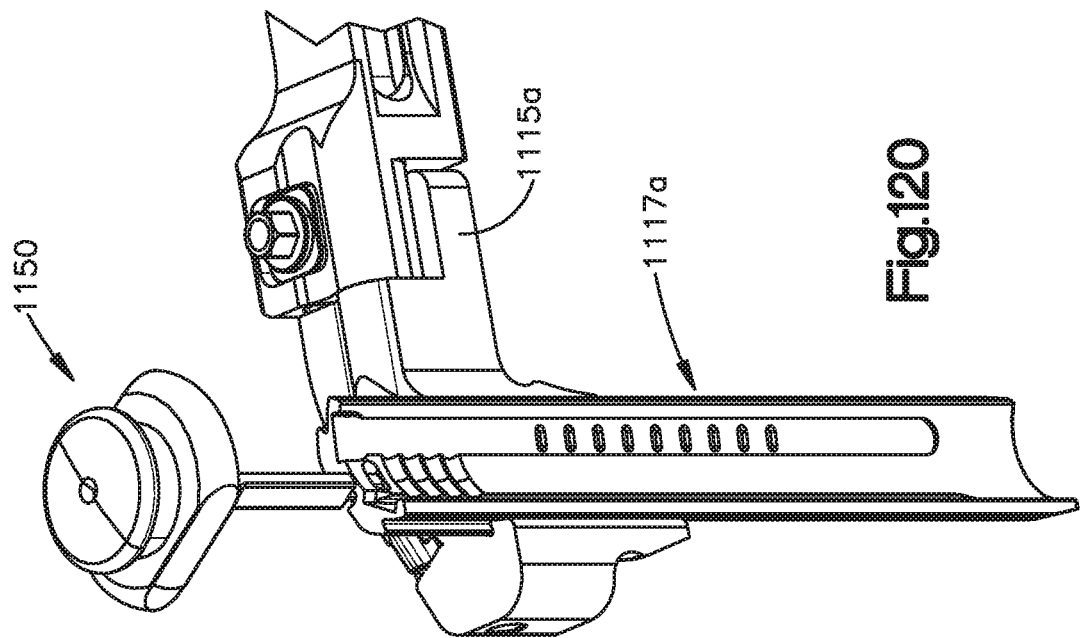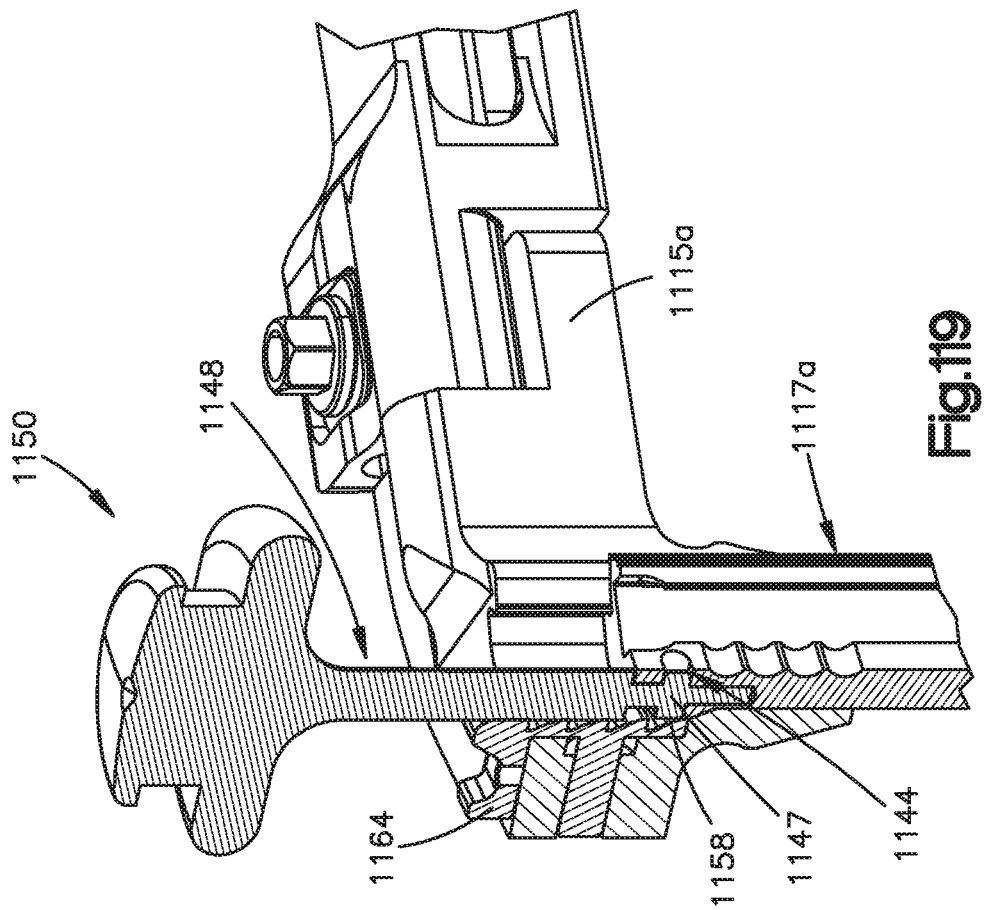

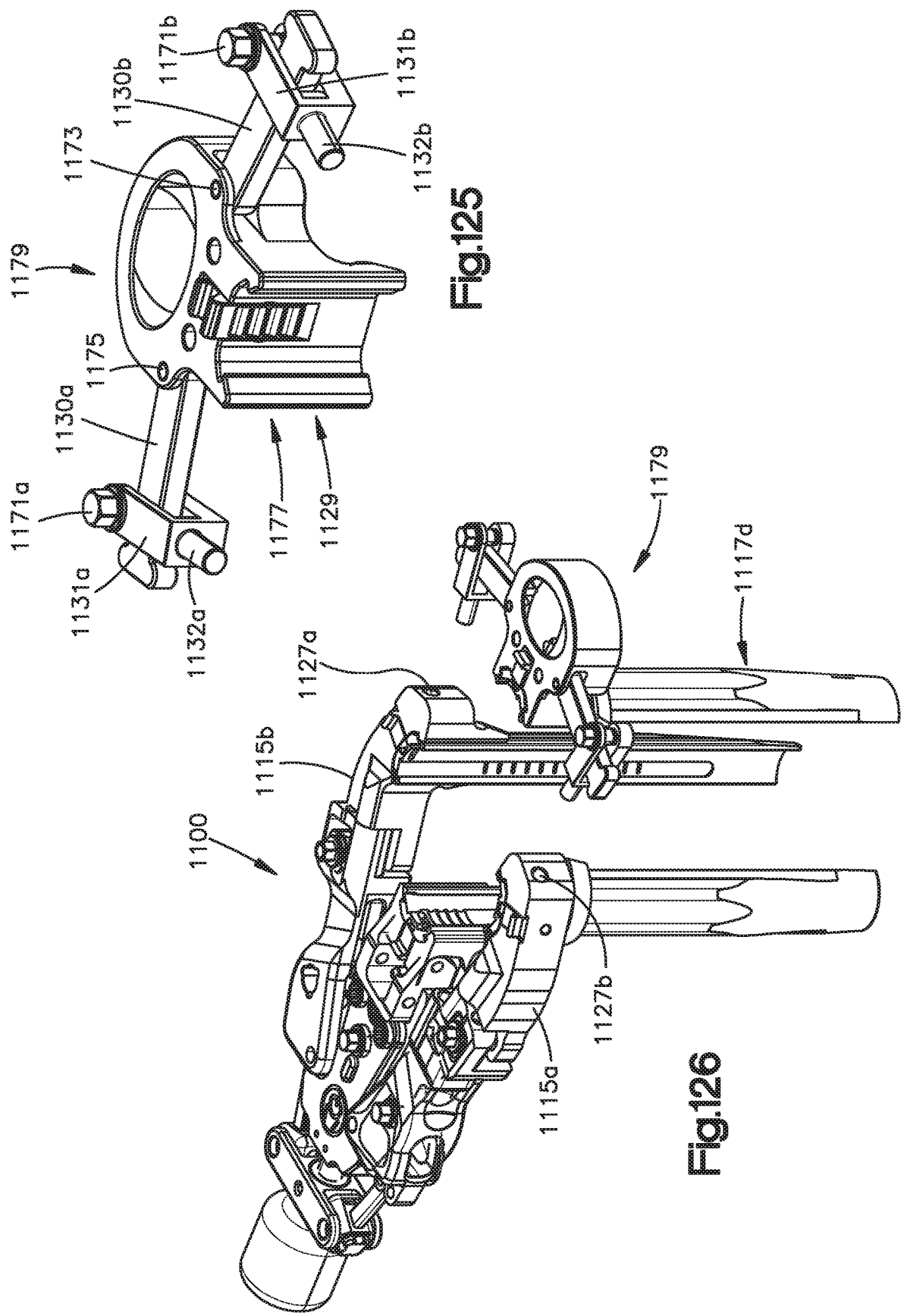

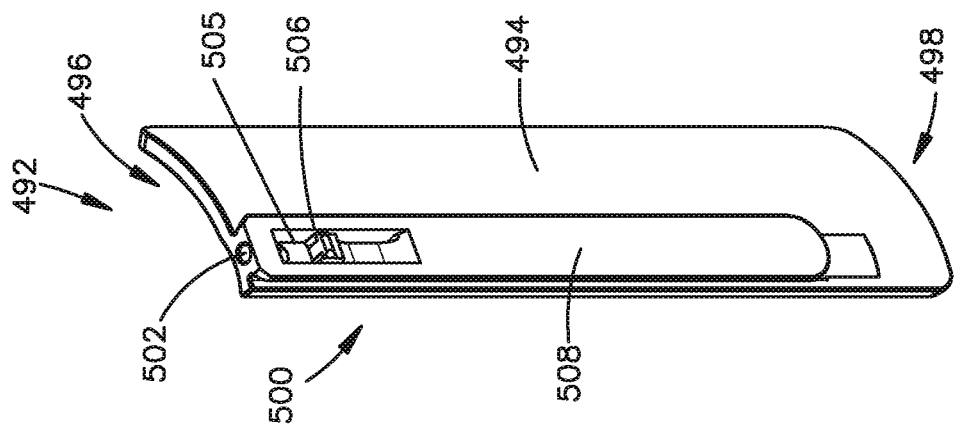
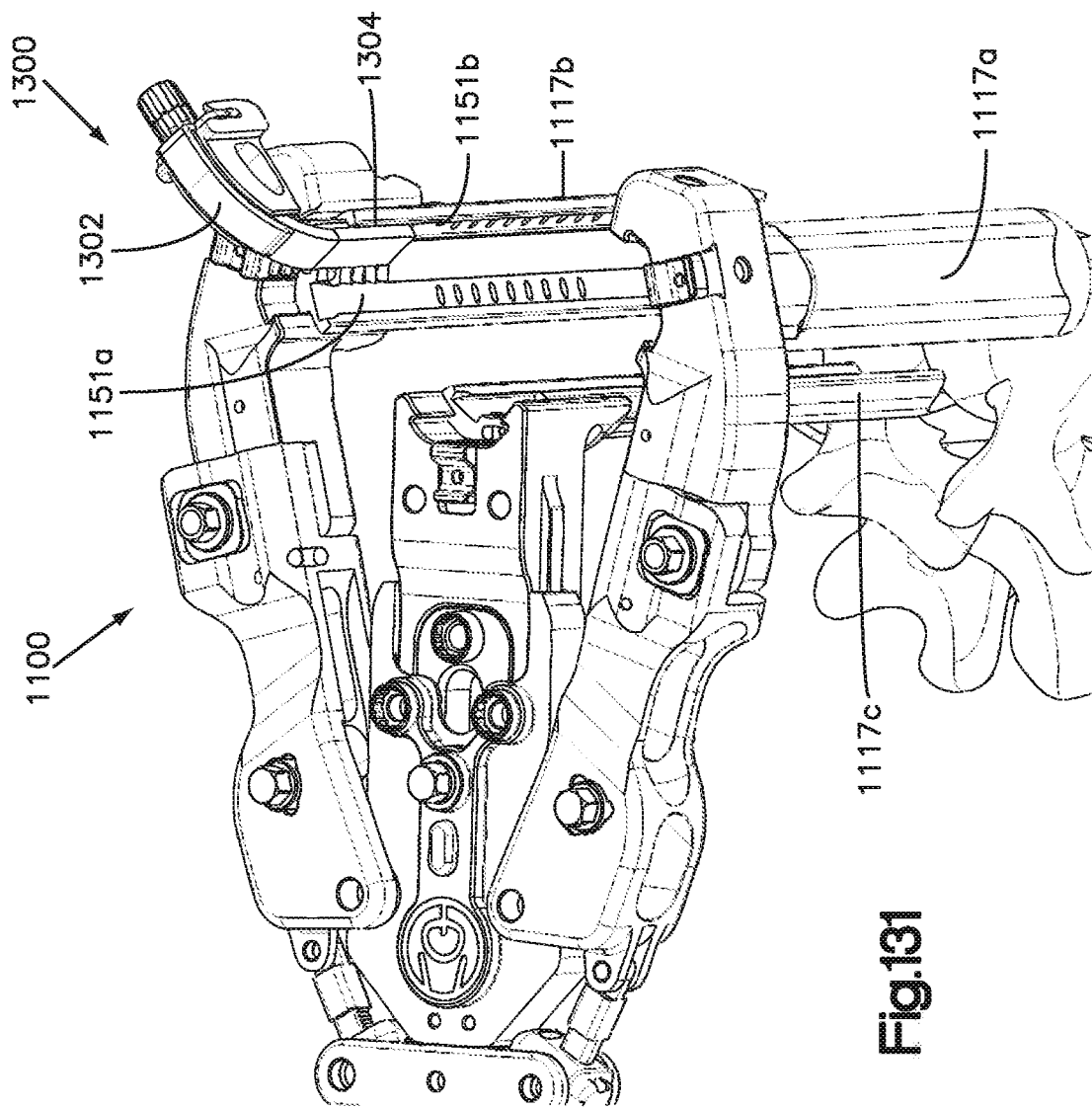
Fig.132
Fig.131

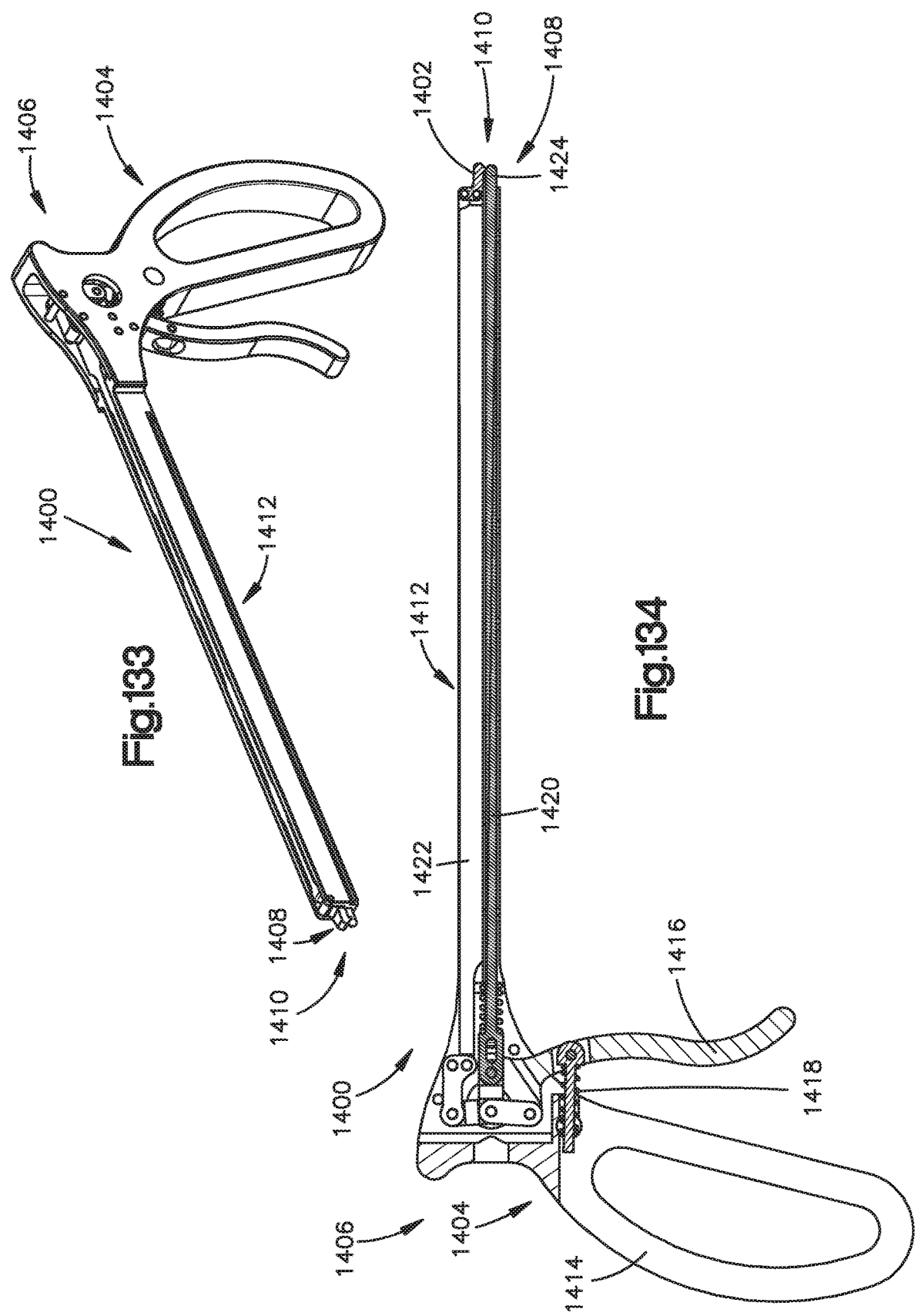

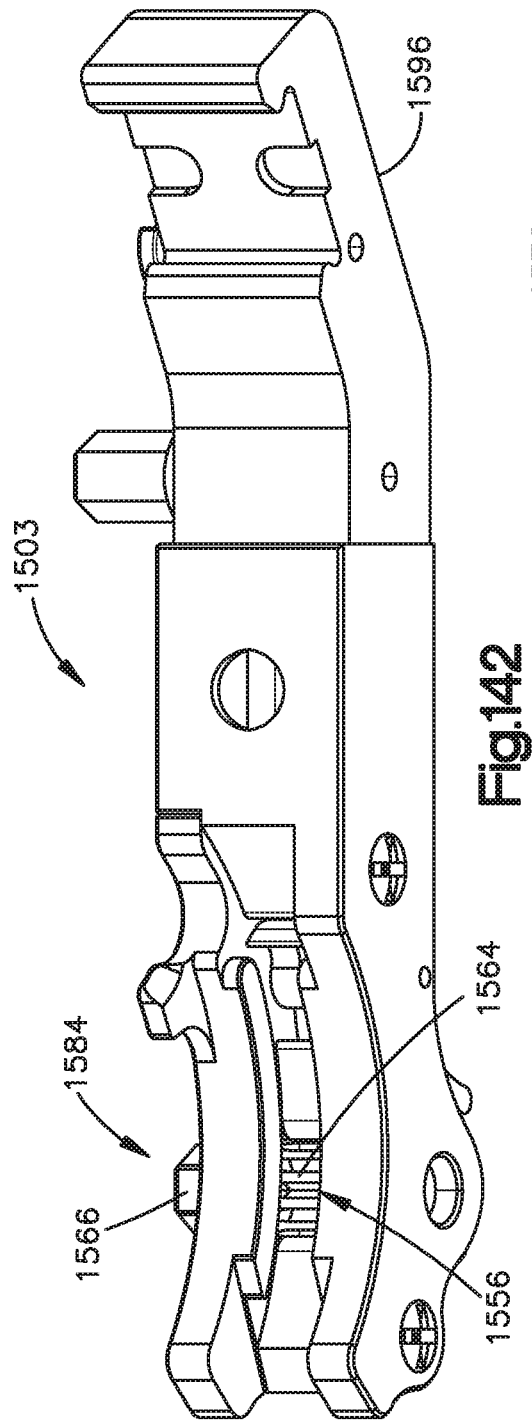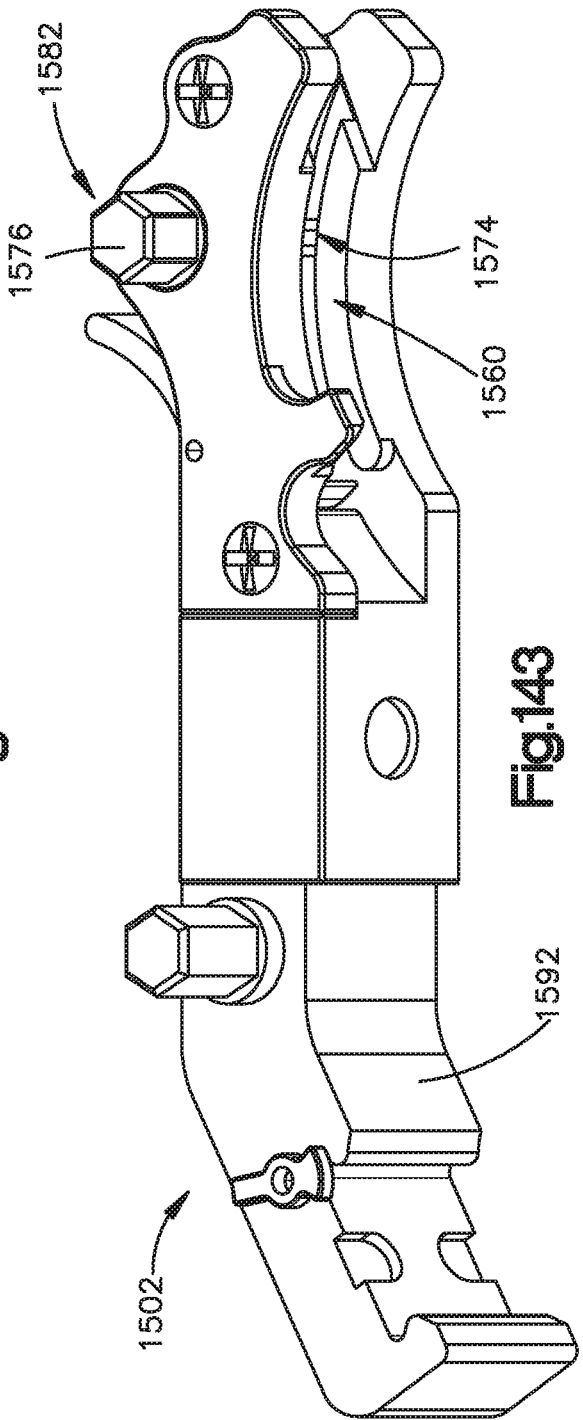

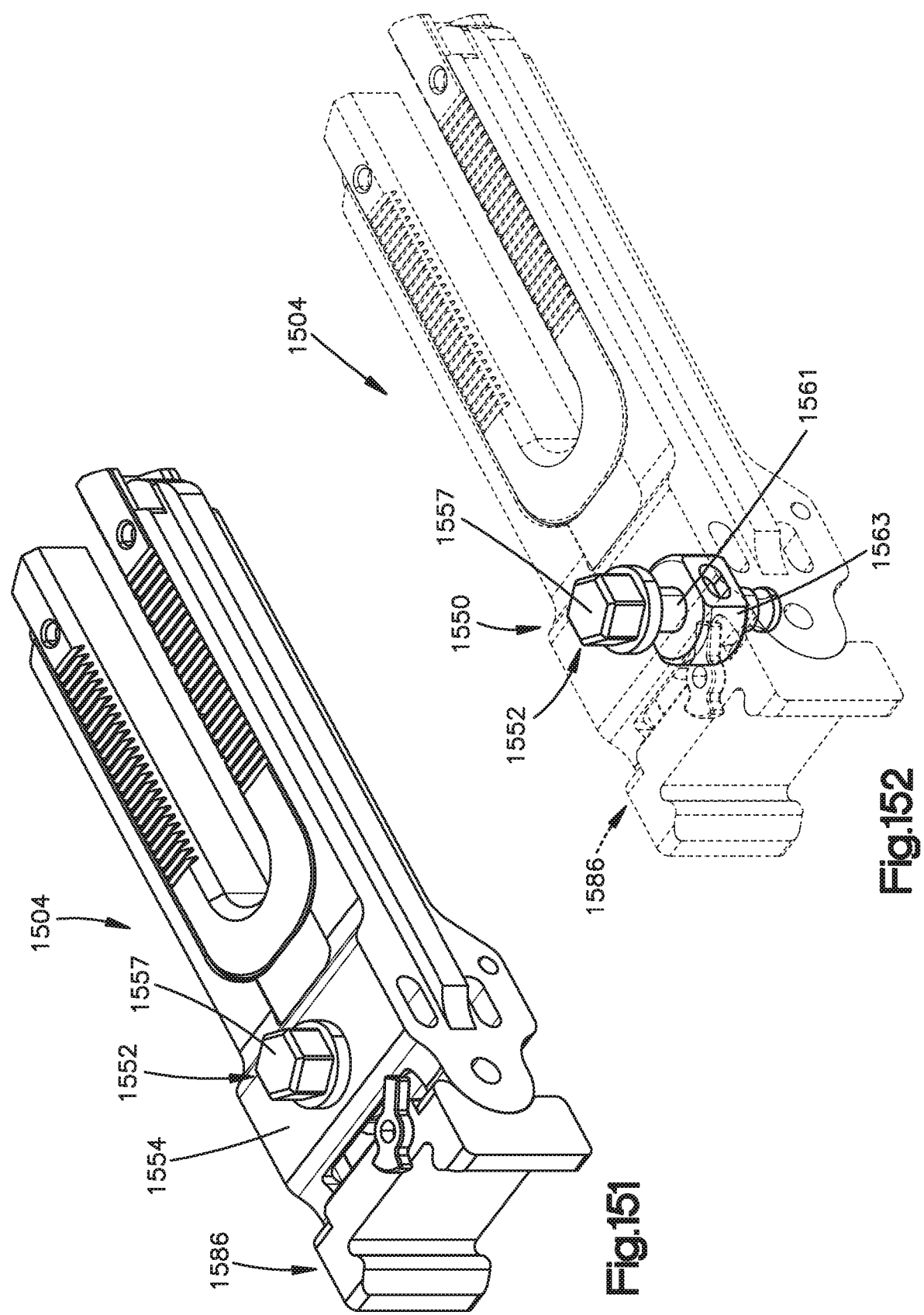

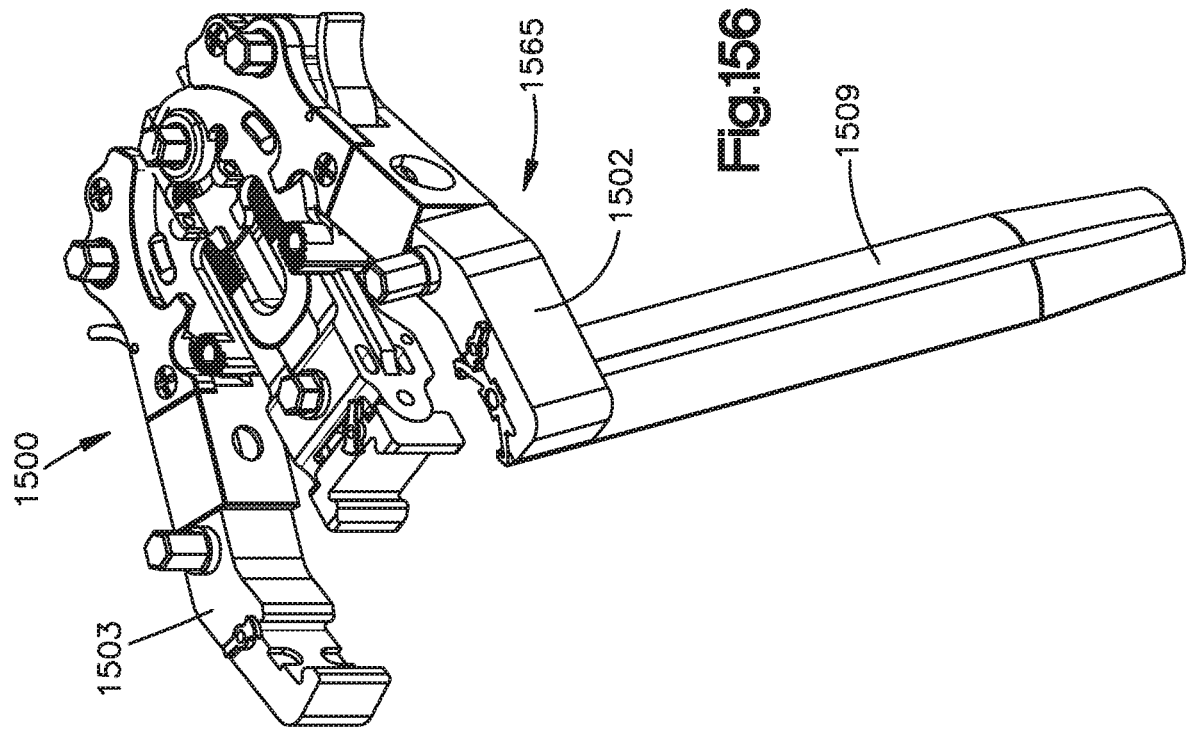
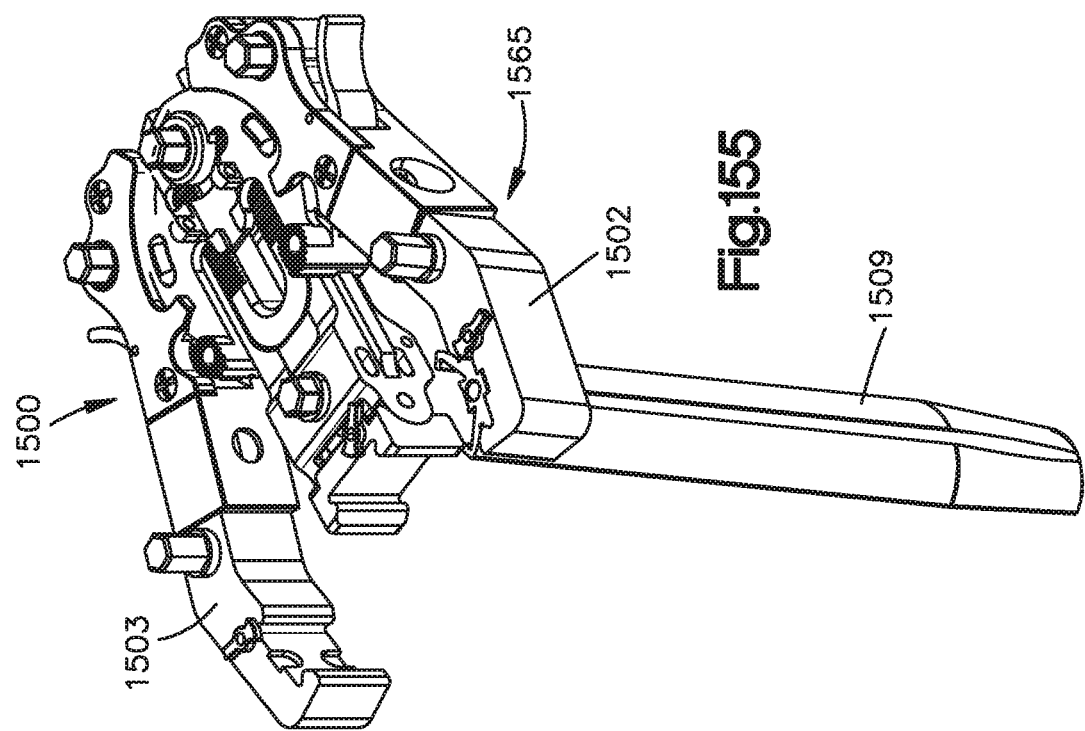

SPINAL ACCESS RETRACTOR

CROSS-REFERENCE TO RELATED APPLICATIONS

This application is a continuation of U.S. patent application Ser. No. 15/370,201, filed on Dec. 6, 2016 which is a divisional of U.S. patent application Ser. No. 13/237,710, filed on Sep. 20, 2011, and claims priority to, and the benefit of, U.S. Provisional Patent Applications Nos. 61/384,453, filed on Sep. 20, 2010, and 61/420,918, filed on Dec. 8, 2010, the contents of each of which are hereby incorporated by reference in their entireties.

TECHNICAL FIELD

The present disclosure generally relates to apparatus, systems, and methods for performing minimally invasive surgery, and more particularly, to retractors, systems, and methods for accessing a surgical site to conduct a surgical procedure.

BACKGROUND

In some surgical procedures, surgeons need to access a target site within the patient's body. To access the desired surgical site, the surgeon may employ open surgery or minimally invasive techniques. Open surgery techniques typically require large incisions and high amounts of tissue displacement to gain access to the surgical target site. Due to the large incisions and high amounts of tissue displacements, patients who undergo open surgery usually require a relatively long recovery time. Minimally invasive techniques, in contrast, involve significantly smaller incisions and require less tissue displacement. As a consequence, patients who undergo minimally invasive procedure have significantly shorter recovery time than patients who undergo opens surgery.

In view of the advantages of minimally invasive procedure over open surgery, the surgical access systems have been developed to access a surgical target site using a minimally invasive approach. Surgical access retractors and systems typically displace or retract tissue to establish an operative corridor to a surgical target site. These retractors also maintain the operative corridor while the surgeon performs the desired surgical procedure.

Surgeons have employed known surgical access retractors and systems in different kinds of surgeries. In spinal surgeries, for example, spinal access systems can be used to retract tissue in order to perform posterior lumbar interbody fusion (PLIF), anterior lumber interbody fusion (ALIF), or any other suitable spinal approach and surgery.

Although a number of surgical access retractors and system have been developed over the years, a need exists for improved spinal access systems and retractors capable of, among other things, displacing tissue in different directions.

SUMMARY

The present disclosure relates to retractors for displacing and holding tissue. In one embodiment, the retractor includes a first arm, a second arm, and a translating member. The first arm comprises a proximal portion and a distal portion. The distal portion is configured to retain a first retractor member. The distal portion is configured to rotate relative to the proximal portion about a first axis. The second arm is configured to retain a second retractor member, such that rotation of the distal portion about the first axis causes the first retractor member to pivot toward or away from the second retractor member when the first retractor member and the second retractor member are coupled to the first arm and the second arm, respectively. The translating member is coupled between the proximal portion and the distal portion. The translating member is configured to receive a drive force that causes the translating member to bias the distal portion to pivot relative to the proximal portion about the first axis. The retractor can further include a support member that retains the proximal portion in a fixed position as the translating member biases the distal portion. The retractor can further include a rotating member that is threadedly coupled to the translating member, wherein the rotating member is configured to rotate about the second axis so as to apply the drive force to the translating member.

In one embodiment, a retractor includes a first arm comprising a proximal portion and a distal portion, the distal portion configured to retain a first retractor member, the distal portion configured to rotate relative to the proximal portion about a first axis. A second arm is configured to retain a second retractor member, such that rotation of the distal portion about the first axis causes the first retractor member to pivot toward or away from the second retractor member when the first retractor member and the second retractor member are coupled to the first arm and the second arm respectively; and a rotating member coupled between the proximal portion and the distal portion, the rotating member configured to rotate about a second axis, wherein rotation of the rotating member about the second axis causes the distal portion to rotate relative to the proximal portion about the first axis. The rotation of the rotating member about the second axis biases a location of the distal portion away from the proximal portion, the location being offset from the first axis. The retractor can further include a pivot member coupled between proximal portion and the distal portion, wherein the pivot member defines the first axis, and rotation of the rotating member about the second axis biases the location of the distal portion away from pivot member. The retractor can further include a translating member connected to the rotating member and configured to translate upon rotation of the rotating member to urge the distal portion to rotate with respect to the proximal portion about the first axis.

In one embodiment, the rotating member defines a threaded bore sized and configured to receive at least a portion of the translating member and wherein the translating member comprises a threaded shaft sized to be positioned within the threaded bore, the threaded shaft being configured to move along threaded bore upon rotation of the rotating member to urge the distal portion to rotate in relation to the proximal portion. The retractor can further include a rotating sleeve surrounding at least a portion of the rotating member, wherein the rotating sleeve rotatably connects the rotating member to the proximal portion and is configured to rotate the rotating member relative to the proximal portion when the threaded shaft moves along the threaded bore.

In another embodiment, the retractor can further include an extension protruding out from the proximal portion, the extension defining an opening configured to receive the rotating member and the rotating sleeve. The retractor can further include a central body connected to the first arm and the second arm. The retractor can further include a third arm configured to retain a third retraction member and movably connected to the central body, wherein the third arm is configured to move longitudinally with respect to the central body. The retractor can further include a rack and pinion mechanism including a pinion connected to the central body and a rack connected to the third arm, wherein the rack and pinion mechanism is configured to move the third arm relative to the central body upon rotation of the pinion. The retractor can further include the third retractor member attached to the third arm, the third retractor member configured to move between a distal position and a proximal position upon rotation of the pinion to retract tissue. The first arm comprises a first distal end, the second arm comprising a second distal end, the first arm and the second arm being pivotally connected to the central body so that the first distal end of the first arm and the second distal end of the second arm are configured to move simultaneously toward or away from each other between a first position and a second position, wherein the first distal end of the first arm and the second distal end of the second arm are farther apart from each other in the second position than in the first position. The retractor can further include a pivot member pivotally connecting the first arm and the second arm to the central body so that the first arm and the second arm are configured to pivot about the pivot member between the first position and the second position.

The retractor can further include a first handle portion connected to a proximal end of the first arm and a second handle portion connected to a proximal end of the second arm, wherein squeezing the first handle portion and the second handle portion together causes the distal end and the second distal end to move away from each other. The retractor can further include the first retractor member attached to the first distal end, and further comprising the second retractor member second retractor member attached to the second distal end, wherein the squeezing the first handle portion and the second handle portion together causes the first retractor member and the second retractor member to move away from each other to bilaterally retract tissue. The first handle portion is pivotally connected to the first arm. The second handle portion is pivotally connected to the second arm. The retractor can further include a connection bar and a knob, the connecting bar having a threaded portion, the knob having a threaded bore configured to receive the threaded portion, wherein rotation of the knob about the threaded portion of the connection bar causes the knob to translate along the connection bar, wherein the knob is configured to move along the connection bar toward or away from the first arm, so that the knob is configured to secure a position of the first arm with respect to the second arm when the knob contacts the first arm. The first retractor member can further include comprises a disc anchor configured to penetrate an intervertebral disc. The disc anchor being can be monolithically formed with the first retractor member.

In one embodiment, the first arm defines a slot that is configured to slidably retain the first retractor member that is configured to retract tissue, and a first engagement member movably connected to the first arm, the first engagement member defining a plurality of recesses, each of the plurality of recesses being selectively configured to securely receive a complementary second engagement member of the first retractor member, the first engagement member configured to move toward the slot so as to engage the second engagement member, thereby causing the second engagement member to be securely received in a select one of the plurality of recesses, and further configured to move away from the slot so as to disengage the second engagement member and allow the second engagement member to slide along the slot. The retractor can further include the first retractor member, the first retractor member defining an outer surface, wherein the second engagement member protrudes out from the outer surface. The plurality of recesses are arranged in a linear row along the second engagement member to allow the first retractor member to be fixed to the arm at different attachment positions.

The retractor can further include a nerve retractor comprising a telescoping assembly, the telescoping assembly comprising a first elongated member and a second elongated member, the second elongated member configured to slide relative to the first elongated member, the second elongated member comprising a tissue retraction member configured to retract tissue. The tissue retractor member is located at a distal end and includes a curved portion and a protrusion extending from the curved portion. The nerve retractor includes a locking mechanism comprising a locking clip configured to engage indentations arranged along opposite sides of the second elongated member to fix a position of the second elongated member relative to the first elongated member. The locking clip includes first and second cantilevered legs arranged on opposite sides of the second elongated member, the first cantilevered leg comprising a third engagement member configured to be selectively positioned in one of the indentations, the second cantilevered leg comprising a fourth engagement member configured to be selectively positioned in one of the indentations. The retractor can further include locking button movable over the locking clip between a locked position, in which the third engagement member and the fourth engagement member securely engage selective indentations, and an unlocked position, in which the third engagement member and the fourth engagement member engage selective indentations to fix the position of the second elongated member with respect to the first elongated member. The nerve retractor further comprises a coupler attached to the telescoping assembly and a handle attached to the coupler. The handle is removably attached to the coupler.

The retractor can further include a holder configured to retain the nerve retractor, the holder configured to be mounted to the retractor. The holder comprises a clamping assembly configured to retain the telescoping assembly, the clamping assembly comprising a first clamping arm and a second clamping arm configured to move toward or away from each other. The clamping assembly defines a space between the first clamping arm and the second clamping arm sized to receive at least a portion of the telescoping assembly. The holder further comprises a second rotating member coupled to the second clamping arm, wherein rotating of the second rotating member causes the second clamping arm to move toward or away the first clamping arm. The second rotating member comprises a threaded shaft and wherein the second clamping arm defines a threaded bore configured to receive the threaded shaft of the second rotating member. The holder comprises an outer housing, housing the second rotating member. The holder is configured to be mounted to the third arm. The third arm comprises a third proximal portion and a third distal portion configured to retain the third retractor member, and wherein the holder is configured to be mounted to the third distal portion. The third distal portion comprises at least one snap fit recess, and wherein the third distal portion comprises at least one snap fit hook, at least one snap fit recess configured to securely receive at least one snap fit hook to connect the holder to the third distal portion. The second elongated member defines an outer surface, the second elongated member comprising a fifth engagement member extending from the outer surface, the fifth engagement member being configured to be received by a selective one of a plurality of indentations defined along an inner surface of the third retractor member to allow the second elongated member to advance incrementally with respect to the third retractor member.

In one embodiment, the holder is configured to be mounted to the first distal end and the second distal end. The holder further a first pivoting arm, and a second pivoting arm, the first pivoting arm and the second pivoting arm pivotally connected to opposite sides of the outer housing, the first pivoting arm connected to the first distal end, the second pivoting arm connected to the second distal end. The holder further comprises a first retaining member and a second retaining member, the first retaining member configured to move along the first pivoting arm, the second retaining member configured to move along the second pivoting arm. The first retaining member comprises a first protrusion, and wherein the second retaining member comprises a second protrusion, the first distal end defining a first connecting slot sized to securely receive the first protrusion, the second distal end defining a second connecting slot sized to securely receive the second protrusion.

In one embodiment, the retractor can further include a disc anchor connected to at least one of the first retractor member, the second retractor member or the third retractor member. The disc anchor can be disc to the third retractor member or any other retractor member. Alternatively, the disc anchor can be removably attached to the third retractor member or any other retractor member. The disc anchor is configured to move along the third retractor member between a retracted position and an extended position. The disc anchor includes a sixth engagement member configured to be received by each of a plurality of indentations arranged along an inner surface of the third retractor member to allow incremental advancement of the disc anchor along the third retractor member. The third retractor member defines a distal-most indentation configured to engage the sixth engagement member to prevent further distal advancement of the disc anchor along the third retractor when the sixth engagement member is positioned within the distal-most indentation. The disc anchor can further include a retaining member configured to slide along a channel defined along on the inner surface of the third retractor member. The channel is defined by a proximal wall and a distal wall of the third retractor member, the disc anchor configured to move to a cleaning position in which the retaining member abuts the distal wall, thereby facilitating cleaning of the disc anchor and the third retractor member. The retractor can further include a tool configured to move the disc anchor along the third retractor member, the tool comprising a rotatable head configured to disengage the sixth engagement member from a selective one of the plurality of indentations to allow the disc anchor to move proximally along the third retractor member to the retracted position.

In one embodiment, the first retractor member defines a first body configured to retract tissue, the first body extending along a first outer perimeter that terminates at opposed first edges, wherein the second retractor member defines a second body configured to retract tissue, the second body extending along a second outer perimeter that terminates at opposed second edges, wherein the retractor defines a fully closed position whereby each of the first retractor member and the second retractor member are unable to be angulated closer to each other and the first outer perimeter is substantially aligned with the second outer perimeter, and the first arm and the second arm are configured to retain the first retractor member and second retractor member such that a first gap is defined between the first retractor member and the second retractor member when the retractor is in the fully closed position. The first gap measures between about 0.5 millimeters and about 2 millimeters. The first gap measures about 1 millimeter. The third retractor member defines a third body configured to retract tissue, the third body extending along a third outer perimeter that terminates at opposed first edges, wherein, in the fully closed position, the first outer perimeter is substantially aligned with the third outer perimeter, and the second outer perimeter is substantially aligned with the third outer perimeter, and the third arm is configured to retain the third retractor member such that a second gap is defined between the first retractor member and the third retractor member, and a third gap is defined between the second retractor member and the third retractor member when the retractor is the fully closed position. The second gap measures between about 0.5 millimeters and about 2 millimeters. The second gap measures about 1 millimeter. The third gap measures between about 0.5 millimeters and about 2 millimeters. The third gap measures about 1 millimeter.

In one embodiment, the retractor can include a leadscrew mechanism including a leadscrew, wherein the leadscrew mechanism is configured to move the first arm and the second arm between the first and second position upon rotation of the leadscrew. The leadscrew mechanism further comprises a follower connected to the leadscrew and the first arm and the second arm, the follower configured to move along the leadscrew upon rotation of the leadscrew. The third arm comprises a third proximal portion and a third distal portion, the distal portion configured to hold the third retraction member, the third distal portion rotatably connected to the to the third distal portion. The retractor can further include a third rotating member connecting the third proximal portion to the third distal portion and a second pivot member pivotally coupling the proximal portion and the third distal portion, wherein rotation of the third rotating member causes the third distal portion to pivot about the second pivot member. The retractor can further include a second translating member comprising a threaded shaft, wherein the third rotating member defines a threaded bore configured to receive the threaded shaft, the threaded bore being sized to receive the threaded shaft of the second translating member, the second translating member being configured to move along the threaded bore upon rotating of the third rotating member, thereby causing the third distal portion to pivot relative to the third proximal portion about the pivot member. The retractor can further include a rack coupled between the follower and the second arm and a rotating member configured mate with the rack, wherein the rotation of the rotating member causes the rotating member to move along the second arm, thereby pivoting the second arm independently of the first arm.

In one embodiment, the retractor includes an arm defining a slot that is configured to slidably retain a retractor member that is configured to retract tissue; and a first engagement member movably connected to the arm, the first engagement member defining a plurality of recesses, each of the plurality of recesses being selectively configured to securely receive a complementary second engagement member of the retractor member, the first engagement member configured to move toward the slot so as to engage the second engagement member, thereby causing the second engagement member to be securely received in a select one of the plurality of recesses, and further configured to move away from the slot so as to disengage the second engagement member and allow the second engagement member to slide along the slot The retractor can further include the first retractor member, the first retractor member defining an outer surface, wherein the second engagement member protrudes out from the outer surface. The plurality of recesses are arranged in a linear row along the second engagement member to allow the first retractor member to be fixed to the arm at different attachment positions. The retractor can further include a central body interconnecting the first arm and the second arm, wherein the first arm and the second arm are removably attached to the central body to facilitate cleaning. The retractor can further include a third arm) removably attached to the central body to facilitate cleaning.

BRIEF DESCRIPTION OF THE DRAWINGS

The foregoing summary, as well as the following detailed description of preferred embodiments, are better understood when read in conjunction with the appended diagrammatic drawings. For the purpose of illustrating the invention, the drawings show embodiments that are preferred. The invention is not limited, however, to the specific instrumentalities disclosed in the drawings. In the drawings:

FIG. 7 is a top view of a portion of the holder assembly of the surgical access retractor illustrated in FIG. 1;

FIG. 8 is an enlarged perspective view of a central body of the surgical access retractor illustrated in FIG. 1;

FIG. 9 is an enlarged perspective view of a connection assembly of the surgical access retractor illustrated in FIG. 1;

FIG. 13 is a front view of a retractor member with a disc anchor inserted in an intervertebral space;

FIG. 14 is a cross-sectional perspective view of a retractor member with the disc anchor illustrated in FIG. 13 in a first or retracted position;

FIG. 15A is a cross-sectional side view of a retractor member with the disc anchor illustrated in FIG. 13 in a second or deployed position;

FIG. 15B is a cross-sectional side view of a retractor member with the disc anchor illustrated in FIG. 13 in a third or cleaning position FIG. 16 is a perspective view of the retractor member illustrated in FIG. 13 with the advancement tool attached to the disc anchor while the disc anchor is in the retracted position;

FIG. 18 is a perspective view of a retractor member illustrated in FIG. 13 with the advancement tool being rotated to disengage the stop to allow the disc anchor to return to the retracted position;

FIG. 19 is a perspective view of retractor member illustrated in FIG. 13 with the advancement tool moving the disc anchor toward the retracted position;

FIG. 20 is a perspective view of a retractor member widener configured to be attached to a retractor member of the surgical access retractor illustrated in FIG. 1;

FIG. 21 is a top view of the surgical access retractor illustrated in FIG. 1 engaging soft tissue without the lateral retractor member shown in FIG. 20;

FIG. 26 is a front view of the distal end of the surgical access retractor illustrated in FIG. 1 positioned close to vertebrae without the retractor member extension shown in FIG. 25;

FIG. 27 is a front view of the distal end of the surgical access retractor illustrated in FIG. 1 positioned close to vertebrae with the retractor member extensions shown in FIG. 25 attached to the retractor members;

FIG. 28 is perspective view of a tissue relocation tool adapted to relocate soft tissue from underneath a retractor member of the surgical access retractor illustrated in FIG. 1;

FIGS. 29-32 are front views illustrating steps for relocating tissue from underneath a retractor member of the surgical access retractor shown in FIG. 1 using the tissue relocation tool illustrated in FIG. 28;

FIGS. 33-35 are top views illustrating steps for removing the tissue relocation tool illustrated in FIG. 28 from the patient;

FIGS. 42-45 are cross-sectional views illustrating the steps of an exemplary method for attaching a retractor member to the retractor member holder shown in FIG. 41 using an insertion tool and telescoping the retractor member towards the surgical site;

FIG. 48 is a perspective view of a distal portion of the telescoping assembly of the tissue retractor illustrated in FIG. 46, showing a locking mechanism in the locked position;

FIG. 49 is a perspective view of a distal portion of the telescoping assembly of the tissue retractor illustrated in FIG. 46, showing a locking mechanism in the unlocked position;

FIG. 50 is a perspective view of a holder for holding the tissue retractor illustrated in FIG. 46;

FIG. 51 is a perspective view of the surgical access retractor shown in FIG. 1 and the holder illustrated in FIG. 50;

FIG. 52 is a perspective phantom view of a holder for holding the tissue retractor in accordance with an alternate embodiment of the present invention;

FIG. 53 is a perspective of a distal portion of the surgical access retractor shown in FIG. 1 and the holder illustrated in FIG. 50 mounted to the surgical access retractor;

FIG. 68 is a sectional perspective view of the surgical retractor illustrated in FIG. 65;

FIG. 69 is a sectional perspective view of the surgical retractor illustrated in FIG. 65 with the central blade angled distally;

FIG. 88 is a perspective side sectional view of the surgical retractor illustrated in FIG. 82;

FIGS. 118-120 are perspective views showing an exemplary method of removing the blade positioned in the blade holder of the surgical retractor shown in FIG. 99 using the tool shown in FIG. 115

FIG. 125 is a perspective view of a blade assembly in accordance with an embodiment of the present invention;

FIG. 126 is a perspective view of the blade assembly shown in FIG. 125 about to be mounted to the surgical retractor shown in FIG. 99;

FIG. 131 is a perspective view of a lighting source mounted to surgical retractor illustrated in FIG. 99;

FIG. 132 is a perspective rear view of the retraction member widener shown in FIG. 20;

FIG. 133 is a perspective view of a holding tool configured to hold the retraction member widener shown in FIG. 132;

FIG. 134 is a cross-sectional side view of the holding tool illustrated in FIG. 133;

FIGS. 135-137 are perspective views illustrates steps of an exemplary method of mounting the retraction member widener shown in FIG. 20 to the surgical retractor illustrated in FIG. 99;

FIG. 138 is a perspective view of a surgical retractor in accordance with an embodiment of the present invention;

FIG. 139 is a perspective view of the surgical retractor illustrated in FIG. 139 with lateral arms in an open position and a central arm in a retracted position;

FIG. 140 is an exploded perspective view of the surgical retractor illustrated in FIG. 138

FIG. 141 is a perspective view of a central body of the surgical retractor illustrated in FIG. 138;

FIG. 142 is a perspective view of a first lateral arm of the surgical retractor illustrated in FIG. 138;

FIG. 143 is a perspective view of a second lateral arm of the surgical retractor illustrated in FIG. 138;

FIG. 144 is a perspective view of a portion of the surgical retractor illustrated in FIG. 138, showing a first lateral arm being mounted to the central body;

Figure 138:
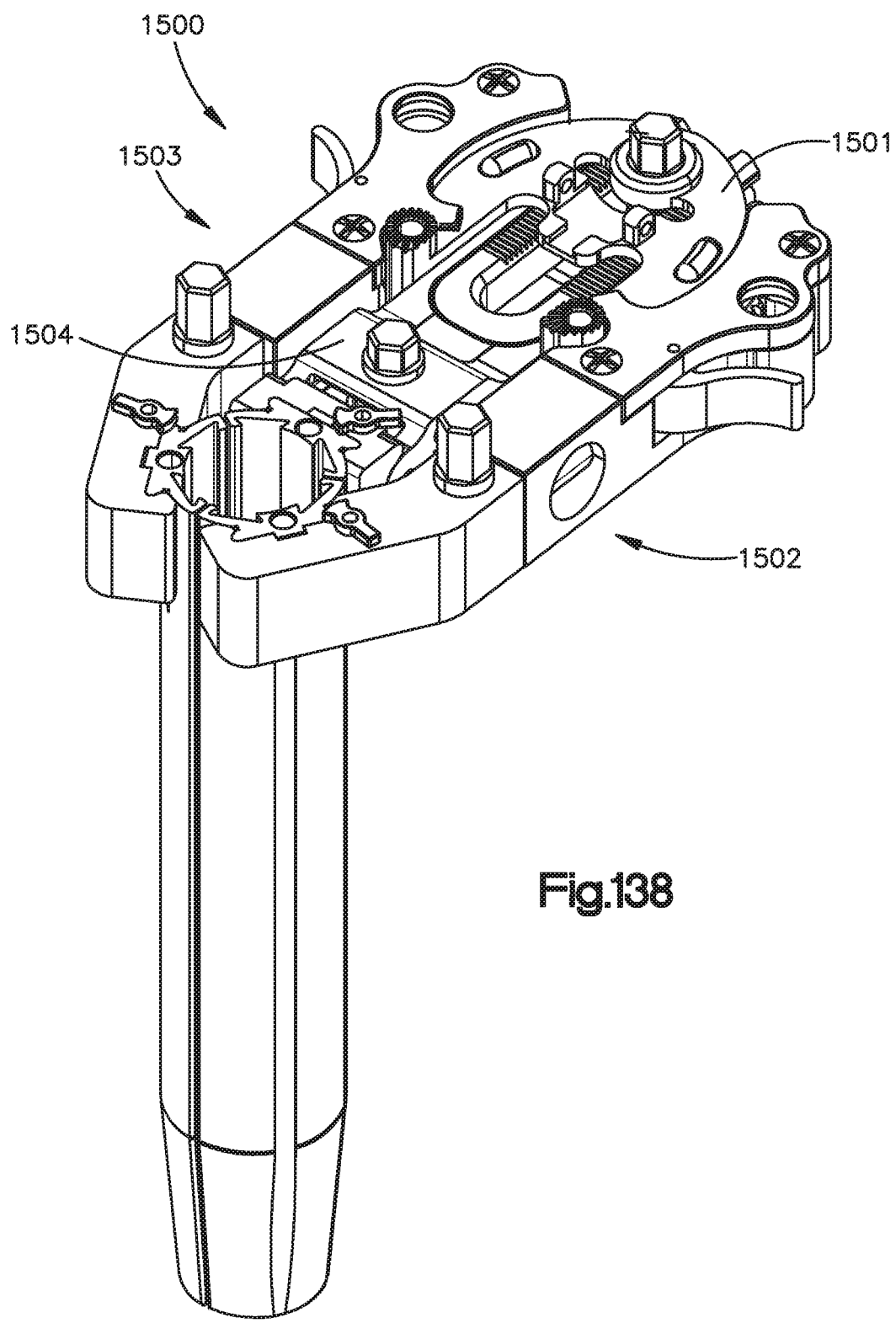
Figure 145:
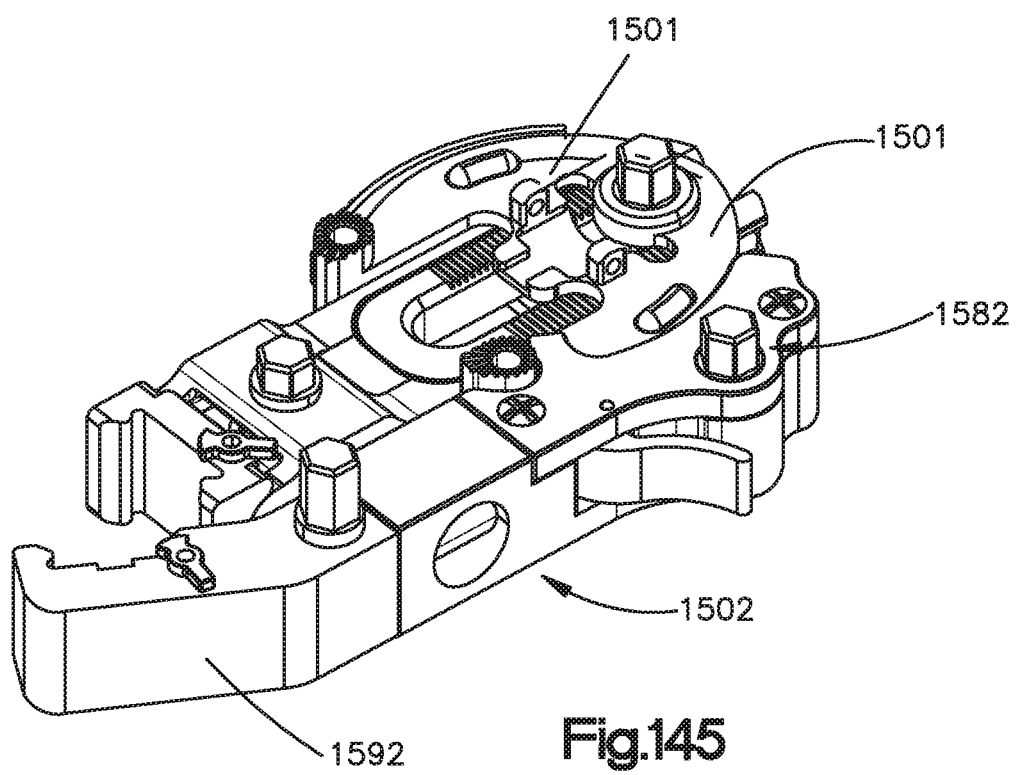
Figure 146:
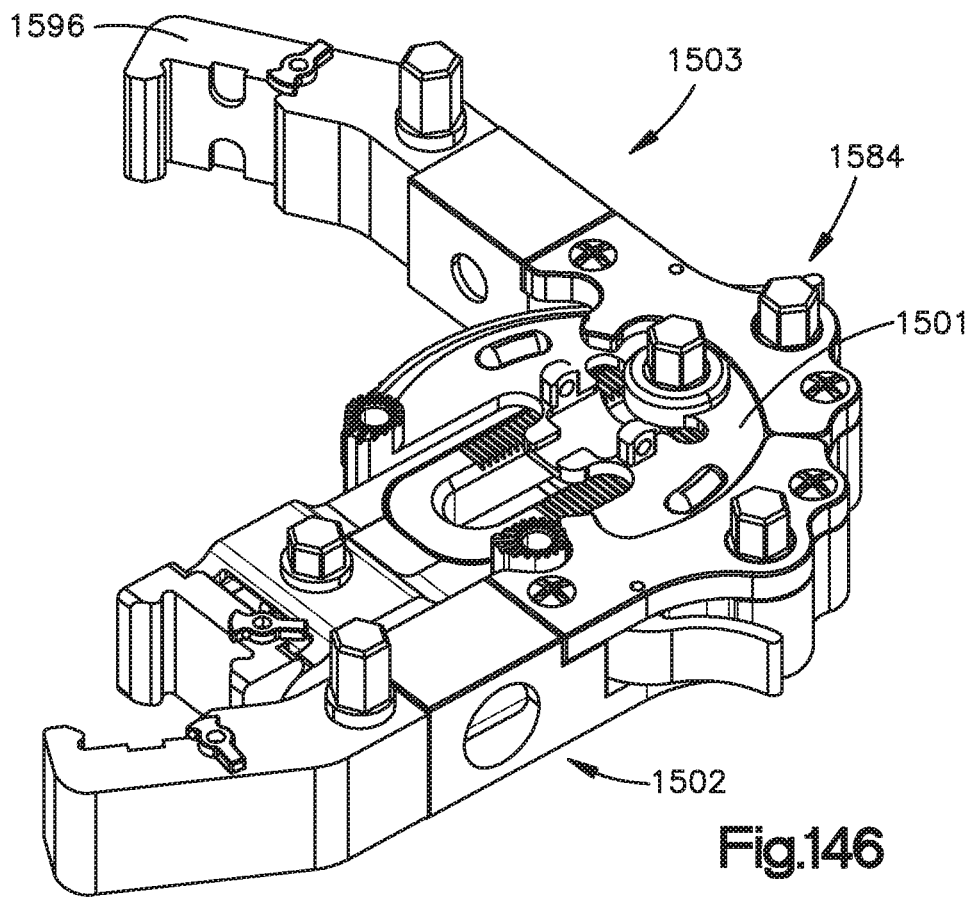
Figure 147:
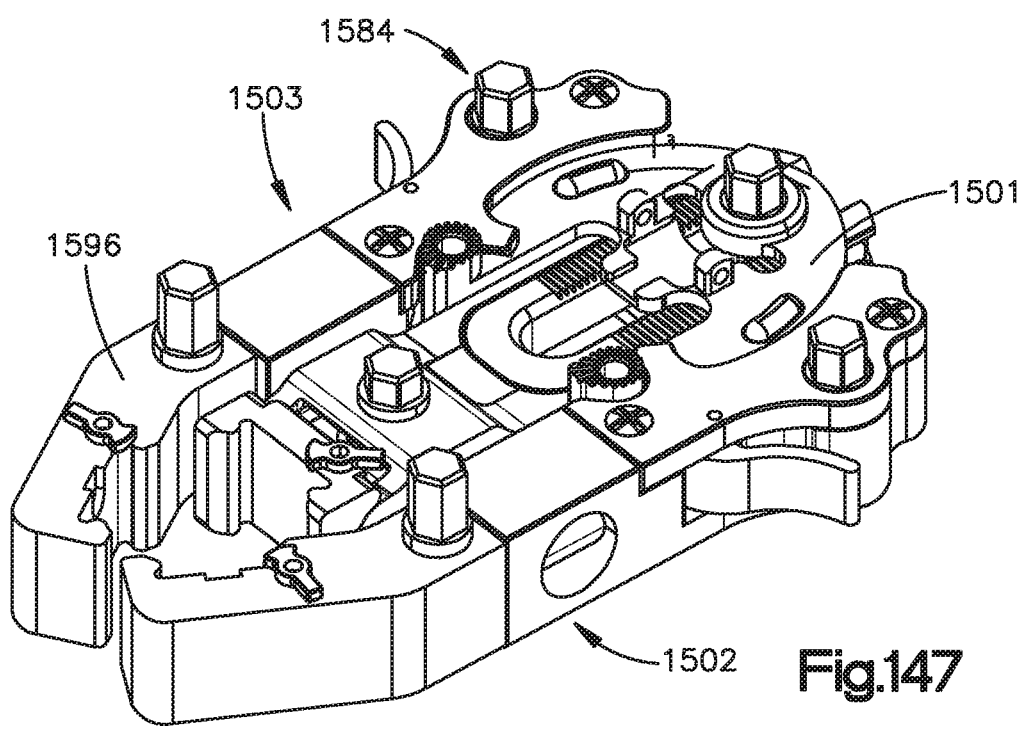
Figure 148:
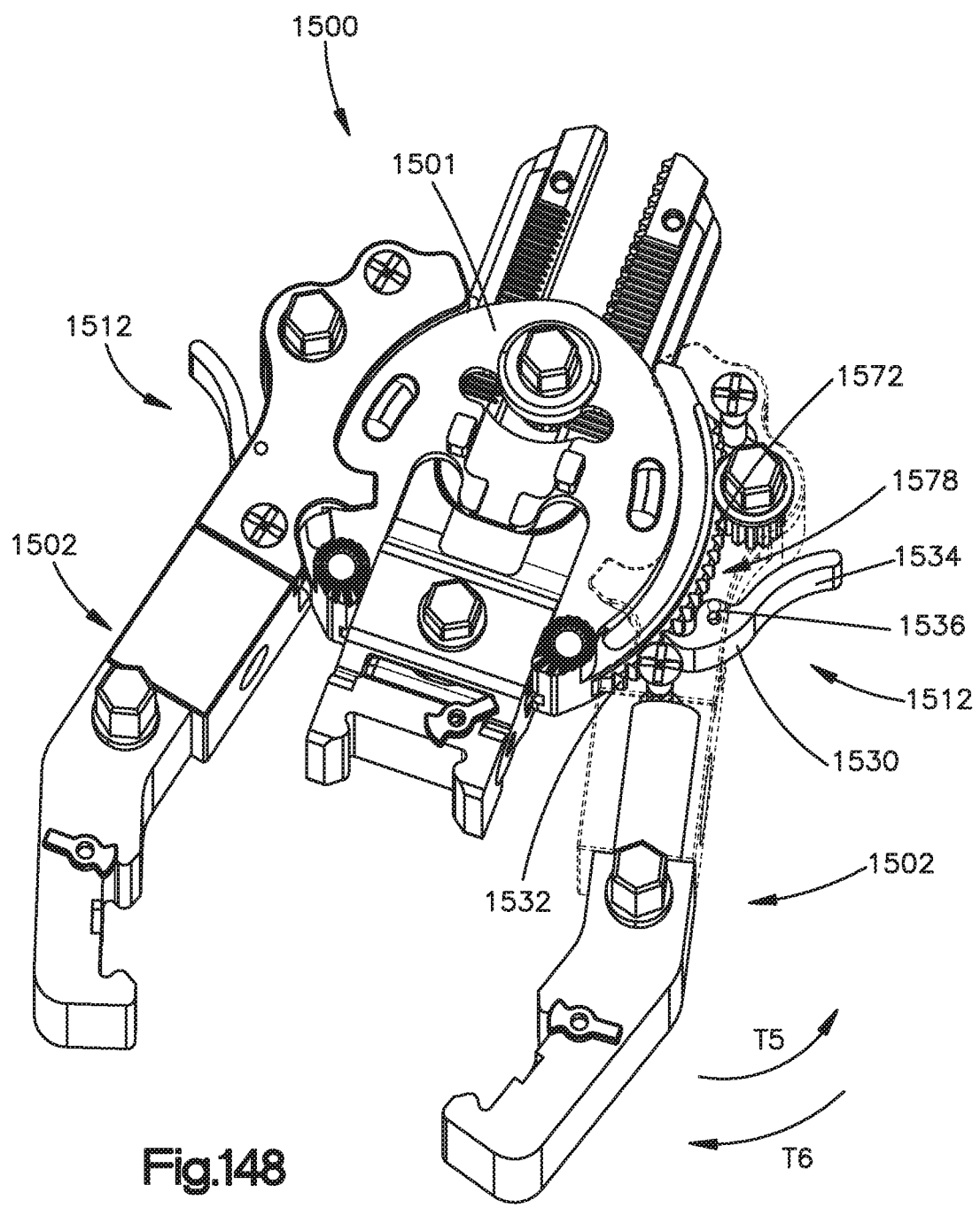
Figure 149:
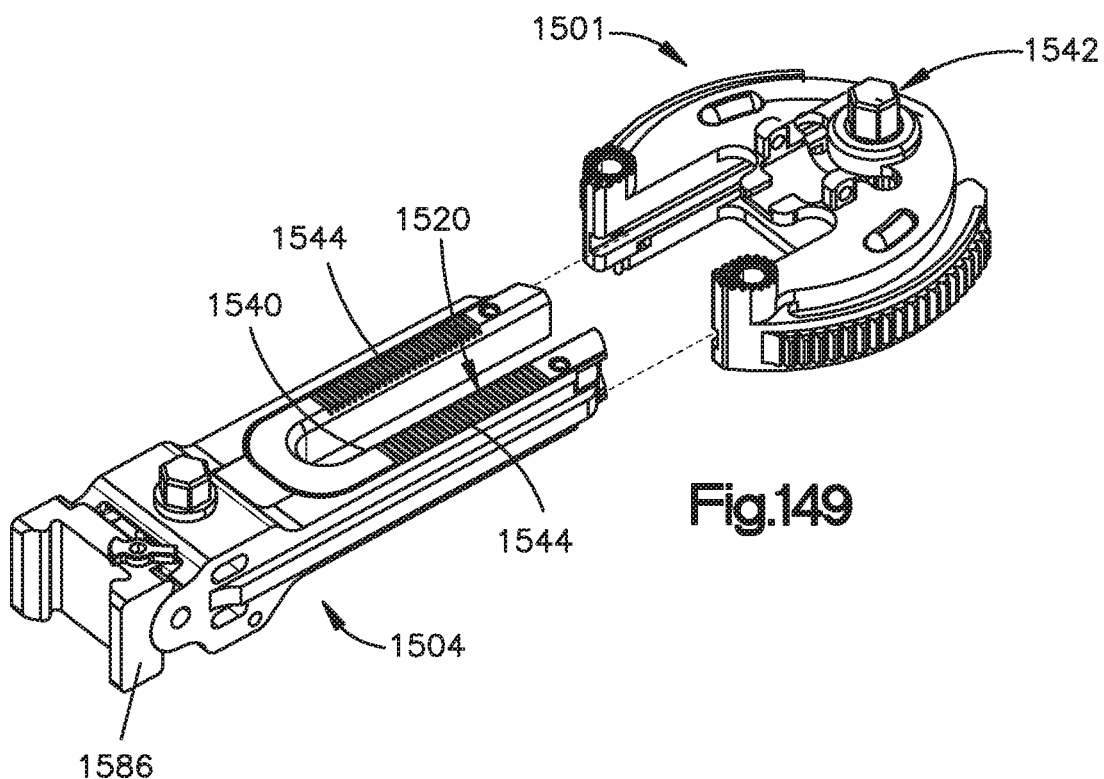
Figure 150:
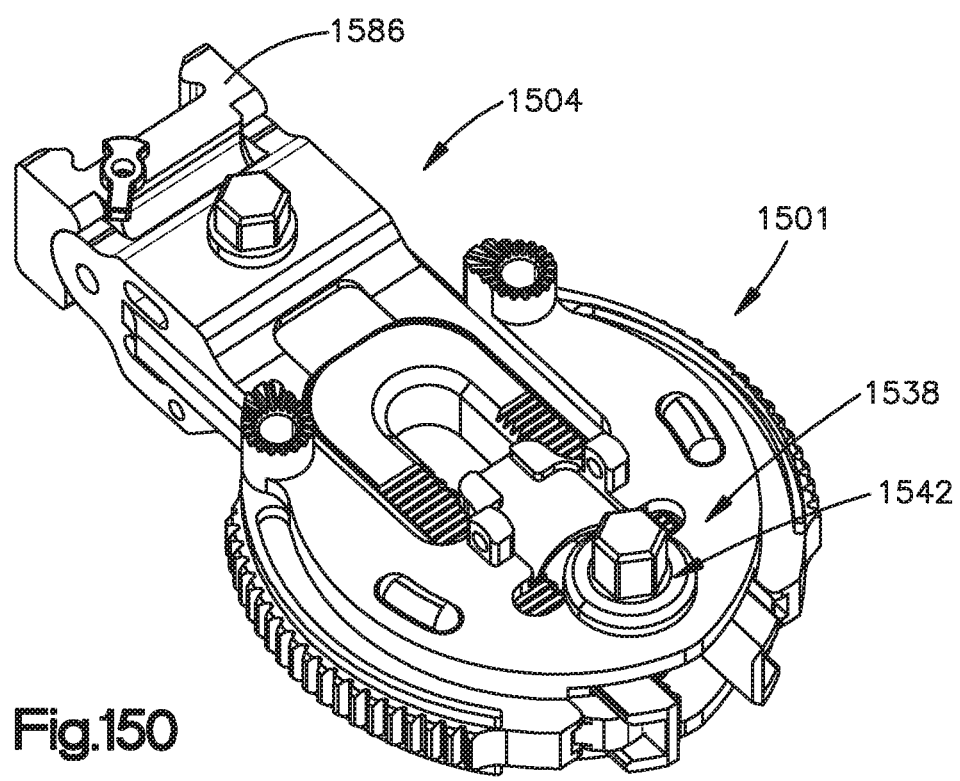

FIG. 145 is a perspective view of a portion of the surgical retractor illustrated in FIG. 138, showing a first lateral arm attached to the central body and in the closed position;

FIG. 146 is a perspective view of a portion of the surgical retractor illustrated in FIG. 138, showing a second lateral arm being mounted to the central body;

FIG. 147 is a perspective view of a portion of the surgical retractor illustrated in FIG. 138, showing a second lateral arm in attached to the central body and in the closed position;

FIG. 148 is a perspective view of the surgical retractor illustrated in FIG. 138, showing a locking mechanism;

FIG. 149 is an exploded perspective view of the central body and the central arm of the surgical retractor illustrated in FIG. 138;

FIG. 150 is a perspective view of the central body and the central arm shown in FIG. 146 assembled together;

FIG. 151 is a perspective view of the central arm

Figure 153:
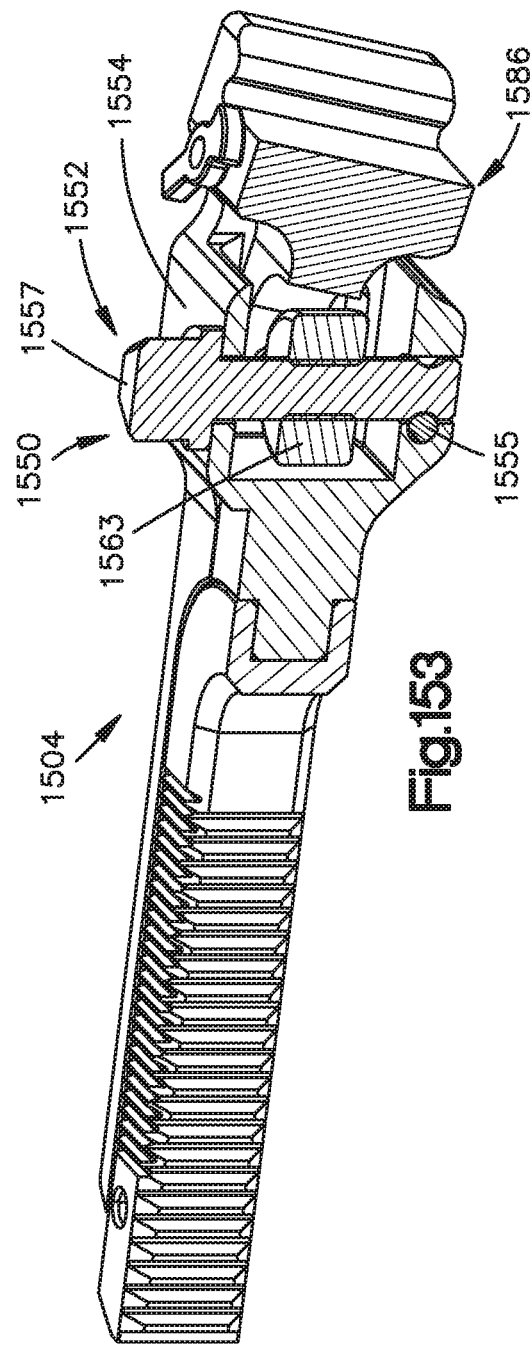
Figure 154:
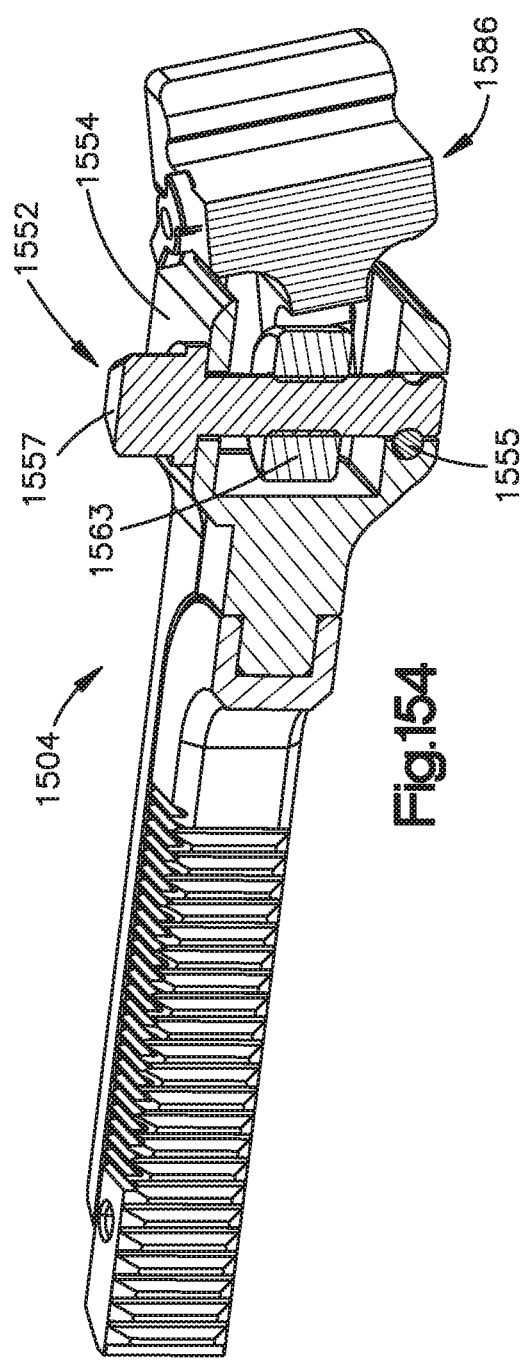

FIG. 152 is a perspective phantom view of the central arm and the blade holder illustrated in FIG. 151, showing an angulation mechanism;

FIG. 153 is a perspective cross-sectional view of the central arm and the blade holder illustrated in FIG. 151, showing an angulation mechanism in a first position;

FIG. 154 is a perspective cross-sectional view of the central arm and the blade holder illustrated in FIG. 151, showing an angulation mechanism in a second position;

FIG. 155 is a perspective view of the surgical retractor illustrated in FIG. 138, showing a blade holder holding a blade; and FIG. 156 is a perspective view of the surgical retractor illustrated in FIG. 138, showing blade holder in an angled position.

DETAILED DESCRIPTION OF ILLUSTRATIVE EMBODIMENTS

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the apparatus and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar importance. For illustration purposes only, FIG. 1 depicts arrows identifying different directions in relation to a spinal column C, namely: arrow L identifies a lateral direction; arrow M identifies a medial direction; arrow R identifies a cranial direction; arrow D identifies a caudal direction; arrow P identifies a posterior direction; and arrow A identifies an anterior direction.

Figure 1:
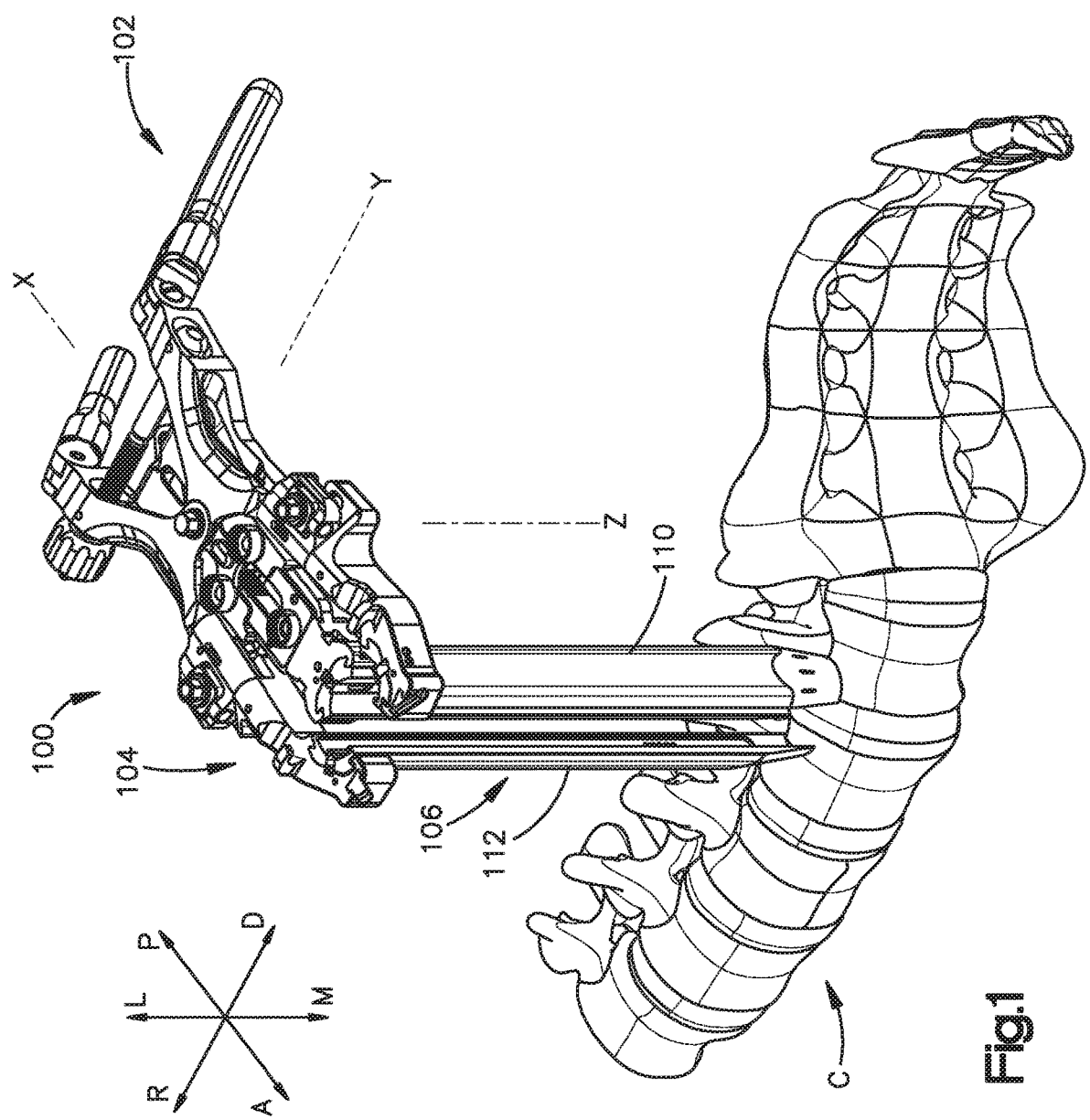
FIG. 1 is a perspective view of a surgical access retractor positioned adjacent a vertebral column constructed in accordance with one embodiment of the present invention.

The retractor and systems described in FIGS. 1-156 can be used to perform surgical procedures in the spinal area including, but not limited to, discectomy, implant insertion, pedicle screw placement, and spinal rod placement. While the description of the retractor will be discussed primarily in relation to spinal surgery, it should be understood that the presently disclosed retractors can be used in other types of surgical procedures. For instance, the retractor can be used where a surgeon wishes to gain access within the body by cutting the skin and can provide an access location for surgical procedures performed on a patient using surgical instruments. In particular, the retractor may hold back soft tissue or organs to allow visibility and/or access for surgical instruments to the location in the patient's body to be operated on by a surgeon and may maintain an incision in a spread apart position so that surgical instruments can be inserted into a patient.

Moreover, the components of any retractor embodiment discussed herein may be made, for example, of metal, plastic, rubber, or combination or composite materials (i.e., a material made of two or more materials). For example, the components may be made from stainless steel, titanium, aluminum, an alloy, carbon fiber composite, or a polymer (e.g., polyvinyl chloride (PVC), polyethylene, polyesters of various sorts, polycarbonate, Teflon coated metal, polyetheretherketone (PEEK), ultra high molecular weight polyethylene (UHMWPE)). In addition, various methods may be used to make the components of the retractors discussed above, including casting, extrusion, injection molding, compression molding, forging, machining, or transfer molding. And, the components may be joined together, for example, by gluing, casting or forging as a single piece, welding or brazing, or mechanically joined by screwing, riveting, or other appropriate means.

Figure 2:
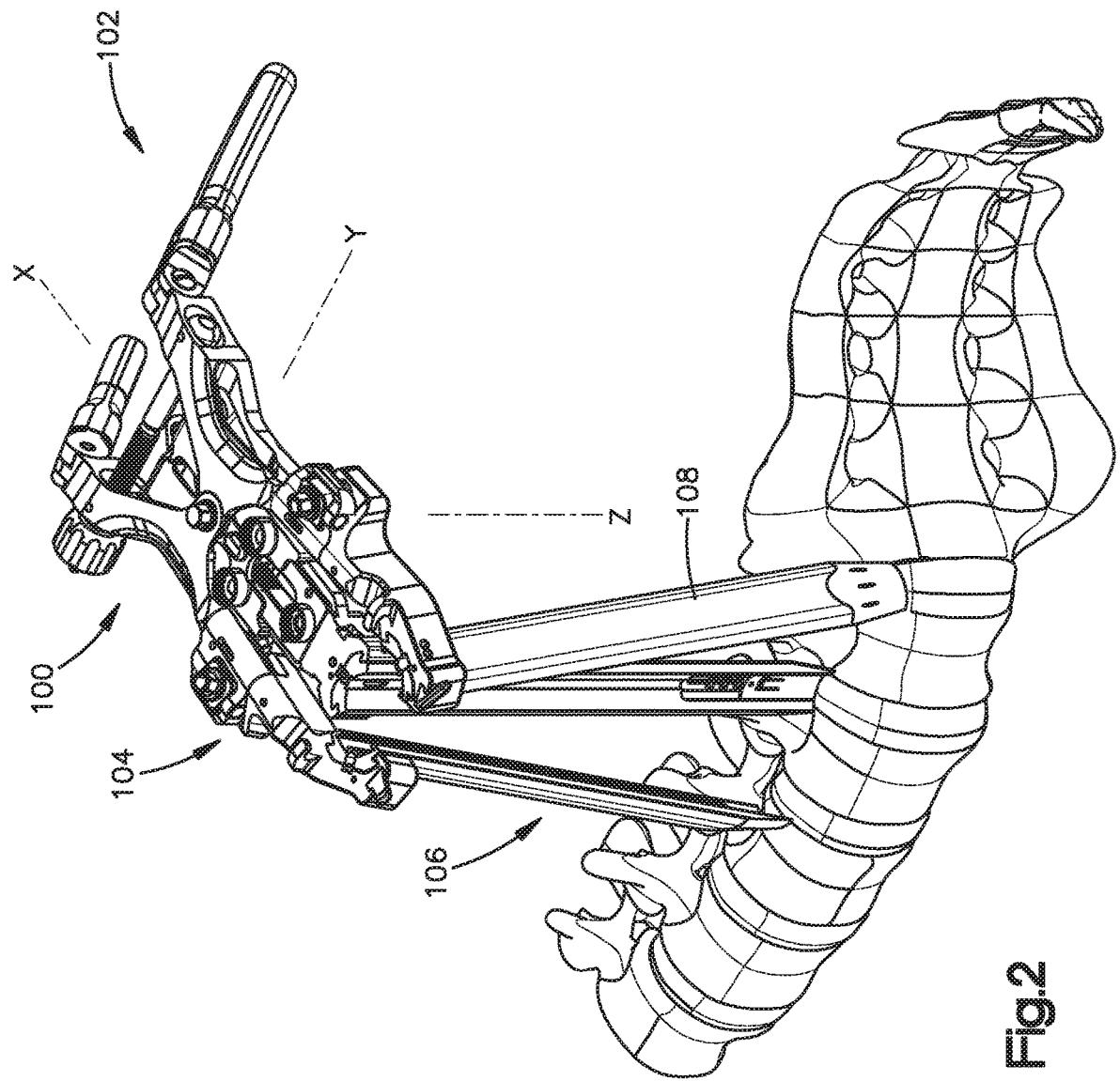
FIG. 2 is a perspective view of the surgical access retractor illustrated in FIG. 1 with retractor members in a spaced apart position.

FIGS. 1-2 depict a surgical access retractor 100 capable of retracting soft tissue to create an access opening. The surgical access retractor 100 defines a longitudinal axis X along its length, a lateral axis Y along its width, and a vertical axis Z along its height. In one exemplary method of use, a clinician can use the surgical access retractor 100 to access a region of the spinal column C. The surgical access retractor 100 can retract tissue bilaterally, unilaterally and/or angularly. To do so, the surgical access retractor 100 includes a plurality of retractor members 106, such as blades, movable relative to one another. Some retractor members 106 can move axially along the lateral axis Y and angularly relative to vertical axis Z. At least one retractor member can move longitudinally along the longitudinal axis X.

To retract tissue bilaterally, two retractor members 106 that are oriented substantially parallel to each other are moved simultaneously away from each about the lateral axis Z from a first or approximated position, in which the retraction members 106 are relatively close to each other, to a second or spaced apart position, in which the retraction members are spaced apart from each other. In unilateral retraction, a first retractor member remains stationary while a second retractor member moves away from the first retractor blade along either the lateral axis Y or the longitudinal axis X. For angular retraction, one or more retractor members 106 pivot relative to the rest of the surgical access retractor 100 with respect to the vertical axis Z, as shown in FIG. 2.

Figure 3:
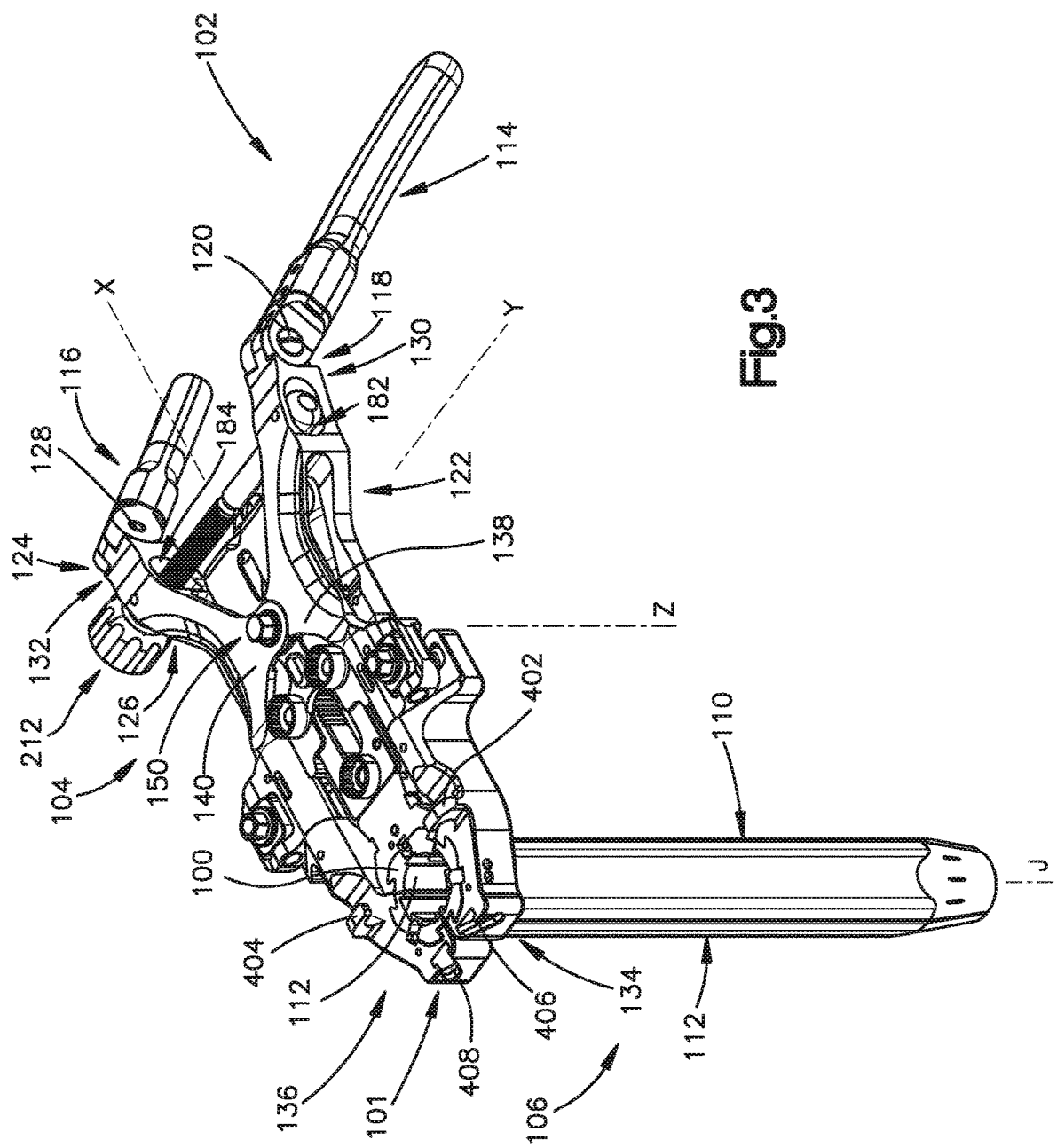
FIG. 3 is a perspective view of the surgical access retractor illustrated in FIG. 1 with the retractor members in a closed position.
Figure 4:
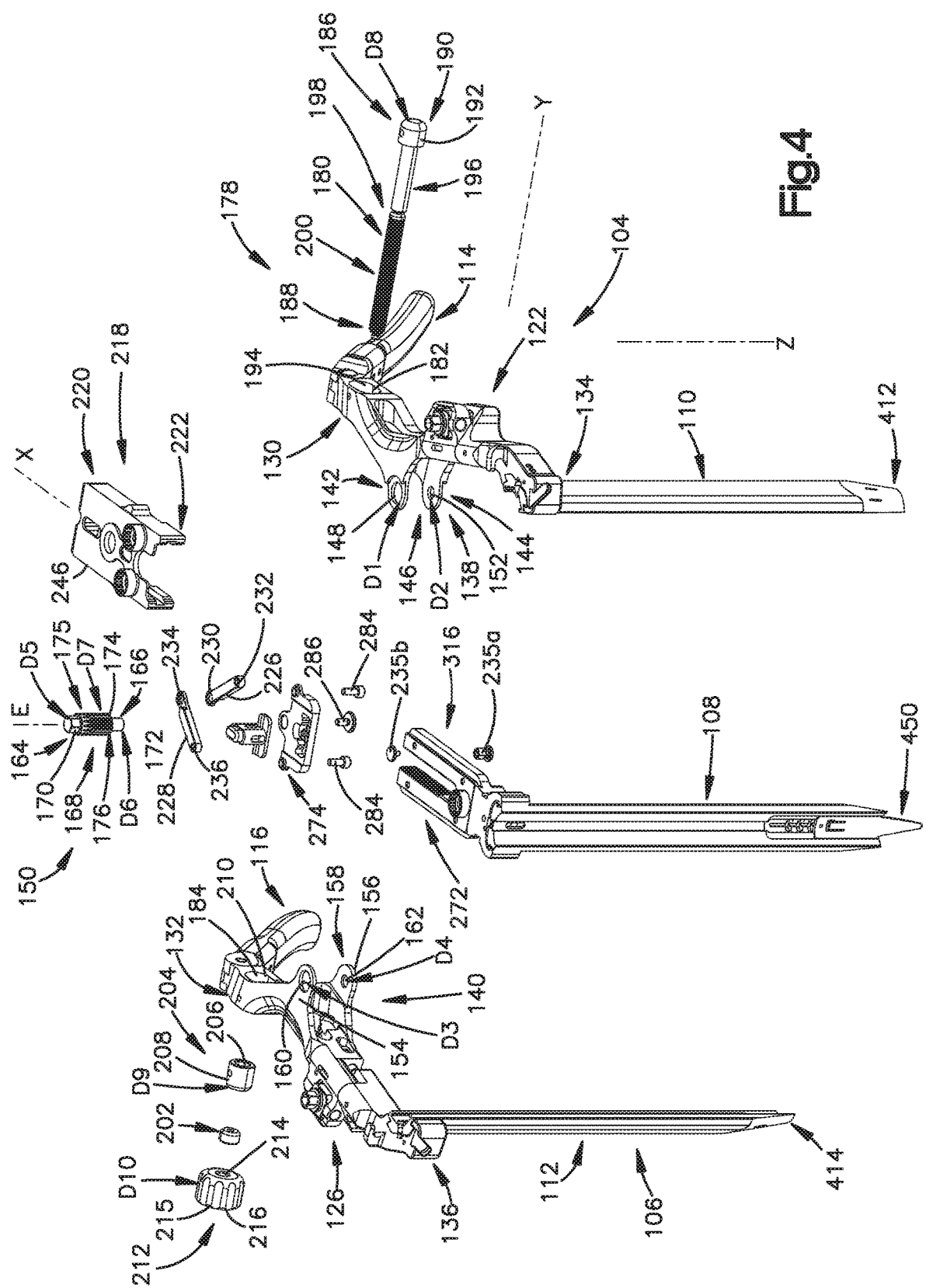
FIG. 4 is an exploded perspective view of the surgical access retractor illustrated in FIG. 1.

With reference to FIGS. 3 and 4, an embodiment of surgical access retractor 100 generally includes a handle assembly 102 and a holder assembly 104 configured to hold and support one or more retractor members 106. Although the depicted embodiment illustrates retractor members 106 as blades, the retractor members 106 may be any other suitable structure capable of displacing soft tissue. For example, the retractor members 106 can be blades, plates, substantially rigid sheets, columns, distractor pins, or panels. The retractor members 106 can be wholly or partly made of aluminum, aluminum alloy, carbon fiber or carbon fiber composites or stainless steel. In the depicted embodiment, surgical access retractor 100 includes a third retractor member 108, a second retractor member 110, and a first retractor member 112. Irrespective of the specific retraction structure employed, one or more retractor members 106 can move relative to the holder assembly 104 upon actuation of the handle assembly 102 or another part of the surgical access retractor 100, as discussed in detail below. In the illustrated embodiment, the holder assembly 104 is adapted to support the retractor members 106 at an orientation substantially perpendicular the longitudinal axis X. It is envisioned, however, that the holder assembly 104 can hold the retractor members 106 at other orientations. For example, the holder assembly 104 can support the retractor members 106 at an oblique angle relative to the longitudinal axis X.

The handle assembly 102 is operatively connected to the holder assembly 104 and includes a first handle portion 116 and a second handle portion 114 each configured to the grabbed by a user. Each of the first handle portion 116 and second handle portion 114 can be a curved rod-shaped like structure. A first pivot joint 118, or any other suitable apparatus or mechanism, pivotally couples the first handle portion 116 to a second arm 122 of the holder assembly 104. In the depicted embodiment, the first pivot joint 118 includes a pivot pin or screw 120 pivotally connecting the second arm 122 to the first handle portion 116. In case of the pivot screw, the pivot screw can be tightened in order to fix to the position of the first handle portion 116 relative to the second arm 112. A second pivot joint 124, or any other suitable apparatus or mechanism, pivotally couples the second handle portion 114 and a first arm 126 of the holder assembly 104. The first arm 126 comprises a proximal portion 127 and a distal portion 374. The distal portion 374 is configured to retain a first retractor member 112. The distal portion 374 is configured to rotate relative to the proximal portion 127 about a first axis 373. In the illustrated embodiment, the second pivot joint 124 includes a pivot pin 128 pivotally connecting the second handle portion 114 to the first arm 126 of the holder assembly 104. As discussed in detail below, the first handle portion 116 and the second handle portion 114 can be squeezed to move two retractor members 106 along the longitudinal axis Y from a first or approximated position, in which the retractor members 106 are relatively close to each other, to a second or open position, in which the retractor members 106 are spaced apart from each other. When the user is not using the first handle portion 116, the first handle portion 116 can be pivoted about the pivot joint 118 relative the second arm 122 to create more working space for the user. In particular, the first handle portion 116 can pivot relative to the longitudinal axis X. Similarly, when the second handle portion 114 is not in use, the user can pivot the second handle portion 114 about the pivot joint 118 relative to the first arm 126 to create more working space.

As discussed above, the holder assembly 104 can include first and second arms 122, 126. Specifically, a first or proximal end 130 of the second arm 122 is pivotally connected to the first handle portion 116, and a first or proximal end 132 of the first arm 126 is pivotally connected to the second handle portion 114. The second arm 122 extends from the pivot joint 118 to a distal end 101 of the surgical access retractor 100. The first arm 126 extends from the pivot joint 124 to the distal end 101 of the surgical access retractor 100. As discussed in detail below, a second or distal end 134 of the second arm 122 is configured to hold and support a retractor member 106. Similarly, a second or distal end 136 of the first arm 126 is configured to hold and support a retractor member 106.

The first and second arms 122 and 126 are pivotally connected to each other. In the exemplary embodiment shown in FIGS. 3 and 4, a pivot member, such as pivot wheel or pinion 150, pivotally couples the second arm 122 and the first arm 126. As a consequence, squeezing the first and second handle portions 116 and 114 together causes the distal ends 134 and 136 of the first and second arms 122 and 126, respectively, to move from a first or approximated position, in which the distal ends 134 and 136 are relatively close to each other, to a second or open position, in which the distal ends are spaced apart from each other. To facilitate this pivotal movement, the second arm 122 includes a connection portion 138 between the proximal end 130 and the distal end 134, and the first arm 126 also includes a connection portion 140 between the proximal end 132 and the distal end 136.

As seen in FIG. 4, the connection portion 138 includes an upper plate or member 142 and a lower plate or member 144. The upper member 142 and the lower member 144 are oriented substantially parallel to each other. The upper member 142 protrudes from the second arm 122 toward the first arm 126 and is spaced apart from the lower member 144 so as to define a space 146. Moreover, the upper member 142 has an opening 148 defining a diameter or cross-sectional dimension D1. Although the figures show opening 148 having a circular shape, opening 148 may have any other suitable shape. For example, opening 148 may be oval, elliptical, polygonal, etc. As discussed in detail below, the opening 148 is sized and adapted to receive at least a portion of a pivot member, such as wheel 150.

The lower member 144 of the connection portion 142 protrudes from the second arm 122 toward the first arm 126 and has an opening 152 defining a diameter or cross-sectional dimension D2. The cross-sectional dimension D1 of opening 148 is larger than the cross-sectional dimension D2 of the opening 152. Although the figures show opening 152 having a circular shape, opening 152 may have any other suitable shape. For example, opening 148 may be oval, elliptical, polygonal, etc. The opening 152 of the lower member 144 is sized and adapted to receive at least a portion of a pivot member, such as wheel 150.

The connection portion 140 of the first arm 126 includes an upper plate or member 154 and a lower plate or member 156. The upper member 154 and the lower member 156 are oriented substantially parallel to each other. Specifically, the upper member 154 and the lower member 156 are spaced apart from one another so as to define a space 158. The upper member 154 protrudes from the first arm 126 toward the second arm 122 and has an opening 160 defining a diameter or cross-sectional dimension D3. Though the figures show opening 160 having a circular shape, opening 160 may have any other suitable shape. For example, opening 160 may be oval, elliptical, polygonal, etc. In the depicted embodiment, the cross-sectional dimension D3 of opening 160 is substantially similar to the cross-sectional dimension D1 of the opening 148. As discussed in detail below, the opening 160 is sized and configured to receive at least a portion of a pivot member 150, such as geared wheel or pinion.

The lower member 156 of the connection portion 140 protrudes from the first arm 126 toward the second arm 122 and has an opening 162 dimensioned and configured to receive at least a portion of a pivot member 150, such as wheel. The opening 162 defines a diameter or cross-sectional dimension D4 that is smaller than the diameter or cross-sectional dimension D3 of the upper member 154. In the depicted embodiment, the diameter or cross-sectional dimension D4 of the lower member 156 is substantially similar to the diameter or cross-sectional dimension D2 of the opening 162 of the lower member 144. Even though the figures show opening 162 having a circular shape, opening 162 may have any other suitable shape. For example, opening may be oval, elliptical, polygonal, etc.

A pivot member, such as wheel 150, is inserted through openings 148, 152, 160, and 162 to pivotally connect the second arm 122 to the first arm 126. In the exemplary embodiment shown in the figures, pivot wheel 150 pivotally couples the first and second arms 122 and 126. The pivot wheel 150 generally includes an upper end portion 164, a lower end portion 166, and a middle portion 168 between the upper and lower end portions. The upper end portion 164 is shaped and configured to be driven by any suitable driving tool, such as hex socket wrench, and has one or more outer lateral walls 170. The outer lateral walls 170 define a diameter or cross-sectional dimension D5. The cross-sectional dimension D5 is smaller than the cross-sectional dimensions D1 and D3 of openings 148 and 160, respectively. Accordingly, the upper end portion 164 can be inserted through openings 148 and 160. In the depicted embodiment, the outer lateral walls 170 of the upper end portion 164 define a hexagonal shaped head adapted to be driven by a hex socket driving tool. Nonetheless, the upper end portion 164 can define other shapes and configurations adapted to be driven by any suitable driving tool. Specifically, a suitable driving tool can engage the upper end portion 164 to rotate the pivot wheel 150 about its central axis E. As discussed in detail below, rotating the pivot wheel 150 about its central axis E in a first direction causes one of the retractor members 106 to move proximally along the longitudinal axis X. Rotation the pivot wheel 150 about its central axis E in a second direction (that is opposite to the first direction) causes the same retractor members 106 to move distally along the longitudinal axis X. Direction is restricted based on the ratchet mechanism 274.

The lower end portion 166 of the pivot wheel 150 has an outer surface 172 defining a diameter or cross-sectional dimension D6. The cross-sectional dimension D6 of the lower end portion 166 is smaller than (or substantially similar to) the cross-sectional dimension D2 and D4 of openings 152 and 162, respectively. Accordingly, the lower end portion 166 of the pivot wheel 150 can be inserted through the openings 152 and 162.

The middle portion of the pivot member 150 is located between the upper end portion 164 and the lower end portion 166 and includes a pinion 175. The pinion 175 includes an outer surface 174 and gear teeth 176 protruding outwardly from the outer surface 174 away from the central axis E. The gear teeth 176 are arranged radially around the outer surface 174 and collectively define a diameter or cross-sectional dimension D7. The cross-sectional dimension D7 is larger than the cross-sectional dimensions D2, and D4 of openings 152, and 162, respectively. As a result, the pivot wheel 150 is secured between the upper members 142 and 154 and the lower members 144 and 156 of the first and second arms 122, 126.

Aside from the pivot wheel 150 (or any other suitable pivot member), a connection mechanism 178 operatively couples the first and second arm 116 and 114. The connection mechanism 178 maintains the first and second arms 116 and 114 substantially aligned along the longitudinal axis Y and includes a connection bar 180 configured and sized to be inserted through openings 182 and 184 of the first and second arms, respectively. The opening 182 is located close to the proximal end 130 of the first arm 114, and the opening 184 is positioned adjacent to the proximal end 132 of second arm 116. When inserted through openings 182 and 184, the connection bar 180 is oriented substantially parallel to the longitudinal axis Y. In addition, the connection bar 180 includes a first end 186 connected to the second arm 122 and a second end 188 connected to the first arm 126.

A pivot fit connector 190, or any other suitable connector, is positioned at the first end 186 of the connection bar 180 and is configured to be pivot fitted within the opening 182. To this end, the pivot fit connection 190 has an outer surface 192 defining a diameter or cross-sectional dimension D8. The cross-sectional dimension D8 of the connector 190 is smaller than the cross-sectional dimension defined by the inner surfaces 194 forming opening 182. Although the figures illustrate a pivot fit connector 190, the surgical access retractor 100 can include any other type of connector capable of connecting the first end 186 of the connection bar 180 to the second arm 122. The connection bar 180 further includes non-threaded portion 196 extending from the pivot fit connector 190. The non-threaded portion 196 is configured and sized to be inserted through the openings 182 and 184 and terminates at an annular recess 198. A threaded portion 200 of the connection bar 180 extends from the annular recess 198 and terminates at the second end 188 of the connection bar.

The connection mechanism 178 further includes a cap 202 adapted to be placed over the second end 188 of the connection bar 180 and a connector 204 configured to secure a portion of the connector bar 180 to the first arm 126 within the opening 184. The connector 204 has a longitudinal opening 206 extending there through. The longitudinal opening 206 of the connector 204 is sized and configured to slidably receive the connection bar 180. In the depicted embodiment, the connector 204 is a pivot fit connector and is therefore configured to be pivot fitted within the opening 184. To this end, the pivot fit connection 204 has an outer surface 208 defining a diameter or cross-sectional dimension D9 that is substantially similar (or equal) to the cross-sectional dimension defined by the inner surfaces 210 forming the opening 184. Although the figures depict a pivot fit connector 204, the connection mechanism 178 can include any other connector suitable for connecting the connection bar 180 to the first arm 126.

The connection mechanism 178 further includes a securing element, illustrated as a knob 212, to secure the position of the first and second arms 122 and 126 relative to each other. The knob 212 has a threaded bore 214 extending there through and an outer surface 216 defining a diameter or cross-sectional dimension D10. Grooves 215 are formed on the outer surface 216 of the knob 212 to facilitate grabbing by a user. The threaded bore 214 is configured and sized to receive the threaded portion 200. The threads formed around bore 214 are configured to mate with the threads of threaded portion 200. Consequently, rotating the knob 212 around the threaded portion 200 in a first direction causes the knob 212 to move along the connection bar 200 toward the second arm 122. Rotating the knob 212 about the threaded portion 200 in a second direction (that is opposite to the first direction) causes the knob to move along the connection bar 180 away from the second arm 122. The diameter or cross-sectional dimension D10 defined by the outer surface 208 is larger than the diameter or cross-sectional dimension defined by the inner surfaces 210 forming the opening 184. Thus, the knob 212 can serve as a mechanical stop when placed abutting the first arm 126 because it cannot be inserted through opening 184.

As discussed in detail below, the user can squeeze first and second handle portions 116 and 114 to pivot the first and second arms 122 and 126 about pivot wheel 150. As the user squeezes the handle portions 116 and 114, the distal ends 134 and 136 of the first and second arms 122 and 126, respectively, move away from each other. Once the distal ends 134 and 136 of the first and second arms 122 and 126, respectively, reach the desired position, the user can rotate the knob 212 in the first direction about the threaded portion 200 to move the knob 212 toward the first arm 126. The user should rotate the knob 212 in the first direction until the knob 212 contacts the first arm 126. At this point, the knob 212 prevents, or at least inhibits, the proximal end 132 of the first arm 126 from moving away from proximal end 130 of the second arm 122, thereby fixing the position of the distal ends 134 and 136 with respect to each other.

Figure 5:
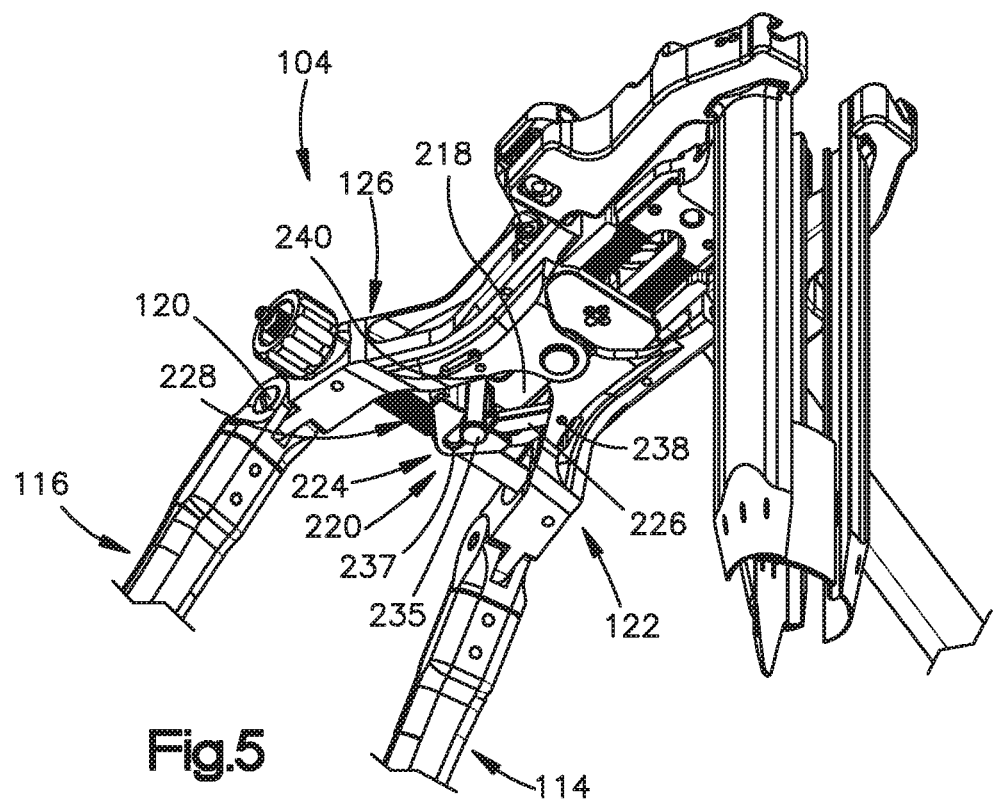
FIG. 5 is a perspective view of a lower portion of the surgical access retractor illustrated in FIG. 1.

With reference to FIGS. 4-7, the holder assembly 104 further includes an elongate central body 218 disposed between the second arm 122 and the first arm 126. The central body 218 has a proximal end portion 220 and a distal end portion 222. As seen in FIG. 5, the proximal end portion 220 of the central body 218 supports a guiding mechanism 224 for guiding the movement of the second arm 122 and the first arm 126. Specifically, the guiding mechanism 224 is configured to allow the first and second arms 122 and 126 to move equidistantly when a user squeezes the first and second handle portions 116 and 114. In the depicted embodiment, the guiding mechanism 224 includes first and second guiding arms 226 and 228 slidably connected to the proximal end portion 220 of the central body 218. The first guiding arm 226 has a proximal end 230 and a distal end 232. Similarly, the second guiding arm 228 has a proximal end 234 and a distal end 236. The proximal ends 230 and 232 of the first and second guiding arms 226 and 228, respectively, are connected to the same sliding member, such as sliding pin 235. As shown in FIG. 4, the sliding pin 235 includes two parts, namely: a lower part 235a and an upper part 235b. The lower part 235a and the upper part 235b are adapted to be connected together and collectively allow the proximal ends proximal ends 230 and 232 of the first and second guiding arms 226 and 228, respectively, to slide along an elongate slot 237 defined on the proximal end portion 220 of the central body 218. The distal end 232 of the first guiding arm 226 is fixed to the second arm 122 at attachment location 238, and the distal end 236 of the second guiding arm 228 is fixed to the first arm 126 at attachment location 240. In the illustrated embodiment, the attachment locations 238 and 240 are positioned at substantially the same distance from the proximal end portion 220 of the central body 218, thereby urging the first and second arms 122 and 126 to move equidistantly when the first and second handle portions 116 and 114 are squeezed together. When the first and second handle portions 116 and 114 are squeezed together, the axes of the distal ends 232 and 236 of the first and second guiding arms 226 and 228, respectively, remain stationary relative to 122 and 126 respectively while the sliding pin 235 urges the proximal ends 230 and 234 of the first and second guiding arms 226 and 228, respectively, to translate and rotate accordingly proximally along the slot 237 of the proximal end portion to allow an equidistant movement of the first and second arms 122 and 126.

With reference to FIGS. 7 and. 8, the central body 218 further includes a top wall 242 connecting first and second side walls 244 and 246. The first and second side walls 244 and 246 are substantially parallel to each other and collectively define a space 248 there between. The opening 252 is located between the first and second side walls 244 and 246. The top wall 242 has an first opening 250 configured and dimensioned to receive at least the upper end portion 164 of the pivot wheel 150 or any other suitable pivot member and a second opening 254. The first opening 250 can have a substantially circular shape such as pivot wheel 150. In the depicted embodiment, second opening 254 has a substantially elliptical shape but it may have other suitable shapes (e.g., circular, rectangular, etc.). The second opening has a diameter or cross-sectional dimension D13. One or more connection members 256 are mounted on the top wall 242 and each is adapted to be connected to a holding or fixation tool or device. In the illustrated embodiment, the central body 218 includes a pair of connection members 256 located adjacent to each other. In the exemplary embodiment shown in FIG. 7, each connection member 256 includes a polygonal socket 258 and a threaded bore 260. The polygonal socket 258 of each connection member 256 leads to the threaded bore 260. Each connection member 256 is adapted to be attached to a fixation tool, such as a table fixation device. The exemplary connection member 256 depicted in FIG. 7 is configured to be attached to a table fixation device including a mating polygonal head and a threaded screw. The central body 218 can nevertheless include other types of connection members capable of being attached to a fixation tool. For example, the connection member 256 can have a hexagon socket configured to be attached to a tool with a hexagon head. Regardless of the specific structural features, the connection member 256 is adapted to be attached to a stationary structure via the holding tool. For example, the connection member 256 can be attached to a table fixation device that is in turn fixed to a surgical or operating table. The top wall 242 of the central body 218 further includes a notch 262 between the two connection members 256. The notch 262 can have a concave configuration or any other suitable configuration or shape. When the retractor member holders or distal portions 362 and 374 are in the closed position and in alignment with the proximal portions (i.e., not angulated) (as described in detail below), a first gap 403 is defined between the retractor member 110 and the retractor member 112. The first gap 403 can measure between about 0.5 millimeters and about 2 millimeters. In one embodiment, the first gap 403 measures 1 millimeter. When the retractor member holders or distal portions 362 and 374 are in the closed position and in alignment with the proximal portions (i.e., not angulated) as described in detail below and the posterior retractor member holder or distal portion 318 is in the distal position (as described in detail below), a second gap 405 is defined between retractor member 108 and retractor member 112 and another third gap 401 is defined between retractor member 108 and 110. The second gap 405 can measure between about 0.5 millimeters and about 2 millimeters. In one embodiment, the second gap 405 measures 1 millimeter. The third gap 401 can measure between about 0.5 millimeters and about 2 millimeters. In one embodiment, the third gap 401 measures 1 millimeter.

The first retractor member 112 defines a first body (399) configured to retract tissue. The first body 399 extends along a first outer perimeter 397 that terminates at opposed first edges 395. The second retractor member 110 defines a second body configured to retract tissue. The second body 393 extends along a second outer perimeter 391 that terminates at opposed second edges 299. When the retractor 100 defines a fully closed position whereby each of the first retractor member 112 and the second retractor member 110 are unable to be angulated closer to each other and the first outer perimeter 397 is substantially aligned with the second outer perimeter 391, and the first arm 126 and the second arm 122 are configured to retain the first retractor member 112 and second retractor member 110 such that the first gap 403 is defined between the first retractor member 112 and the second retractor member 110 when the retractor 100 is in the fully closed position. The first gap 403 can measure between about 0.5 millimeters and about 2 millimeters. The first gap 403 can measure about 1 millimeter. The third retractor member 108 defines a third body 389 configured to retract tissue. The third body 389 extends along a third outer perimeter 387 that terminates at opposed first edges 385. In the fully closed position, the first outer perimeter 397 is substantially aligned with the third outer perimeter 387, and the second outer perimeter 391 is substantially aligned with the third outer perimeter 387, and the third arm 316 is configured to retain the third retractor member 108 such that the second gap 405 is defined between the first retractor member 112 and the third retractor member 108, and the third gap 401 is defined between the second retractor member 110 and the third retractor member 108 when the retractor 100 is the fully closed position. The second gap 405 can measure between about 0.5 millimeters and about 2 millimeters. The second gap 405 can measure about 1 millimeter. The third gap 401 can measure between about 0.5 millimeters and about 2 millimeters. The third gap 401 can measure about 1 millimeter.

With reference to FIG. 8, the central body 218 also includes a first guide track 264 formed on an inner surface 268 of the first side wall 244 and a second guide track 266 formed on an inner surface 270 of the second side wall 246. In the depicted embodiment, the first and second guide tracks 264 and 266 can be substantially linear grooves extending between the proximal end portion 220 and the distal end portion 222 of the central body 218. The guide tracks 264 and 266, however, can have other suitable shapes and configurations. In addition to the guide tracks 264 and 266, the central body 218 includes a protrusion 280 extending outwardly from each side wall 244 and 266. Each protrusion 280 defines an inner longitudinal bore (not shown).

Referring again to FIG. 4, the central body 218 is operatively connected to a rack and pinion mechanism 272 through a connection assembly 274. Instead of the rack and pinion mechanism 272, the central body 218 can be connected to any other mechanism capable of moving the third arm 316 longitudinally along the axis X. The rack and pinion mechanism 272 is configured to move at least one of the retractor members 106 proximally or distally along longitudinal axis X, as discussed in detail below. The connection assembly 274 couples the rack and pinion mechanism 272 and the central body 218 while allowing at least a portion of the rack and pinion mechanism 272 to move proximal and distally relative to the central body 218. Fasteners, such as pins 284 and 286, help connect the connection assembly 274 to the rack and pinion mechanism 272 and the central body 218.

With reference to FIG. 9, the connection assembly 274 includes a bottom member 276 adapted to be positioned underneath the rack and pinion mechanism 272 (FIG. 4) and an upper member 278 configured to at least partially pass through the translation mechanism 272. The bottom member 276 can have a substantially planar configuration, having a proximal end 296 and a distal end 298, and includes first and second extensions 288 and 290 protruding outwardly from opposite sides of the bottom member 276. The first extension 288 defines a hole 292 sized and adapted to receive at least a portion of a fastener, such as one of the pins 284 (FIG. 4). In the illustrated embodiment, a pin 294 (FIG. 4) is inserted through the hole 292 and the inner bore of the protrusions (FIG. 8) formed on the side wall 244 of the central body 218 to fix the connection assembly 274 to the central body 218. The second extension 290 also defines a hole 294 sized and adapted to receive at least a portion of a fastener, such as one of the pins 284 (FIG. 4). In the depicted embodiment, a pin 284 (FIG. 4) is inserted through the hole 294 and the inner bore of the protrusion 284 (FIG. 8) formed on the side wall 246 of the central body 218 to fix the connection assembly 274 to the central body 218. The bottom member 276 includes a third extension 300 protruding from its proximal end 296. The third extension 300 defines a hole 302 configured and sized to receive at least a portion of a fastener, such as the pin 286 (FIG. 4). In the depicted embodiment, the pin 286 (FIG. 4) is inserted through the hole 302 and is attached to the lower end portion 166 (FIG. 4) of the pivot wheel 150 in order to fix the pivot wheel 150 to the connection assembly 274. Moreover, the upper end portion 164 (FIG. 4) of the pivot wheel 150 extends through the first opening 250 (FIG. 8) of the central body 218. As a consequence, the pivot wheel 150 (FIG. 4) cannot translate in any direction. The pivot wheel (FIG. 4) can only rotate about its central axis E.

With continued reference to FIG. 9, the bottom member 276 of the connection assembly 274 has a top surface 306 and an opposite bottom surface 308. A recess 304 is formed on the top surface 306 of the bottom member 276. The recess 304 is shaped and sized to tightly and securely receive a lower portion 306 of the upper member 278. Consequently, the lower portion 306 of the upper member 278 is press fitted within the recess 304. In the illustrated embodiment, the lower portion 306 has a substantially planar configuration. However, the lower portion 306 of the upper member 278 may have other suitable shapes and configurations. The upper member 278 further includes a column 310 extending upwardly from the lower portion 306. The column 310 has a main section 312 and an upper section 314. The main section 312 has a diameter or cross-sectional dimension D11, and the upper section has a diameter or cross-sectional dimension D12. The cross-sectional dimension D12 is larger than the cross-sectional dimension D11. Moreover, the cross-sectional dimension D12 of the main section 312 is larger than the cross-sectional dimension D13 (FIG. 8) of the second opening 254 of the central body 218. The cross-sectional dimension D13 (FIG. 8) of the second opening 254, however, is larger or substantially similar to the cross-sectional dimension D12 of the upper section 314 of the column 310. Consequently, the upper section 314 can be inserted through the second opening 254 (FIG. 8) of the central body 218 to restrict the movement of the central body 218 relative to the connection assembly 274 along longitudinal axis X (FIG. 4).

Figure 10:
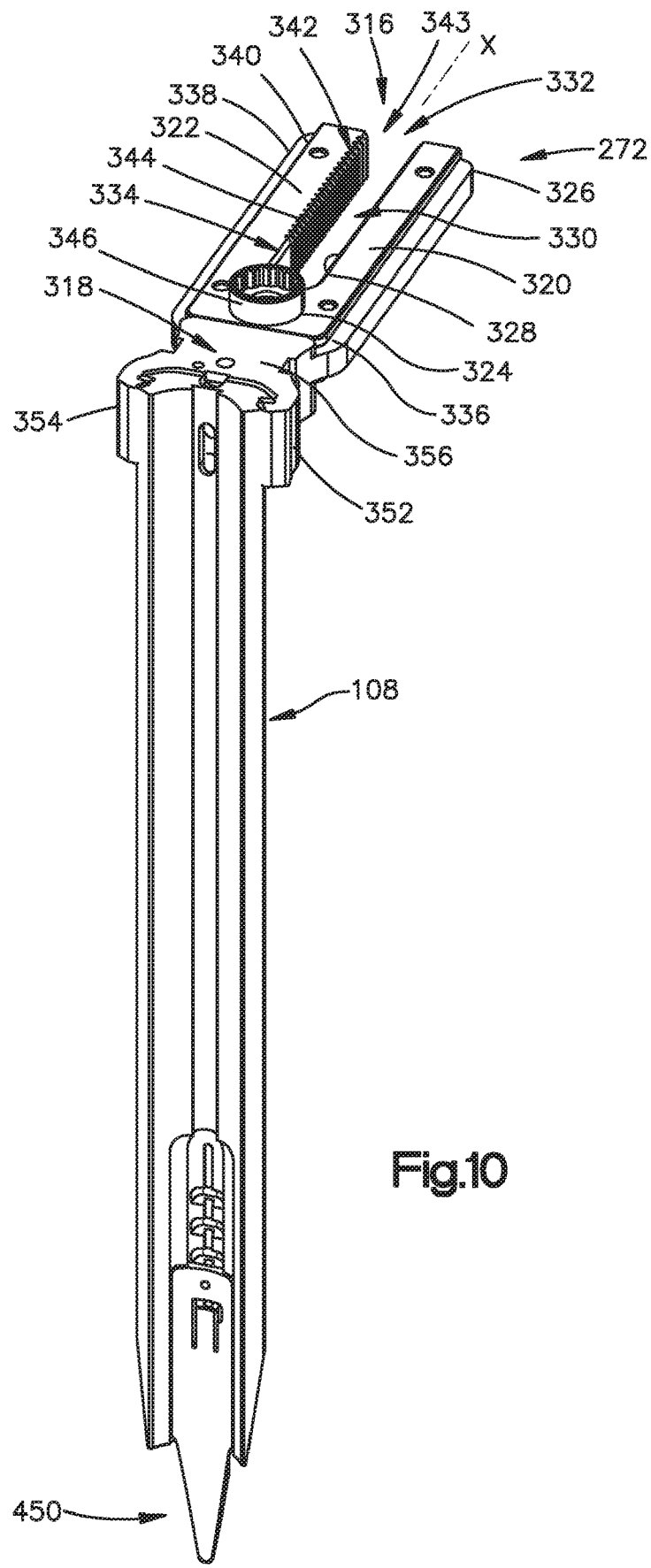
FIG. 10 is an enlarged perspective view of a retractor member holder attached to a part of a translation mechanism of the surgical access retractor illustrated in FIG. 1.

Referring to FIG. 10, in the depicted embodiment, the rack and pinion mechanism 272 includes a third arm 316 adapted to operatively mate with pivot wheel 150. The third arm 316 includes a proximal portion 315 and a distal portion 318, such as a retractor member holder, configured to retain retraction member 108. The third arm 316 can move longitudinally proximal or distally along the longitudinal axis X. The third arm 316 includes a first leg 320 and a second leg 322, and distal connecting portion 324 coupling the first and second legs 320 and 322. The first leg 320 and the second leg 322 are substantially parallel to each other and collectively form an open slot 330. The open slot 330 is formed between the first and second legs 320 and 322 and has an open proximal end 332 and a close distal end 334. Moreover, the slot 330 is shaped, sized, and configured to receive the middle portion 168 (FIG. 4) of the pivot wheel 150 and the main section 312 (FIG. 9) of the column 310.

With continued reference to FIG. 10, the first and second legs 320 and 322 are adapted to move longitudinally within the space 248 (FIG. 8) of the central body 218 along the longitudinal axis X. To facilitate and guide the longitudinal movement of the first and legs 320 and 322, each of the first and second legs 320 and 322 includes first and second guide protrusions 336 and 338, respectively. The first guide protrusion 336 extends radially outward from an outer side wall 326 of the first leg 320 and is configured to be slidably received within the first guide track 264 (FIG. 10) of the central body 218. The second guide protrusion 338 extends radially outward from an outer side wall 340 of the second leg 322 and is configured to be slidably received within the second guide track 266 (FIG. 8) of the central body 218. In operation, the first and second guide protrusions 336 and 338 can slide through the first and second guide tracks 264 and 266 (FIG. 8), respectively, to guide the longitudinal movement of the third arm 316 through the space 248 (FIG. 8) of the central body 218.

With continued reference to FIG. 10, the first leg 320 further has an inner side wall 328 facing the open slot 330. In the depicted embodiment, the inner side wall 328 has a substantially planar configuration and, therefore, does not have teeth. The second leg 322 also has an inner side wall 342 facing the open slot 330. A rack 343 includes teeth 344 protruding from the inner side wall 342. The teeth 344 are arranged at least along a portion of the length of the inner side wall 342. The teeth 344 are configured to mate with the gear teeth 176 (FIG. 4) of the pivot wheel 150. Since gear teeth 176 (FIG. 4) mate with the teeth 344 when the surgical access is fully assembled, the rotation of pivot wheel 150 (FIG. 4) about its central axis E, causes the third arm 316 to move axially along the longitudinal axis X. Specifically, rotating the pivot wheel 150 (FIG. 4) in a first direction about its central axis E causes the third arm 316 to move proximally (i.e., toward first and second handle portions 116 and 114 (FIG. 3)). Rotating the pivot wheel 150 (FIG. 4) in a second direction (that is opposite to the first direction) about its central axis E causes the third arm 316 to move distally (i.e., toward the distal ends 134 and 136 (FIG. 4) of the first and second arms 122 and 126, respectively).

In the embodiment illustrated in FIG. 10, a connection member 346 can be mounted onto the distal connecting portion 324. The structure and operation of the connection member 346 can be substantially similar to the structure and operation of connection member 256 (FIG. 7). As seen in FIG. 7, the connection member 346 can include a polygonal socket 348 and a threaded bore 350. The polygonal socket 348 of connection member 346 leads to the threaded bore 350. The connection member 346 is adapted to be attached to a fixation tool, such as a table fixation device. The third arm 316 (FIG. 10) can therefore be connected to a stationary structure, such as a surgical or operating table. This connection allows the third arm 316 (FIG. 10) to be moved relative to a stationary structure, such as an operating table, in order to provide more control to the user of the surgical access retractor 100.

With reference to FIGS. 7 and 10, the distal connecting portion 324 of the proximal portion 315 is attached to the third distal portion 318. Consequently, the third distal portion 318 is adapted to move axially when the third arm 316 moves axially upon rotation of the pivot wheel 150. The third distal portion 318 is configured to hold and support a retractor member 106. In the illustrated embodiment, the third distal portion 318 is adapted to hold and support the third retractor member 108 and includes a main body 356 and first and second hooks 352 and 354 extending distally from opposite sides of the main body 356. The first and second hooks 352 and 354 are spaced apart from each and collectively form a groove 358 between them. The groove 358 is shaped and sized to receive the third retractor member 108. The third retractor member 108 is pressed fitted in the groove 358, so that the retractor member holder 318 can securely hold the third retractor member 108. The third distal portion 318 can further include a retention member 360, such as a snap fit socket, configured for the retaining accessories to be used during a surgical procedure. For example, the retention member 360 can be a snap fit socket adapted to securely receive a snap fit protrusion of a light clip.

Since the third retractor member 108 is attached to the third distal portion 318, the third retractor member 108 is adapted to move proximally upon rotation of the pivot wheel 150 (FIG. 4) in a first direction about its central axis E. Moreover, the third retractor member 108 is adapted to move distally upon rotation of the pivot wheel 150 (FIG. 4) in a second direction (that is opposite to the first direction) about its central axis E. The third distal portion 318 can be wholly or partly made of a suitable radiolucent material and can have a dark color in order to prevent glaring during use. Suitable radiolucent materials include, but are not limited to, aluminum, aluminum alloys, carbon fiber, and carbon fibers composites.

With reference to FIG. 7, the first and second arms 122 and 126 also include retraction member holders configured to hold and support a retractor member 106, such as a blade. The first arm 126 comprises the proximal portion 127 and the distal portion 374, such as a retractor member holder. The distal portion 374 is configured to retain a first retractor member 112. The second arm 122 comprises a proximal portion 125 and a distal portion 362, such as a retractor member holder, adjacent the distal end 134. The distal portion 362 is configured to retain a retractor member 110. In the illustrated embodiment, the distal portion 362 is adapted to hold and support a second or cranial retractor member 110 and includes a main body 364 and first and second hooks 366 and 368 extending from the main body 364. The first and second hooks 366 and 368 are spaced apart from each other and collectively form a groove 370 between them. The groove 370 is shaped and sized to receive the second retractor member 110. The second retractor member 110 is tightly fitted in the groove 370 such that the distal portion 362 can securely hold the second retractor member 110. The distal portion 362 can further include a retention member 372, such as spring-loaded clip, that locks into the second retractor member 110 to prevent the retractor member 110 from escaping the distal portion 362. The distal portion 362 can be wholly or partly made of a suitable radiolucent material and can have a dark color in order to prevent glaring during use. Suitable radiolucent materials include, but are not limited to, aluminum, aluminum alloys, carbon fiber, and carbon fibers composites.

The first arm 126 includes a distal portion 374, such as a retractor member holder, adjacent the distal end 136. In the illustrated embodiment, the distal portion 374 is adapted to hold and support a first retractor member 112 and includes a main body 376 and first and second hooks 378 and 380 extending from the main body 376. The first and second hooks 378 and 380 are spaced apart from each other and collectively form a groove 382 between them. The groove 382 is shaped and sized to receive the first retractor member 112. The first retractor member 112 is tightly fitted in the groove 382 such that the distal portion 374 can securely hold the first retractor member 112. The distal portion 374 can further include a retention member 384, such as a spring-loaded clip, that locks into the first retractor member 112 to prevent the first retractor member 112 from escaping the distal portion 374. For example, the retention member 384 can be a snap fit socket adapted to securely receive a snap fit protrusion of a light clip. The distal portion 374 can be wholly or partly made of a suitable radiolucent material and can have a dark color in order to prevent glaring during use. Suitable radiolucent materials include, but are not limited to, aluminum, aluminum alloys, carbon fiber, and carbon fibers composites.

As discussed above, the distal ends 134 and 136 of the first and second arms 122 and 126, respectively, move away from each other when the handle portions 116 and 114 (FIG. 3) are squeezed together. Consequently, moving the handle portions 116 and 114 (FIG. 3) toward each other causes the retractor members 110 and 112 to move away from each other from a first or approximated position (see FIG. 7) in which retractor members 110 and 112 are positioned adjacent to each other, to a second or open position (see FIG. 1) in which the retractor members 110 and 112 are spaced apart from each other. Conversely, when the handle portions 116 and 114 (FIG. 3) move away from each other, the retractor members 110 and 112 move toward each other from the second or open position (see FIG. 1) toward the first or approximated position (see FIG. 7). When the retractor members 110 and 112 are in the first or approximated position, the retractor members 108, 110, and 112 collectively form a passageway 410 extending along a longitudinal axis J (see FIG. 3). The passageway 410 is configured and dimensioned to receive any suitable medical apparatus, such as surgical distractors. The passageway 410 can have a diameter or cross-sectional dimension ranging between about 12 and 18 millimeters. In one specific embodiment, the diameter or cross-sectional dimension of the passageway can be about 16 millimeters.

With continued reference to FIG. 7, the second retractor member 110 can include one or more slots 386 extending along its length. The slots 386 are formed on inner surface 390 of the second retractor member 110 and each is configured to receive any suitable surgical device. Similarly, first retractor member 112 can include one or more slots 388 extending along its length. The slots 388 are formed on an inner surface 392 of the first retractor member 112 and each is configured to receive any surgical device.

The second retractor member 110 further includes a slot 394 leading to retention member 372 and sized and adapted to receive a surgical accessory such as a tubular fiber optic cable configured to illuminate a surgical field. The slot 394 is formed on an outer surface 398 of the second retractor member 110 and allows a user to reach the retention member 372 (using, for example, a tool) to disengage the retention member 372 from the second retractor member 110, thereby permitting removal of the second retractor member 110 from the distal portion 362.

The first retractor member 112 includes a slot 396 leading to retention member 384 and sized and configured to receive a surgical accessory such as a tubular fiber optic cable adapted to illuminate a surgical field. The slot 396 is formed on an outer surface 400 of the first retractor member 112 and allows a user to reach the retention member 384 (using, for example, a tool) to disengage the retention member 384 from the first retractor member 112, thereby permitting removal of the first retractor member 112 from the distal portion 374.

The distal portion 362 can further include a holding member, such as a hook 402 (see also FIG. 3), for holding surgical accessories. The hook 402 can, for example, hold a conventional light clip. The distal portion 374 can also include a holding member, such as hook 404 (see also FIG. 3), for holding surgical accessories. For instance, the hook 404 can hold a conventional light clip.

The second arm 122 can further include a retention feature, such as a second connecting slot 406, for holding another surgical device. This retention feature can hold, for example, another soft tissue retractor. In the illustrated embodiment, the second connecting slot 406 is located at the distal end 134 of the second arm 122 and is oriented at an oblique angle with respect to the longitudinal axis Z (see FIG. 3). The first arm 126 can also include a retention feature, such as first connecting slot 408, for holding another surgical device. For instance, this retention feature can hold another soft tissue retractor. In the depicted embodiment, the first connecting slot 408 is located at the distal end 136 of the first arm 126 and is oriented at an oblique angle relative to the longitudinal axis Z (see FIG. 3).

The retractor members 110 and 112 can be wholly or partly made of a radiolucent material. Suitable radiolucent materials for the retractor members 110 and 112 include, but are not limited to, aluminum, aluminum alloys, carbon fiber, and carbon fiber composites. Each of the retractor members 110 and 112 can include one or more radiopaque markers (not shown) at or near their corresponding distal ends 412 and 414 (see FIG. 4) to allow the clinician to observe the distal ends 412 and 414 under fluoroscopy. The radiopaque markers can be, for example, radiopaque pins inserted at or near the distal ends 412 and 414 of the retractor members 110 and 112, respectively. The radiopaque markers can be wholly or partly made of any suitable radiopaque material. Suitable radiopaque materials include, but are not limited to, titanium, titanium alloys, stainless steel, and tantalum.

With reference to FIGS. 6 and 11A-12C, each of the first and second arms 122 and 126 includes an angulation mechanism 416 for pivoting distal portion 362 or distal portion 374 with respect to the rest of the arm (122 or 126) and longitudinal axis Z. The angulation mechanism 416 of the first and second arms 122 and 126 are identical. Thus, in the interest of brevity, only the angulation mechanism 416 of the first arm 126 is discussed herein.

The angulation mechanism 416 is configured to rotate the third retractor member holder or distal portion 374 relative to a proximal portion 127 of the second arm 122 between a first or straight position (FIGS. 11A and 12A), in which the proximal portion 127 is substantially aligned with the distal portion 374, and a first angled position (FIGS. 11B and 12B), in which the distal portion 374 is oriented at an oblique angle relative the proximal portion 127. When the distal portion 374 is in the first angled position, the first retractor member 112 is oriented at an oblique angle relative to the longitudinal axis Z. Specifically, the distal portion 374 is rotatably coupled to the proximal portion 127. Thus, the distal portion 374 is configured to rotate relative to the proximal portion 127 about axis 373.

In the depicted embodiment, the angulation mechanism 416 includes a rotating member 418, such as rotating nut, disposed within an extension 129 of the proximal portion 127 of the first arm 126. The extension 129 protrudes outwardly or laterally from the proximal portion 127. The rotating member 418 rotatably couples the proximal portion 127 to the retraction member holder or distal portion 374. Specifically, the rotating member 418 is at least partially disposed within an opening 131 of the extension 129. A rotating sleeve 426 rotatably couples the rotating member 418 to the extension 129. Thus, the rotating sleeve 426 rotatably couples the rotating member 418 to the proximal portion 127. It should thus be appreciated that the rotataing member 418 provides a support member that supports the proximal portion 127 in a desired, for instance fixed, position. The support member is configured to retain the proximal portion 127 in a fixed position as the translating member 430 biases the distal portion 127. The opening 131 is sized and configured to receive the rotating member 418 and the rotating sleeve 426. In the depicted embodiment, the rotating sleeve 426 surrounds at least a portion of rotating member 418 and includes one or more pivot members 428, such as pivot pins, rotatably connecting the rotating member 418 to the extension 129. Thus, the rotating sleeve 426 rotatably connects the rotating member 418 to the proximal portion 127. The diameter or cross-sectional dimension of the opening 131 of the extension 129 is larger than the diameter or cross-sectional dimension of the rotating member 418 and the rotating sleeve 426. As a result, the rotating member 418 and the rotating sleeve 426 can pivot concomitantly about the pivot member 428 within the opening 131 of the extension 129.

Furthermore, the rotating sleeve 426 is configured to pivot the rotating member 418 when the threaded shaft 434 of a translating member 430 moves along the threaded bore 422 along the second axis L. The rotating member 418 is coupled between the proximal portion 127 and the distal portion 374. In addition, the rotating member 418 is configured to rotate about a second axis L, wherein rotation of the rotating member 418 about the second axis L causes the distal portion 374 to rotate relative to the proximal portion 127 about the first axis 373.

The angulation mechanism 416 further includes a translating member 430 that extends along the second axis L, and is configured to receive a drive force that causes the translating member 430 to translate along the second axis L so as to bias, directly or indirectly, the distal portion 374 to move with respect to, for instance pivot away from, the proximal portion 127. It should be appreciated that the rotating member 418 is configured to support, directly or indirectly, the proximal portion 127 in a desired, for instance fixed, position as the distal portion 374 moves relative to the proximal portion 127. Thus, the rotating member 418 can be referred to as a support member configured to support, directly or indirectly, the proximal portion 127 in a desired, for instance fixed, position as the distal portion 374 moves relative to the proximal portion 127. Alternatively, the retractor 100 can define any suitable alternative support structure that is configured to support, directly or indirectly, the proximal portion 127 in a desired, for instance fixed, position as the distal portion 374 moves relative to the proximal portion 127

In accordance with one embodiment, the rotating member 418 is configured to be rotated along the second axis L so as to apply the drive force to the translating member 430. The translating member 418 is configured to receive a drive force that causes the translating member 418 to bias the distal portion 374 to pivot relative to the proximal portion 127 about the first axis 373 In accordance with another embodiment, the drive force can be a torsional force about the second axis L that is applied to the translating member 430 that causes the translating member 430 to rotate relative to the rotating member 430, thereby causing the translating member 430 to translate relative to the rotating member 418, and thus further relative to the proximal portion 127, so as to bias the distal portion 374 to move relative to the proximal portion. In accordance with another embodiment, the drive force can be a translation force applied to the translating member 430 substantially along the second axis L that causes the translating member 430 to translate along the second axis L and bias the distal portion 374 to move, e.g., pivot, relative to the proximal portion 127 (for instance, when the translating member 430 is not threadedly coupled to the rotating member 418). The rotating member 418 can be threadedly coupled to the translating member 430, wherein the rotating member 418 is configured to rotate about the second axis L so as to apply the drive force to the translating member 430.

Figure 12A:
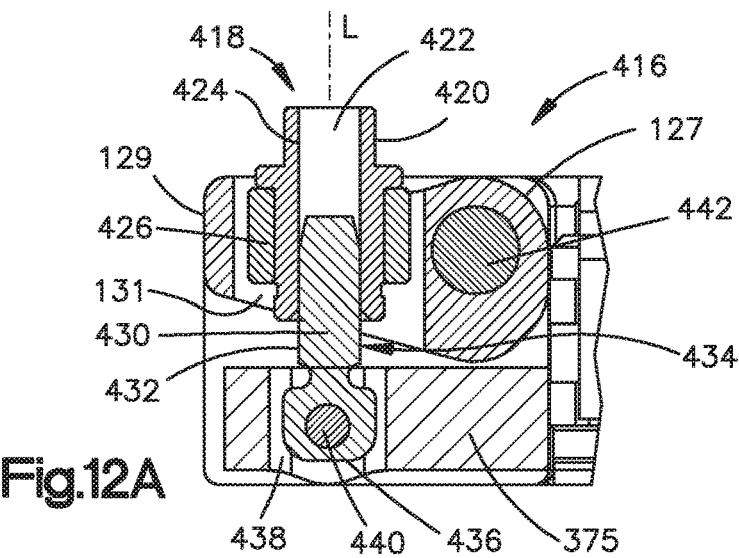
FIG. 12A is a cross-sectional view of the arm shown in FIG. 11A, taken along section line 12A-12A of FIG. 11A.
Figure 12B:
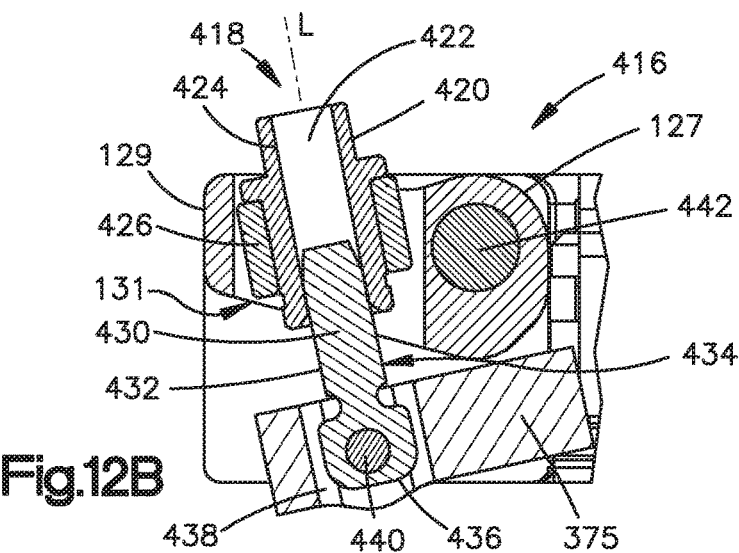
FIG. 12B is a cross-sectional view of the arm shown in FIG. 11B in the first angled position, taken along section line 12B-12B of FIG. 11B.
Figure 12C:
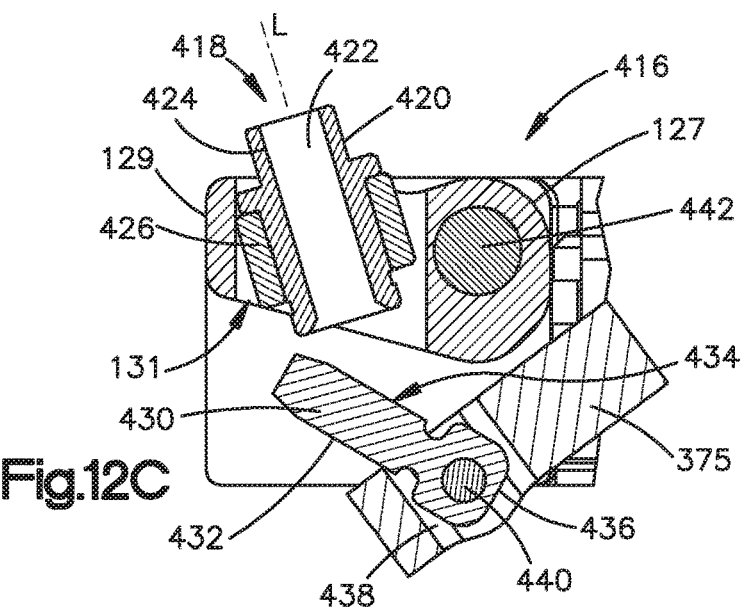
FIG. 12C is a cross-sectional view of the arm shown in FIG. 11C in the second angled position, taken along section line 12C-12C of FIG. 11C.
Figure 17:
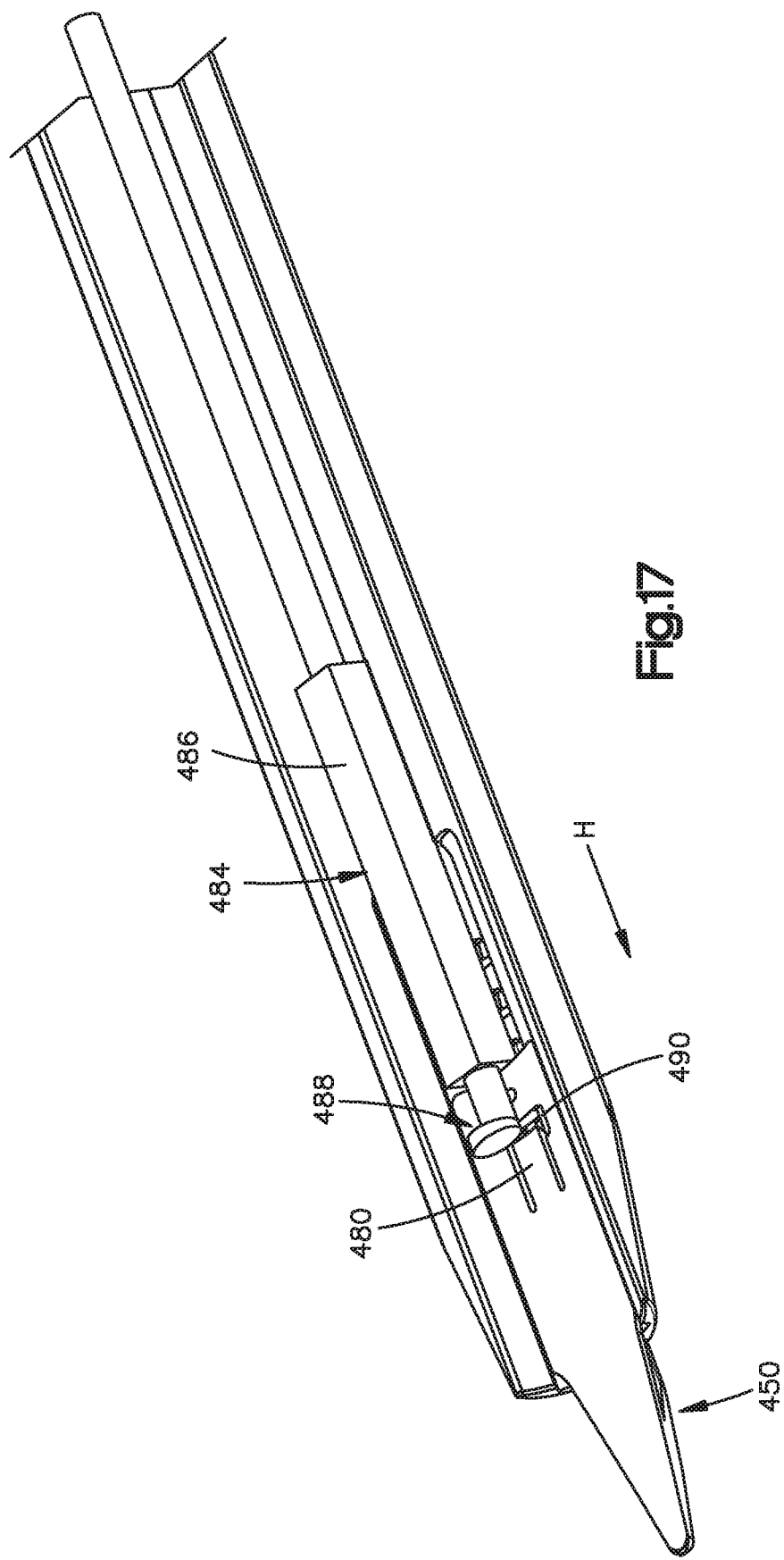
FIG. 17 is a perspective view of a retractor member illustrated in FIG. 13 with the advancement tool attached to the disc anchor while the disc anchor is in the deployed position.

Furthermore, the rotating member 418 is configured to be rotated about its central axis L and can include a head 420 adapted to be driven by a tool. The axis 373 and the axis L are positioned at different. For example, head 420 can have a hexagonal configuration or any other suitable configuration. The rotating member 418 further includes a longitudinal threaded bore 422 formed by an inner surface 424. At least a portion of the inner surface 424 includes threads (not shown) adapted to mate outer threads (not shown) of a translating member 430. The translating member 430 may be a translating pin as illustrated in FIGS. 12A-12C.

The translating member 430 includes a threaded shaft 434 configured and sized to fit within the longitudinal bore 422 of the rotating member 418. The shaft 434 has an outer surface 432 having outer threads (not shown) configured to mate with the inner threads (not shown) of the rotating member 418. Thus, turning the rotating member 418 about axis L in a first direction as shown by arrow W (FIG. 11A) causes the translating member 430 to move through the longitudinal threaded bore 422 away from the head 420. Conversely, turning the rotating member 418 about axis L in a direction opposite to the direction indicated by arrow W (FIG. 11A) causes the translating member 430 to move toward head 420. The translating member 430 is connected to the rotating member 418 and configured to translate upon rotation of the rotating member 418 to urge the distal portion 374 to rotate with respect to the proximal portion 127 about the first axis 373.

The translating member 430 includes a lower connection portion 436 pivotally connected to a location 375, such as an extension or base, of the distal portion 374. The location 375 includes an opening 438 configured and sized to receive the lower connection portion 436. A pivot member 440, such as a pivot pin, pivotally connects the lower connection portion 436 of the translating member 430 to the location 375 of the distal portion 374. The diameter or cross-sectional dimension of the opening 438 is larger than the diameter or cross-sectional dimension of the lower connection portion 436 so that the lower connection portion 436 can freely pivot within the opening 438. The rotation of the rotating member 418 about the second axis L biases the location 375 of the distal portion 374 away from the proximal portion 127. The location 375 is offset from the first axis 373.

The third retractor member holder or distal portion 374 is rotatably connected to the proximal portion 127 of the first arm 126 through a pivot member 442. Thus, the distal portion 374 is configured to rotate about the pivot member 442 relative to the proximal portion 127. The pivot member 442 can be a pivot pin. Regardless of its specific structure, the pivot member 442 extends through the distal portion 374 and the proximal portion 127 of the first arm 126 and allows the distal portion 374 to pivot relative to the proximal portion 127 of the first arm 126. When the distal portion 374 pivots with respect to the proximal portion 127 of the first arm 126, the location 375 also pivots relative to the extension 129 of the proximal portion 129.

Figure 11A:
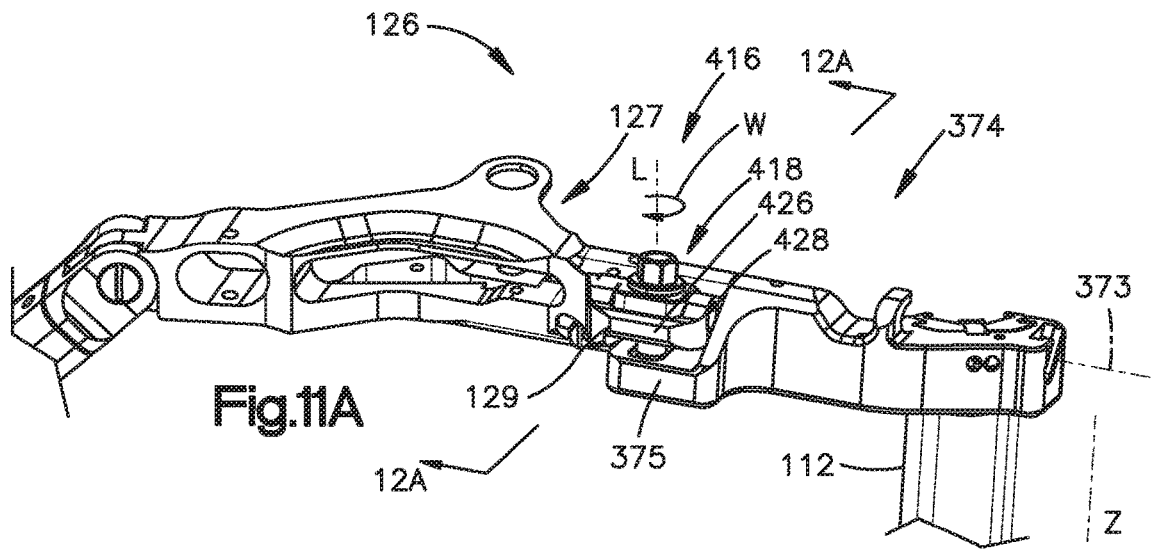
FIG. 11A is a perspective view of an arm of the surgical access retractor illustrated in FIG. 1, the arm having a proximal portion and a distal portion.
Figure 11B:
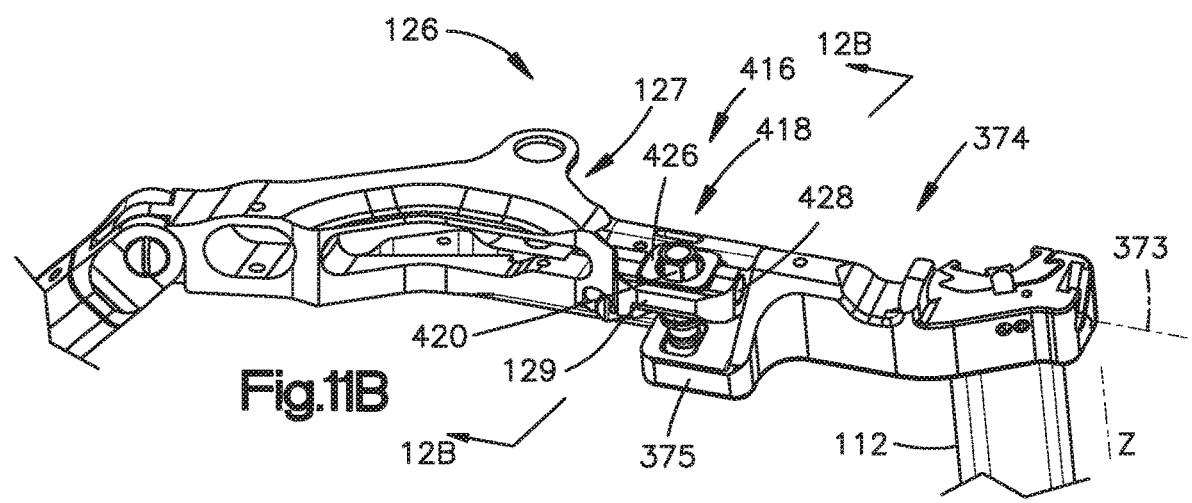
FIG. 11B is a perspective view of the arm shown in FIG. 11A. showing the distal portion of the arm angled in a first angled position.

The distal portion 374 can be pivoted from a first position relative to the proximal portion 127 to a second position relative to the proximal portion 127. In accordance with one embodiment, the first position can be a or straight position, such that the distal portion 374 is co-extensive with, or alternatively parallel to, the proximal portion 127 (FIGS. 11A and 12A), and the second position can be to a first angled position, whereby the distal portion 374 defines a non-zero angle with respect to the proximal portion 127 (FIGS. 11B and 12B). A torsional force applied to the by turning the rotating member 418 can cause the rotating member 418 to rotate about the second axis L along in the direction indicated by arrow W so as to pivot the distal portion 374 from the first position to the second position. Upon rotation of the rotating member 418 about axis L in the direction indicated by arrow W. (FIG. 11A), the translating member 430 moves through the threaded bore 422 away from the head 420. As the translating member 30 moves away from the head 420, the rotating sleeve 426 pivots within the opening 131 about pivot member 428. The rotating member 418 then pivots concomitantly with the rotating sleeve 426. While pivoting, the rotating member 418 exerts a force on the location 375 (via the translating member 430), causing the distal portion 374 to pivot about the pivot member 442.

Figure 6:
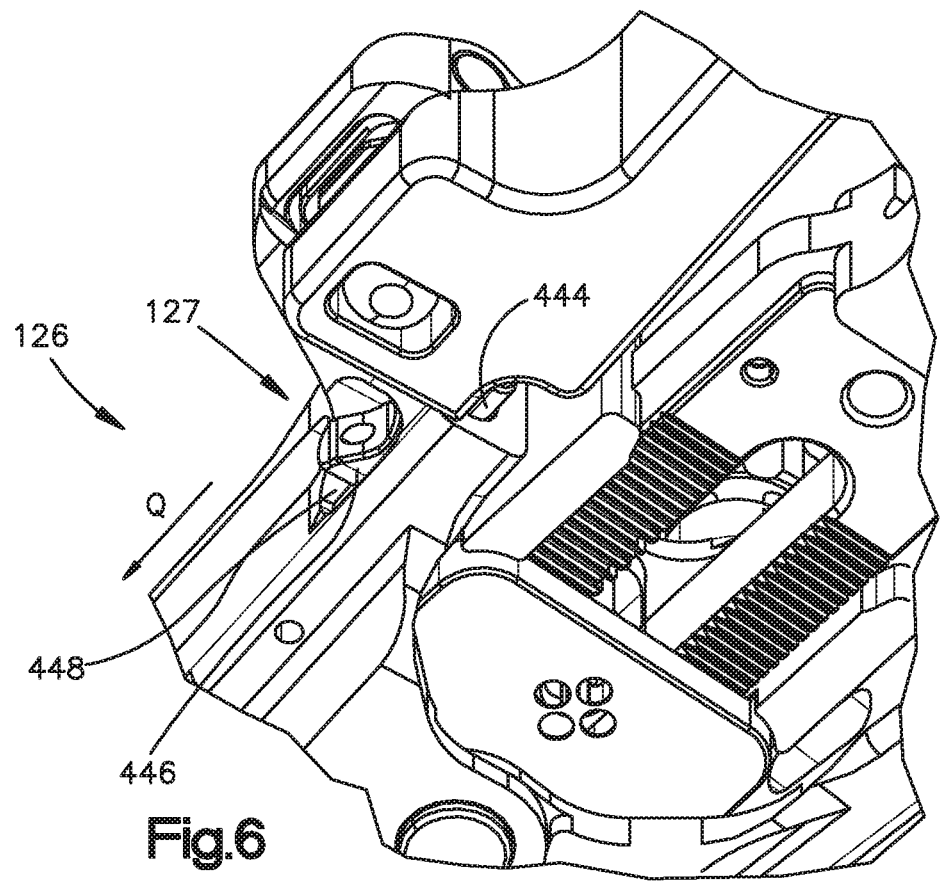
FIG. 6 is an enlarged perspective view of a portion of a holder assembly of the surgical access retractor illustrated in FIG. 1.
Figure 11C:
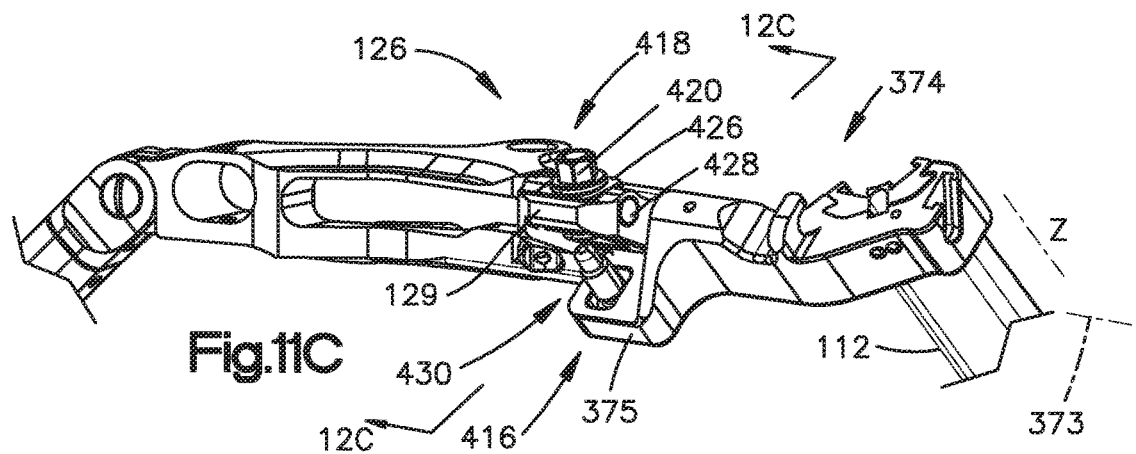
FIG. 11C is a perspective view of the arm shown in FIG. 11A in a second angled position.
Figure 11D:
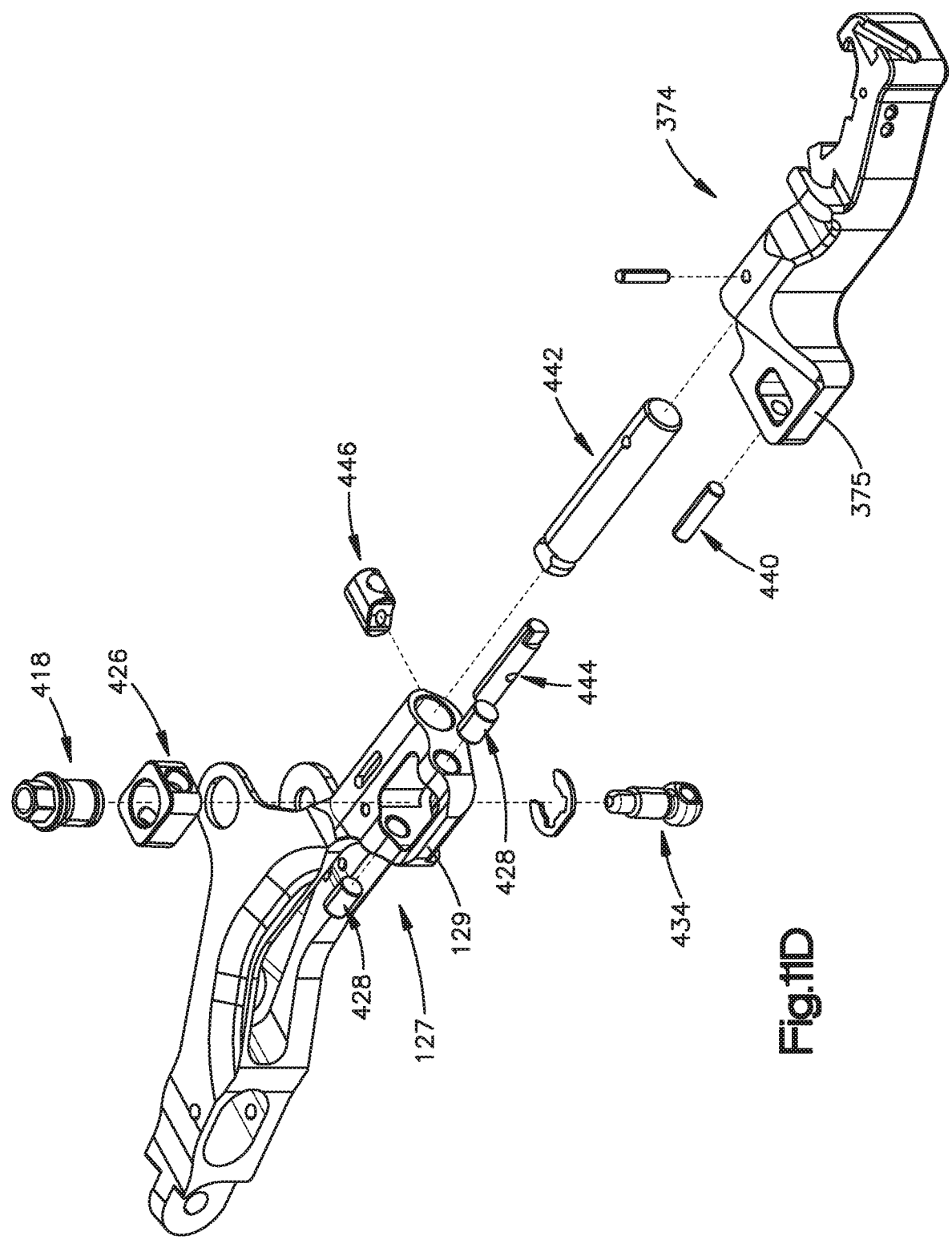
FIG. 11D is a perspective exploded view of the arm shown in FIG. 11A.

With specific reference to FIGS. 6, 11C and 12C, the angulation mechanism 416 includes a spring loaded mechanical stop 444 that prevents, or at least inhibits, the third retractor member holder 474 from being angled beyond the first angled position shown in FIGS. 11B and 12B. When the distal portion 374 reaches the first angled position (FIGS. 11B and 12B), the mechanical stop 444 abuts a portion of the distal portion 374, thereby preventing further angulation. The spring loaded mechanical stop 444 is operatively connected to a button 446 slidably disposed within a slot 448 of the proximal portion 127 of the first arm 126. A user can slide button 446 in a direction indicated by arrow Q to move the mechanical stop 444 also in the direction indicated by arrow Q. As this point, the mechanical stop 444 no longer blocks further angulation of the distal portion 374 relative to the proximal portion 127. Once the mechanical stop has been withdrawn, the rotating member 418 can be further turned about axis L in the direction indicated by arrow W (FIG. 11A) to move the translating member 430 out of the longitudinal threaded bore 422 of the rotating member 418. At this juncture, the distal portion 374 can be removed from the proximal portion 127 of the first arm 126 to prepare the surgical access retractor for another use. This preparation can entail cleansing the distal portion 374 or replacing the old distal portion 374 with a new one.

The first arm 126 comprises a proximal portion 127 and a distal portion 374. The distal portion 374 is configured to retain the first retractor member 112. The distal portion 374 is configured to rotate relative to the proximal portion 127 about a first axis 373. The second arm 122 is configured to retain the second retractor member 110, such that rotation of the distal portion 374 about the first axis 373 causes the first retractor member 112 to pivot toward or away from the second retractor member 110 when the first retractor member 112 and the second retractor member 110 are coupled to the first arm 126 and the second arm 122, respectively; and a rotating member 418 coupled between the proximal portion 127 and the distal portion 374. The rotating member 418 is configured to rotate about a second axis L, wherein rotation of the rotating member 418 about the second axis L causes the distal portion 374 to rotate relative to the proximal portion 127 about the first axis 373. The second arm 122 is configured to retain the second retractor member 110, such that rotation of the distal portion 374 about the first axis 373 causes the first retractor member 112 to pivot toward or away from the second retractor member 110 when the first retractor member 112 and the second retractor member 110 are coupled to the first arm 126 and the second arm 122, respectively. The rotating member 418 is coupled between the proximal portion 127 and the distal portion 374. The rotating member 418 is configured to rotate about a second axis L, wherein rotation of the rotating member 418 about the second axis L causes the distal portion 374 to rotate relative to the proximal portion 127 about the first axis 373.

The rotation of the rotating member 418 about the second axis 831 biases a location 375 of the distal portion away from the proximal portion 127. The location 375 is offset from the first axis (373, 821). The retractor further comprises 100 a pivot member 442 coupled between proximal portion 127 and the distal portion 374. The pivot member 442 defines the first axis 373. The rotation of the rotating member 418 about the second axis L biases the location 375 of the distal portion 374 away from pivot member 442. The retractor 100 can further include the translating member 430 connected to the rotating member 418 and configured to translate upon rotation of the rotating member 418) to urge the distal portion 374 to rotate with respect to the proximal portion 127 about the first axis 373. The rotating member 418 defines the threaded bore 422. The threaded bore 422 is sized and configured to receive at least a portion of the translating member 430. The translating member 430 comprises the threaded shaft 434 sized to be positioned within the threaded bore 422. The threaded shaft 434 is configured to move along threaded bore 422 upon rotation of the rotating member 418 to urge the distal portion 374 to rotate in relation to the proximal portion 127.

The retractor 100 can further comprise the rotating sleeve 426 surrounding at least a portion of the rotating member 418. The rotating sleeve (426) rotatably connects the rotating member 418 to the proximal portion 127 and is configured to rotate the rotating member 418 relative to the proximal portion 127 when the threaded shaft 434 moves along the threaded bore 422. The retractor 100 can further comprise the extension 129 protruding out from the proximal portion 127. The extension 129 defines the opening 131 sized configured to receive the rotating member 418 and the rotating sleeve 426. The retractor 100 can further include a central body 218 connected to the first arm 126 and the second arm 122. The retractor 100 can further include the third arm 316, which is configured to retain a third retraction member 108. The third arm 316 is movably connected to the central body 218. The third arm 316 is configured to move longitudinally with respect to the central body 218. The retractor 100 can further include the rack and pinion mechanism 272, which includes the pinion 175 connected to the central body 218 and the rack 343 connected to the third arm 316. The rack and pinion mechanism 272 is configured to move the third arm 316 relative to the central body 218 upon rotation of the pinion 175. The retractor 100 can further include the third retractor member 108 attached to the third arm 316. The third retractor member 108 is configured to move between a distal position and a proximal position upon rotation of the pinion 175 to unilaterally retract tissue.

The first arm 126 comprises the first distal end 136, and the second arm 122 comprising the second distal end 134. The first arm 126 and the second arm 122 are pivotally connected to the central body 218 so that the first distal end 136 of the first arm 126 and the second distal end 134 of the second arm 122 are configured to move simultaneously toward or away from each other between a first position and a second position. The first distal end 136 of the first arm 126 and the second distal end 134 of the second arm 122 are farther apart from each other in the second position than in the first position. The retractor 100 can further include a pivot member 150 pivotally connecting the first arm 126 and the second arm 122 to the central body 218 so that the first arm 126 and the second arm 122 are configured to pivot about the pivot member 150 between the first position and the second position. The retractor 100 can further include the first handle portion 116 connected to the proximal end 132 of the first arm 126 and a second handle portion 114 connected to a proximal end 130 of the second arm 122. Squeezing the first handle portion 116 and the second handle portion 114 together causes the distal end 134 and the second distal end 134 to move away from each other. The retractor 100 can further include the first retractor member 112 attached to the first distal end 136. The retractor 100 can further include the second retractor member 110 attached to the second distal end 134. Squeezing the first handle portion 116 and the second handle portion 114 together causes the first retractor member 112 and the second retractor member 110 to move away from each other to bilaterally retract tissue. The first handle portion 116 is pivotally connected to the first arm 126. The second handle portion 114 is pivotally connected to the second arm 122. The retractor 100 can further include the connection bar 180 and the knob 212. The connecting bar 180 has the threaded portion 200. The knob 212 has the threaded bore 214, which is configured to threadedly receive threaded portion 200. The rotation of the knob 212 about the threaded portion 200 of the connection bar 180 causes the knob 212 to translate along the connection bar 180. The knob 212 is configured to move along the connection bar 180 toward or away from the first arm 126, so that the knob 212 is configured to secure the position of the first arm 126 with respect to the second arm 122 when the knob 212 contacts the first arm 126.

With reference to FIGS. 13-19, at least one of the retractor members 106 can include a disc anchor 450. In the illustrated embodiment, the disc anchor 450 is a shim and can move along an inner surface of a retractor member 106 between a first or retracted position (FIG. 14) and a second or extended position (FIG. 13). The disc anchor 450 can be permanently or removably attached to any of the illustrated retractor members 106, namely retractor members 108, 110 or 112 (FIG. 4). In the retracted position, the disc anchor 450 does not extend past the distal end of the retractor member 106. In the extended position, the disc anchor 450 extends past the distal end of the retractor member 106 to penetrate an intervertebral disc between two vertebrae V. When the disc anchor 450 penetrates the intervertebral disc, it fixes the retractor member 106 to that intervertebral disc in order to help maintain the position of the surgical access retractor 100 in relation to the patient.

In the depicted embodiment, the disc anchor 450 is movably mounted on an inner surface 417 off the first or posterior retractor member 108 adjacent its distal end 415. The disc anchor 450 can be permanently attached to the third retractor member 108 (or any other blade) or removably attached to the third retractor member 108 (or any other blade). The third retractor member 108 defines a longitudinal axis G along its length and includes a central groove 452 extending along the length of the retractor member 108. The central groove 452 is in communication with a channel 454 on the inner surface 417. An array of indentations 456 is disposed along the channel 454. Each indentation 456 is formed by a proximal wall 458, a bottom wall 460, and a distal wall 462. In all the slots 456, except for the distal-most slot 464, the proximal wall 458 is oriented substantially perpendicular relative to the longitudinal axis G, the bottom wall 460 is substantially parallel to the longitudinal axis G, and the distal wall 162 is tapered and therefore defines an acute angled relative to the longitudinal axis G. The distal-most indentation 464 is formed by a proximal wall 466, a bottom wall 468, and a distal wall 470. The proximal wall 466 and the distal wall 470 are each oriented substantially perpendicular to the longitudinal axis G. The bottom wall 468 is oriented substantially parallel to the longitudinal axis G.

The disc anchor 450 includes has a substantially planar configuration and is sized and configured to fit within the channel 456. Thus, the disc anchor 450 is flushed with the inner surface 417 of the retractor member 108, thereby allowing the retractor member 108 to retract more tissue because no portion of the disc anchor 450 occupies the opening space formed within the blades 108, 110, and 112. The disc anchor 450 includes a main body 472 and a tapered distal end 474 extending from the main body 472. The tapered distal end 474 is adapted to penetrate an intervertebral disc. The disc anchor 450 further includes a retaining member 476, such as a retaining pin or deformed tab, protruding from a proximal portion 478. The retaining member 476 is configured and sized to slide along the channel 454 to guide the disc anchor 450 along the retractor member 108.

The disc anchor 450 further includes a biasing member 480 configured for engaging the indentations 456 and 464. In the depicted embodiment, the biasing member 480 is a leaf spring formed as a cutout of the disc anchor 450. However, the disc anchor 480 can include other types of biasing members. The biasing member 480 includes a sixth engagement member 482 illustrated in the figures as protrusion extending from an end of the biasing member 480. The sixth engagement member 482 is sized and configured to fit within the indentations 456 and 464 and allows incremental distal movement of the disc anchor 450. The disc anchor 450 can be urged distally in the direction indicated by arrow H (FIG. 15A). When advanced distally, the biasing member 480 biases the engagement member 480 toward the indentations. Thus, the disc anchor 450 can be advanced distally until the sixth engagement member 482 reaches an indentation 456. At this point, the indentation 456 acts as stop and interrupts the distal advancement of the disc anchor 450. However, the disc anchor 450 can be further advanced distally because the distal walls 462 of the indentations 456 have a tapered. Nonetheless, the disc anchor 450 cannot be easily advanced proximally in the direction indicated by arrow I (FIG. 15A) because the proximal wall 458, which is oriented substantially perpendicular to the longitudinal axis G, acts as a mechanical stop, preventing, at least inhibiting, proximal movement of the disc anchor. 450. When the sixth engagement member 482 of the disc anchor 450 reaches the distal-most indentation 464, the disc anchor 450 cannot easily move distally or proximally because the proximal and distal walls 466 and 470 are oriented substantially perpendicular to the longitudinal axis G and act as a mechanical stop. At this point, the disc anchor 450 has reached its extended position.

The disc anchor 450 is connected to at least one of the first retractor member 112, the second retractor member 110 or the third retractor member 108. The disc anchor 450 can be permanently or removably attached to the third retractor member 108. The disc anchor 450 is configured to move along the third retractor member 108 between a retracted position and an extended position. The disc anchor 450 includes the sixth engagement member 482. The sixth engagement member 482 is configured to be received by each of a plurality of indentations 456 arranged along the inner surface 417 of the third retractor member 108 to allow incremental advancement of the disc anchor 450 along the third retractor member 108. The third retractor member 108 defines the distal-most indentation 464, which is configured to engage the sixth engagement member 482 to prevent further distal advancement of the disc anchor 450 along the third retractor 108 when the sixth engagement member 482 is positioned within the distal-most indentation 464. The disc anchor 450 further comprises the retaining member 476 configured to slide along the channel 454 defined along on the inner surface 417 of the third retractor member 108. The channel 454 is defined by a proximal wall 454a and a distal wall 454b of the third retractor member 108. The disc anchor 450 is configured to move to a cleaning position in which the retaining member 476 abuts the distal wall 454b, thereby facilitating cleaning of the disc anchor 450 and the third retractor member 108. In the cleaning position, the gap between the disc anchor 450 and the third retractor member 108 is minimized. A tool 484 is configured to move the disc anchor 450 along the third retractor member 108. The tool 484 includes the rotatable head 488, which is configured to disengage the sixth engagement member 482 from a selective one of the plurality of indentations 456 to allow the disc anchor 450 to move proximally along the third retractor member 108 to the retracted position.

FIG. 16 illustrate a tool 484 for moving the disc anchor proximally and distally along the retractor member 108. The tool 484 includes an elongated member 486 and a rotatable head 488. The rotatable head 488 is configured as an eccentric wedge-shaped wheel and can fit within a slot 490 of the disc anchor 450 formed the engagement member 485 and the biasing member 480. To move the disc anchor distally from the retracted position (FIG. 16) to the extended position (FIG. 17), the rotatable head 488 is inserted in slot 490 and the tool 484 is advanced distally in the direction indicated by arrow H. The tool 484 can also be used to move the disc anchor 450 proximally in the direction indicated by arrow I from an extended position (FIG. 19) to a retracted position (FIG. 20). To do so, the rotatable head 488 is inserted in the slot 490 and, then, the head 488 is rotated until it lifts the engagement member 482 out of indention 464 (or any other indentation). Subsequently, the tool 484 is advanced proximally in the direction indicated by arrow I to urge the disc anchor 450 from the extended position (FIG. 19) to the retracted position (FIG. 20).

The tool 484 can be used to move the disc anchor 450 further distally (as described above) to a cleaning position. (FIG. 15B) The channel 454 is defined by a proximal wall 454a and a distal wall 454b of the third retractor member 108 and is configured to move to a cleaning position (FIG. 15B) in which the retaining member 476 abuts the distal wall 454b, thereby facilitating cleaning of the disc anchor 450 and the third retractor member 108.

Figure 22:
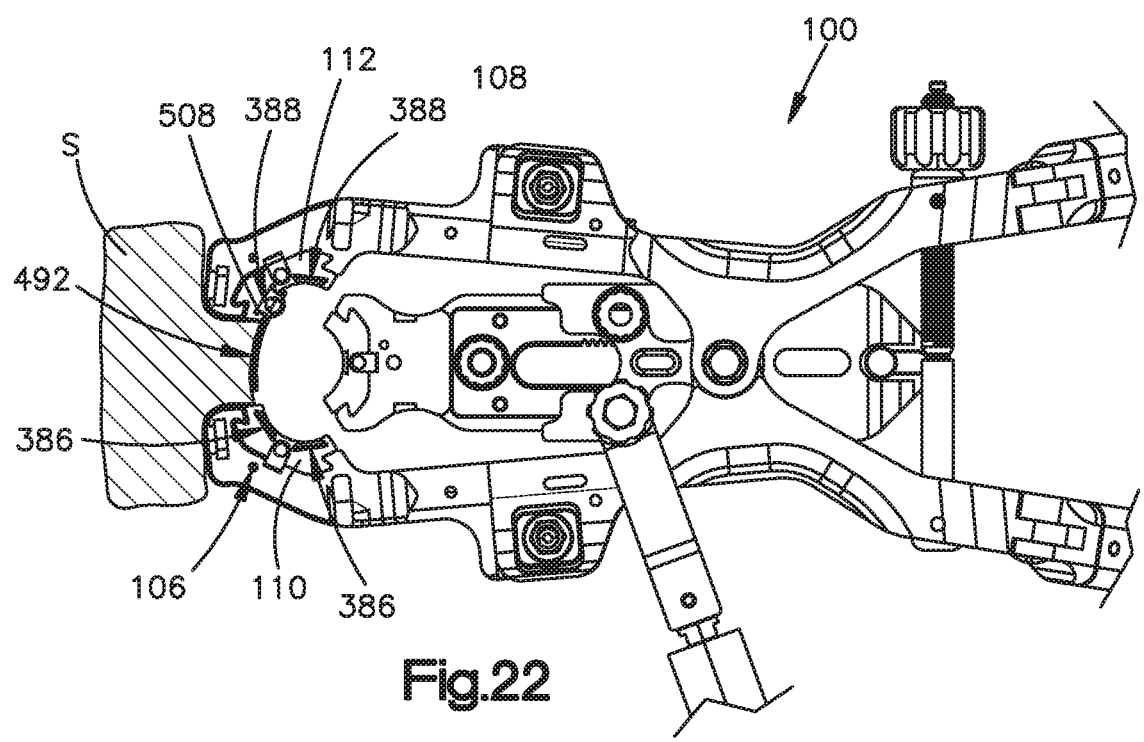
FIG. 22 is a top view of the surgical access retractor illustrated in FIG. 1 engaging soft tissue with the lateral retractor member shown in FIG. 20.

With reference to FIGS. 20-22, the surgical access retractor 100 can further include a lateral retractor member 492 configured to prevent, or at least inhibit, soft tissue S from entering the passageway 410 formed within the retractor members 106 when the retractor members 106 are in the open position. As shown in FIG. 21, the soft tissue S may enter the passageway 410 formed within the retractor members 108, 110, and 112 when the retractor members are in the open position. The lateral retractor member 492 can be attached to one of the retractor members 108, 110, or 112 to block soft tissue from entering the passageway 410 when the retractor members 108, 110, and 112 are in the open position, as shown in FIG. 22.

In the illustrated embodiment, the lateral retractor member or winglet 492 includes a curved or flat body 494 adapted to displace soft tissue. The body 494 has a proximal end 496 and a distal end. In addition, the body 494 includes a connection assembly 500 at its proximal end 496. In the depicted embodiment, the connection assembly 500 includes a threaded bore 502 adapted to mate with a threaded portion of an insertion tool (not shown) and a biasing member 504 adjacent the threaded bore 502. The biasing member 504 is adapted to bias an engagement member 506 toward an inner portion of the body 494. In the depicted embodiment, the engagement member 506 is cantilevered from the body 494. The engagement member 506 can be a protrusion and is configured to engage a slot of the blade to maintain the lateral retractor member 492 attached to the blade. The lateral retractor member 492 further includes a guiding member 508, such as a guiding protrusion, extending from an outer wall of the body 494. The guiding member 508 is shaped, sized, and adapted to be inserted through one of the slots 386 or 386 of the retractor member 110 or 112, respectively, such that the lateral retractor member 492 can be slid along the retractor member 110 or 112. Once the lateral retractor member 492 is inserted in one of the slots 386 or 386, the lateral retractor member 492 can block, or at least inhibit, soft tissue from entering the passageway 410 when the retractor members 110 and 112 are in the open position, as shown in FIG. 22.

Figure 23:
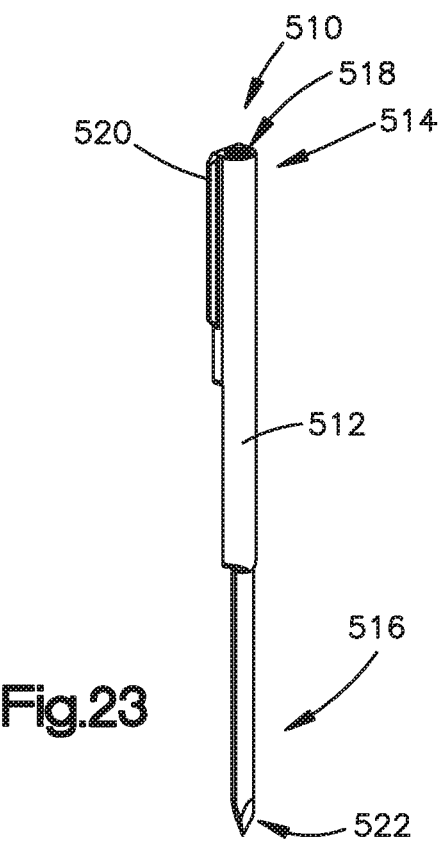
FIG. 23 is a perspective view of a bone anchor adapted to be connected to the surgical access retractor illustrated in FIG. 1.
Figure 24:
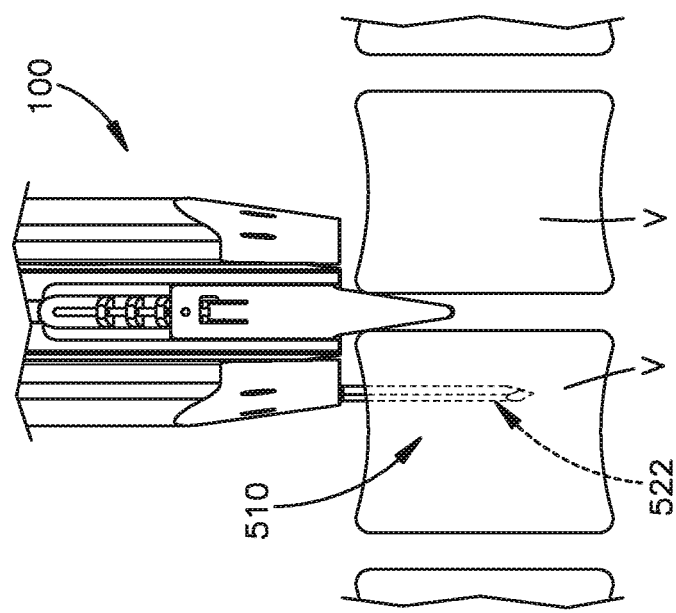
FIG. 24 is a front view of a distal portion of the surgical access retractor illustrated in FIG. 1 with the bone anchor shown in FIG. 23 inserted through a vertebral body.

With reference to FIGS. 23 and 24, a bone anchor 510 can be connected to the surgical access retractor 100 and serves to fix the surgical access retractor 100 to a vertebral body V. The bone anchor 510 can be a pin (as shown in FIG. 23) and includes a body 512 having a proximal end 514 and a distal end 516. The body 512 can have a cylindrical shape and includes a threaded bore 518 at its proximal end 514. The threaded bore 518 is adapted to mate with a threaded portion of an insertion tool (not shown). The body 512 further includes a guiding member 520 sized, shaped, and adapted to be inserted through one of the slots 386, 388, 394 or 396 (see FIG. 7) of blades 110 or 112. In the depicted embodiment, the guiding member 520 is a guiding protrusion extending outwardly from an outer surface of the body 512. The guiding member 520 allows a user to slide the bone anchor 510 along the retractor member 110 or 112. The bone anchor 510 further includes a sharp distal tip 522 adapted to penetrate a bone, such as a vertebral body V. During use, the bone anchor 520 is moved distally along the retractor member 110 or 112 until the sharp distal tip 522 penetrates a vertebral body V. As a result, the surgical access retractor 100 is fixed to a vertebral body V.

Figure 25:
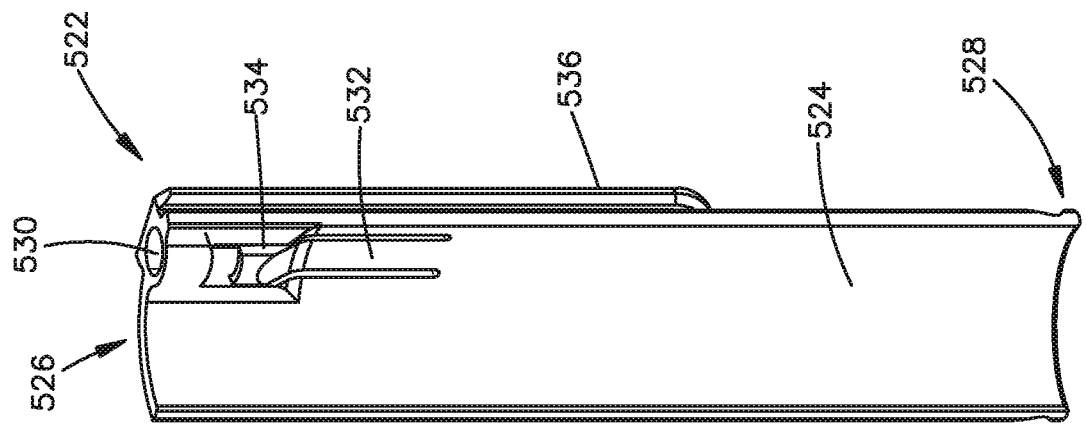
FIG. 25 is a perspective view of a retractor member extension adapted to be connected to a retractor member of the surgical access retractor illustrated in FIG. 1.

With reference to FIGS. 25-27, a retractor member extension 523 can be attached to a retractor member 106, such as retractor member 110 or 112, to extend the length of the retractor member 106. In operation, the retractor member extension 523 can prevent, or at least inhibit, soft tissue S from being positioned underneath the retractor members 110 and 112 if a blade with an inappropriate length was selected. As seen in FIG. 26, a soft tissue can slide underneath the retractor members 110 and 112 if the blade with the wrong length is chosen. A user, however, can remove the soft tissue underneath the retractor members 110 and 112 and attach the retractor member extension 523 to the retractor members 110 and 112 to prevent the soft tissue from creeping underneath the blades, as shown in FIG. 27. In the depicted embodiment, the retractor member extension 523 includes a curved body 524, which curvature can match the curvature of the retractor member 110 or 112. The body 524 has a proximal end 526 and a distal end 528. A threaded bore 530 is disposed at the proximal end 526 of the body 524 and is adapted to mate with an outer thread portion of an insertion tool (not shown). The body 524 further includes a biasing member 532 adjacent the threaded bore 530. The biasing member 532 can be a leaf spring and is adapted to bias an engagement member 534 toward an inner portion of the body 524. The engagement member 534 can be a protrusion and is configured to engage a slot of the insertion tool (not shown) to maintain the retractor member extension 523 attached to the insertion tool. The retractor member extension 523 further includes a guiding member 536, such as a guiding protrusion, extending from an outer wall of the body 524. The guiding member 536 is shaped, sized, and adapted to be inserted through one of the slots 386 or 386 of the retractor members 110 or 112, respectively, such that the retractor member extension 523 can be slid along the retractor member 110 or 112. Before using sliding the retractor member extension 523 along retractor member 110 or 112, the soft tissue S underneath the distal end of the retractor members 110 and 112 should be removed. A number of tools can be used to remove such soft tissue.

With reference to FIG. 28, a tissue removal tool or scoop 538 can be used to remove soft tissue from underneath a retractor member 110 or 112 (FIG. 4) before advancing the retractor member extension 523 (FIG. 25) in a distal direction as described above. The tissue removal tool or scoop 538 includes a handle 540 at its proximal end 542, a tissue removal member 544 at its distal end 544, and an elongated member 548, such as a rod, between the handle 540 and the tissue removal member 544. The tissue removal member 544 includes a substantially flat plate 550. The plate 550 has a curved configuration such that it forms an open space 552 having substantially the same shape as a retractor member 108, 110, or 112. Accordingly, each of the retractor member 108, 110 and 112 is shaped and sized to fit within the open space 552 formed by the plate 550 of the tissue removal tool 538.

With reference to FIGS. 29-31, the tissue removal tool 538 can remove the tissue from underneath a retractor member 108, 110 or 112. As seen in FIG. 29, soft tissue can creep underneath the blade (110 or 112). To remove this soft tissue, the tissue removal tool 538 is inserted through the passageway 410 formed between blades 110 and 112 as seen in FIG. 30. During this insertion, the entire tissue removal member 546 is positioned within the passageway 410. Once the tissue removal member 546 has reach the target site (i.e., next to the soft tissue underneath the retractor member 110 or 112), the tissue removal tool 538 is rotated to turn the tissue removal member 546. As the tissue removal member 546 turns underneath the blade (110 or 112), it displaces the soft tissue located underneath that blade as seen in FIG. 31. The tissue removal tool 546 is rotated until the tissue removal member 546 surrounds an outside surface of the retractor member 110 or 112 as seen in FIG. 32. The retractor member extension 523 (FIG. 25) can then be advanced distally to prevent, or at least inhibit soft tissue, from being positioned underneath a retractor member 110 or 112 as discussed in detail above.

With reference to FIGS. 33 and 35, the tissue removal tool 538 can be removed from the surgical site after advancing the retraction member extension 523 (FIG. 25) distally. After displacing soft tissue using the tissue removal tool 538, the tissue removal member 546 is positioned around an outer surface of the retractor member 110 or 112 (that is, outside the passageway 410 formed between the blades 110 and 112) as seen in FIG. 33. To safely remove the tissue removal tool 538, the tissue removal member 546 should be placed at least partially within the passageway 410. To do so, the tissue removal member 538 is turned in the direction indicated by arrow T1, so that the tissue removal member 546 slides away from the retractor member 110 or 112 along the outer surface of that blade as seen in FIG. 34. As the tissue removal tool 538 is further rotated in the direction indicated by arrow T1, the tissue removal member 546 is substantially positioned within the passageway 410 as shown in FIG. 35. The user can then safely remove the tissue removal tool 538 from the surgical site through the passageway 410.

Figure 36:
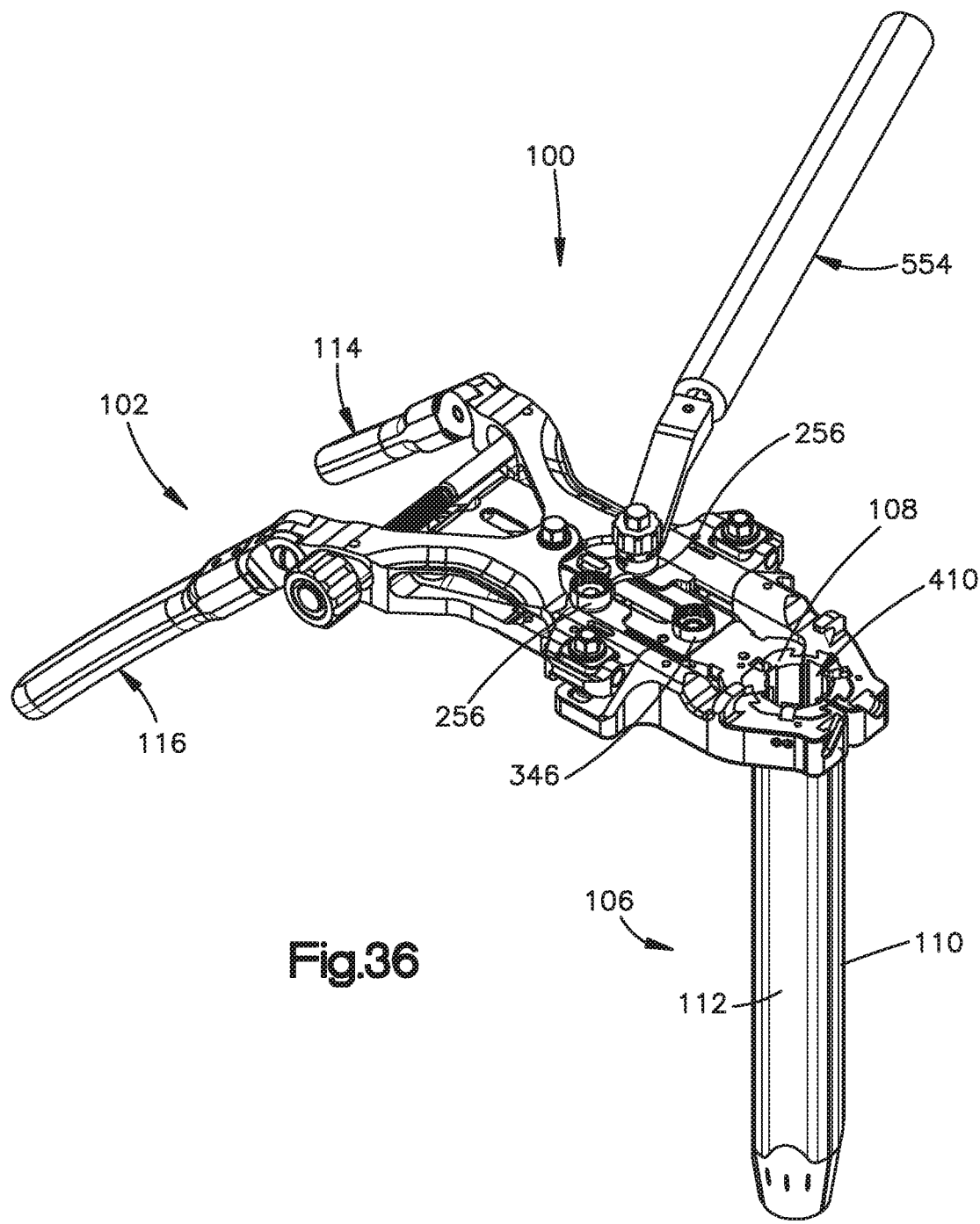
FIGS. 36-39 are perspective views illustrating steps of an exemplary method for retracting soft tissue using the surgical access retractor illustrated in FIG. 1.

FIGS. 36-39 illustrate an exemplary method for accessing a surgical target site using the surgical access retractor 100. The clinician can employ the surgical access retractor 100 to access, for example, the cervical, thoracic, or lumbar regions of the spinal column C (FIG. 1) using any suitable approach. Suitable approaches include, but are not limited to, anterior, posterior, posterior oblique, anterior oblique, and lateral approaches. The retractor members 106 of the surgical access retractor 100 should be inserted into a patient's body while the retractor members 106 are in the closed or approximated position as shown in FIG. 36. The user can use any suitable approach to insert the retractor members 106 into a patient's body. In an exemplary process, a Kirschner wire is introduced through a patient's skin and is advanced until it reaches the desired surgical target site (e.g., an intervertebral disc). Then, one or more tissue dilators are placed over the Kirschner wire. The dilators are subsequently advanced toward to the surgical target site in order to displace soft tissue. The retractor members 106 are then placed over the dilators and advanced toward the surgical target site. The retractor members 106 should be in the closed approximated position (FIG. 36) when placed over the dilators. At this point, the dilators are positioned within the passageway 410 formed within the retractors 106. The dilators are then withdrawn from the patient through the passageway 410. A table fixation tool 554 can be attached to the surgical access retractor 100 via the connection members 256 or 346 (as described in detail above) in order to fix the surgical access retractor 100 to an operating table. The table fixation tool 554 can be pre-attached to the operating table.

Figure 37:
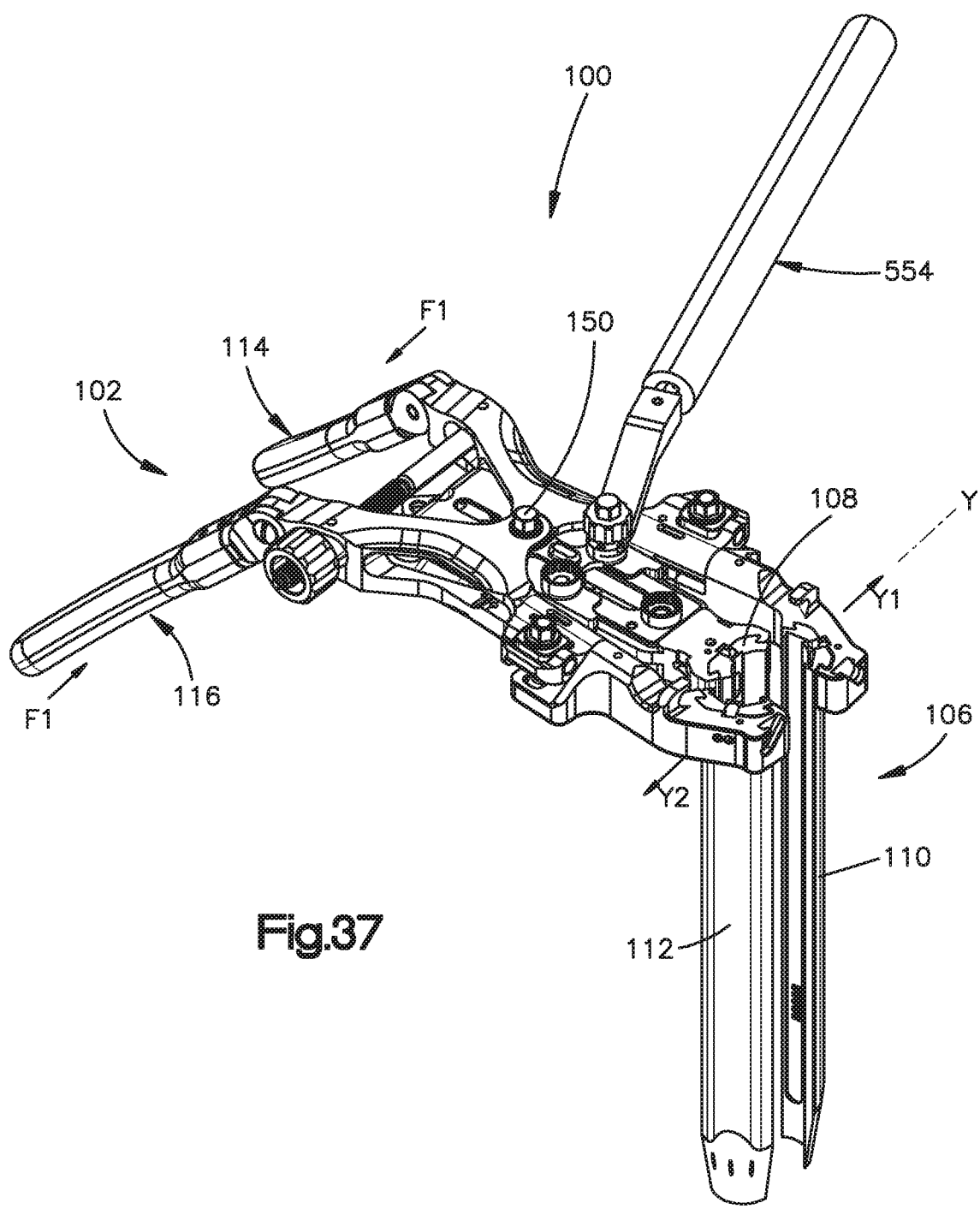

As seen in FIG. 37, the handle 102 is then actuated to move at least two retractor members 106 away from each other along the longitudinal axis Y. Specifically, a squeezing force F1 can be applied to handle portions 116 and 114 to simultaneously move retractor member 110 in the direction indicated by arrow Y1 and retractor member 112 in the direction indicated by arrow Y2, such that the retractor members 110 and 112 move relative to each other from a first or closed position (FIG. 36) to a second or open position (FIG. 37). This movement of the retractor members 110 and 112 causes bilateral retraction of the soft tissue.

Figure 38:
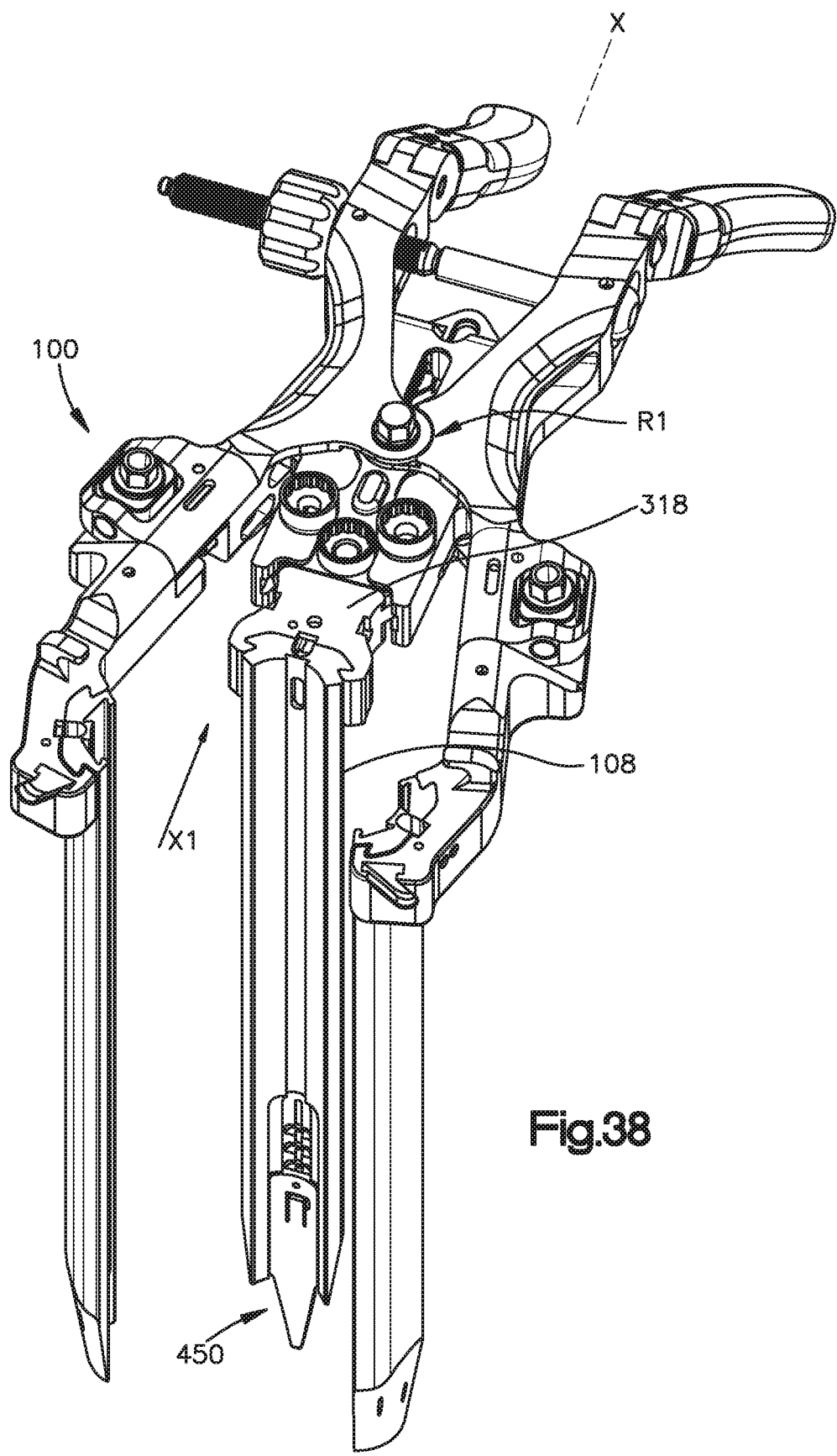
Figure 39:
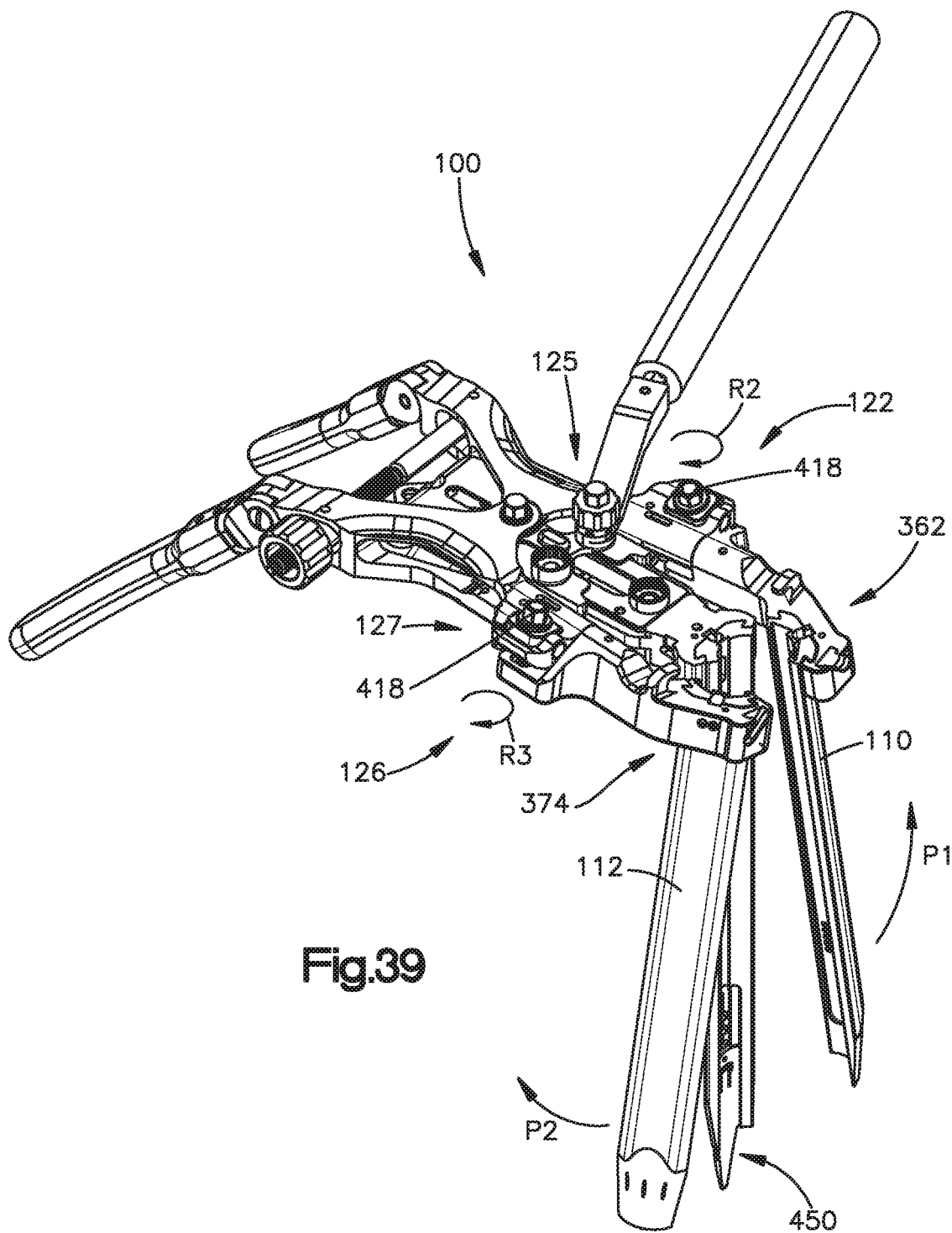

The first or posterior retractor member 108 can be moved from a first or distal position (FIG. 37) to a second or proximal position (FIG. 38) to unilaterally retract tissue. To do so, the user can rotate pivot member 150 in the direction indicated by arrow R1. Upon rotation of pivot member 150, the third distal portion 318 moves along the longitudinal axis X in the direction indicate by arrow X1 (i.e., proximal direction), thereby moving the retractor member 108 from the distal position (FIG. 37) to the proximal position (FIG. 38).

The surgical access retractor 100 can also angularly retract soft tissue at the surgical target site. To do so, the user turns the rotating member 418 of the second arm 122 in the direction indicated by arrow R2. This rotation of rotating member 418 causes the distal portion 362, such a retractor member holder, to pivot relative to the proximal portion 125 of the second arm 122. Consequently, retractor member or retractor member 110 moves in the direction indicated by arrow P1 to angularly retract tissue at the surgical target site. Similarly, turning the rotating member 418 of the first arm 126 in the direction indicated by arrow R3 causes the distal portion 374 to pivot relative to the proximal portion 127 of the first arm 126. Consequently, the retractor member 112 moves in the direction indicated by arrow P2 to angularly retract tissue at the surgical target site. Hence, the second arm 122 is configured to retain a second retractor member 110, such that rotation of the distal portion 374 about the first axis 373 causes the first retractor member 112 to pivot toward or away from the second retractor member 110 when the first retractor member 112 and the second retractor member 110 are coupled to the first arm 126 and the second arm 122, respectively.

Figure 40:
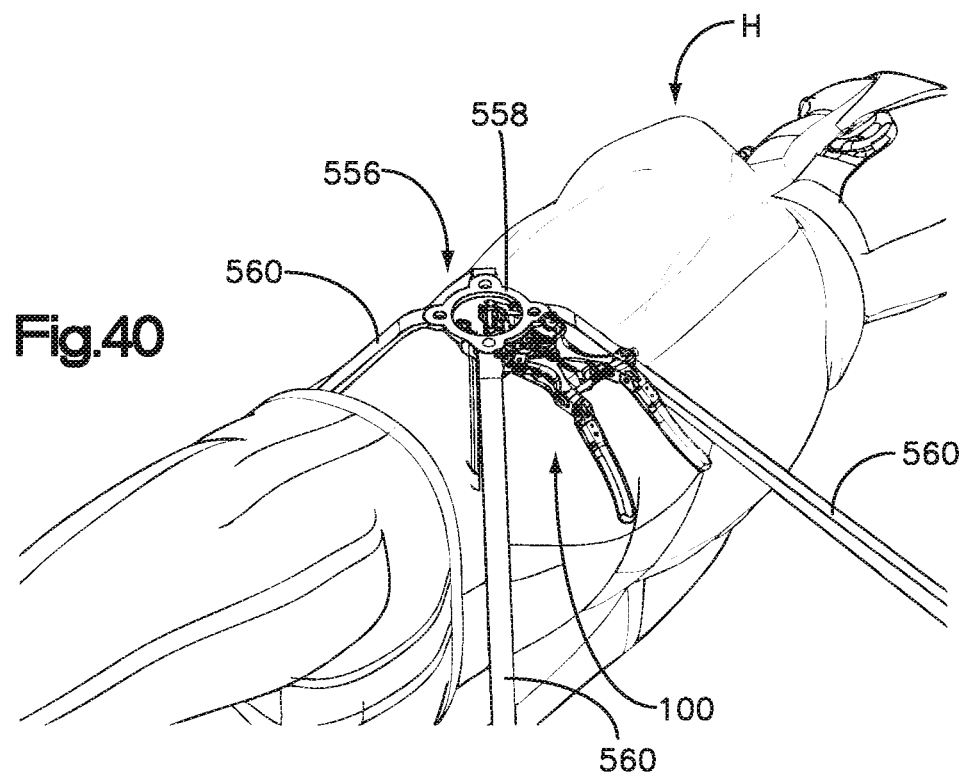
FIG. 40 is a perspective view of a holding system holding the surgical access retractor 100 illustrated in FIG. 1 above a patient lying down on an operating table.

With reference to FIG. 40, a holding system 556 is configured to compress the surgical access retractor 100 downwardly toward the body H of a patient in order to fix the position of the surgical access retractor 100 in relation to the surgical target site. The holding system 556 includes a center portion 558 and a plurality of belt or straps 560 extending radially from the center portion 558. The straps 560 are configured to be attached to an operating table (not shown) using any suitable means. For example, a knot can be formed at the end of the strap 560 to attach that end of the strap 560 to a rail of an operating table (not shown). In the exemplary embodiment, the holding system 556 includes four straps 560 equidistantly disposed relative to one another. However, the holding system 556 can have, for example, three straps 560 equidistantly disposed relative to one another. All the straps 560 are attached to the center portion 558. The center portion 558 can have a ring-like shape and is adapted to be placed over the surgical access retractor 100 or can be a connection feature on the retractor 11 to allow for attachment of the straps 560. When the center portion 558 is placed over the surgical access retractor 100 and the straps 560 are tightly attached to the operating table, the center portion 558 presses the surgical access retractor 100 downwardly toward the body H of the patient to fix the position of the surgical access retractor 100 in relation to the patient.

Figure 41:
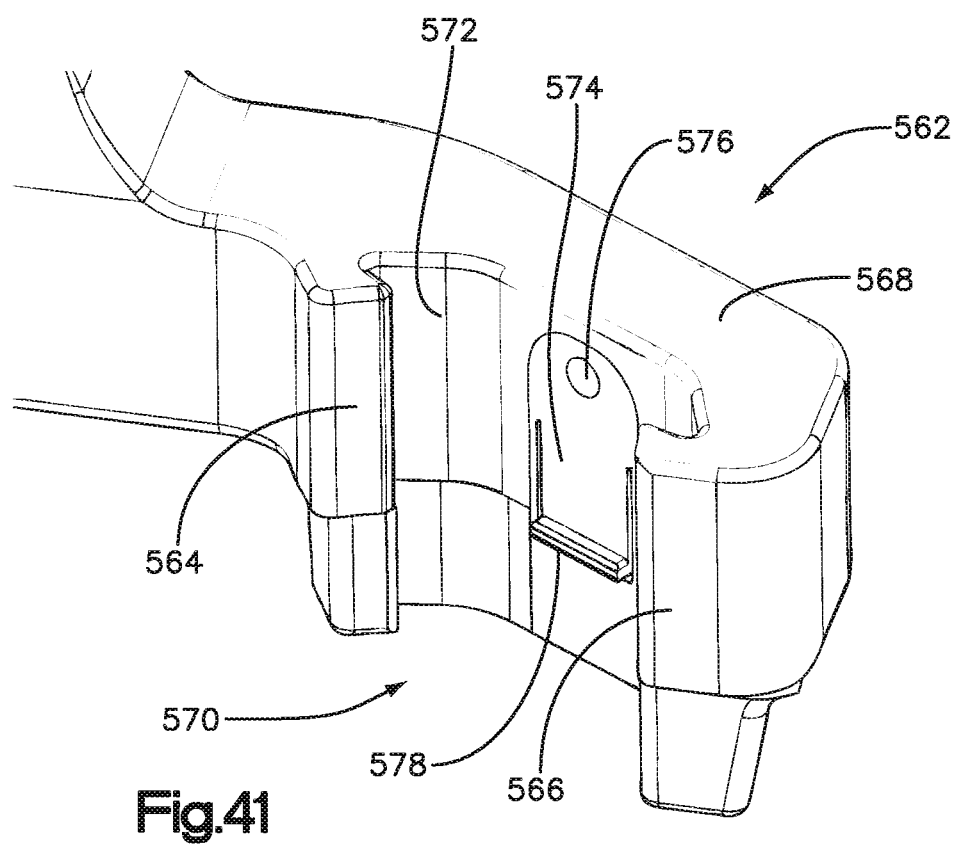
FIG. 41 is a perspective view of alternate retractor member holder for the surgical access retractor illustrated in FIG. 1 which allows for telescoping of the retractor members.

With reference to FIG. 41, an alternate retractor member holder 562 is configured to hold and support a retractor member 106 (FIG. 4), such as blades 110 or 112. The retractor member holder 562 includes a main body 568 and first and second hooks 564 and 566 extending from the main body 568. The first and second hooks 564 and 566 are spaced apart from each other and define a pocket or space 570 between them. The pocket 570 is at least partially formed by an inner surface 572 of the main body 568. The retractor member holder 562 further includes a biasing member 574 mounted on the inner surface 572 of the main body 568. In the illustrated embodiment, the biasing member 574 is a leaf spring formed by a cutout. However, the biasing member 574 can have any other suitable structure. An engagement member 578 is located at an end of the biasing member 574. In the depicted embodiment, the engagement member 578 is a protrusion extending toward the pocket 570 and away from the inner surface 572. The biasing member 574 biases the engagement member 578 away from the inner surface 572. In use, the engagement member 578 is adapted to engage a recess or indentation of a retractor member 160, such as a blade, in order to connect the retractor member 106 to the retractor member holder 562. A retaining member 576, such as a retaining pin, connects the biasing member to the main body 568 of the retractor member holder 562.

With reference to FIGS. 42-45, retractor member holder 562 can be used with an insertion tool 580. The insertion tool 580 is adapted to attach telescoping blade 113 to the retractor member holder 562. The telescoping blade 113 includes a plurality of indentations 115 each shaped and configured to receive the engagement member 578. The indentations 115 are arranged along an outer surface 117 of the telescoping blade 113 and allow the blade 113 to be attached to the retractor member holder 562 at different positions along its length. Accordingly, the blade 113 can be attached to the retractor member holder 562 at different attachment positions along the length of the blade 113.

The insertion tool 580 is adapted to insert the blade 113 into the pocket 570 of the retractor blade member 562 and move the blade 113 from one attachment position to another attachment position. In the illustrated embodiment, the insertion tool 580 includes a handle 582 at its proximal end 584 and elongated member 586 configured and dimensioned to be receive within a longitudinal opening 119 of the blade 113. The longitudinal opening 119 has an enlarged portion 121 having a larger diameter or cross-sectional dimension that the rest of the opening 119. The enlarged portion 121 of the opening 119 is at least partially formed by a proximal shoulder 123 and a distal shoulder 133 as seen in FIG. 43.

The elongated member 586 includes an engagement portion 588 adapted to engage the engagement member 578 to remove it from an indentation 115. The engagement portion 578 has a diameter or cross-sectional dimension D14 in a first transverse direction (FIG. 42) and a larger diameter or cross-sectional dimension D15 in a second transverse direction (FIG. 43). The cross-sectional dimension D15 is larger than the cross-sectional dimension D15. Thus, the engagement portion 588 of elongated member 586 is adapted to urge the engagement member 578 out of an indentation 115 when the insertion tool 580 is turned from a first position (FIG. 42) to a second position (FIG. 43).

In order to attach the blade 113 to the retractor member holder 562, the elongated member 586 of the insertion tool 580 is inserted into the longitudinal opening 119. Then, the insertion tool 580 is advanced toward the blade 113 such that at least one indentation 115 is positioned adjacent the engagement member 578. The insertion tool 580 is then rotated until the engagement member 578 is positioned within one of the indentations 115.

Once the blade 113 has been connected to the retractor member holder 562, the blade 113 can be move to another attachment position. To do so, the insertion tool 580 is inserted into the longitudinal bore 119 of the blade 113 and is then rotated (e.g., 90 degrees) in the direction indicated by arrow R4. Upon rotation of the insertion tool 580, the engagement portion 588 moves from the first position (FIG. 42) to the second position (FIG. 43) and urges the engagement member 578 out of an indentation 115 of the blade 113 as seen in FIG. 43. The insertion tool 580 is then advanced forward in the direction indicated by arrow T3. As a result, the engagement portion 588 of the elongated member 586 contacts the distal shoulder 133 of the blade 113 and advances the blade forward in the direction indicated by arrow T4 as shown in FIG. 43. Once the blade 113 has been advanced to the desire position, the insertion tool 582 is rotated (e.g., 90 degrees) in the direction indicated by arrow R5 as seen in FIG. 44. Upon rotation of the insertion tool 580, the engagement portion 588 of the elongated member 586 rotates from the second position (FIG. 44) to the first position (FIG. 45) to allow the engagement member 578 to move into an indentation 115. As discussed above, the biasing member 574 is configured to bias the engagement member 578 toward an indentation 115.

Figure 46:
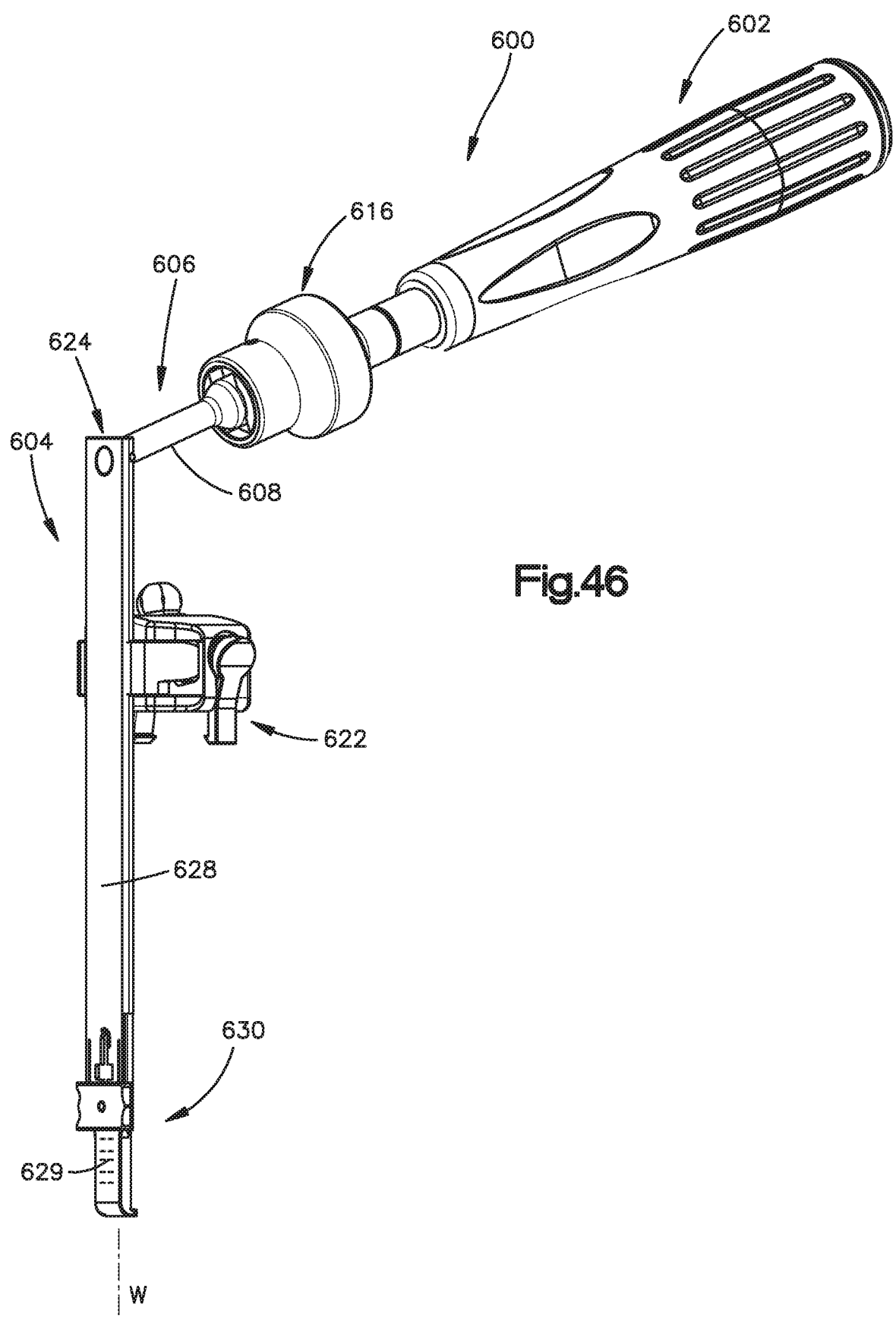
FIG. 46 is a perspective view of a tissue retractor according to an embodiment of the present invention.
Figure 47:
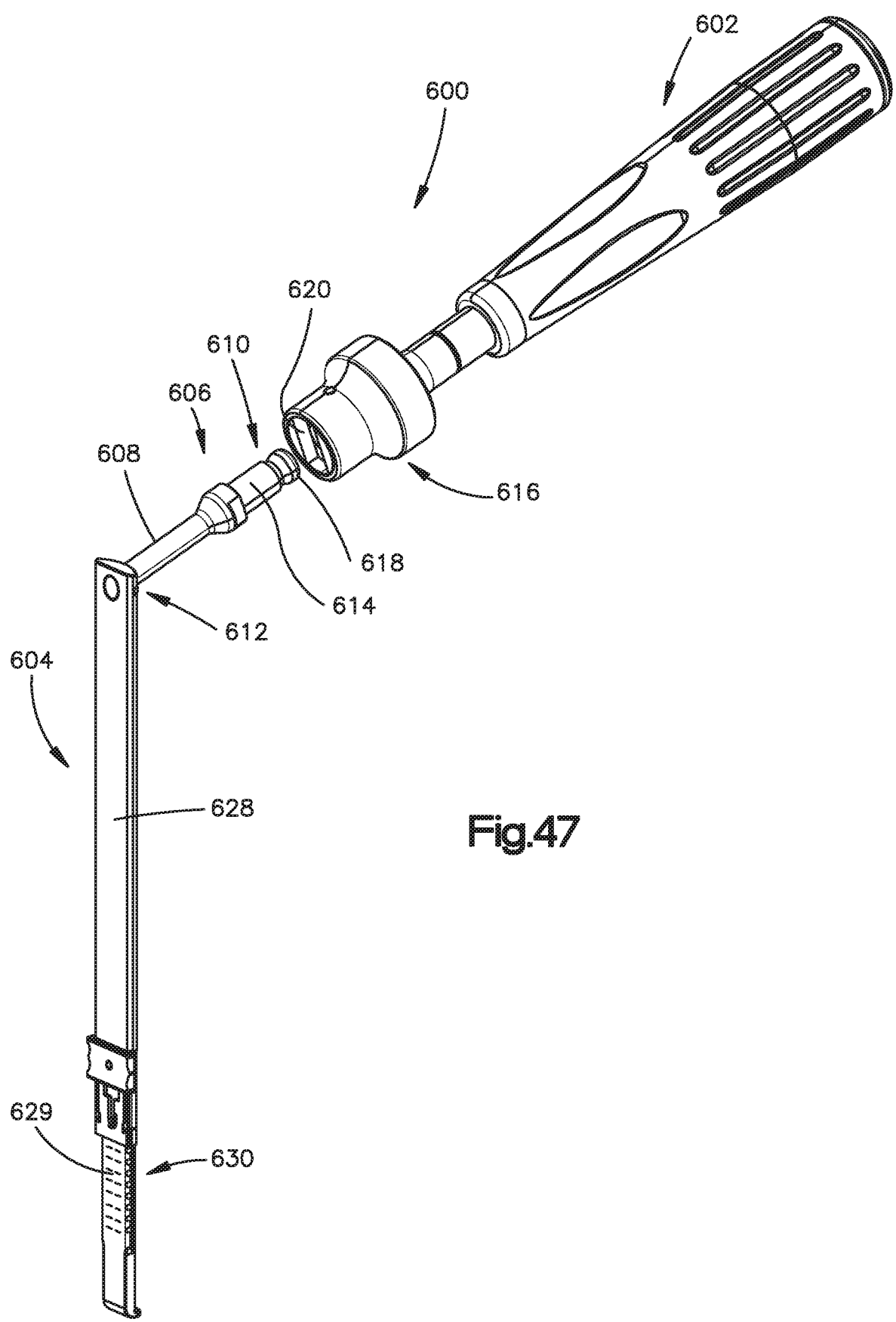
FIG. 47 is a perspective view of the tissue retractor illustrated in FIG. 46, showing a handle detached from a shaft of the tissue retractor.

With reference to FIGS. 46 and 47, a tissue or nerve retractor 600 is configured to move and hold soft or hard tissue and, therefore, create a working space in the surgical field. The tissue retractor 600 is can be used in conjunction with the surgical access retractor 100 (FIG. 1) and includes a detachable handle 602 configured to be grabbed by a user, an elongated telescoping assembly 604, and a holder 622 adapted to hold the telescoping assembly 604 and to be mounted onto the surgical access retractor 100 (FIG. 1) as discussed in detail below. The telescoping assembly 604 can be made of a substantially rigid material. In the depicted embodiment, the telescoping assembly 604 defines a longitudinal axis 625 along its length and has a substantially planar configuration. However, the tissue retractor 600 can include other kinds of telescoping members. A coupler 606 detachably connects the handle 602 to the telescoping assembly 604. The coupler 606 includes a shaft 608 having a proximal end 610 and a distal end 612. The distal end 612 of the shaft 608 is attached to the telescoping assembly 604, and the proximal end 610 includes a connection portion 614 shaped and configured to be connected to a locking member 616 of the handle 602. The connection portion 614 can include a snap fit protrusion 618 shaped and dimensioned to be tightly positioned within a snap fit socket 620 of the locking member 616 in order to connect the handle 602 to the coupler 606. The handle 602, however, can be (permanently or detachably) attached to the telescoping assembly 604 using any suitable apparatus, mechanism, or means. The telescoping assembly 604 has a first end portion 624 attached to the coupler 606 and a second end portion 626 configured to hold and displace soft or hard tissue.

With reference to FIGS. 48 and 49, the telescoping assembly 604 includes a first elongated member or shaft 628 that remains stationary relative to the coupler 606 (FIG. 46) and a second elongated member or shaft 630 configured to move along the longitudinal axis 625 relative to the first elongated member 628. Moreover, the second elongated member 630 can slide in relation to the first elongated member 628 in a telescoping fashion. The second elongated member 630 is at least partially disposed within the first elongated member 628 and includes a tissue retraction member 632 at its distal end 634. The tissue retraction member 632 is adapted to move and hold soft or hard tissue. In the illustrated embodiment, the tissue retraction member 632 includes a curved portion 636 and a protrusion 638 extending from the curved portion 636. The protrusions 638 is oriented substantially perpendicular to the longitudinal axis 625 (FIG. 46) defined along the length of the telescoping assembly 604. The tissue retraction member 632 is wholly or partly made of a substantially rigid material and is adapted to move and hold hard or soft tissue.

The second end portion 626 of the telescoping assembly 604 further includes a locking mechanism 640 to fix the position of the second elongated member 630 with respect to the first elongated member 628. In the illustrated embodiment, the locking mechanism 640 includes a locking clip 642 adapted to engage indentations 650 arranged along opposite sides of the second elongated member 630 and a locking button 644 movable over the locking clip 642 along the longitudinal axis 625 (FIG. 46) between an unlocked position (FIG. 49) and a locked position (FIG. 48). The locking clip 642 includes first and second cantilevered legs 646 and 648 arranged on opposite sides of the second elongated member 630. Each cantilevered leg 646 and 648 includes an engagement member 652, 654, respectively. Each engagement member 652 and 654 is configured and sized to engage one of the indentions 650. In the illustrated embodiment, engagement members 652 and 654 are protrusions. The cantilevered leg 646 biases the engagement member 652 away from the indentations 650. Similarly, the cantilevered leg 648 biases the engagement member 654 away from the indentations 650.

The locking button 644 can be positioned over the locking clip 642 to urge the engagement members 652 and 654 into indentions 650 to thereby fix the position of the second elongated member 630 relative to the first elongated member 628. In the depicted embodiment, locking button 644 includes a guiding member 656, such as a guiding pin, configured and dimensioned to slide along a slot 658 formed on the locking clip 642. With the aid of this guiding member 656, the locking button 644 can move between an unlocked position (FIG. 49) and a locked position (FIG. 48). In the unlocked position, the locking button 644 is not positioned over the engagement members 652 and 654 and, therefore, the engagement members 652 and 654 do not engage indentations 650. As a result, the second elongated member 630 can move freely with respect to the first elongated member 628. In the locked position, the locking button 644 is disposed over the engagement members 652 and 654 and, therefore, each of the engagement members 652 and 654 are positioned within an indentation 650. Consequently, the second elongated member 630 is fixed relative to the first elongated member 628 when the locking button 644 is in the locked position. As seen in FIG. 47, the second elongated member 630 can include length markings 629 to help the user determine how much he or she has to extend the second elongated member 630 relative to the first elongated member first elongated member 628.

Any of the retractor described herein can further include the nerve retractor 600, which includes the telescoping assembly 604. The telescoping assembly 604 includes the first elongated member 628 and the second elongated member 630. The second elongated member 630 is configured to slide relative to the first elongated member 628. The second elongated member 628 includes the tissue retraction member 632 configured to retract tissue. The tissue retractor member 632 is located at the distal end 634 and includes the curved portion 636 and a protrusion 638 extending from the curved portion 636. The nerve retractor includes the locking mechanism 640, which includes the locking clip 642. The locking clip 642 is configured to engage the indentations 650 arranged along opposite sides of the second elongated member 630 to fix the position of the second elongated member 630 relative to the first elongated member 628. The locking clip 642 includes first and second cantilevered legs 646 and 648 arranged on opposite sides of the second elongated member 630. The first cantilevered leg 646 includes the third engagement member 652 configured to be selectively positioned in one of the indentations 650. The second cantilevered leg 648 includes the fourth engagement member 654 configured to be selectively positioned in one of the indentations 650. A locking button 642 is movable over the locking clip 642 between a locked position, in which the third engagement member 652 and the fourth engagement member 654 securely engage selective indentations 650, and an unlocked position, in which the third engagement member 652 and the fourth engagement member 654 engage selective indentations 650 to fix the position of the second elongated member 630 with respect to the first elongated member 628. The nerve retractor 600 further comprises the coupler 606 attached to the telescoping assembly 604 and the handle 602 attached to the coupler 606. The handle 602 is removably attached to the coupler 606.

With reference to FIGS. 50-54, a holder 622 is configured to hold the tissue retractor 600 and to be attached to the surgical access retractor 100. In the depicted embodiment, the holder 622 includes an outer housing 660, a clamping assembly 662 configured to hold the telescoping assembly 604 (FIG. 46) of the tissue retractor 600, a locking mechanism 664 configured to lock the clamping assembly 604, and a mounting mechanism 666 adapted to connect the holder 622 to the surgical access retractor 100. The outer housing 660 houses at least a portion of the clamping assembly 662, the locking mechanism 664, and the mounting mechanism 666.

The clamping assembly 662 includes first and second clamping arms 668 and 670 configured to collectively hold the telescoping assembly 604. The first and second clamping arms 668 and 670 can move toward and away from each other. Alternatively, only one of the clamping arms 668 and 670 can move away and toward the other arm. Irrespective of its specific structure and operation, the clamping assembly 662 defines a space 672 between the first and second clamping arms 668 and 670 sized and configured to receive at least a portion of the telescoping assembly 604 (FIG. 46).

As discussed above, the locking mechanism 664 can fix the position of the first and second clamping arms 668 and 678 in relation to each other. In the embodiment depicted in FIG. 52, the locking mechanism 664 includes a rotating member 674 coupled to the second arm 670. The rotating member 674 can be a screw including a head 676 adapted to be driven by a tool and threaded shaft 678 operatively connected to a proximal portion 680 of the second arm 670. The proximal portion 680 of the second clamping arm 670 includes a threaded bore 682 configured and sized to mate with the threaded shaft 678. An end 684 (that is opposite to the head 676) of the threaded shaft 678 is attached to an inner surface 686 of the housing 660. In operation, the locking mechanism 664 has a locked position and an unlocked position. To fix a telescoping assembly 604 (FIG. 47) within the space 672 defined by the clamping assembly 662, the rotating member 674 is rotated via the head 676 in the direction indicated by arrow R6. Upon rotation of the rotating member 674, the proximal portion 680 of the second arm 670 moves toward the inner surface 686 along the threaded shaft 678. As a consequence, the second arm 670 moves toward the first arm 668 until it is firmly pressed against the telescoping assembly 604 positioned in the space 672. Before or after attaching the tissue retractor (FIG. 46) to the holder 622, the holder 622 can be connected to the surgical access retractor 100 via the mounting mechanism 666.

FIGS. 50, 51, and 53 show an embodiment of the mounting mechanism 666, and FIG. 52 shows an alternative embodiment. In the embodiment shown in FIGS. 50, 51, and 53, the mounting mechanism 666 allows the holder 622 to be connected to third distal portion 318 and includes a first and second snap fit hooks 688 operatively connected to opposite sides of the housing 660. A biasing member 692, such as a coil spring, biases the snap fit hook 688 to a locked position as seen in FIG. 50. The third distal portion 318 includes a pair of snap fit recesses 690 shaped and configured to securely receive a portion of the snap fit hooks 688. The snap fit recesses 690 are located on opposite sides of the third distal portion 318 and each is shaped and configured to securely receive a snap fit hook 688. When the snap fit recesses 690 receive the snap fit hooks 688 (as shown in FIG. 5), the holder 622 is securely mounted to the surgical access retractor 100.

In the embodiment shown in FIG. 52, a mounting mechanism 667 allows the holder 622 to be connected to the distal ends 134 and 136 (FIG. 7) of the first and second arms 122 and 126 of the surgical access retractor 100. The mounting mechanism 667 can includes one or more extensions 669 on each side of the housing 660. Each extension 669 includes a bore 671 sized and configured to receive a connection member (not shown) such as a screw, rod, or nut. The particulars of the mounting mechanism 667 are described in detail below.

Figure 54:
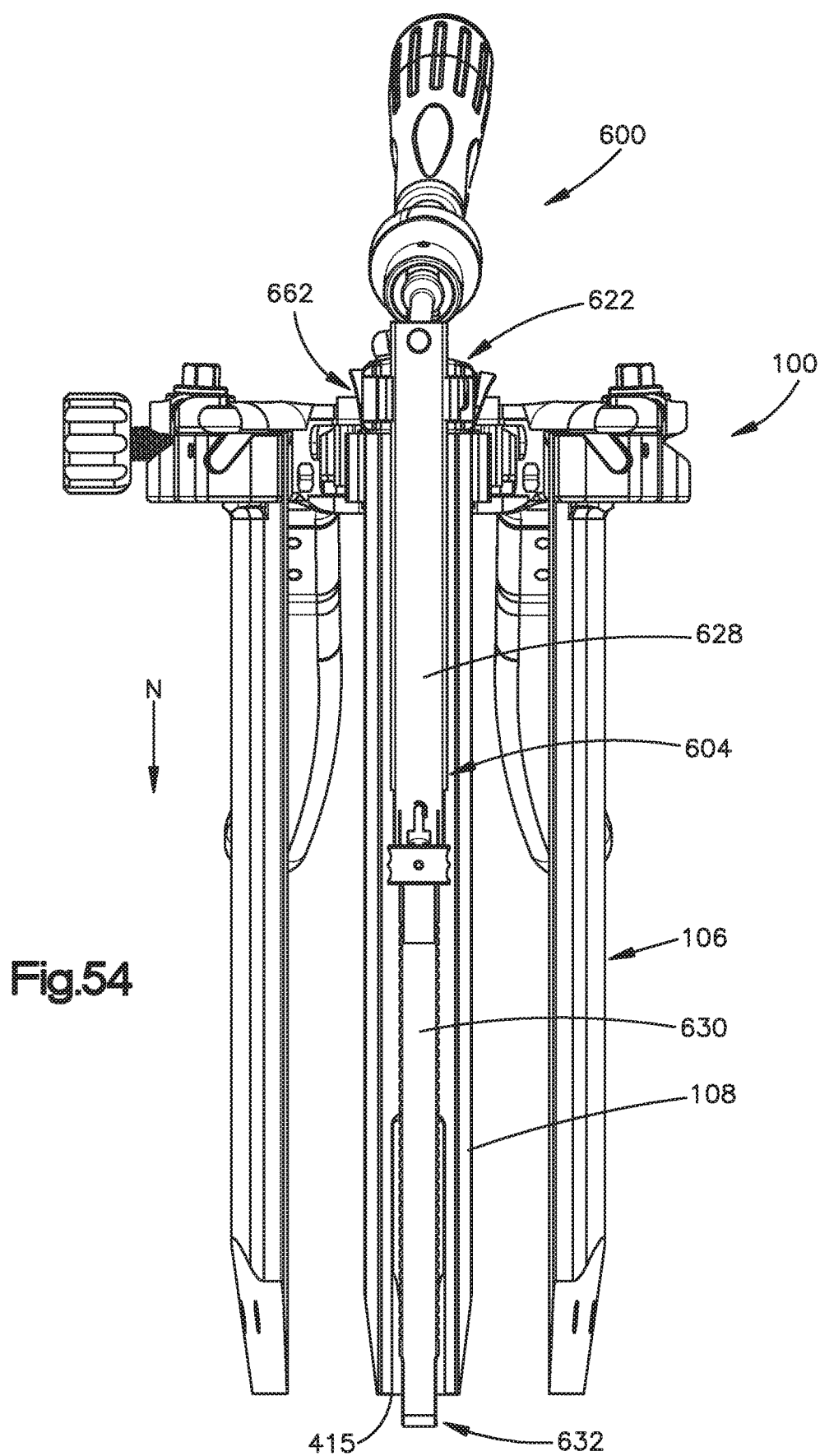
FIG. 54 is a front view of the tissue retractor illustrated in FIG. 46 mounted to the surgical access retractor illustrated in FIG. 1.
Figure 55:
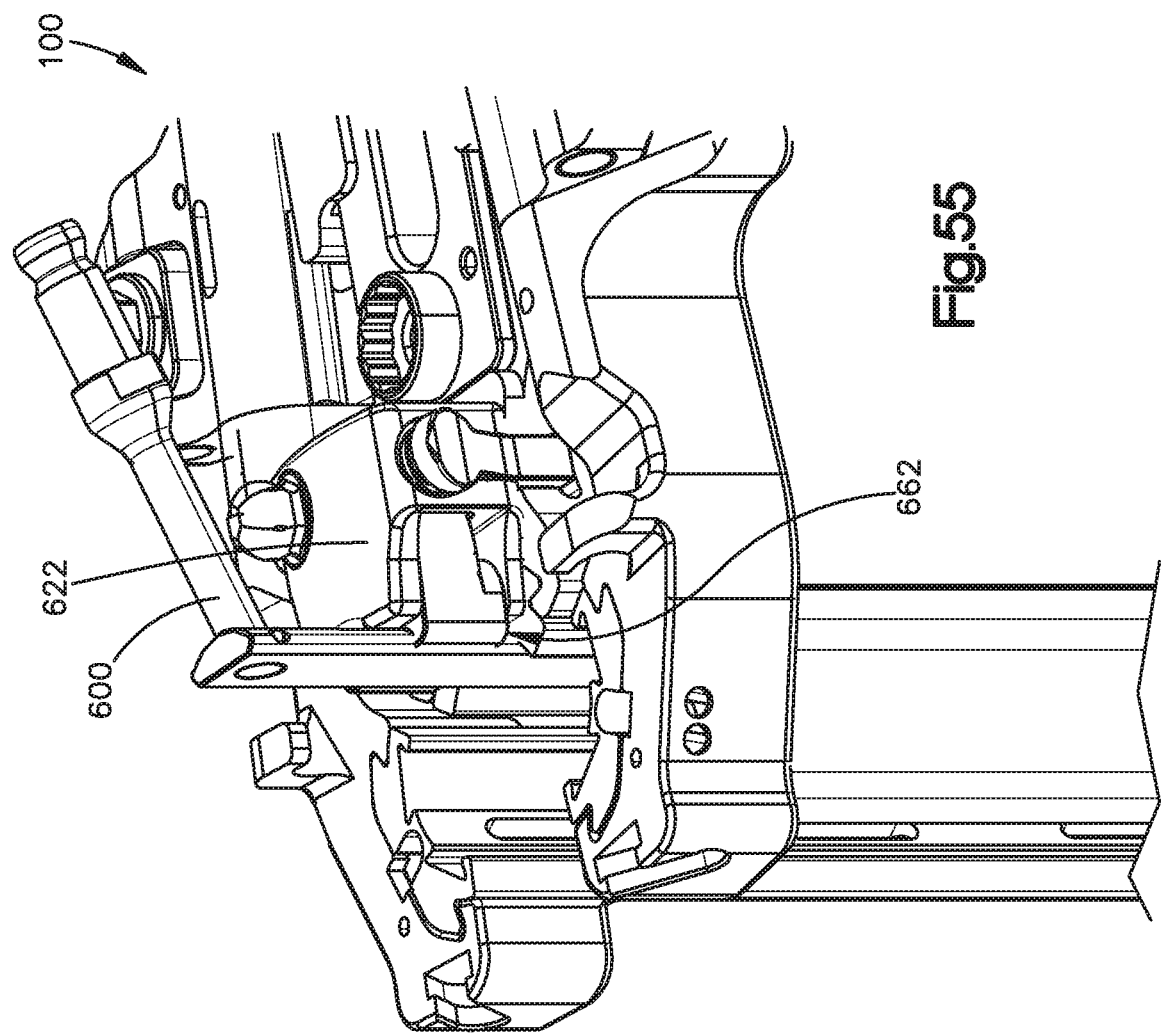
FIG. 55 is a perspective view of the tissue retractor illustrated in FIG. 46 mounted to a distal portion of the surgical access retractor illustrated in FIG. 1.
Figure 56:
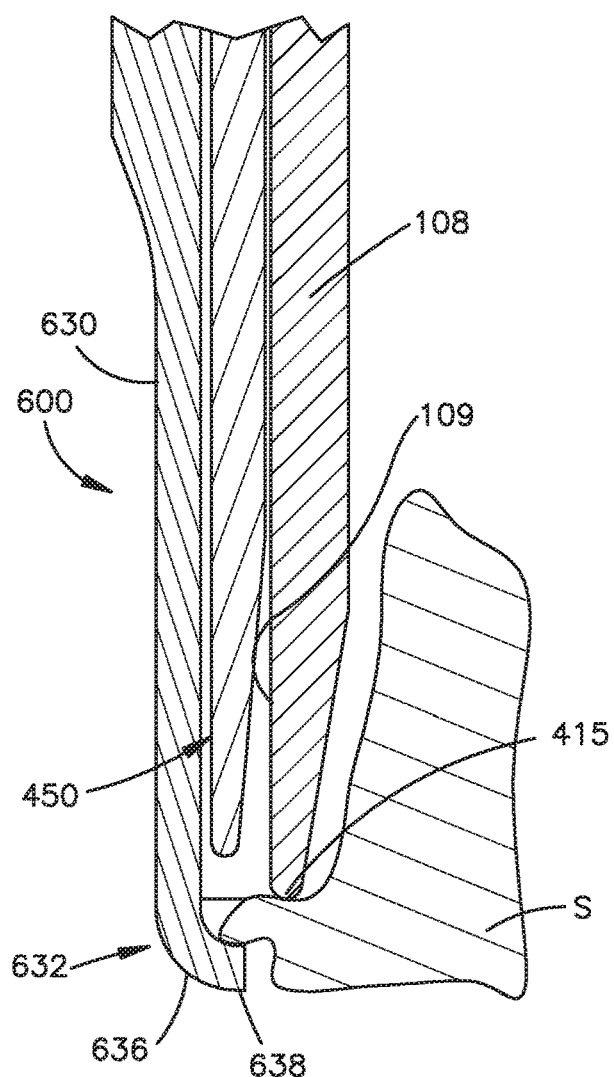
FIG. 56 is a cross-sectional side view of a distal portion of the tissue retractor illustrated in FIG. 46 pushing tissue behind a blade of the surgical access retractor shown in FIG. 1.

With reference to FIGS. 54-56, the tissue retractor 600 can hold move and hold tissue behind a retractor member 106, such as retractor member 108, to enlarge the surgical operating field. In use the telescoping assembly 604, as described above, to adjust its length as desired. In particular, the second elongated member 630 can be move relative to the first elongated member 628 to until the telescoping assembly 604 has the desired length. Then, the second elongated member 630 is fixed in relation to the first elongated member 628 using the locking mechanism 640 as described above. The telescoping assembly 604 is then attached to the clamping assembly 662 of the holder 622. The holder 622 can already be mounted to the surgical access retractor 100 as described above. The telescoping assembly 604 is then advanced in the direction indicated by arrow N until the tissue retraction member 632 extends beyond the distal end 415 of retractor member 108. At this point, the protrusion 638 of the tissue removal member 623 moves and holds at least some tissue S away from the inner surface 109 of the retractor member 108 as depicted in FIG. 56.

The tissue retractor 600 can alternatively be used without connecting it to the surgical access retractor 100. In this exemplary method of use, the telescoping assembly 604 is advanced along the inner surface 109 of the retractor member 108 in the direction indicated by arrow N until the tissue retraction member 632 extends beyond the distal end 415 of retractor member 108. Then, the tissue retractor 600 is pulled back (i.e. proximally) so that the tissue removal member 623 can urge tissue S away from the inner surface 109 of the retractor member 108.

Figure 57:
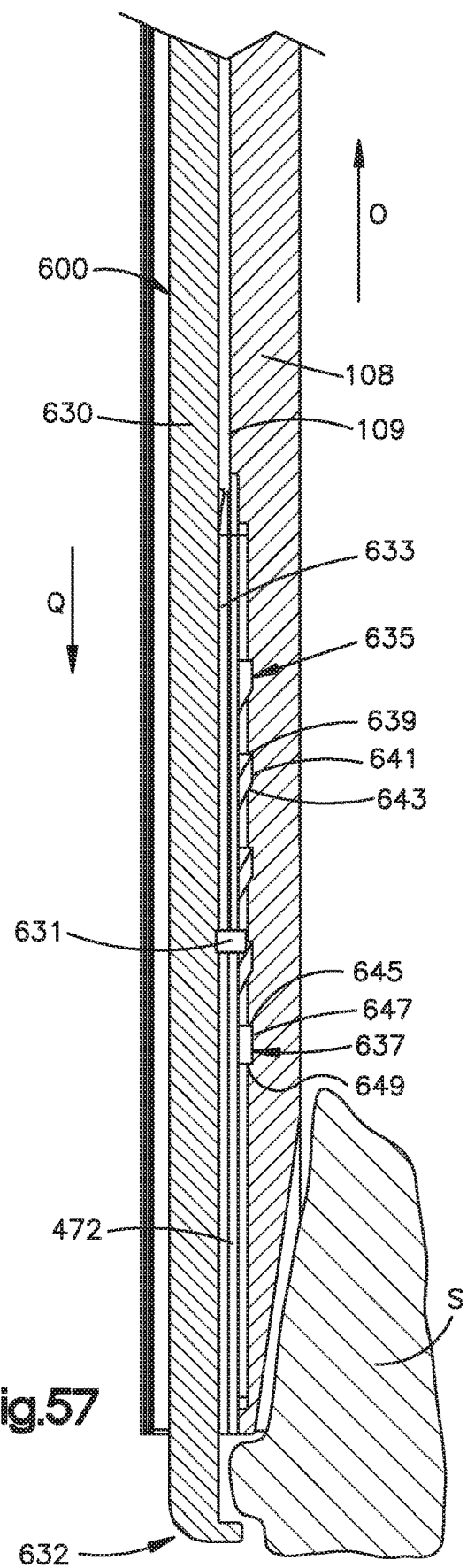
FIG. 57 is a cross-sectional side view of a distal portion of a tissue retractor in accordance with an alternate embodiment of the present invention.

FIG. 57 shows an alternate embodiment of the tissue retractor 600. In this embodiment, the second elongated member 630 includes an engagement member 631 extending from an inner surface 633 thereof. In the depicted embodiment, the engagement member 631 is a protrusion. The engagement member 631 is adapted and sized to be received within indentations 635 and 637 arranged along the inner surface 109 of the retractor member 108 (or any other retractor member 106). The indentations 635 are formed by a proximal wall 639, a bottom wall 641, and a distal wall 643. The proximal wall 639 is oriented substantially perpendicular to the inner surface 109. The bottom wall 641 is oriented substantially parallel to the inner surface 109. The distal wall 643 is oriented at an oblique angle relative to the inner surface 109. The angled orientation of the distal wall 643 allows the second elongated member 630 to move in the direction indicated by arrow Q because the engagement member 631 can slide out of the indentation 633. However, the orientation of the proximal wall 639 prevents, or at least inhibits, the second elongated member 630 from moving in the direction indicated by arrow O because the proximal wall 639 acts as a mechanical stop and prevents, or at least inhibits, the engagement member 631 from moving in the direction indicated by arrow O. The distal-most indentation 637 is formed by a proximal wall 645 oriented substantially perpendicular to the inner surface 109, a bottom wall 647 oriented substantially parallel to the inner surface 109, and a distal wall 649 oriented substantially perpendicular to the inner surface 109. The orientations of the proximal wall 645 and distal wall 649 prevent, or at least inhibits, the second elongated member 630 from moving in the direction indicated by arrow Q and O because the proximal wall 645 and distal wall 649 function as mechanical stops and block the engagement member 631 from moving in either direction. The most-distal indentation 637 therefore limits the distal movement of the second elongated member 630 in relation to the retractor member 108.

The holder 622 is configured to retain the nerve retractor 600. The holder 622 is configured to be mounted to the retractor. The holder 622 comprises a clamping assembly (662) configured to retain the telescoping assembly 604. The clamping assembly 662 includes the first clamping arm 668 and the second clamping arm 670 configured to move toward or away from each other. The clamping assembly 662 defines a space 672 between the first clamping arm 668 and the second clamping arm 670 sized to receive at least a portion of the telescoping assembly 604. The holder 622 further comprises the second rotating member 674 coupled to the second clamping arm 670. Rotating the second rotating member 674 causes the second clamping arm 670 to move toward or away the first clamping arm 668. The second rotating member 674 comprises a threaded shaft 678. The second clamping arm 670 defines the threaded bore 682, which is configured to receive the threaded shaft 678 of the second rotating member 674. The holder 622 comprises the outer housing 660 housing the second rotating member 674. The holder 622 is configured to be mounted to the third arm 316. The third arm 316 comprises the third proximal portion 315 and the third distal portion 318, which is configured to retain the third retractor member 108. The holder 622 is configured to be mounted to the third distal portion 318. The third distal portion 318 comprises at least one snap fit recess 690. The third distal portion 318 comprises at least one snap fit hook 688. The at least one snap fit recess 690 configured to securely receive the at least one snap fit hook 688 to connect the holder 622 to the third distal portion 318. The second elongated member 630 defines the outer surface 633. The second elongated member 630 includes the fifth engagement member 631 extending from the outer surface 633. The fifth engagement member 631 is configured to be received by a selective one of the plurality of indentations 635 defined along the inner surface 109 of the third retractor member 108 to allow the second elongated member 630 to advance incrementally with respect to the third retractor member 108.

Figure 58:
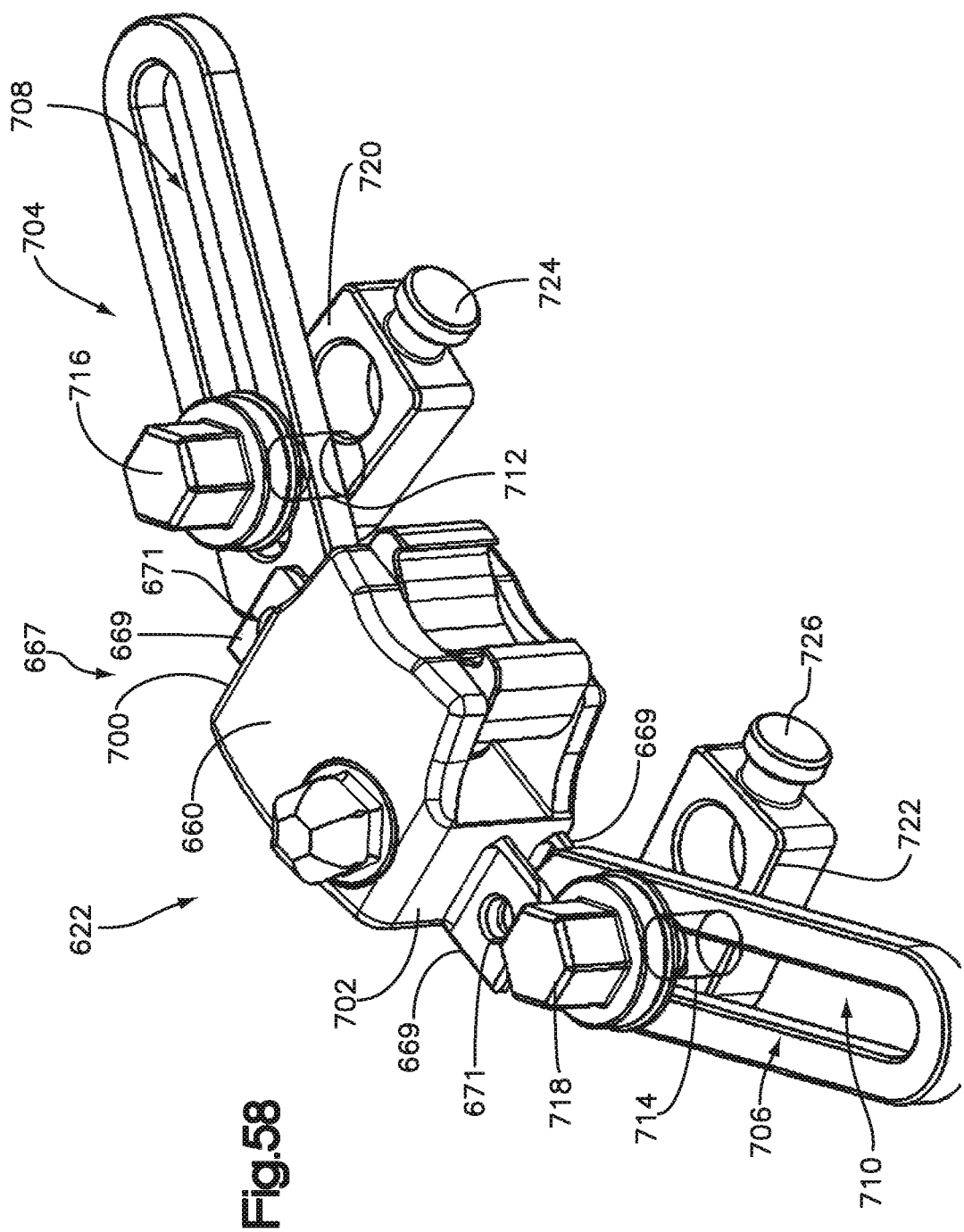
FIG. 58 is perspective view of alternative holder for holding the tissue retractor illustrated in FIG. 46.
Figure 59:
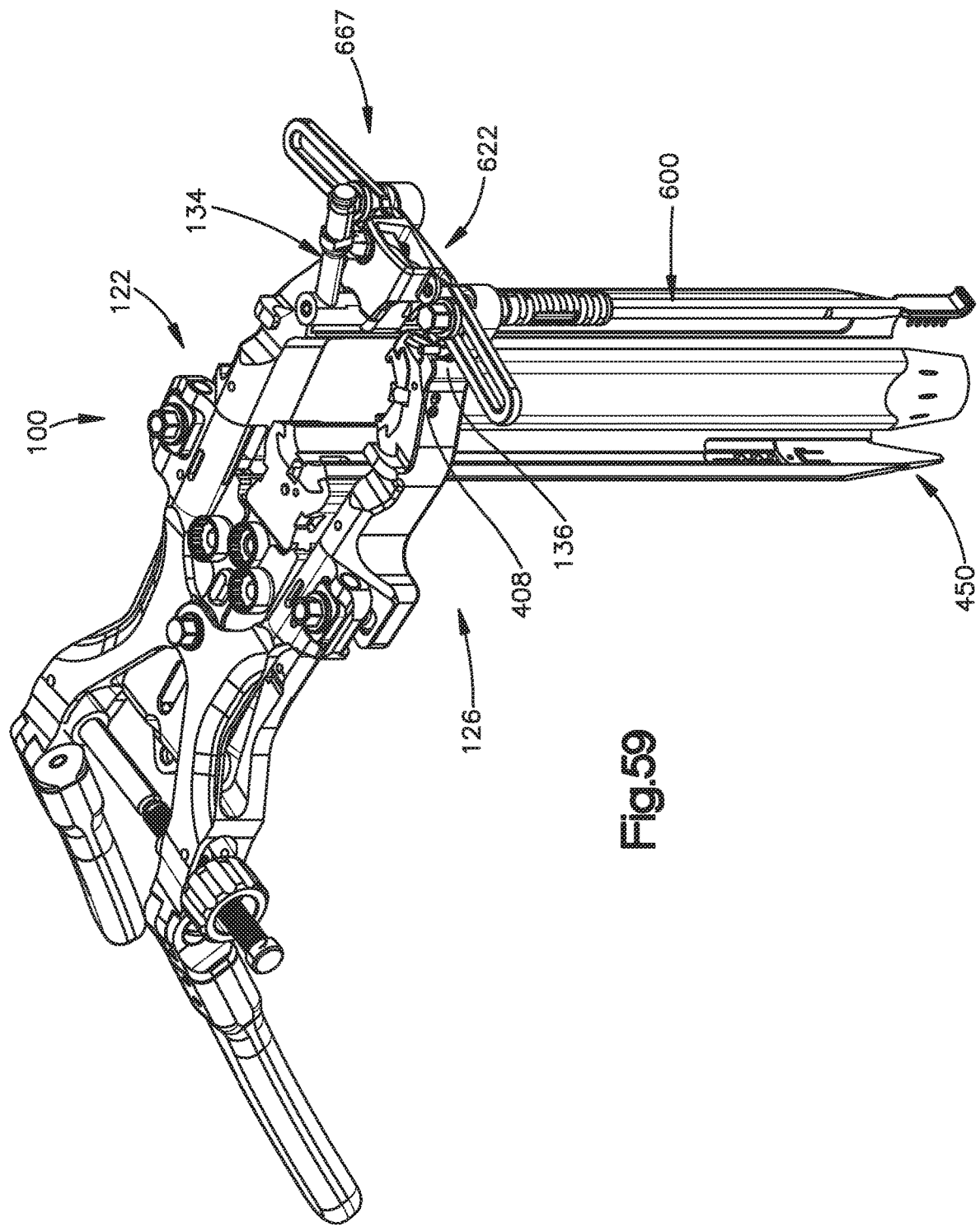
FIG. 59 is a perspective view of the holder illustrated in FIG. 58 mounted to the surgical access retractor shown in FIG. 1.

With reference to FIG. 58-59, the holder 622 can alternatively include the mounting mechanism 667 discussed above with respect to FIG. 52. The mounting mechanism 667 allows the holder 622 to be connected to the distal ends 134 and 136 (FIG. 7) of the first and second arms 122 and 126 of the surgical access retractor 100. In the illustrated embodiment, the mounting mechanism 667 includes one or more extensions 669 on each side wall 700 and 702 of the housing 660. A pair of extensions 669 spaced apart from each other can be attached to each side wall 700 and 702 of the housing 660. Each extension 669 includes a bore 671 sized and configured to receive a connection member (not shown) such as a screw, pin, or nut adapted to connect the extensions 669 to an pivoting arm 704 or 706.

The mounting mechanism 667 includes first and second pivoting arms 704 and 706 each connected to a side wall 700 or 702 of the housing 660 via the extensions 669. Each of the first and second pivoting arms 702 and 704 defines a guiding slot 708, 710, respectively. Each guiding slot 708 and 710 is sized and configured to slidably receive a guiding member 712 and 714, respectively. The guiding member 712 can be a pin or a rod and is adapted to slide along guiding slot 708. Similarly, the guiding member 714 can be a pin or a rod and is adapted to slide along the guiding slot 710. A first fixation member 716, such as a nut, is attached to an end of the guiding member 712 and is configured to fix the position of the guiding member 712 with respect to the guiding slot 708. A first retaining member 720 is attached to the opposite end of the guiding member 712 and is adapted to be attached to the distal end 136 of the first arm 126. In addition, the first retaining member 720 includes a first boss or protrusion 724 shaped and dimensioned to be inserted in the first connecting slot 408 of the first arm 126 in order to connect the holder 622 to the surgical access retractor 100. A second fixation member 718, such as a nut, is attached to an end of the guiding member 714 and is configured to fix the position of the guiding member 714 relative to the guiding slot 710. A second retaining member 722 is attached to the opposite end of the guiding member 714 and is adapted to be attached to the distal end 134 of the second arm 122. Moreover, the second retaining member 722 includes boss or protrusion 716 shaped and dimensioned to be inserted in the second connecting slot 406 (FIG. 7) of the second arm 122 in order to connect the holder 622 to the surgical access retractor 100.

Figure 60:
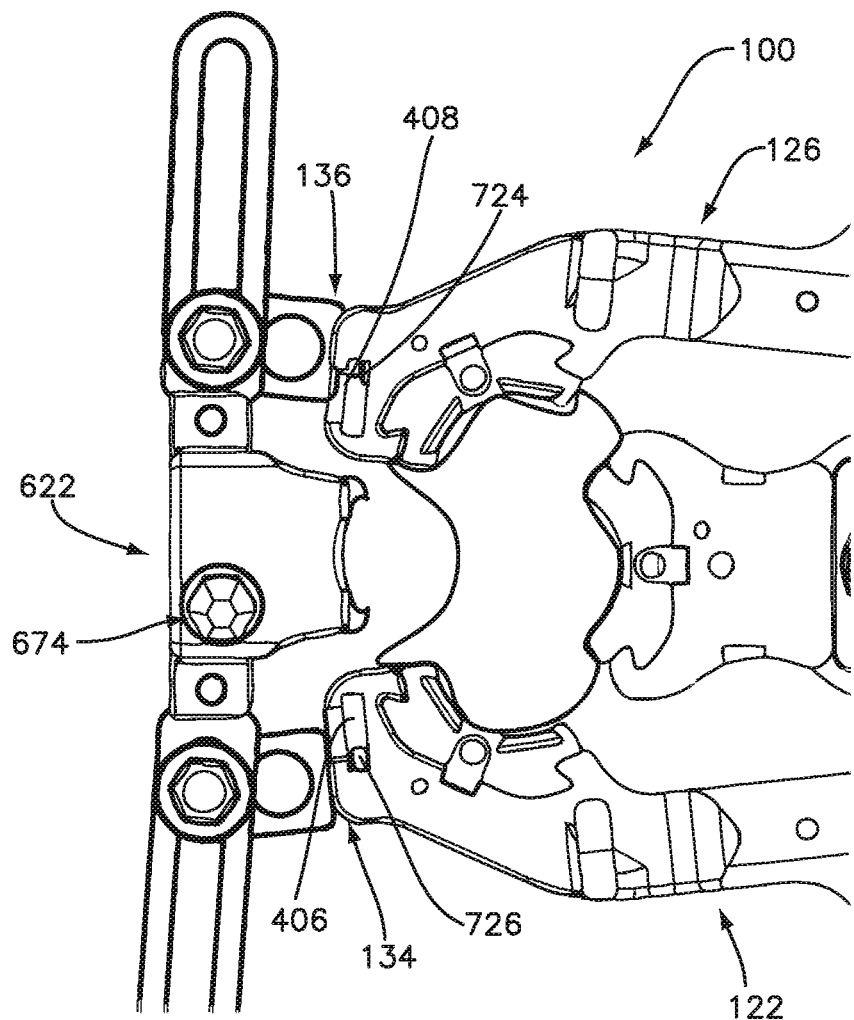
FIGS. 60-64 are top views illustrating step of an exemplary method for retracting tissue using the tissue retractor shown in FIG. 46 and the holder shown in FIG. 58.
Figure 61:
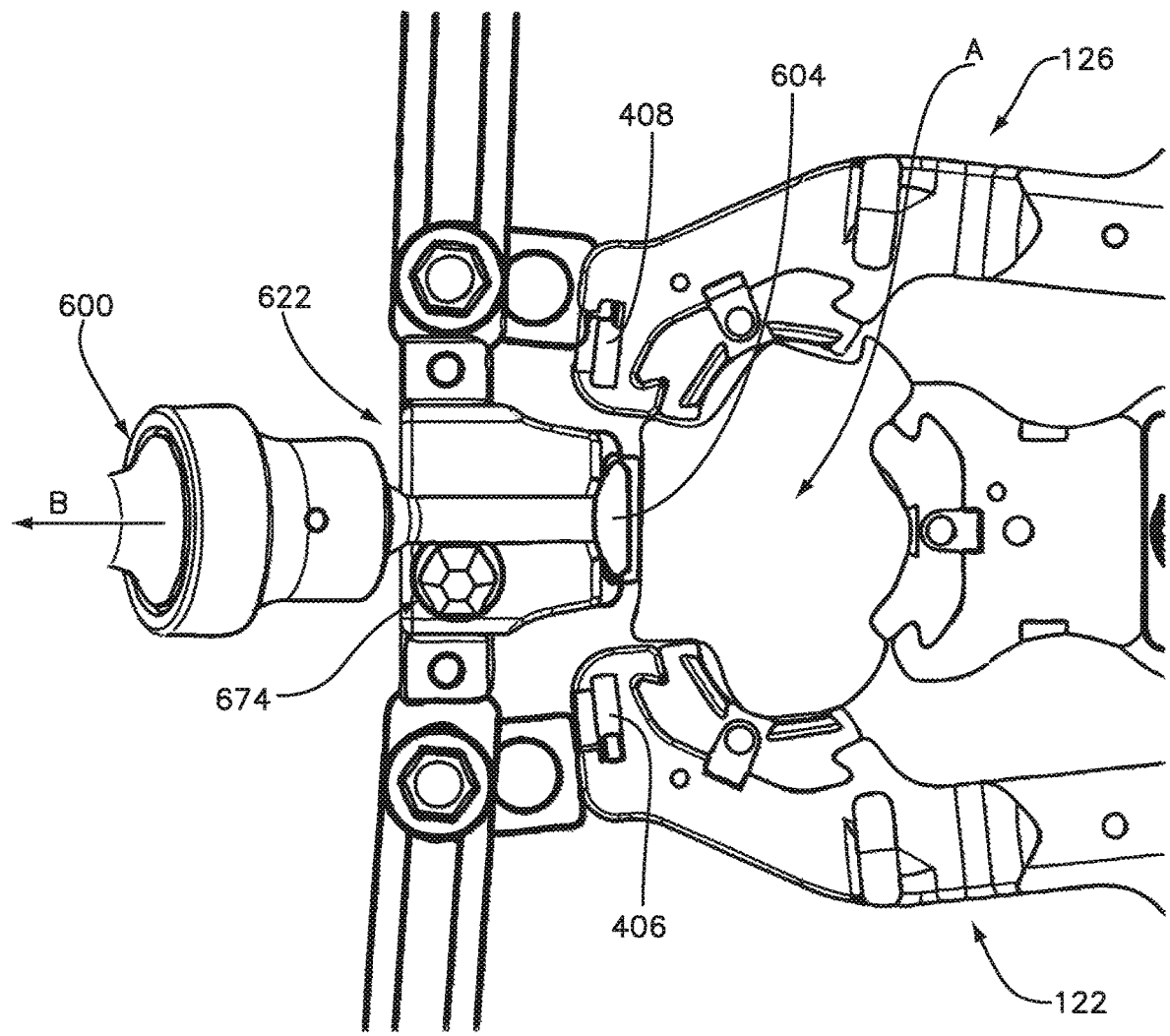
Figure 62:
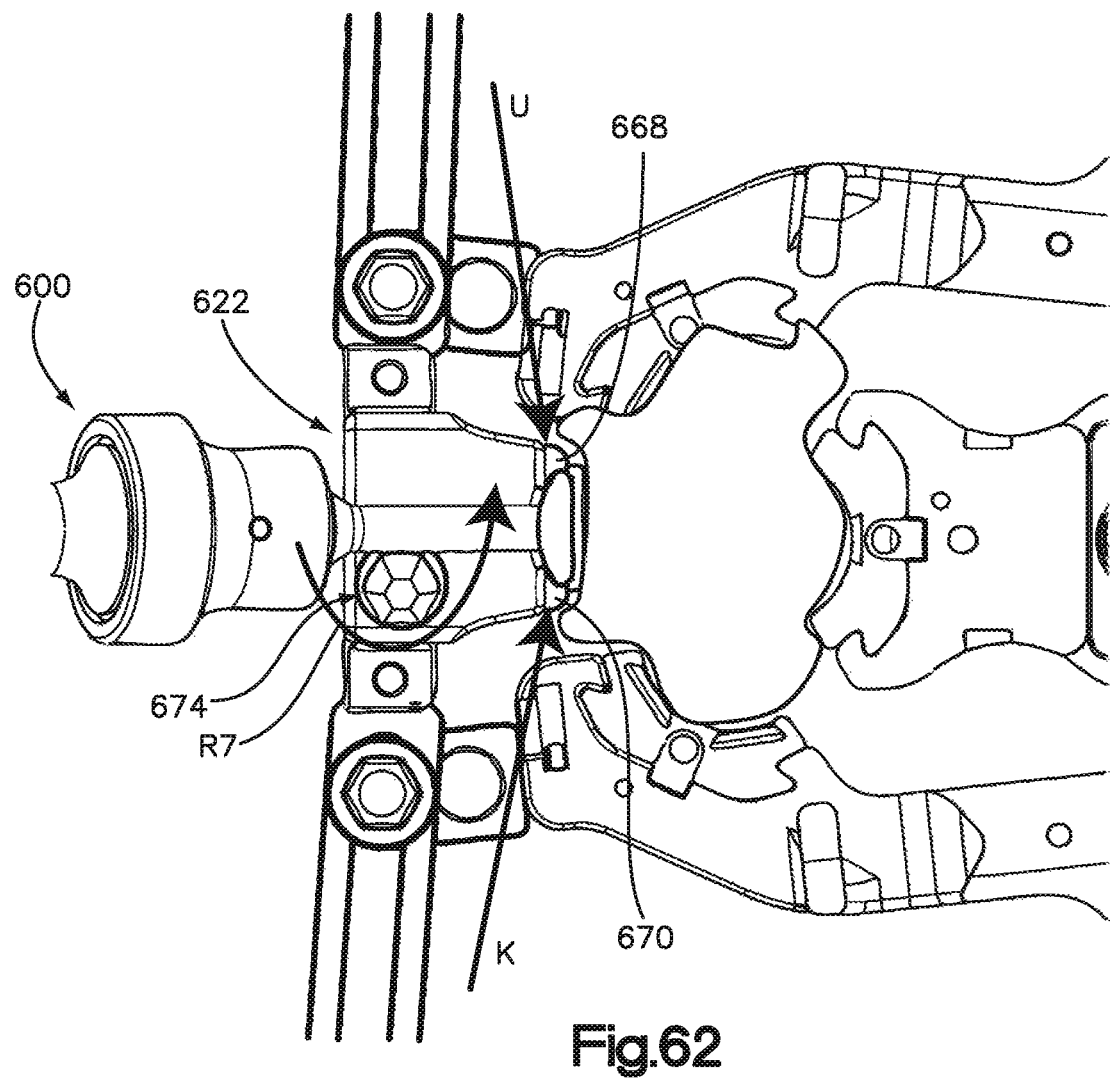
Figure 63:
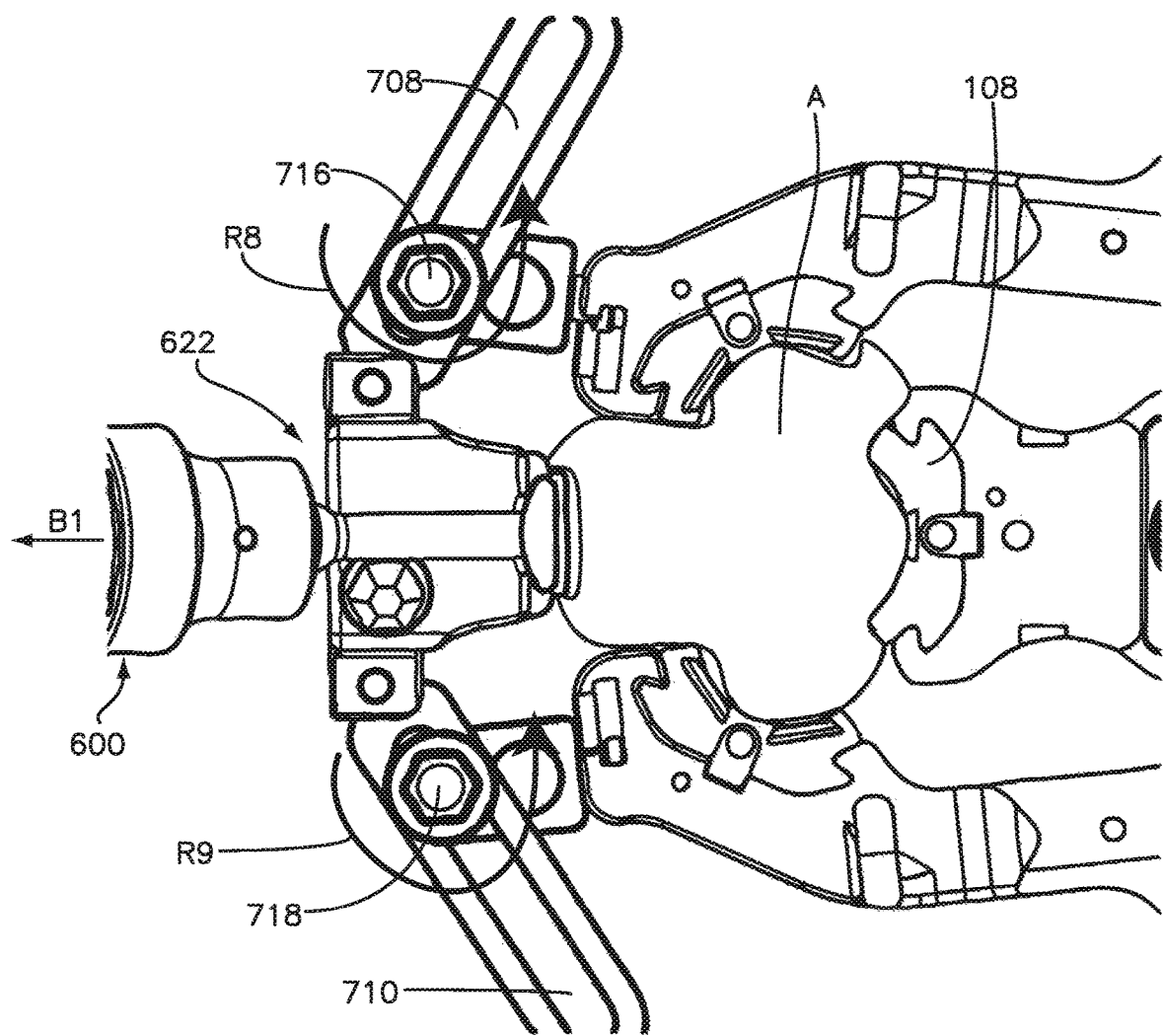
Figure 64:
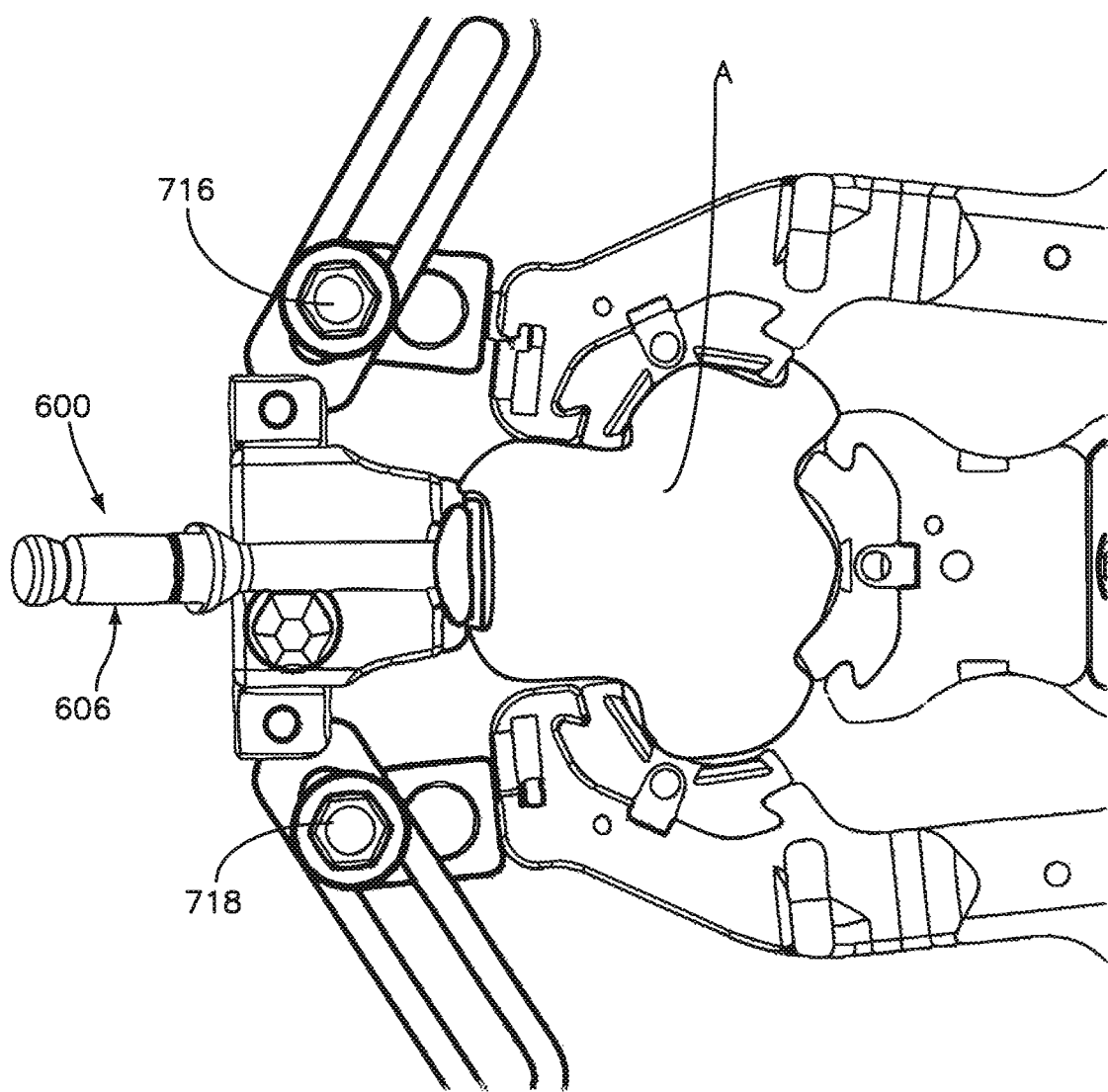

FIGS. 60-64 illustrate an exemplary method of retracting and holding tissue with tissue retractor 600 attached to the surgical access retractor 100 through the holder 622 having mounting mechanism 667. First, the holder 622 is attached to the surgical access retractor 100 by inserting a second boss or protrusion 726 into the second connecting slot 406 and the first boss or protrusion 724 into the first connecting slot 408 as seen in FIG. 60. Subsequently, the telescoping assembly 604 of the tissue retractor 600 is inserted in the space 672 (FIG. 52) of the clamping assembly 662. The tissue retractor 600 is then pulled back in the direction indicated by arrow B to securely position within the clamping assembly 662 as seen in FIG. 61. Then, as seen in FIG. 62, the rotating member 674 is rotated in the direction indicated by arrow R7 to move first and second clamping arms 668 and 670 closer to each other in the direction indicated by arrows K and U, respectively, in order to securely attached the tissue retractor 600 to the holder 622. The tissue retractor 600 is then pulled back in the direction indicated by arrow B1 to retract tissue away from the retractor member 108, thereby enlarging the surgical operating field A, as seen in FIG. 63. As the tissue retractor 600 is pulled back, the guiding members 712 and 714 (FIG. 58) slide along the slots 708 and 710, respectively, thereby allowing the holder 622 to move in the direction indicated by arrow B1. Then, the first fixation member 716 is rotated in the direction indicated by arrow R8 to fix the position of the guiding member 712 with respect to the slot 708 as seen in FIG. 63. Similarly, the second fixation member 718 is rotated in the direction indicated by arrow R9 to fix the position of the guiding member 714 relative to the slot 710. Next, the handle 602 (FIG. 46) of the tissue retractor 600 is detached from the coupler 606 to enhance the user's field of view to the surgical operating field A.

The holder 622 is configured to be mounted to the first distal end 136 and the second distal end 134. The holder 622 further comprises the first pivoting arm 704 and the second pivoting arm 706. The first pivoting arm 704 and the second pivoting arm 706 pivotally connected to opposite sides of the outer housing 660. The first pivoting arm 704 is connected to the first distal end 136. The second pivoting arm 706 is connected to the second distal end 164. The holder 622 further comprises the first retaining member 720 and the second retaining member 722. The first retaining member 720 is configured to move along the first pivoting arm 704. The second retaining member 722 is configured to move along the second pivoting arm 706. The first retaining member 720 comprises the first protrusion 724. The second retaining member 722 comprises the second protrusion 726. The first distal end 136 defines the first connecting slot 408 sized to securely receive the first protrusion 724. The second distal end 134 defines the second connecting slot 406 sized to securely receive the second protrusion 724.

Figure 65:
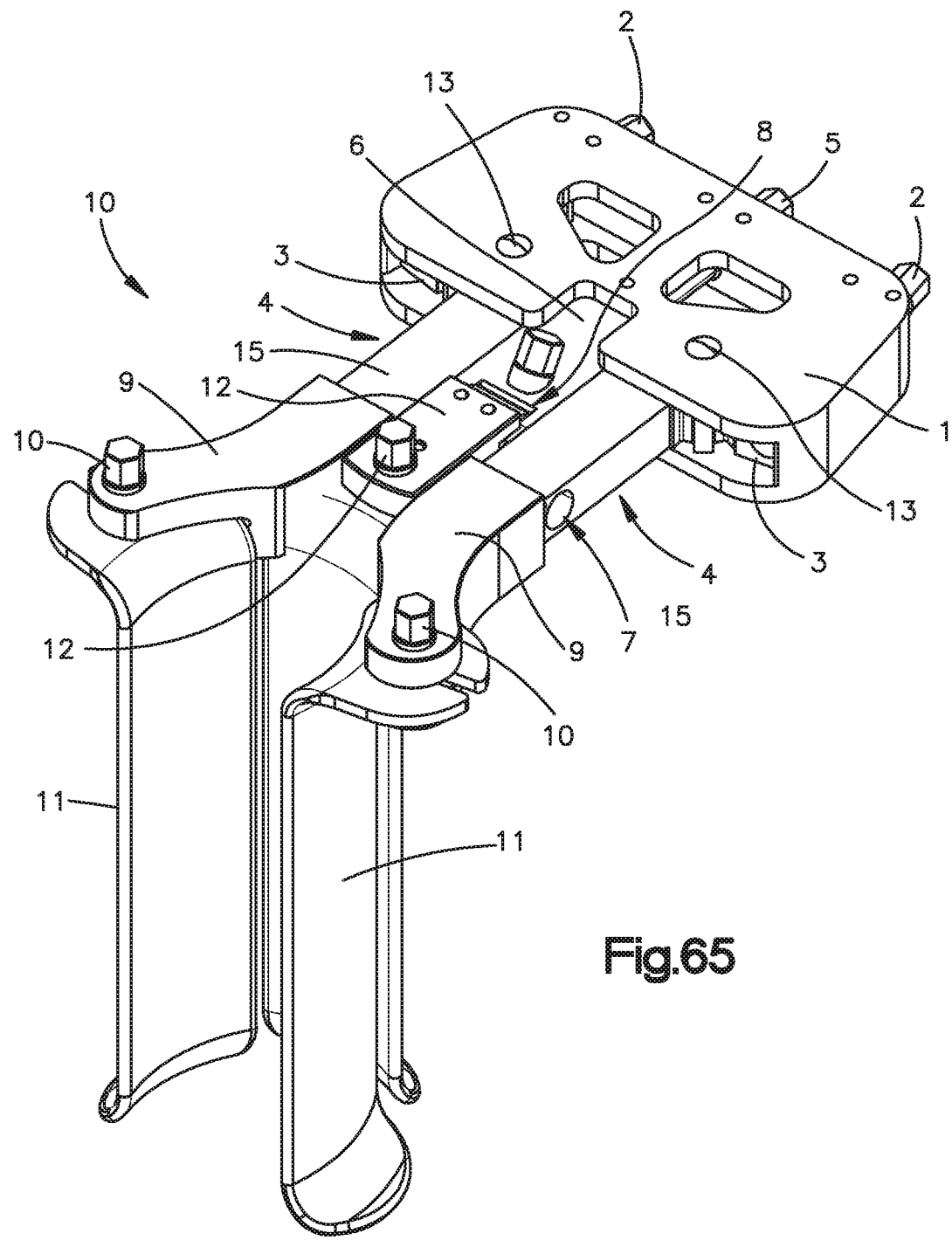
FIG. 65 is a perspective view of a surgical retractor in accordance with an embodiment of the present invention.
Figure 66:
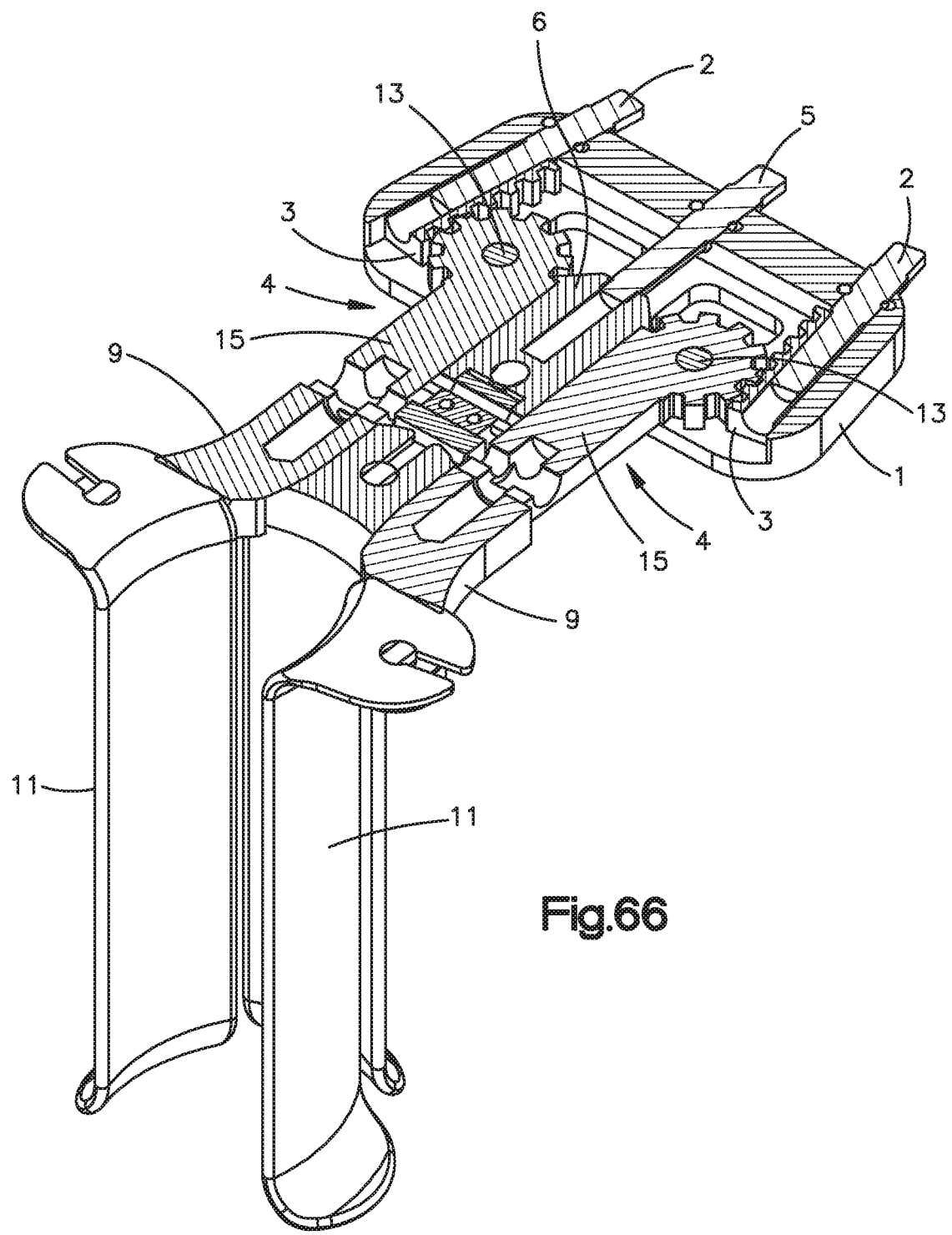
FIG. 66 is a perspective cutout view of the surgical retractor illustrated in FIG. 65.
Figure 67:
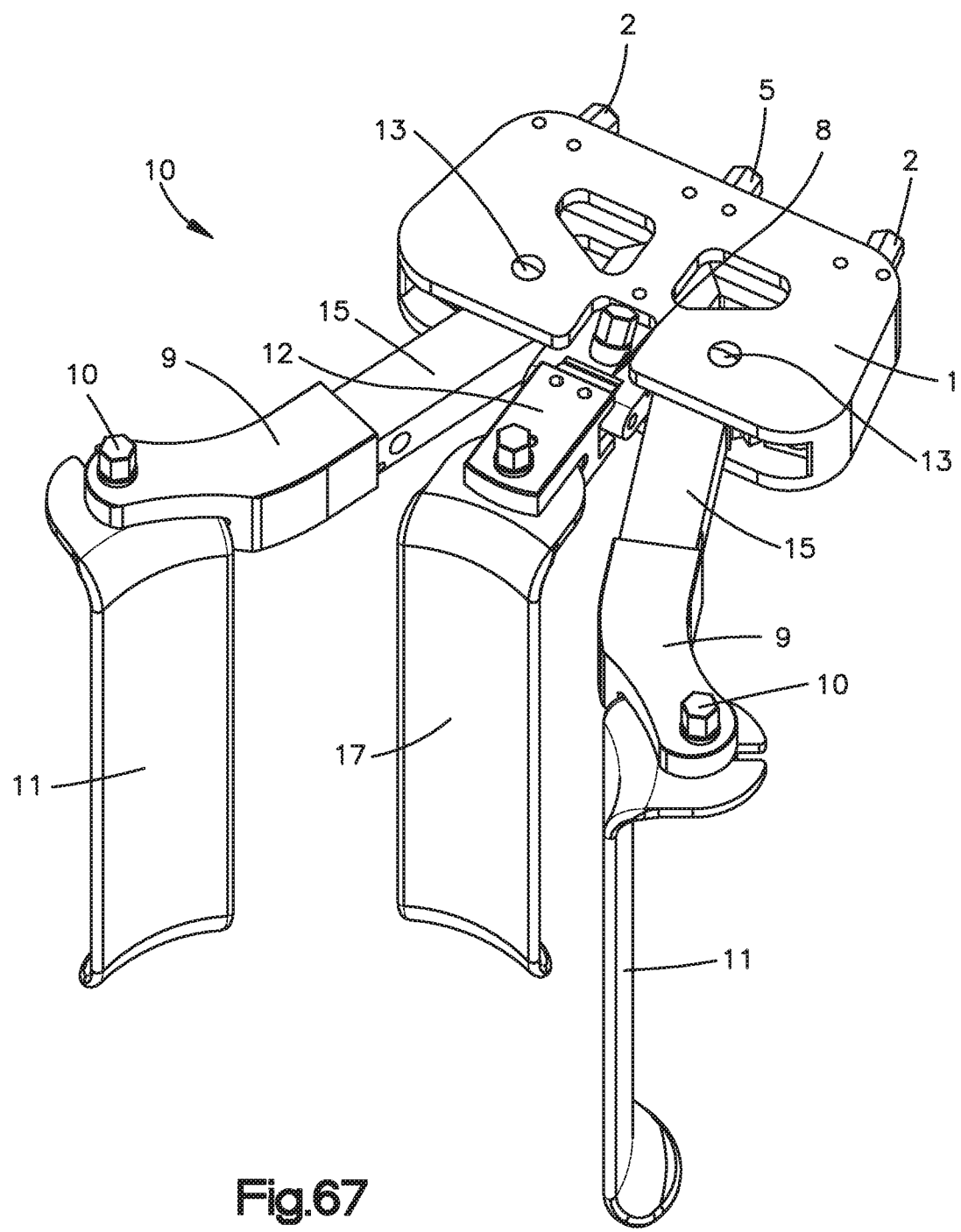
FIG. 67 is a perspective view of the surgical retractor illustrated in FIG. 65 with the blades spaced apart from one another.
Figure 70:
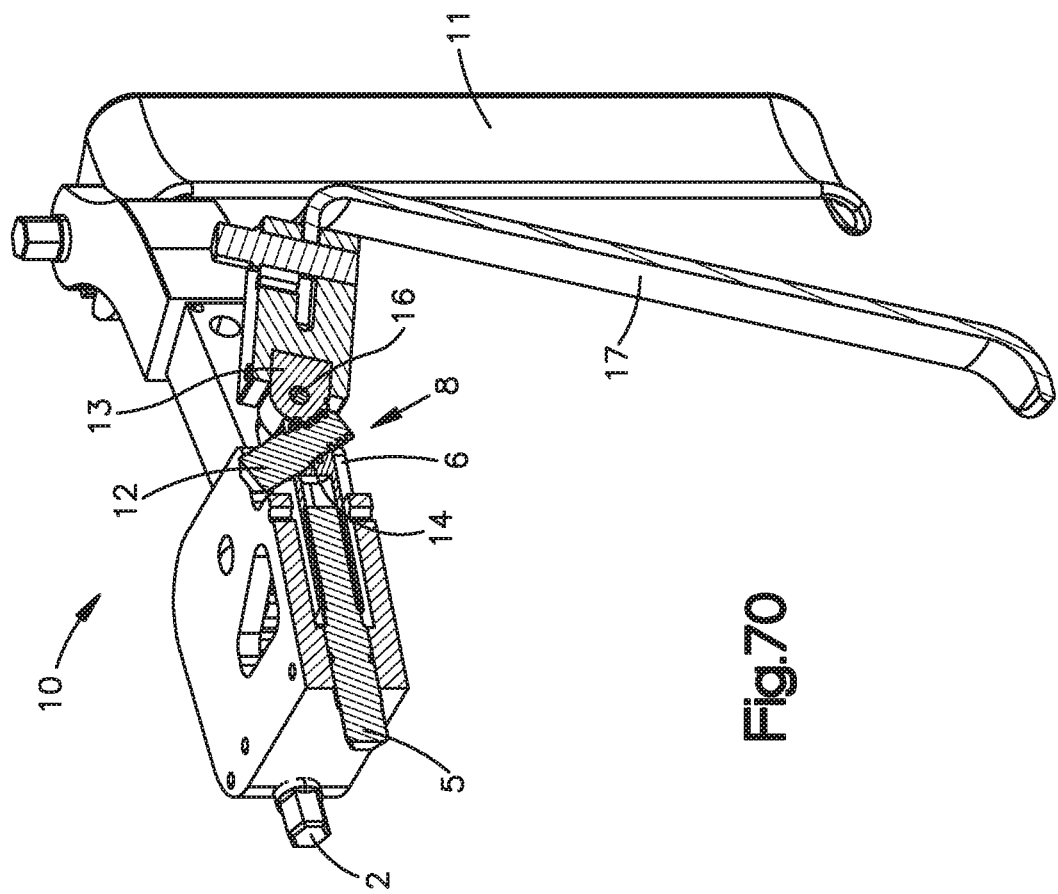
FIG. 70 is a sectional perspective view of the surgical retractor illustrated in FIG. 65 with the central blade angled proximally.
Figure 71:
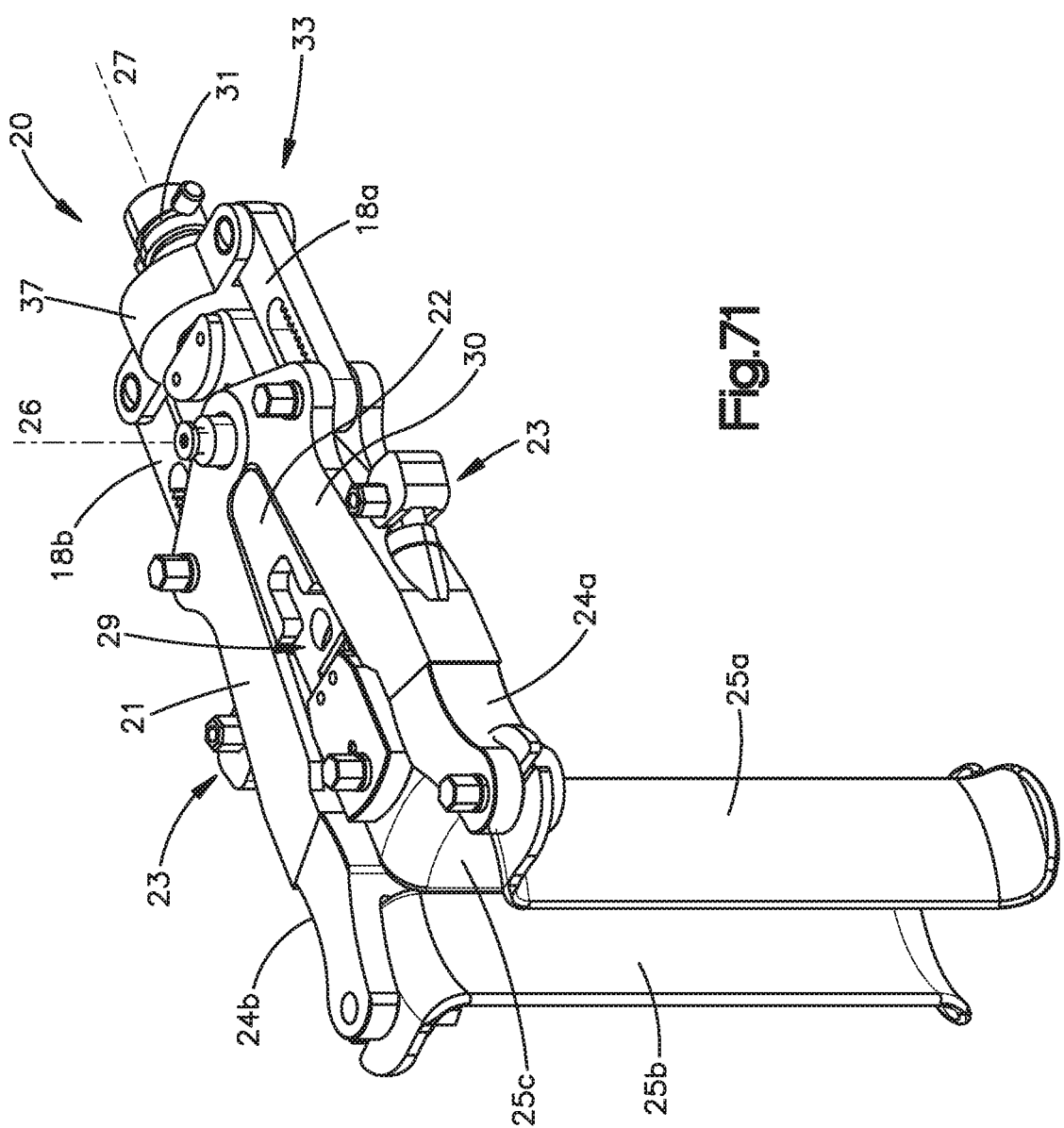
FIG. 71 is a perspective view of a surgical retractor in accordance with an embodiment of the present invention.

With reference to FIGS. 65-67, an embodiment of a surgical retractor 10 comprises a central frame or housing 1, two identical geared arms 4 at least partially disposed within the central frame 1, two identical geared racks 3 at least partially disposed within the central frame 1, and a central threaded nut 5, and two lateral threaded nuts 2. The central nut 5 is disposed along the center of the central frame 1, while the two lateral threaded nuts 2 are positioned on opposite sides of the central frame 1. The geared arms 4 are fixed to the frame 1 but are free to rotate around a fixed axis due to being pinned accordingly. For instance, the geared arms 4 can pivotally connected to the central frame 1 by pivot pins 13. The threaded nuts 2 and 5 are also fixed to the frame 1 but are also free to rotate around a fixed axis, again due to being pinned accordingly. In order to indirectly connect the threaded nuts 2 to the geared arms 4, the geared racks 3 are threaded onto the threaded nuts 2 and, once sufficiently threaded, the gears of racks 3 engage with the gears of arms 4. Thereby, rotation of the threaded nuts 2 results in translation of the geared racks 3, which in turn causes rotation of the geared arms 4. Each geared arms 4 includes a substantially rigid elongated portion or shaft 15 connected to a radiolucent blade holder 9. The connecting shaft 15 is coupled with a spring button and ratchet mechanism 7, which allows for controlled rotation of the blade holder 9 around the shaft 15. Attached to the blade holder 9 is a radiolucent blade 11. This connection is achieved using a connecting mechanism 10, which comprised of a rotatable eccentric rod which in it minor dimension allows for blade insertion but the major dimension does not. Hence once the blade has been inserted along the minor dimension, the rod is then rotated such that its major dimension restricts detachment of the blade. Further to the two lateral gear arms 4, there is a central arm 6 that is threaded to the threaded nut 5 and free to rotate around its longitudinal axis within frame 1. The height of the central arm 6 is the same as the opening in frame 1 into which it is placed to thread onto threaded nut 5. Rotation of threaded nut 5 while threaded to central arm 6 results in translation of central arm 6 in either the proximal or distal direction. Each turning nut operates a different blade and when all are nuts are turned to one extreme, the retractor 10 is in the closed position (FIG. 65) and when they are turned to the other extreme, the retractor 10 is considered open (FIG. 67). Each individual blade 11 can be positioned anywhere within these extremes, independent of each other.

With reference to FIG. 67-70, the central arm 6 is connected to a radiolucent blade holder 73 by a worm gear mechanism 8, which allows for rotation of the radiolucent blade holder 73 in both the proximal and distal direction. This is achieved using a worm gear mechanism 8, whereby a threaded nut 12 is turned against a longitudinally toothed cylindrical part 13 that is connected to the blade holder 73. The threaded nut 12 is fixed from translation by pins 14. Turning the threaded nut 12 results in rotation of the toothed cylindrical part about a set axis 16. Rotation of the threaded nut 12 in clockwise and counterclockwise direction causes rotation of the blade holder 73 in either the proximal direction (FIG. 70) or distal direction (FIG. 69). The retractor 10 would typically be rigidly held such that the surrounding tissue conforms to the retraction rather than the retractor conforming to the surrounding tissue. The embodiment described above might thus provide for radiolucency (achieved through the use of radiolucent materials such as aluminum, carbon fire composites or other materials); unilateral blade retraction which can allow the user to selectively choose in which direction retraction is needed; easy disassembly for reprocessing and cleaning; angulation of all blades in both inward and outward direction; accommodation of multiple types and sizes of blades (for posterior, anterior, lateral access of lumbar, thoracic or cervical spine), etc.

Figure 72:
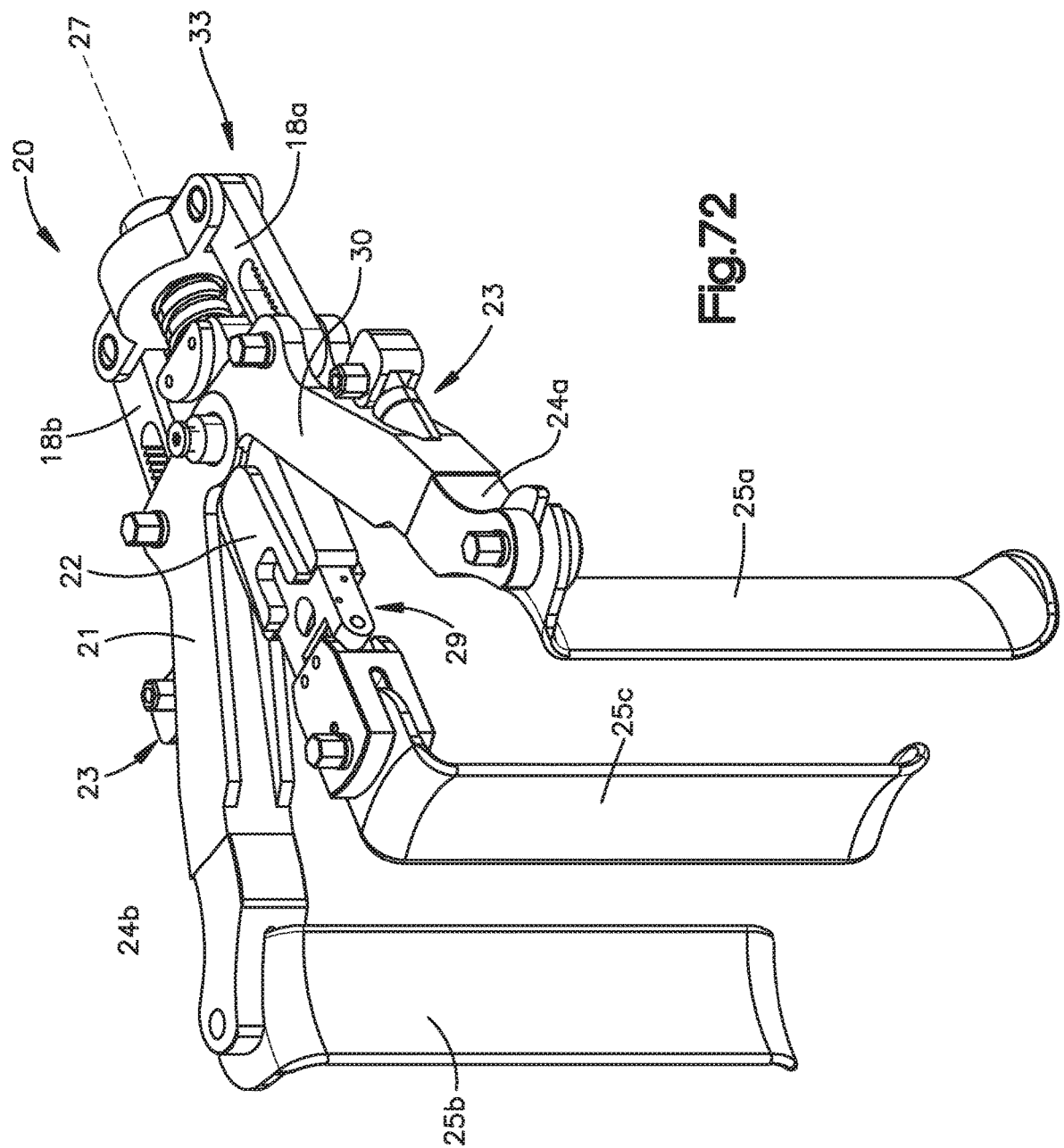
FIG. 72 is a perspective view of the surgical retractor illustrated in FIG. 71 with the blades in an open position.

With reference to FIGS. 71-74, a retractor 20 involves the use of a leadscrew mechanism 33 to provide bilateral retraction but also a geared mechanism on the lateral sides of the retractor to additionally offer unilateral retraction. In brief, the retraction 20 includes a cannulated leadscrew 31, which is pinned to a central body 22. It is free to rotate about axis 27 but is restricted from translation by these pins. The retractor 20 includes a first arm 21 and a second arm 30 each attached to the central body 22. These first and second arms 21 and 30 are connected to the central body 22 and to each other along a vertical axis 26. An indirect connection between the leadscrew 31 and each of the first and second arms 21 and 30 is achieved through a follower 37 and two lateral connection bars 18*a* and 18*b*. Upon rotation of the leadscrew 31, the follower 37 is forced to translate because it is threaded to the leadscrew 31. As the follower 31 translates, it pulls the connection bars 18*a* and 18*b*, which are fixed to the follower 31 and to the first and second arms 21 and 30 via pins that allow rotation. These connections allow for the translation of the follower 31 to be converted into bilateral expansion of the first and second arms 21 and 30. In other words, the rotation of the leadscrew 21 causes the first and second arms 21 and 30 to move from a first or closed position (FIG. 71) to a second or open position (FIG. 72). Further indirectly attached to the lateral arms are distal arms 24*a* and 24*b*, which are held by the blade rotation mechanism 23. To these distal arms 24*a* and 24*b*, the blades 25*a*, 25*b*, and 25*c*, are attached in a similar way as described in the embodiment shown in FIG. 65. The third, central arm 29 loosely fits into the central body 22. In order to achieve retraction of the central arm 29, it is connected to a central threaded bar 28, which is pinned to the central body independent of the leadscrew 31. This central threaded bar 28 is located along the longitudinal axis 27 of the leadscrew 31, which is cannulated. At the proximal end of the central threaded bar 28, there is a connection 32 for a driving device to achieve rotation. Rotation of the central threaded bar 28 causes translation of the central arm 29. A similar mechanism of angulation of the third blade 25*c* to that described in the embodiment shown in FIG. 65 is incorporated into this embodiment.

Figure 73:
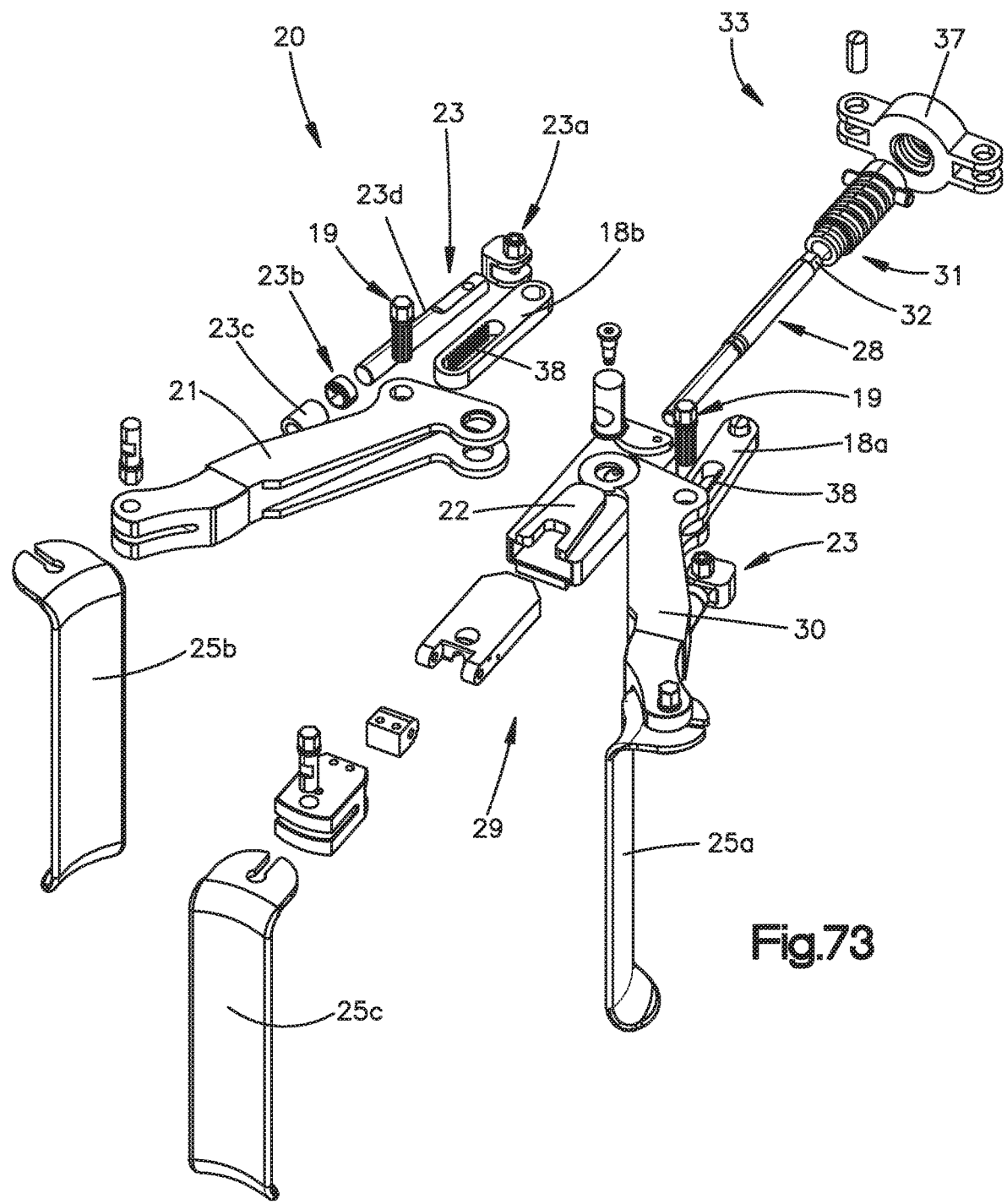
FIG. 73 is an exploded perspective view of the surgical retractor illustrated in FIG. 71.
Figure 74:
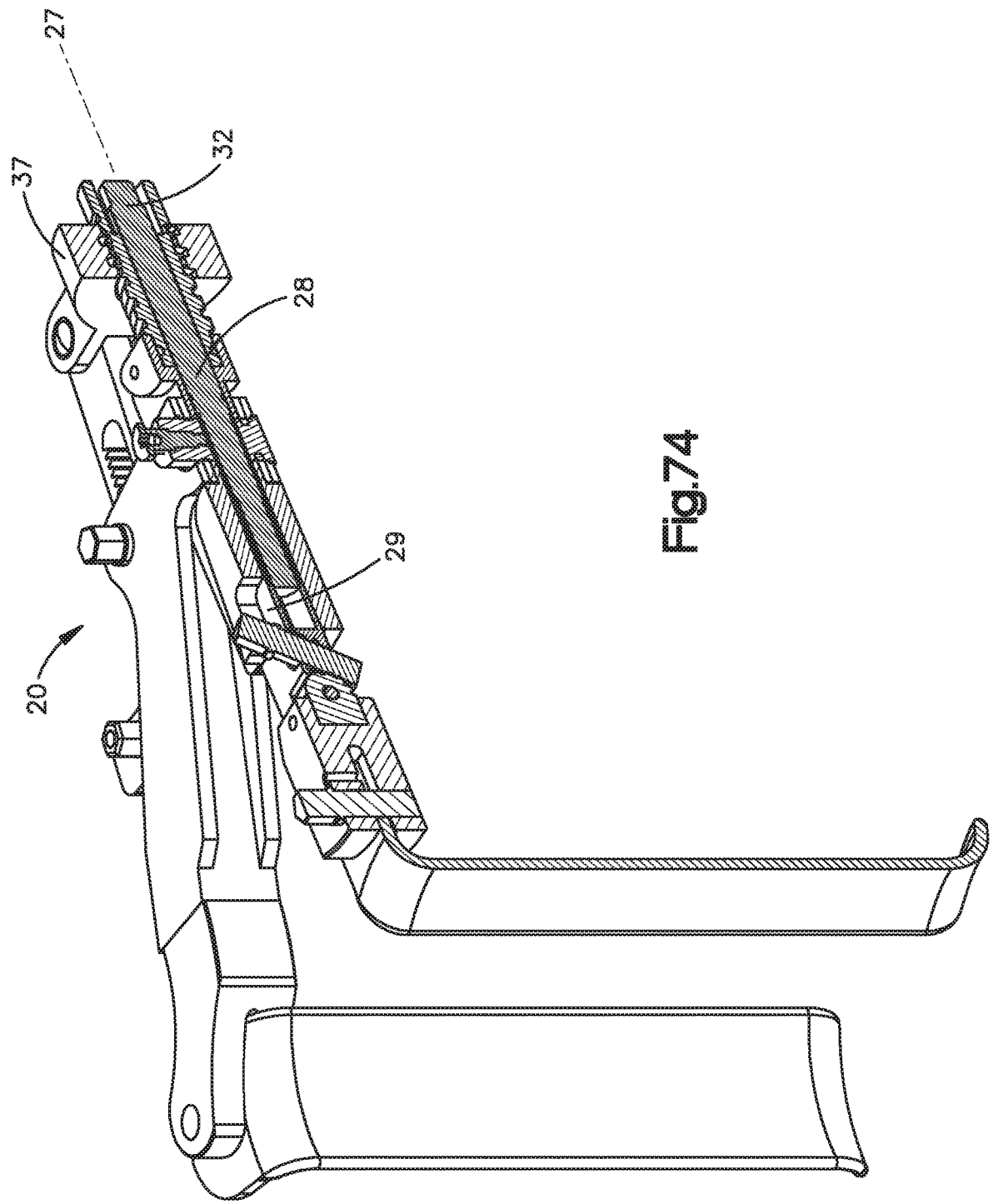
FIG. 74 is a sectional perspective view of the surgical retractor illustrated in FIG. 71.
Figure 75:
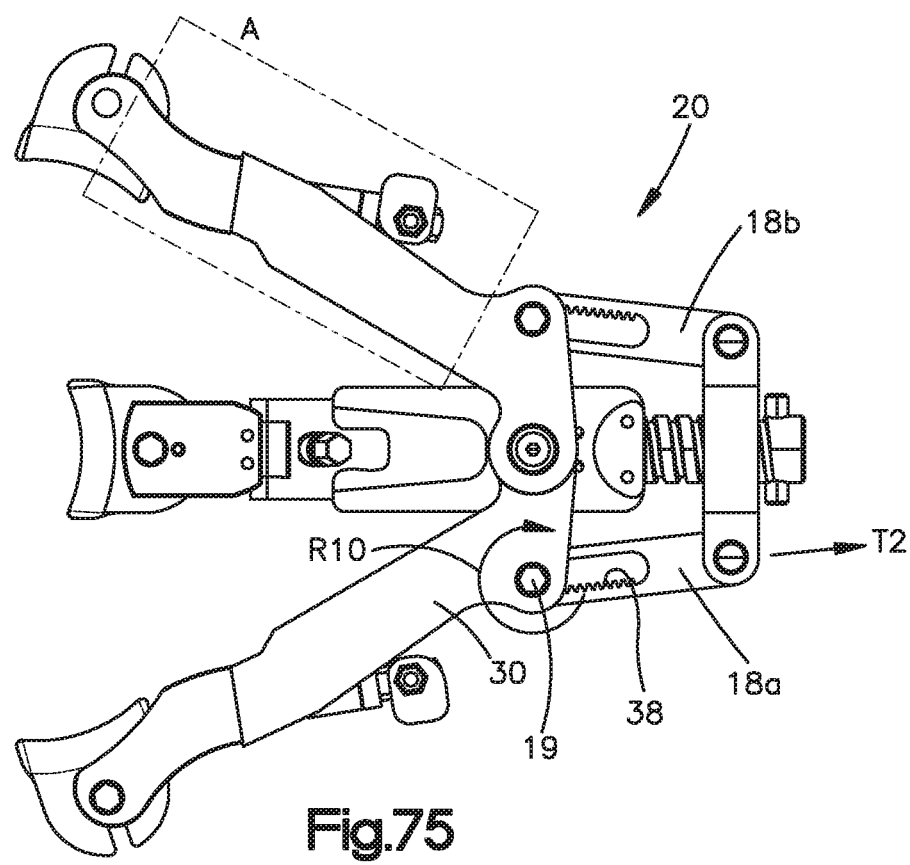
FIG. 75 is a top view of the surgical retractor illustrated in FIG. 71.

With reference to FIGS. 73 and 75, in addition to bilateral retraction, the retractor 20 allows for unilateral retraction of both lateral blades 25*a* and 25*b* independently. This is achieved using a rack and pinion mechanism located at the both junctions between the follower 37 and the connection bars 18*a* and 18*b*. The retractor 20 includes a rack or teeth 38 coupled between the follower 37 and the second arm 30. In addition, the retractor 20 includes a rotating member or pinion 19, such as a gear nut 19 configured mate with the rack or teeth 38. The rotation of the rotating member 19 causes the rotating member (19) to move along the second arm (30) in the direction indicated by arrow T2, thereby pivoting the second arm 30 independently of the first arm 21. Specifically, upon turning of the rotating member or pinion 19 (e.g. geared nut 19) in the direction indicated by arrow R10, it engages teeth or rack 38 of the internal surface of the connection bar 18*a* (or 18*b*). This causes translation of the connection bar 18*a* (or 18*b*) in the direction indicated by arrow T2, which in turn causes further retraction of the second arm 30 (or first arm 21) attached to it. This position is then locked using a ratchet or spring mounted mechanism.

The leadscrew mechanism 33 can include the leadscrew 31. The leadscrew mechanism 33 is configured to move the first arm 21 and the second arm 30 between the first and second position upon rotation of the leadscrew 31. The leadscrew mechanism 33 further includes the follower 37, which is connected to the leadscrew 31 and the first arm 21 and the second arm 30. The follower 37 is configured to move along the leadscrew 31 upon rotation of the leadscrew 31.

Figure 76:
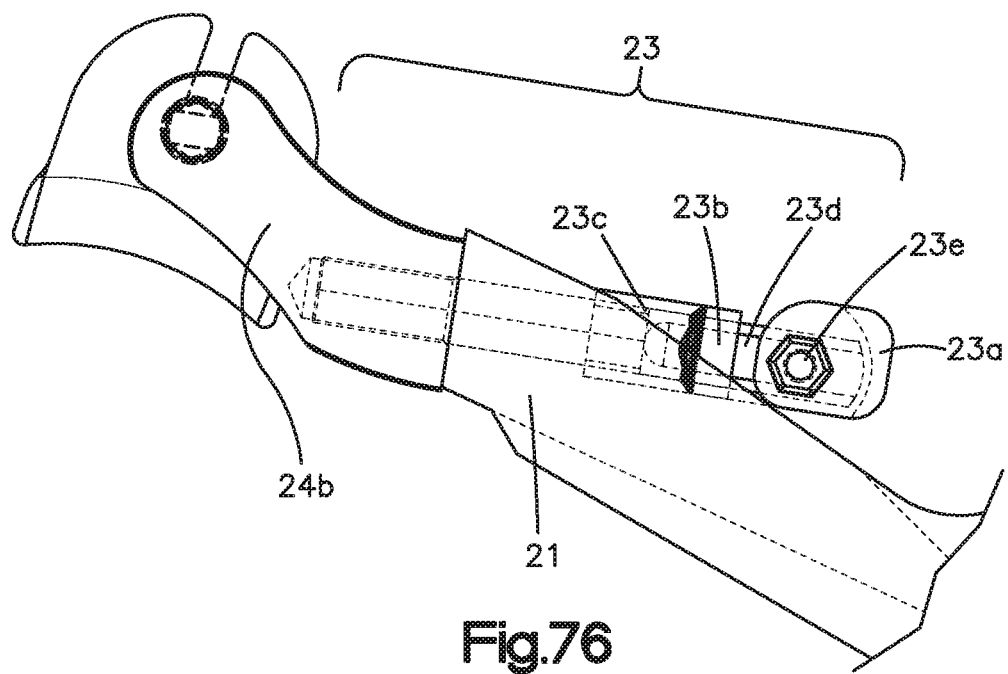
FIG. 76 is an enlarged top view of a portion of the surgical retractor illustrated in FIG. 71, taken around section A.
Figure 77:
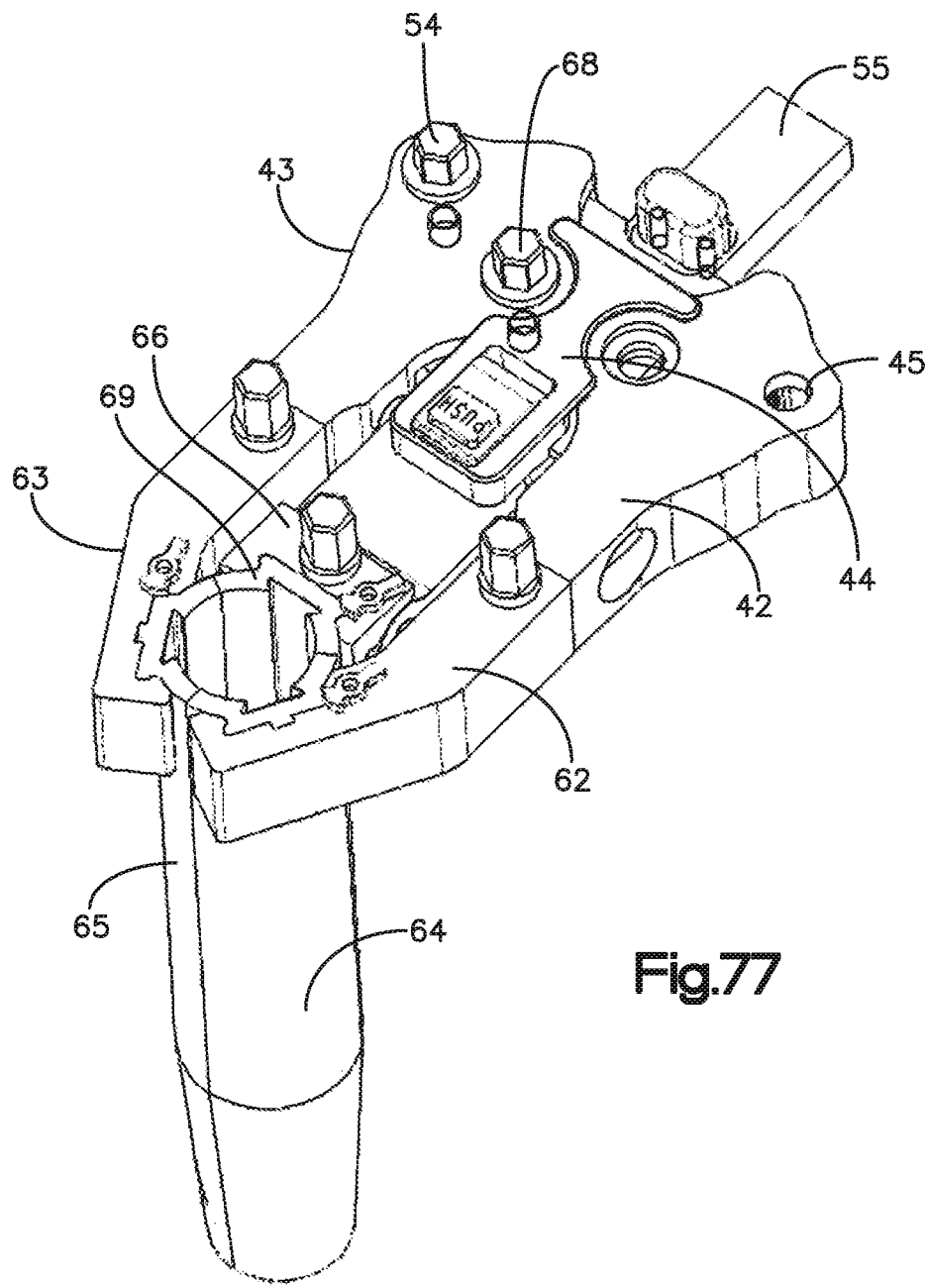
FIG. 77 is a perspective view of a surgical retractor in accordance with an embodiment of the present invention.
Figure 78:
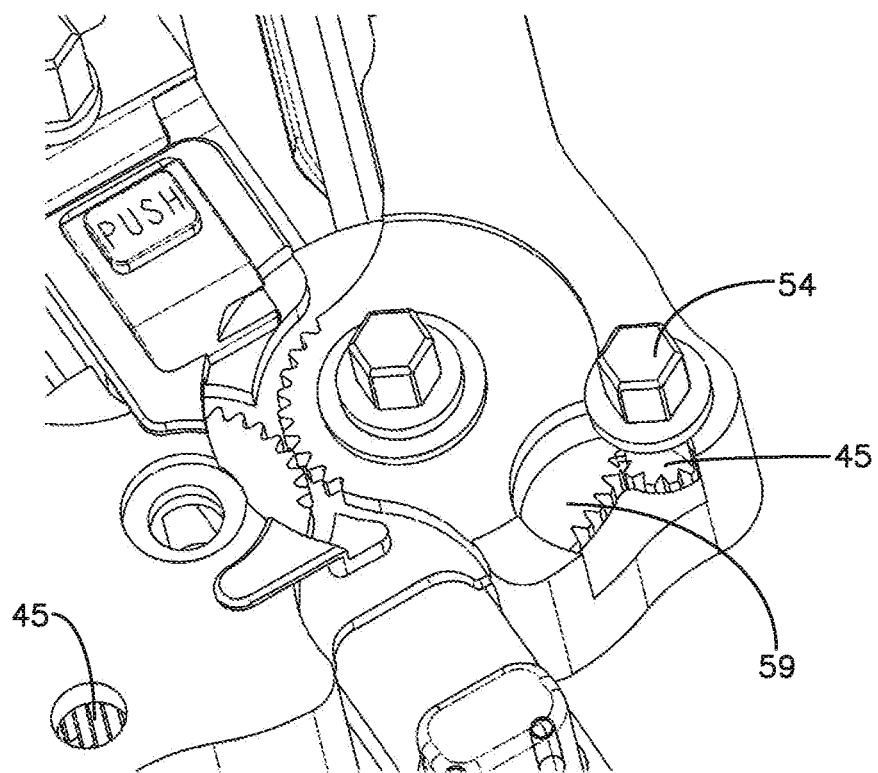
FIG. 78 is a perspective top cutout view of a portion of the surgical retractor illustrated in FIG. 77.
Figure 79:
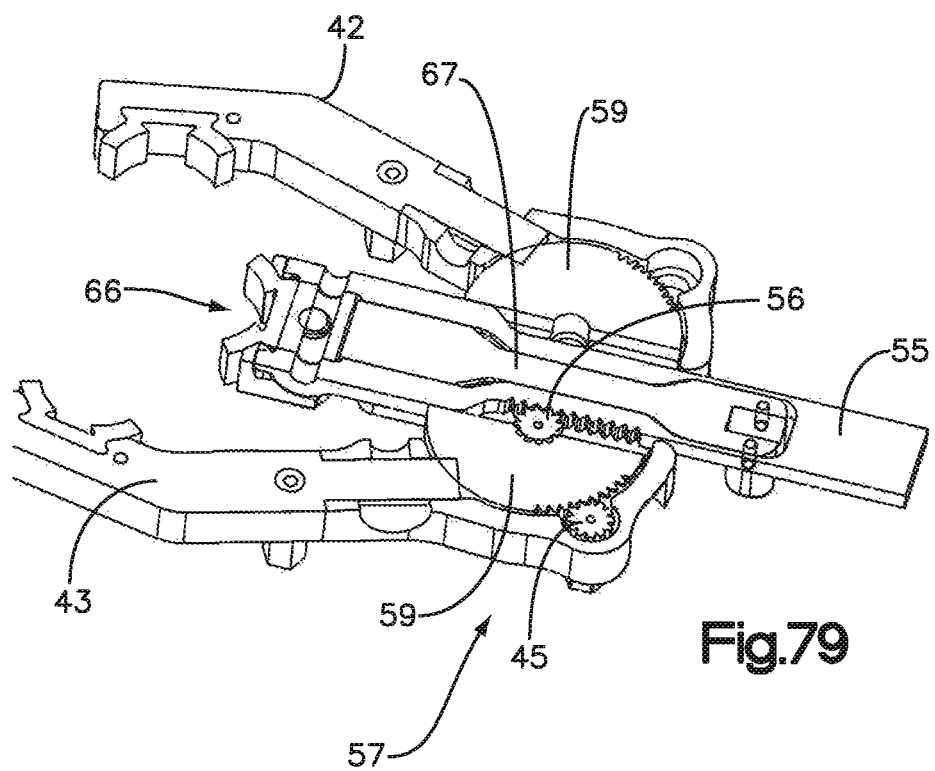
FIG. 79 is a perspective bottom cutout view of the surgical retractor illustrated in FIG. 77.

FIG. 76 illustrates one possible mechanism of blade rotation for the lateral arms 23. Briefly, a turning shaft 23*e* is rigidly connected to the distal arm 24*b*. This can be achieved through press fit and pinning or threading and gluing or any other method. This assembly is then fitted into the distal end of a hole in the first arm 21. Rigidly connected to the proximal end of the hole in the lateral arm 24b is a connector 23c (see also FIG. 73) with a toothed female conical feature on its proximal side. Then another connector 23b with a toothed male conical feature on its distal end is placed onto the proximal side of the turning shaft 23. Finally, a cam head 23a is attached to the proximal end of the turning shaft 23d. This can be achieved using a press fit pin which allows for rotation of the cam head 23a around the proximal end of the assembly. In order to achieve rotation, a driver is placed into the hexagonal driver interface 23e of the cam head 23a. This engaged driver is then used to indirectly turn the lateral blades via the turning shaft 23d. In order to lock the lateral arm 24b (or 24a) and associated blade 25b (or 25a), the driver is rotated to engage the cam head 23a onto the male connector 23b and cause a further engagement of the male and female connectors 23b and 23c respectively. The toothed conical surface of the connectors 23b and 23c prevents loosening or slipping of the blades when under lateral forces. The embodiment described above might thus provide for radiolucency at distal end to allow for better visualization under fluoroscopy; an option for bilateral and unilateral retraction of the lateral blades; accommodation of various types of blades (cervical, thoracic or lumbar) as well as various lengths of blades for different approaches; angulation of all blades inward and outward, etc.

Figure 80:
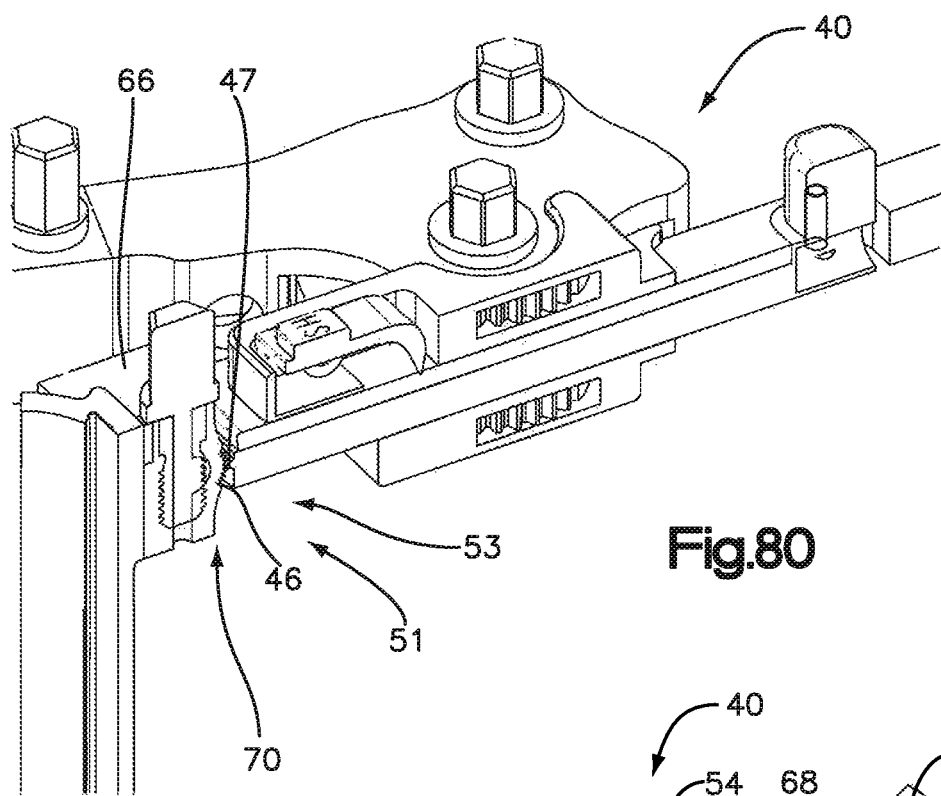
FIG. 80 is a perspective sectional view of a portion of the surgical retractor illustrated in FIG. 77.
Figure 81:
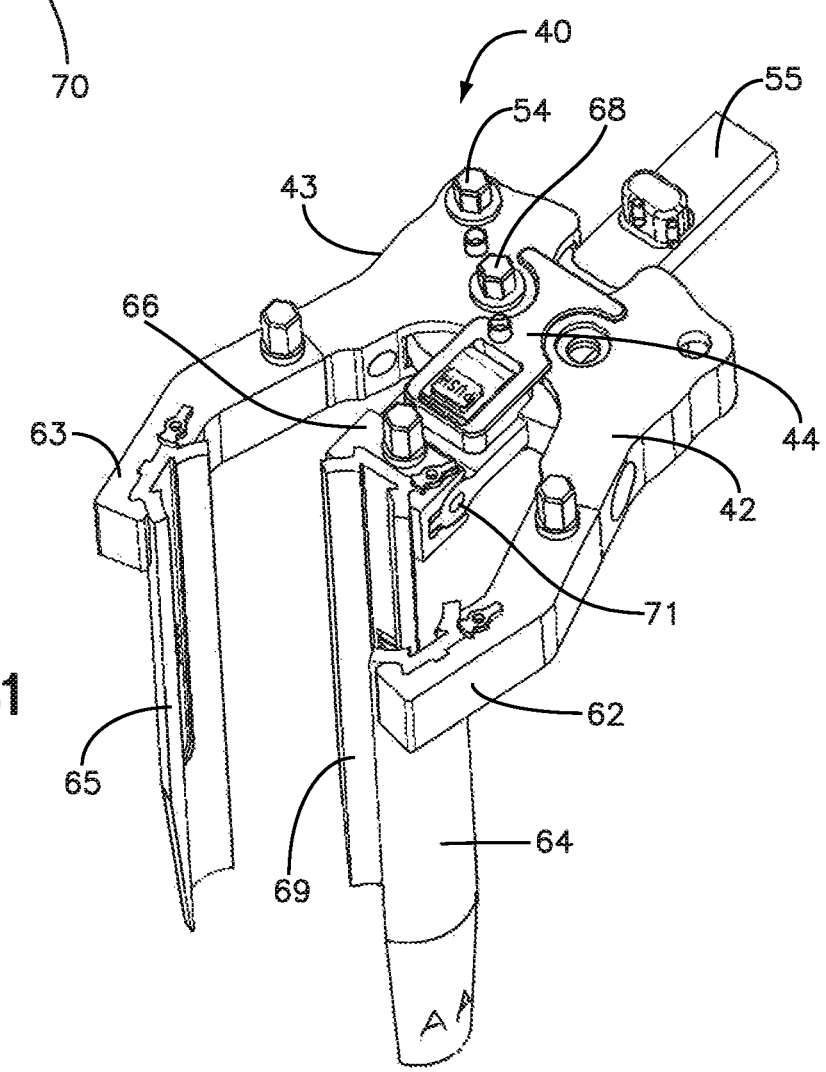
FIG. 81 is a perspective view of the surgical retractor illustrated in FIG. 77 with the blades in the open position.

With reference to FIGS. 77-81, in yet another embodiment, a gear mechanism is used which offers bilateral retraction. In brief, the retractor 40 includes geared arms 42 and 43, which are mounted onto a central body 44. The geared arms 42 and 43 are fixed to the central body 44 such that their gears mesh at the midline of the central body 44. At the posterior lateral portion of each geared arm 42 and 43, there is a gear wheel 45 with a socket connection 54. The gear wheel 45 is part of a ratchet mechanism. In operation, the gear wheel 45 meshes with a toothed part 59 located at the posterior lateral portion of the central body 44, FIG. 13). The toothed part 59 can have a substantially semi-circular shape and its teeth are located along an outer curved surface. The gear wheel 45 and the toothed part 59 together form the ratchet mechanism 57, which maintains the position of the geared arms 42 and 43 when retracted/rotated. Upon turning of the gear wheel 5, the entire geared arm 43 (or 42) is forced to rotate around its connection point to the central body 44. As the geared arm 43 rotates, it forces the opposing geared arm 42 to rotate. Thus, the rotation of the gear wheel 45 (via socket connection 54) causes the geared arms 42 to move from a first or closed position (FIG. 77) to a second or open position (FIG. 81). Blade holders 62 and 63 are attached to the distal ends of gear arms 42 and 43, respectively. Blade holder 62 is configured to hold and support a first blade 64, and blade holder 63 is configured to hold and support a blade 65. Hence, the rotation of the rotation of the gear wheel 45 (via socket connection 54) causes the first and second blades 64 and 65 to move away from each other from a first or closed position (FIG. 77) to a second or open position (FIG. 81).

The central geared arm 55 is connected to a blade holder 66. The blade holder 66 is configured to hold and support a central blade 69. In order to retract the third central geared arm 55 (and thus the central blade 69), a rack and pinion mechanism 67 is used. The rack and pinion mechanism 67 includes a gear wheel 56 with a socket connection 68. The gear wheel 56 is used as the connector between the central geared arm 55 and the central body 44. The geared wheel 56 functions as a pinion and, therefore, its rotation results in translation of the third central arm 55, which functions as a rack. Given that the central arm 55 is operatively connected to the central blade 69, the rotation of the geared wheel 56 (via socket connection 68) causes the blade 69 to move longitudinally between a first or distal position (FIG. 77) and second or proximal position (FIG. 81).

Central blade angulation is also controlled by a ratchet mechanism 70 which involves the release of the ratchet mechanism. The proximal end 51 of the blade holder 66 has a toothed cylindrical edge 46. A single tooth 47 protrudes from the distal end 53 of the central arm 55. The ratchet mechanism 70 includes the toothed cylindrical edge 46 of the blade holder 66 and single tooth 47 of the central arm 55. The central arm 55 is biased distally by any suitable biasing member, such as a spring, so that the tooth 47 engages the toothed cylindrical edge 46 as shown in FIG. 80. The central arm 55 can be moved proximally against the influence of the biasing member to disengage the protruding tooth 47. When the tooth 47 is disengaged from the toothed cylindrical edge 46, the blade holder 66 (along with the blade 69) can be manually rotated about at a fixed axis 71. The central arm 55 can be released to allow the biasing member to urge the tooth 47 distally, causing the tooth 47 to engage the toothed cylindrical edge 46. When the tooth 47 engages the toothed cylindrical edge 46, the ratchet mechanism locks the blade holder 66 (and the blade 69) in the prescribed position. The embodiment described above might thus provide for radiolucency at distal end to allow for better visualization under fluoroscopy; option for controlled bilateral retraction of the lateral blades; accommodation of various types of blades (cervical, thoracic or lumbar) as well as various lengths of blades for different approaches; angulation of all blades inward and outward, etc.

As another alternative, attachment of distraction pins to the arms rather than blades would allow the device to be used as a distraction tool in order to aid in interbody device placement. This would typically be more suited to open procedures.

Figure 82:
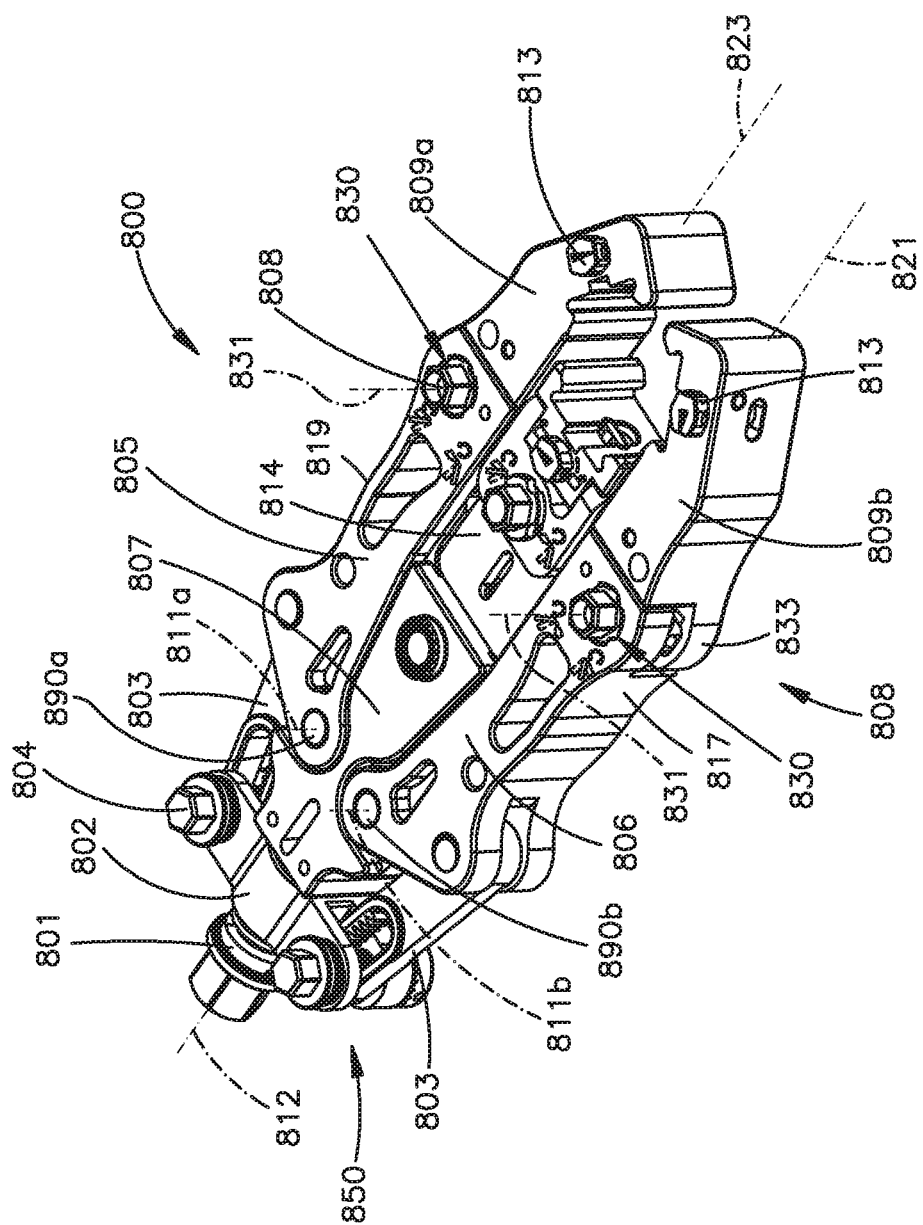
FIG. 82 is a perspective view of a surgical retractor in accordance with an embodiment of the present invention.
Figure 83:
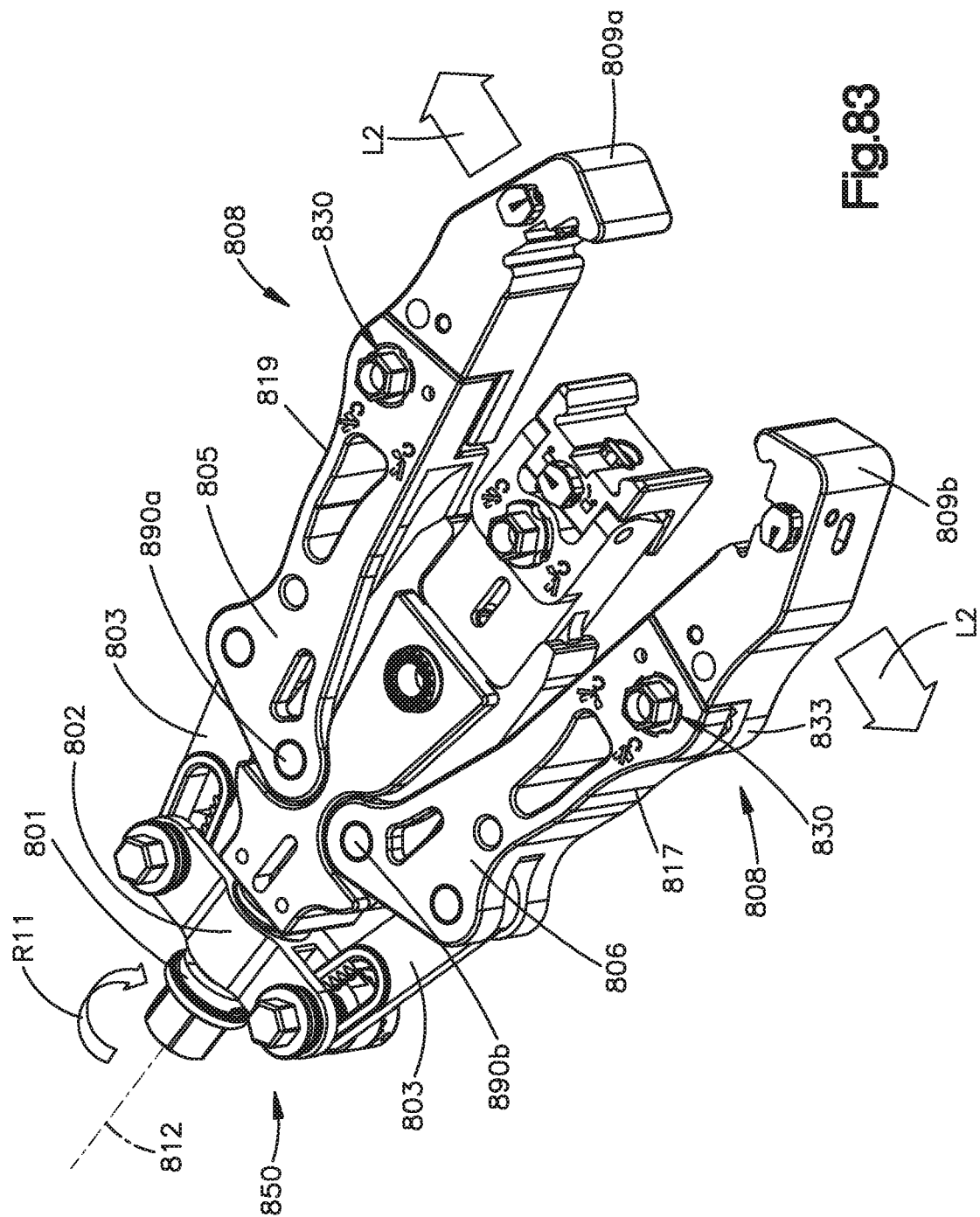
FIG. 83 is a perspective view of the surgical retractor illustrated in FIG. 82 with the movable arms in an open position.

With reference to FIGS. 82-83, a retractor 800 according to an embodiment of the present disclosures includes a first mechanism capable of performing bilateral tissue retraction and a second mechanism capable of performing unilateral tissue retraction. In the depicted embodiment, the retractor 800 includes a leadscrew mechanism 850 for bilateral tissue retraction and a geared mechanism for unilateral tissue retraction. The retractor 800 includes a cannulated leadscrew 801 coupled to a central body 807. The leadscrew 801 can be operatively connected to the central body 807 via a pair of pins and can rotate about an axis 812. However, translation of the leadscrew 801 is restricted by the pins. The retractor 800 further includes a first arm 806 and a second arm 805. The first arm 806 and the second arm 805 are attached to the central body 807. The first and second arms 806 and 805 are coupled to the lateral sides of the central body 807 along a vertical axis 811a and 811b. An indirect connection between the leadscrew 801 and each of the first and second arms 806 and 805 is provided through a follower 802 and two lateral connection bars 803.

The follower 802 has an inner thread (not shown) configured to mate with the outer threads of the leadscrew 801. Hence, upon rotation of the leadscrew 801 about axis 812, the follower 802 is forced to translate because the inner threads of the follower 802 mate with the outer threads of the leadscrew 801. As the follower 802 translates, it pulls a pair of connection bars 803a and 803b, which are fixed to the follower 802 and the first and second arms 806 and 805. The first and second arms 806 and 805 are pivotally connected to the connection bars 803a and 803b by a pair of pins 890a, 890, respectively. These connections allow for the translation of the follower 802 to be converted into bilateral expansion of the first and second arms 806 and 805. Specifically, the rotation of the leadscrew 801 about axis 812 in the direction indicated by arrow R11 causes the first and second arms 806 and 805 to move simultaneously away from each other in the direction indicated by arrows L2 from a first or closed position (FIG. 82) to a second or open position (FIG. 83).

The leadscrew mechanism 850 includes the leadscrew 801). The leadscrew mechanism 850 is configured to move the first arm 806 and the second arm 805 between the first and second position upon rotation of the leadscrew 801. The leadscrew mechanism 850 further comprises the follower 802, which is connected to the leadscrew 801 and the first arm 806 and the second arm 805. The follower 802 is configured to move along the leadscrew 801 upon rotation of the leadscrew 801.

Figure 84:
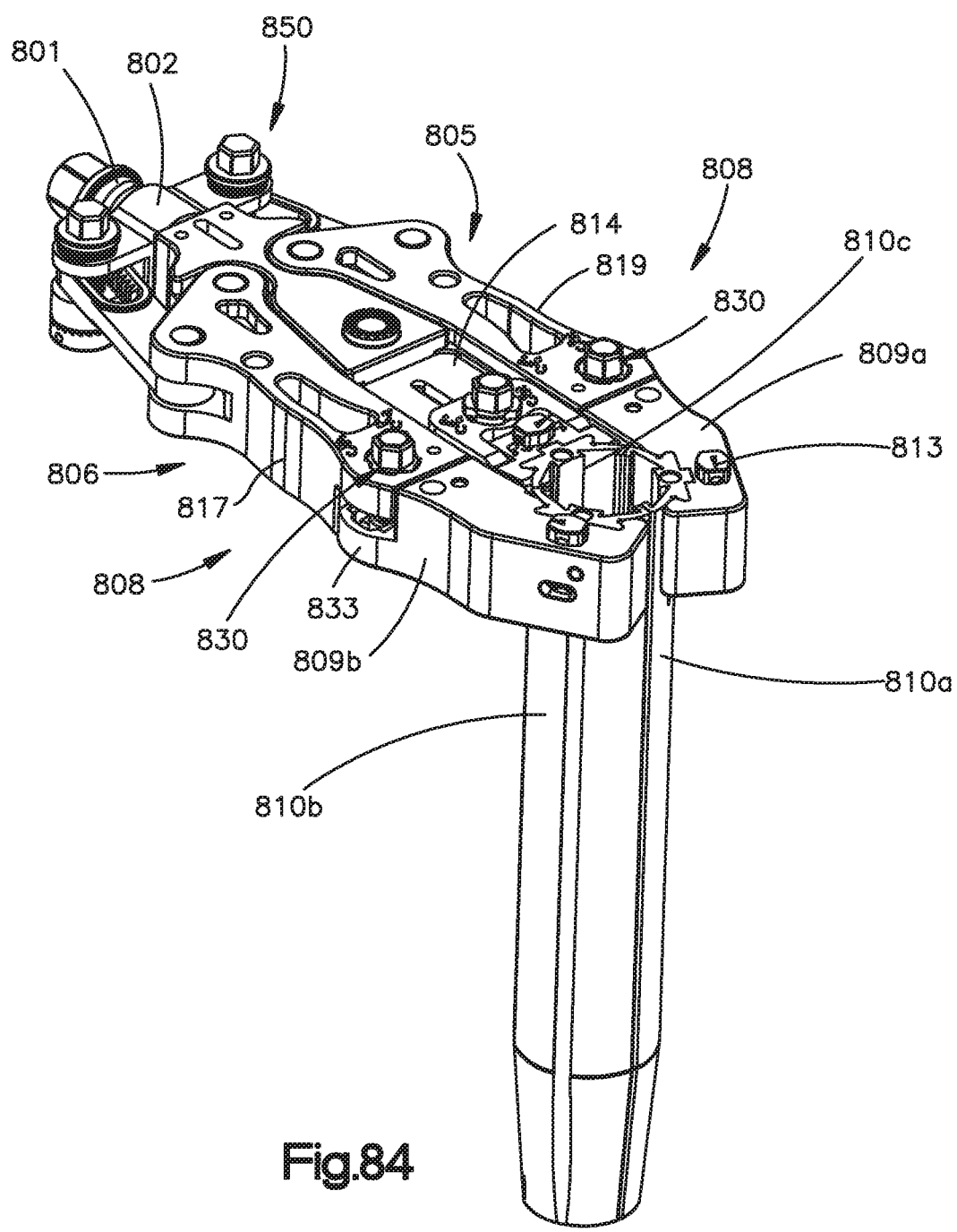
FIG. 84 is a perspective view of the surgical retractor illustrated in FIG. 84, showing blade holding a plurality of blades.

With reference to FIG. 84, the first arm 806 includes a proximal portion 817 and a distal portion 809b configured to retain a first retractor member 810b, such as a blade. The second arm 805 includes a proximal portion 819 and a distal portion 809a configured to retain a second retraction member 810a, such as a blade. An angulation mechanism 808 rotatably connects the proximal portion 817 to the distal portion 809b. The distal portion 809b is configured to rotate relative to the proximal portion 817 about a first axis 821. Another angulation mechanism 808 rotatably connects the proximal portion 819 to the distal portion 809b. Both angulation mechanism 808 include a rotating member 830 substantially similar or identical to the rotating member 418 depicted in FIGS. 11A-12. Each rotating member 830 is configured to rotate about a second axis 831. The distal portion 809b is configured to rotate about an axis 823. The angulation mechanism 808 is substantially similar or identical to the angulation mechanism 416 depicted in FIGS. 11A-12C. As seen in FIG. 84, retractor members 810a and 810b to distal arms 809a and 809b, respectively via a blade attachment mechanism 813. Similarly, the blade 10c is attached to the third arm 814 using a blade attachment mechanism 813.

Figure 87:
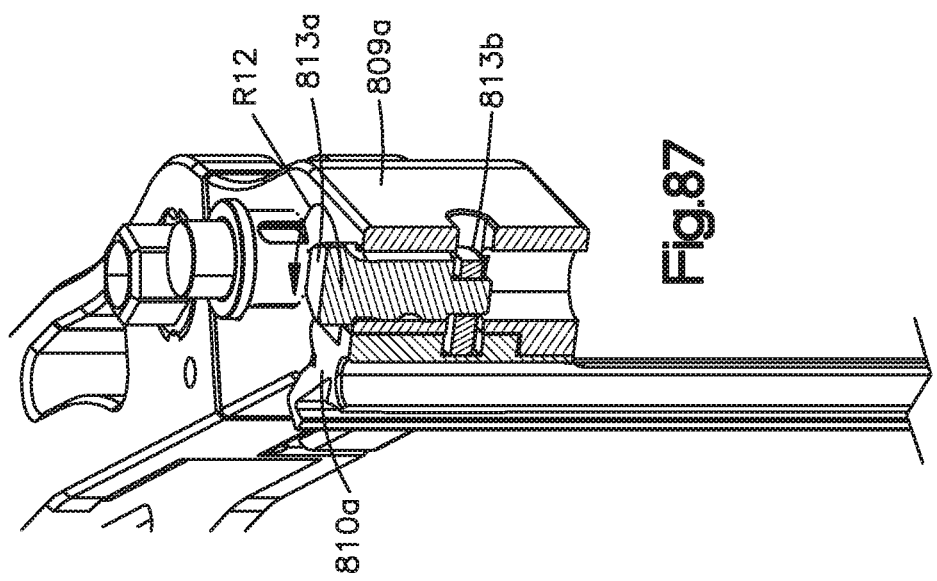
FIG. 87 is a perspective front sectional view of the distal portion of the surgical retractor as shown in FIG. 85 with the blade attached to the retractor.
Figure 86:
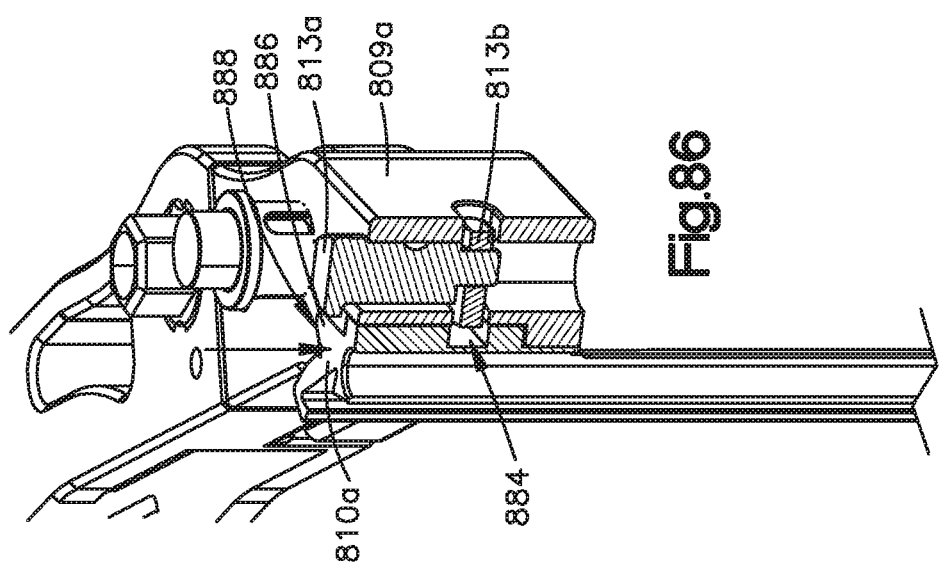
FIG. 86 is a perspective sectional view of the distal portion of the surgical retractor as shown in FIG. 85 with the blade mounted (but not attached) to the retractor.
Figure 85:
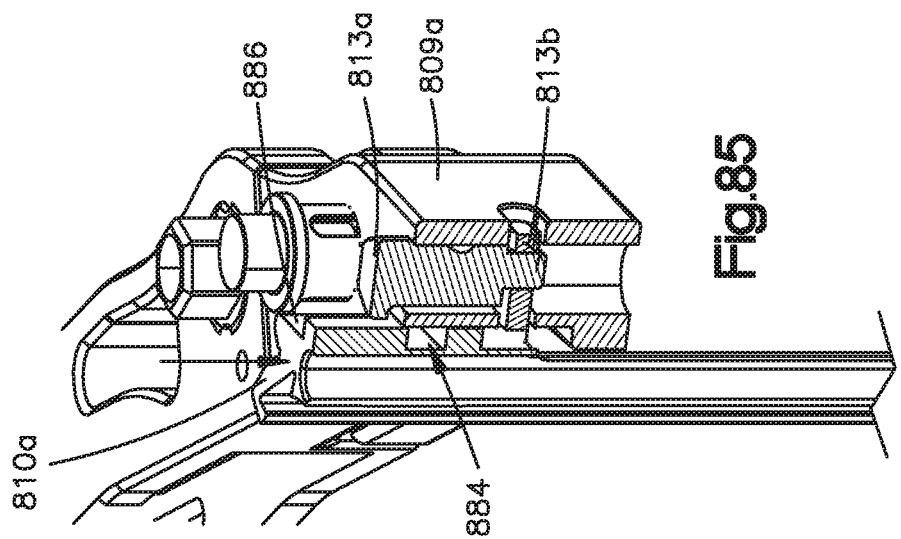
FIG. 85 is a perspective sectional view a distal portion of the surgical retractor illustrated in FIG. 84 while a blade is attached to it.

With reference to FIGS. 85 and 86, a blade attachment mechanism 813 is configured to connect a retractor members 810a, 810b or 810c to the lateral arm 809a and 809b or a central arm 814. In the interest of brevity, only one blade attachment mechanism 813 is described in the present disclosure. However, all the blade attachment mechanisms 813 have the same structure. In the illustrated embodiment, the blade attachment mechanism 813 includes a cam 813a and a follower 813b. The follower 813b is operatively connected to the cam 813 such that rotation of the cam 813 causes translation of the follower 813b. The distal arm 809a has a slot 888 shaped and dimensioned to receive a connection member 886 protruding from an outer surface of the retractor member 810a. The connection member 886 has a recess 884 shaped and dimensioned to receive the follower 813b. To connect the blade 810 to the arm 809a, the connection member 886 of the retractor member 810a is inserted into the slot 888 of the arm 809 as seen in FIGS. 85 and 86. Then, the cam 813a is rotated in the direction indicated by arrow R12, thereby forcing the follower 813b to translate such that it positioned inside the recess 884 of the retractor member 810a as shown in FIG. 87. Once the follower 813b is positioned within the recess 884, the retractor member 810a locked to the arm 809a.

With reference to FIG. 88, the third, third arm 814 loosely fits into the central body 807. In order to achieve retraction, the third arm 814 is connected to a central threaded bar 815, which is pinned to the central body 807 independently of the leadscrew 801. The central threaded bar 815 is located along the longitudinal axis 812 of the cannulated leadscrew 801. A connection 816 adapted to be attached to a driving tool is provided at the proximal end of the central threaded bar 815. Any suitable driving tool can be attached to the connection 816 to rotate the central threaded bar 815. Rotation of the central threaded bar 815 about axis 812 causes translation of the central arm 814. Thus, upon rotation of the central threaded bar 815, the third arm 814 (along with the blade 810c attached to it) moves longitudinally from a first or proximal position to a second or distal position.

Figure 89:
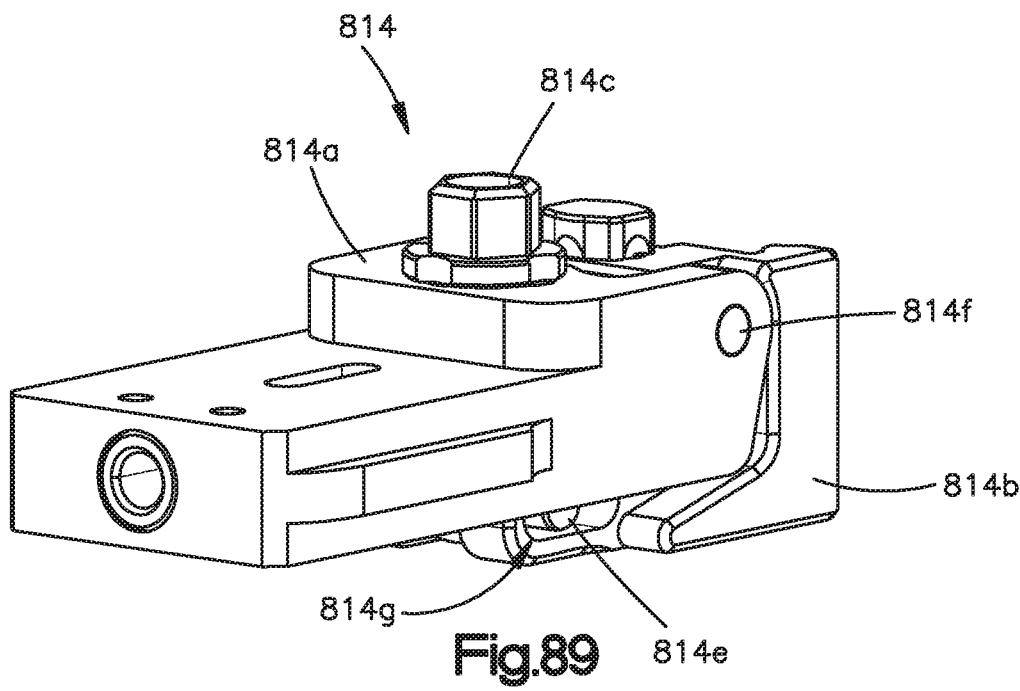
FIG. 89 is a perspective view of a central arm of the surgical retractor illustrated in FIG. 82.
Figure 90:
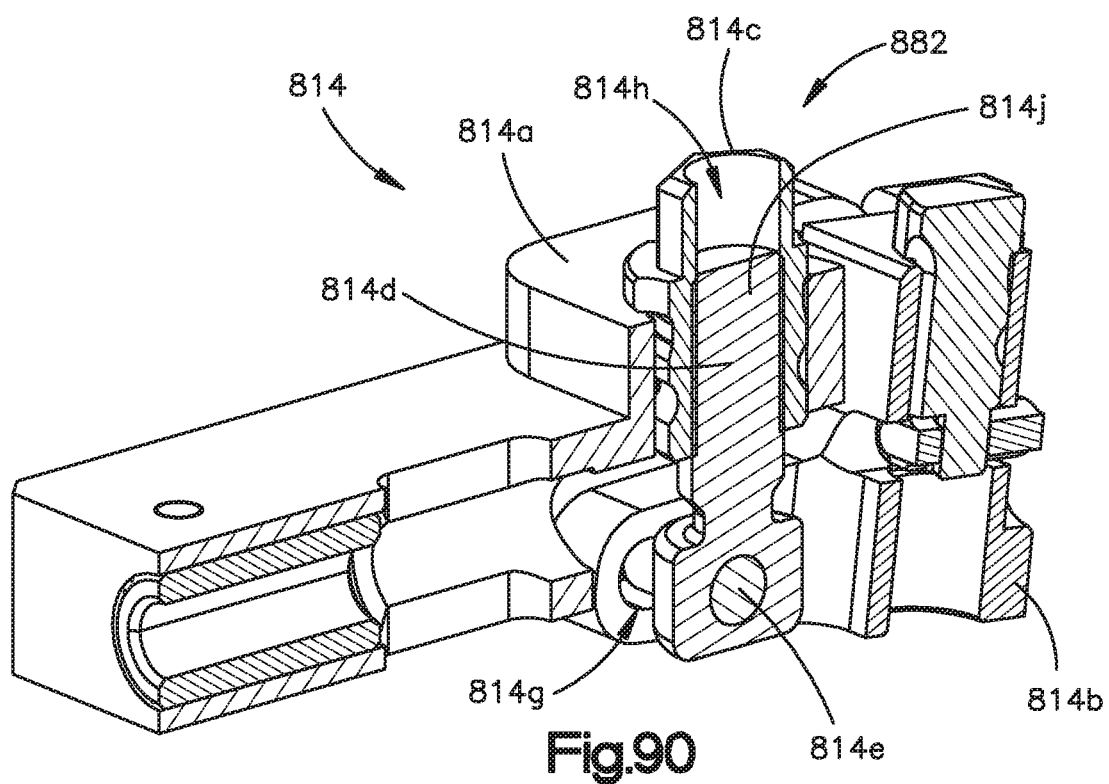
FIG. 90 is a perspective side sectional view of the central arm illustrated in FIG. 89.
Figure 92:
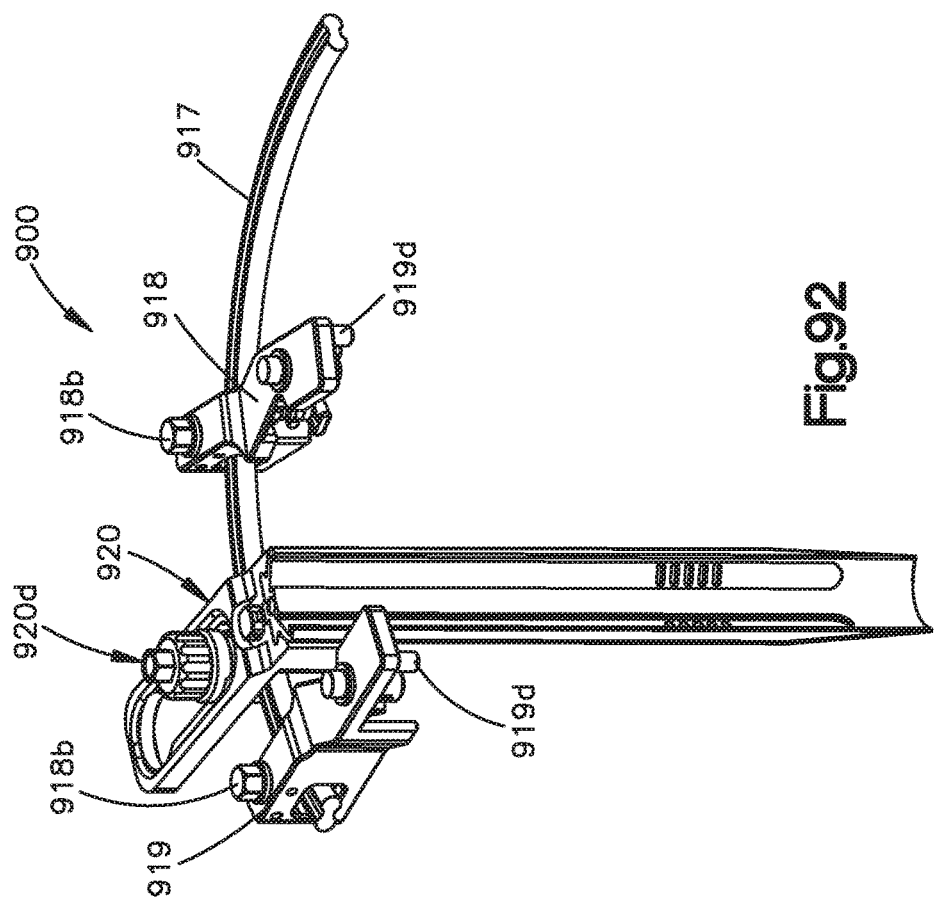
FIG. 92 is a perspective view of a blade assembly in accordance with an embodiment of the present invention.

With reference to FIGS. 89 and 90, a proximal portion 814a of the third arm 814 can be pivotally coupled to a third distal portion 814b, such as blade or retraction member holder, configured to hold a retractor member 810c, such as blade (FIG. 84). A blade angulation mechanism 882 includes a third rotating member 814c, such as a nut, a second translating member 814d, a transmission pin 814e, and a second pivot member or fulcrum pin 814f The translating member 814 can include a threaded shaft 814j. The third distal portion 814b of the third arm 814, which can be blade or retraction member holder, is adapted to retain retraction member, such as retractor members 810a, 810b, or 810c. The third proximal portion 814a can be part of the third arm 814 (FIG. 82) and is operatively connected to the third distal portion 814b via the second pivot member or fulcrum pin 814f The second pivot member or fulcrum pin 814f pivotally couples the third proximal portion 814a to the third distal portion 814b. Accordingly, the third distal portion 814b can pivot relative to the third proximal portion 814a about the pivot member or fulcrum pin 814f Pinned to the third distal portion 814b is the third rotating member or nut 814c. The third rotating member 814c has a threaded bore 814h. The third rotating member or nut 814c has inner threads (around the threaded bore 814h) adapted to mate with outer threads of a threaded shaft 814j of the translating shaft 814j. Thus, rotation of the third rotating member or nut 814c causes the second translating member 814d to translate along the length of the third rotating member or nut 814c. The second translating member 814d contains the transmission pin 814e, which protrudes on either side of the second translating member 814d such that it fits into the elongated slots 814g on the third distal portion 814b.

To achieve blade angulation, which is possible for all three blades, the same driving device as used for the third blade retraction is utilized. The driving device is used to rotate the third rotating member or nut 814c, which thereby results in the translation of the second translating member 814d due to the thread connection and its inability to rotate. As the second translating member 814d translates along the length of the third rotating nut 814c, the transmission pin 814e also translates concomitantly with the second translating member 814d. While translating, the transmission pin 814e applies a force on the third distal portion 814b that results in a moment generated about the second pivot member or fulcrum pin 814f, thereby causing the third distal portion 814b to angulate relative to the proximal portion 814a. The direction of angulation is controlled by the direction in which the third rotating member 814c is turned. Angulation can be achieved in both directions. Since a blade can be attached to the third distal portion 814b, the rotation of the third rotating member 814c also causes angulation of the attached blade relative to the third proximal portion 814a.

An additional benefit of the present embodiment of the retractor 800 is the ability to angulate one blade outwards (e.g. cranial) and the other inwards (caudal). This allows for an oblique access route to the spine which is useful in the lateral approach for lumbar segments L4-L5 where the iliac crest can be an obstacle to direct lateral access.

The third arm 814 comprises the third proximal portion 814a and the third distal portion 814b. The third distal portion 814b is configured to hold the third retraction member 810c. The third distal portion 814b is rotatably connected to the to the third distal portion 814b. The third rotating member 814c connects the third proximal portion 814a to the third distal portion 814b. The second pivot member 814f pivotally couples the proximal portion 814a and the third distal portion 814b. The rotation of the third rotating member 814c causes the third distal portion 814b to pivot about the second pivot member 814f The second translating member 814d comprises the threaded shaft 814j. The third rotating member 814c defines a threaded bore 814h configured to receive the threaded shaft 814j. The threaded bore 814h is sized to receive the threaded shaft 814j of the second translating member 814d. The second translating member 814d is configured to move along the threaded bore 814h upon rotating of the third rotating member, thereby causing the third distal portion 814b to pivot relative to the third proximal portion 814b about the pivot member 814f.

Figure 91:
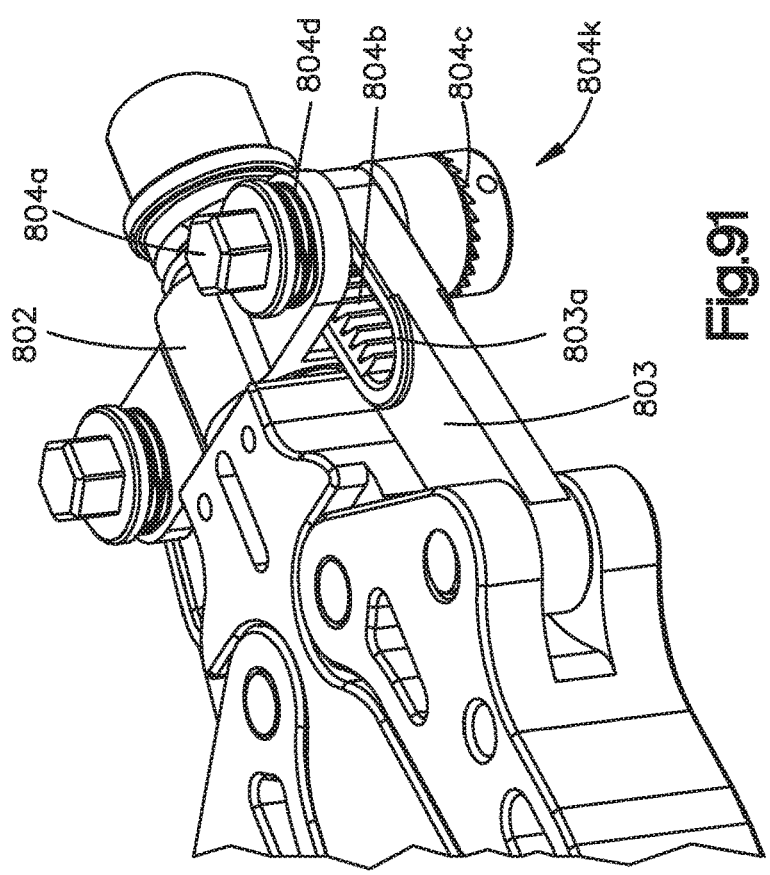
FIG. 91 is a perspective view of a proximal portion of the surgical retractor illustrated in FIG. 82.
Figure 93:
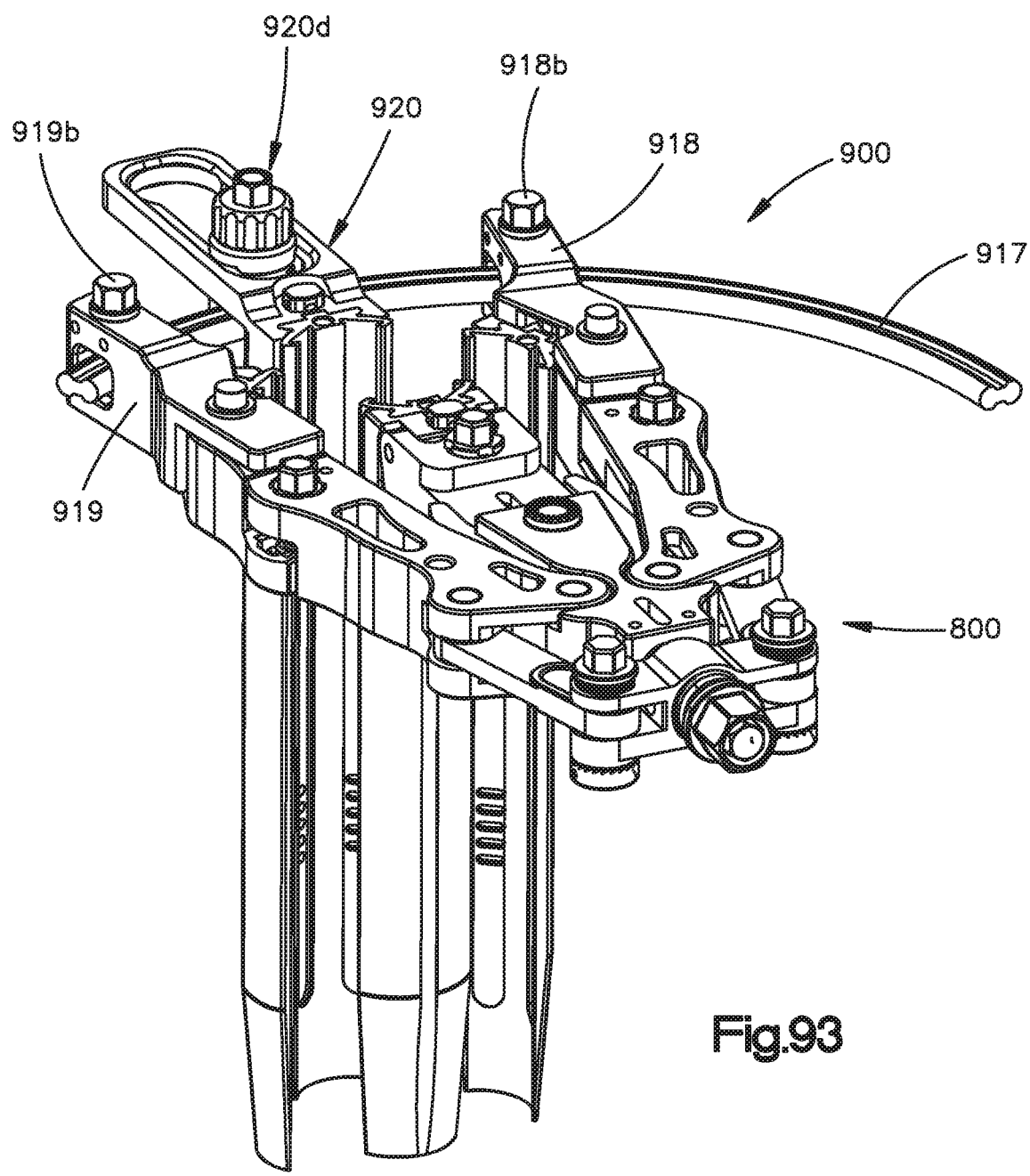
FIG. 93 is a perspective view of the blade assembly shown in FIG. 92 mounted to the surgical retractor illustrated in FIG. 82.
Figure 94:
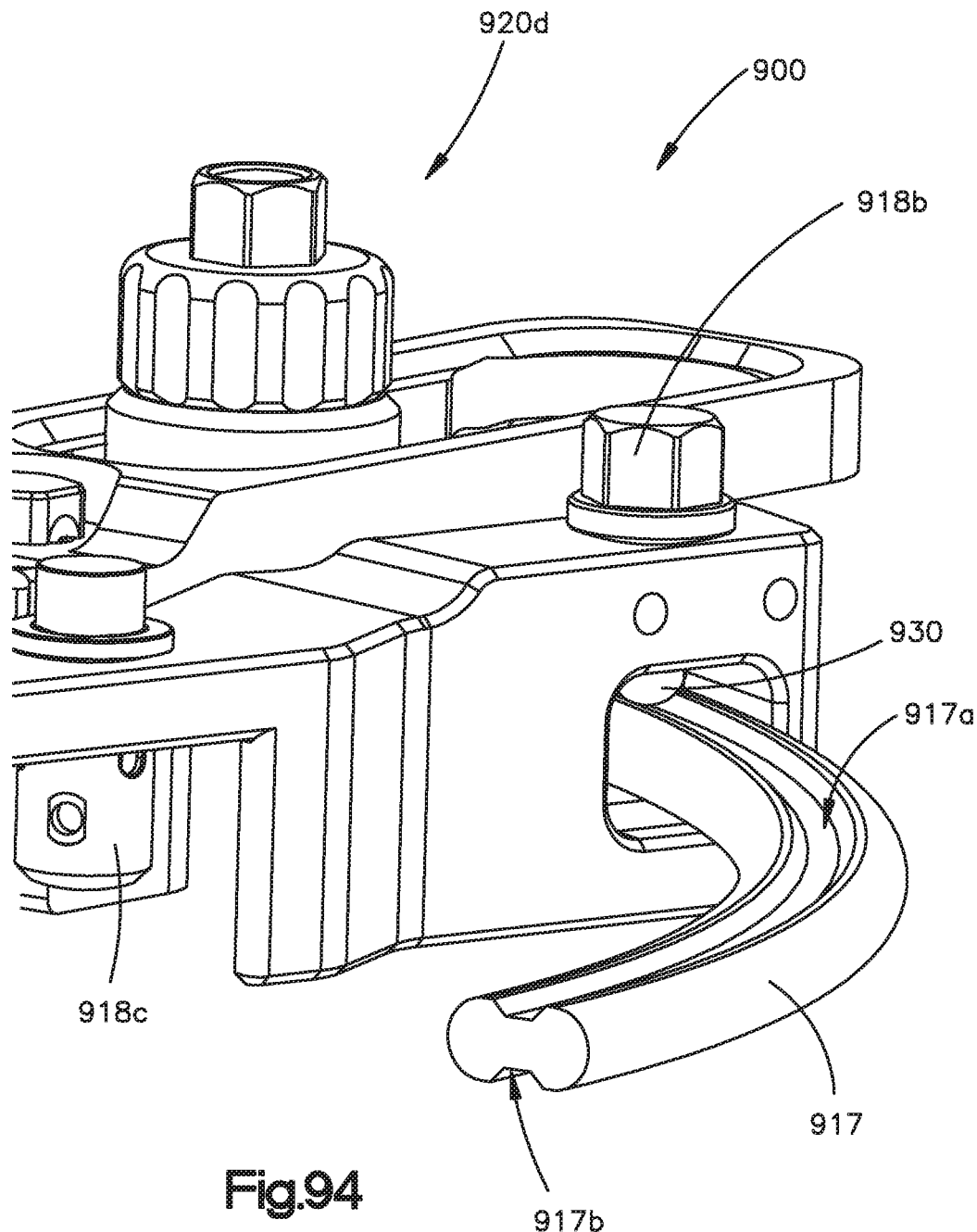
FIG. 94 is a perspective sectional side view of a portion of the blade assembly illustrated in FIG. 92.
Figure 95:
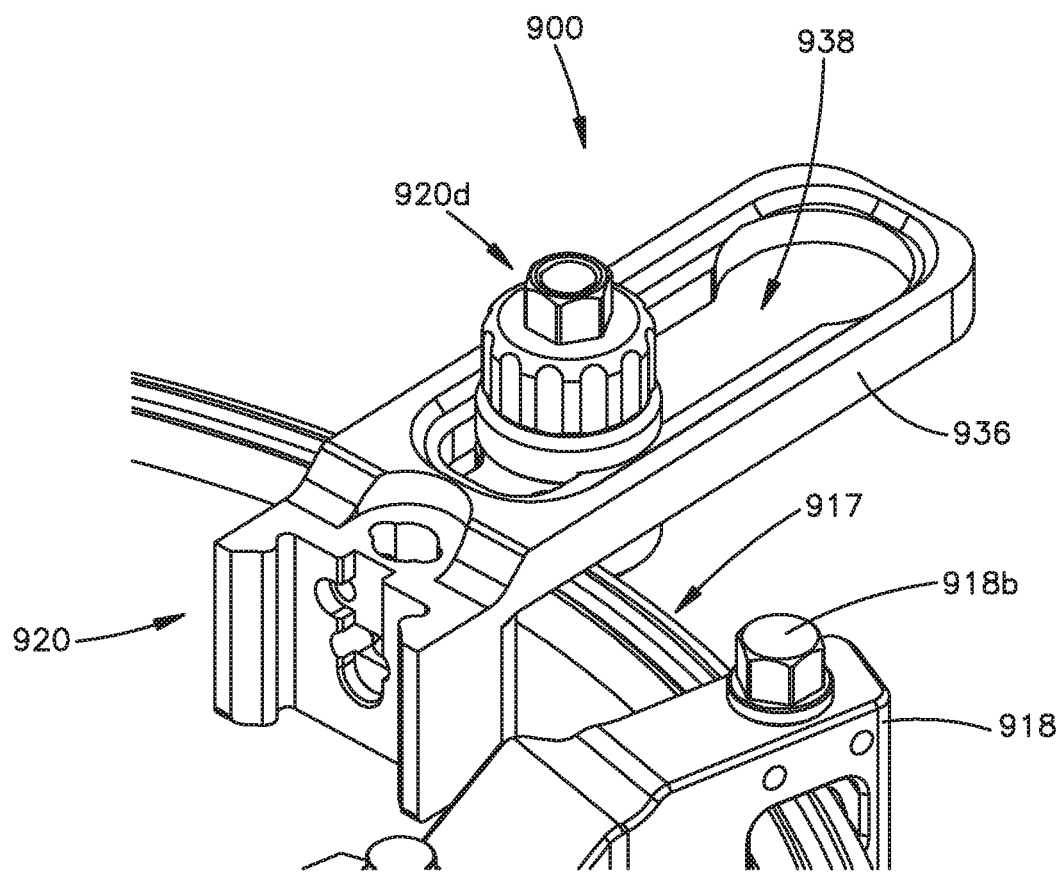
FIG. 95 is a perspective upper view of a portion of the blade assembly illustrated in FIG. 92.
Figure 96:
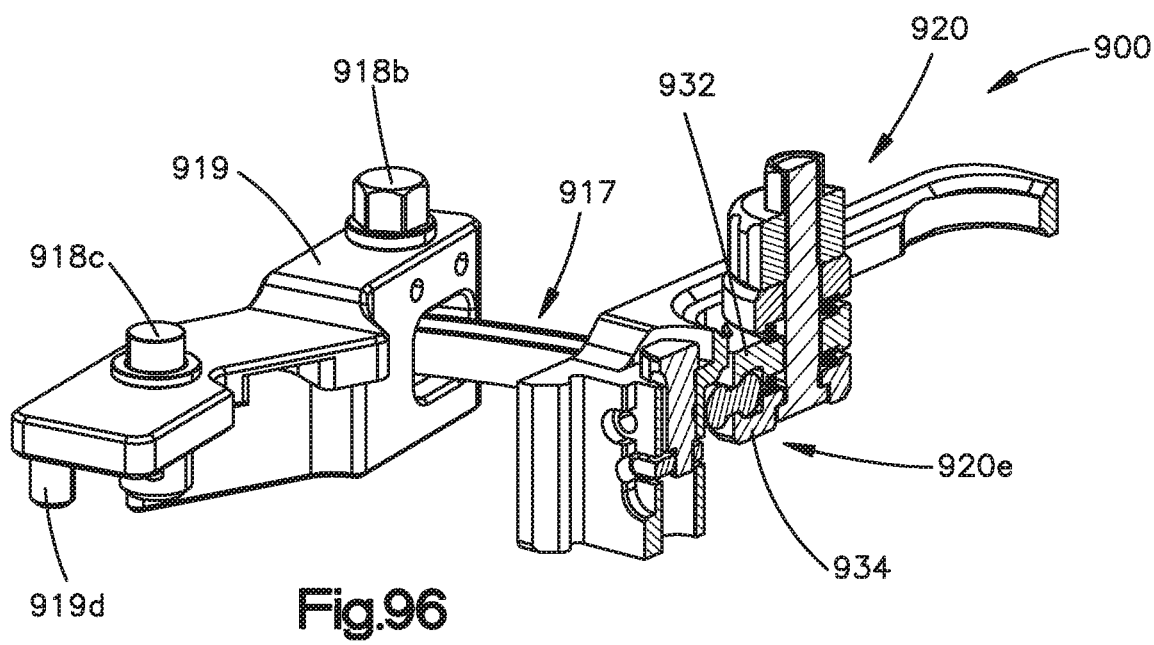
FIG. 96 is a perspective side sectional view of the blade assembly illustrated in FIG. 92.

With reference to FIG. 91, the present embodiment of the retractor 800 allows for independent unilateral retraction of lateral arms 809a and 809b (FIG. 82), which is achieved using a rack and pinion mechanism 804k located at both junctions between the follower 802 and the connection bar 803. The rack and pinion mechanism 804k includes a toothed shaft or pinion 804b and teeth 803a arranged along an inner surface of the connection bar 803. The teeth 803 collectively form the rack of the rack and pinion mechanism 804k. The toothed shaft 804b includes a head 804a adapted to be connected to a driving tool. Moreover, the toothed shaft 804b is operatively connected to a ratchet 804c. Upon turning of the pinion head 804a, the toothed shaft 804b engages the teeth 803a on the internal surface of the connection bar 803, which in turn causes further retraction of the lateral arm 809a or 809b (FIG. 82) attached to it. This position of the lateral arm 809a or 809b (FIG. 82) is then locked using a ratchet 804c and biasing member or spring 804d within the rack and pinion mechanism 804k. The biasing member 804d biases the ratchet 804c toward the toothed shaft 804b. When the ratchet 804c engages the toothed shaft 804b, it prevents the toothed shaft from rotating, thereby locking the position of the lateral arm 809a or 809b (FIG. 82).

The first arm 806 includes a proximal portion 817 and a distal portion 809b. The distal portion 809b is configured to retain the first retractor member 810b. The distal portion 809b is configured to rotate relative to the proximal portion 817 about the first axis 821. The second arm 805 is configured to retain the second retractor member 810a such that rotation of the distal portion 809b about the first axis 821 causes the first retractor member 810b to pivot toward or away from the second retractor member 810a when the first retractor member 810b and the second retractor member 810a are coupled to the first arm 806 and the second arm 805, respectively. The rotating member 830 is coupled between the proximal portion 817 and the distal portion 809b. The rotating member 830 is configured to rotate about a second axis 831, wherein rotation of the rotating member 830 about the second axis 831 causes the distal portion 809b to rotate relative to the proximal portion 817 about the first axis 821.

In operation, the rotation of the rotating member 830 about the second axis 831 biases a location of the distal portion 809b away from the proximal portion 817. The location 833 is offset from the first axis 821.

With reference to FIGS. 92-97, in addition to the three arms on the retractor, there is the possibility to attach a fourth blade using the fourth blade assembly 900. The fourth blade mechanism 900 includes a guide rail 917, a first or right attachment arm 918, a second or left attachment arm 919, and a blade holder 920. The guide rail 917 can be substantially curved I-beam having an adequate arc length to accommodate expansion of the retractor 800. Thus, the central portion of the I-beam shaped guide rail 917 defines an upper channel 917a and a lower channel 917b (see FIG. 94). The upper channel 917a is configured and sized to slidably receive a substantially spherical end 930 of a rotating member or nut 918b. Each arm 918 and 919 has a rotating member 918b attached to it. The arms 918 and 919 can therefore be moved along guide rail 917 because the ends 930 of the rotating members 918b can slide along the upper channel 917a of the guide rail 917. The substantially I-beam shape of the guide rail 917 also allows first and second clamping arms 932 and 934 (see FIG. 96) of the blade holder 920 to hold the guide rail 917. Specifically, the first clamping arm 932 can be at least partially disposed in the upper channel 917a (FIG. 94) and the second clamping arm 934 (FIG. 96) can be at least partially positioned in the lower channel 917b (FIG. 94) in order to clamp the guide rail 917 and therefore connect the blade holder 920 to the guide rail 917. The first and second clamping arms 932 and 934 collectively form a clamping assembly 920e.

Each of the arms 918 and 919 includes a first retaining member or pin 918c (FIG. 94) and a second retaining member or pin 919d (FIG. 96) each being adapted to be inserted in holes (not shown) of the surgical retractor 900 (FIG. 82). The retention member 919d can be used as a rotation stop, and the retention member 918c can be used to prevent the fourth blade assembly 900 from separating unintentionally from the retractor 800. This is achieved using a simple ball plunger mechanism known to persons experienced in the art. There is also the possibility to load a fifth and potentially a sixth blade if the situation requires so.

The blade 913 can be attached to the blade holder 920 in an identical manner to that used for the other blades described in the present disclosure. The blade 913 can be retracted by physically unlocking the blade holder 920 from the guide rail 917. A tightening knob or fixation member 920d is operatively attached to the clamping assembly 920 such that turning the tightening knob or fixation member 920d releases the clamping assembly 920e from the guide rail 917. Thus, the blade holder 920 can be released from the guide rail 917 by turning the tightening knob or fixation member 920d. The tightening knob or fixation member 920d disposed on a guide track 936. The guide track 936 has a slot 938 adapted to slidably receive at least a portion of the fixation member 920d. The fixation member 920d can therefore slide along the slot 938 of the guide track 936. After releasing the blade holder 920 from the guide rail 917, the blade 913 can be manually retracted by sliding the fixation member 920d along the slot 938. The fixation member 920d can then be tightened once the appropriate retraction has been achieved.

Figure 97:
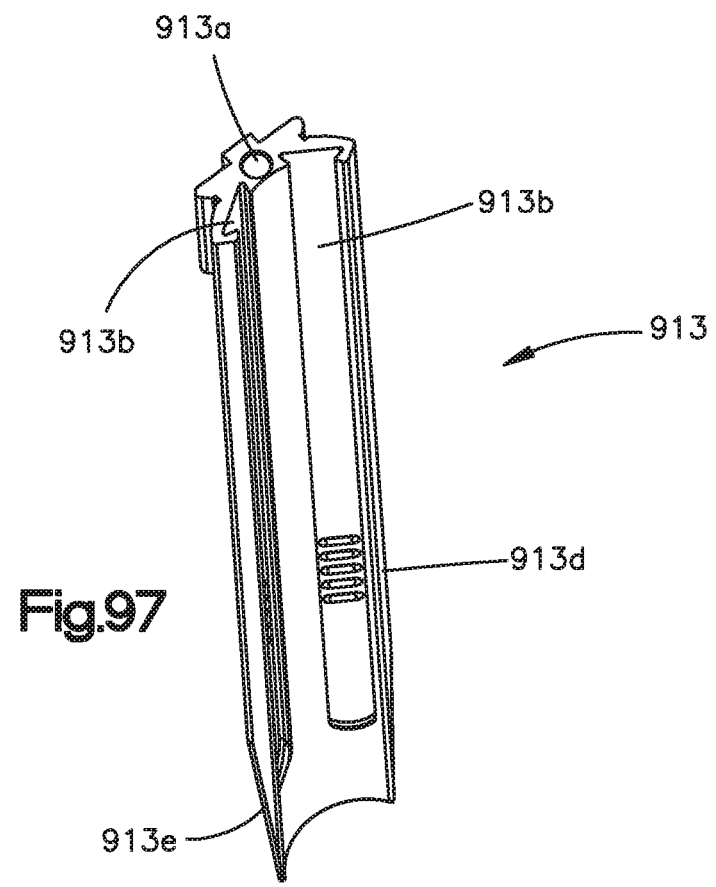
FIG. 97 is a perspective view of a blade of the blade assembly illustrated in FIG. 92.

With specific reference to FIG. 97, the blade 913 can be mounted to the retractor 800 or blade holder 920 using any of the blade attachment mechanisms described above. The blade 913 has a longitudinal bore 913a sized and configured to receive any suitable tool or instrument. For example, the hole 913 can receive a stimulating probe in order to check for neural activity in the vicinity of the blade 913. In order to prevent shunting of the stimulating current, the blade 913 can be wholly or partly made of a non-conductive material (e.g., carbon fiber, PEEK reinforced carbon fiber, PEEK, polymer coated aluminium, amongst others). The blades can be wholly or partly made of a radiolucent material to improve visibility under fluoroscopy.

Additionally, the blade 913 allow for the insertion of various accessories along two longitudinal slots 913b extending along its inner surface. The slots 913b can have a substantially dovetail shape. Any suitable accessory can be inserted through the slots 913b. Suitable accessories may include, but are not limited to, a light, blade extensions, interdiscal anchors, and bone anchors. The presence of two slots 913b per blade allows for multiple accessories to be introduced. In order to retain the accessories, recesses or indentations 913d are formed on an inner surface of the blade 913 along one or more slots 913b. In order to minimize tissue disruption at the spine, the blade 913 cha have a distal tapered tip 913e.

Some additional advantages provided by the present embodiment of the retractor 11 include radiolucency at distal end that allows for better visualization under fluoroscopy, radiolucent blades, the option for bilateral and/or unilateral retraction of the lateral blades, accommodation of various types of blades (such as cervical, thoracic, and lumbar) as well as various lengths of blades for different anatomical approaches, the ability of each blade to angulate both inwards and outwards, the ability to provide oblique access via the angulation of one blade outwards and another blade inwards, the use of a single driver instrument to achieve all adjustments to the retractor 100, the ability to incorporate a fourth blade if desired, the ability to utilize additional instruments within the blade including, but not limited, to a light, blade extensions, and irrigation, and the ability to use a neuromonitoring probe through the blade to assess neural activity in the vicinity of the blades.

The arms 809a and 809b (FIG. 82) can also include the angulation mechanism 416 described in above with respect to FIGS. 11A-12C in order to angulate the blades attached to those arms.

Figure 98:
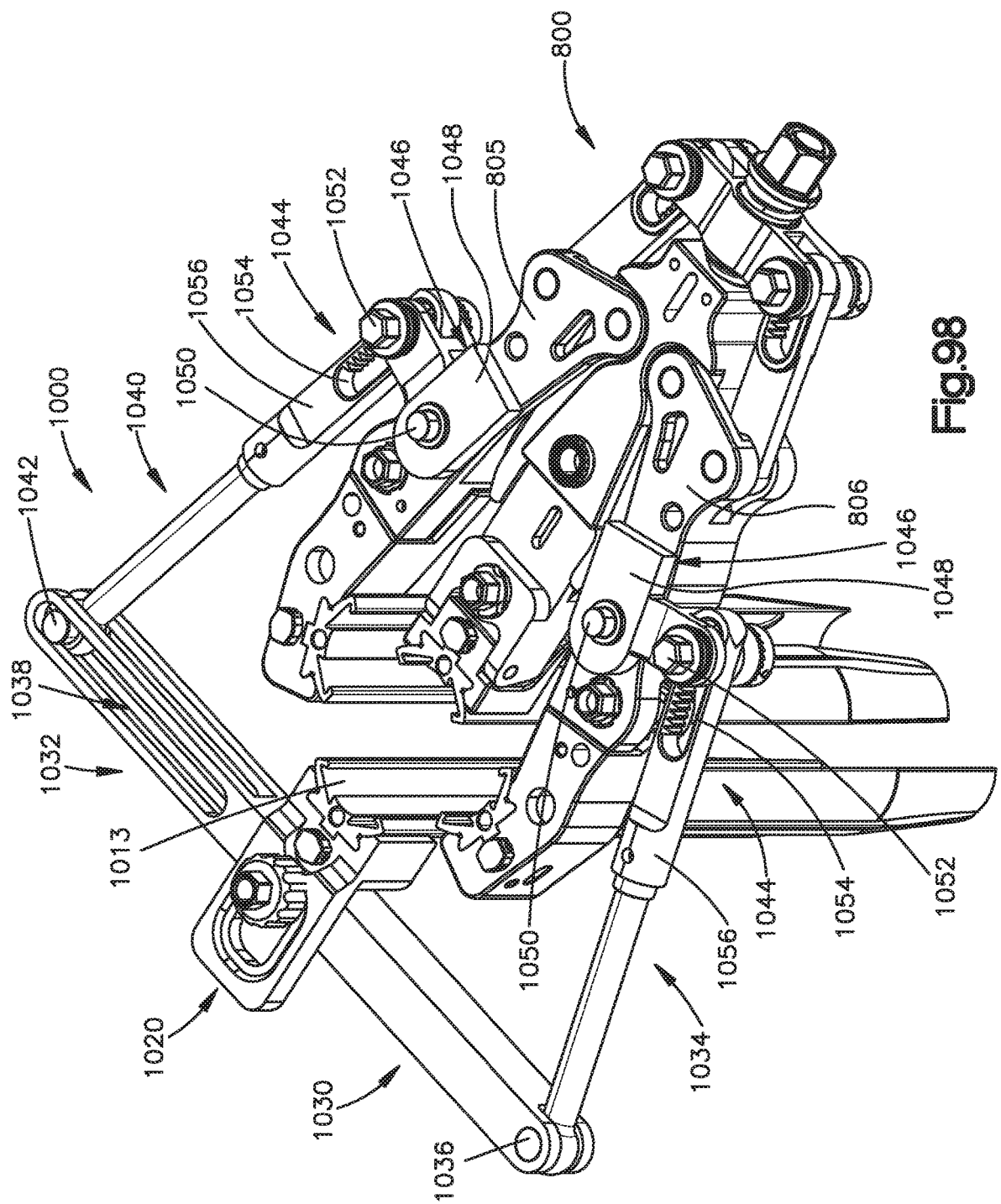
FIG. 98 is a perspective view of a blade assembly mounted to the surgical retractor illustrated in FIG. 82.

FIG. 98 illustrates an alternative embodiment of a blade assembly 1000 adapted to be mounted to retractor 800 or any other suitable retractor. The blade assembly 1000 includes a blade holder 1020 substantially similar (or identical) to the blade holder 920 shown in FIG. 93. The blade holder 920 is configured to hold a blade 1013 as described above with respect to FIG. 93 and is coupled to a connection bar 1028. The connection bar 1028 has a first portion 1030 positioned on one side of the blade holder 1020 and a second portion 1032 disposed on the opposite side of the blade holder 1020. The first portion 1030 is substantially pivotally connected to a first arm 1034 by a pivot member 1036, such as a pin. The first arm 1034 can therefore pivot about pivot member 1036 relative to the first portion 1030 of the connection bar. The second portion 1032 of the connection bar 1030 has a slot 1038 and is pivotally and slidably connected to a second arm 1040. The second arm 1040 includes a connection member 1042, such as a pin, slidably disposed in the slot 1038 of the second portion 1032 of the connection bar 1030. Accordingly, the connection member 1042 of the second arm 1040 can slide along the second portion 1032 of the connection bar 1030.

Each of the first and second arms 1034 and 1040 includes rack and pinion mechanism 1044 configured to be attached to a corresponding first and second 806 and 805 of the retractor 800. Each rack and pinion mechanism 1044 can include a lateral arm connector 1046 configured to be coupled to a first or second arm 806 or 805. The lateral arm connector 1046 can include a plate 1048 adapted to be placed on top of the first or second arm 806 or 805 and a retaining member 1050 configured to be securely received within an opening (not shown) of the first or second arm 806 or 805.

Each rack and pinion mechanism 1044 can be substantially similar to the ratchet mechanism 804k shown in FIG. 91 and generally includes a geared rotating member or pinion 1052 and a rack 1054 (i.e., teeth) formed along an inner portion of a connection bar 1056. The connection bar 1056 is adapted to move upon rotation of the pinion 1052. Specifically, when rotated, the pinion 1052 engages the rack 1054, causing the connection bar 1056 to move proximally or distally depending on the direction of rotation of the pinion 1052.

The slot 1038 of the connection bar 1030 allows expansion of the blade assembly 1000. Rotation of the pinion 1052 results in translation of the arm 1040 or 1034, which in turn results in retraction of the blade 1013 attached to the blade holder 1013. There exists the ability to load a fifth blade and sixth blade if the situation requires so.

Some advantages of the present embodiment with respect to the previous embodiment include the ability to disassemble the lateral arms of the retractor for washing and sterilization, and all mechanisms for attachment of the fourth blade are located out of the fluoroscopic field of view.

Figure 99:
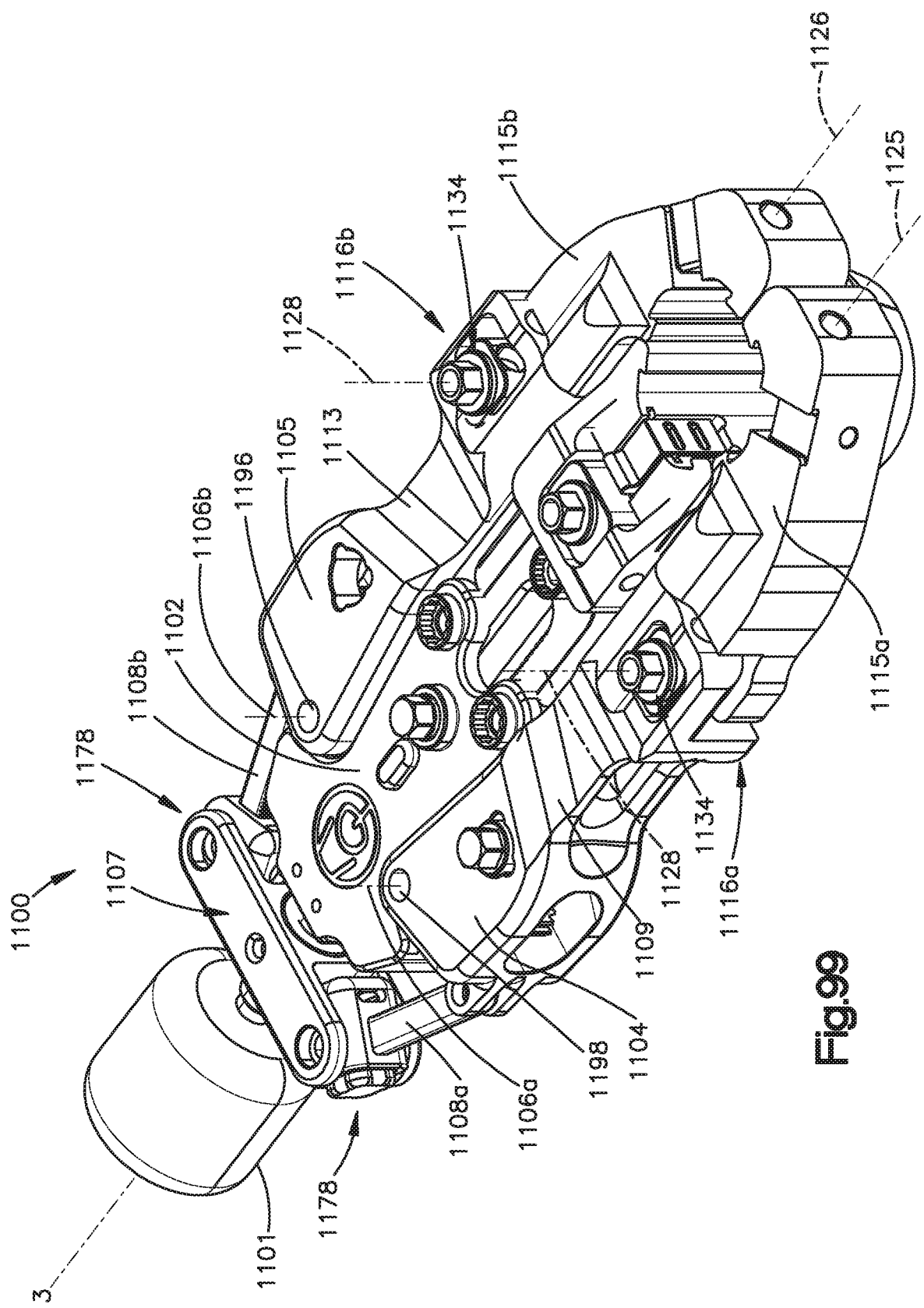
FIG. 99 is a perspective view of a surgical retractor in accordance with an embodiment of the present invention.
Figure 100:
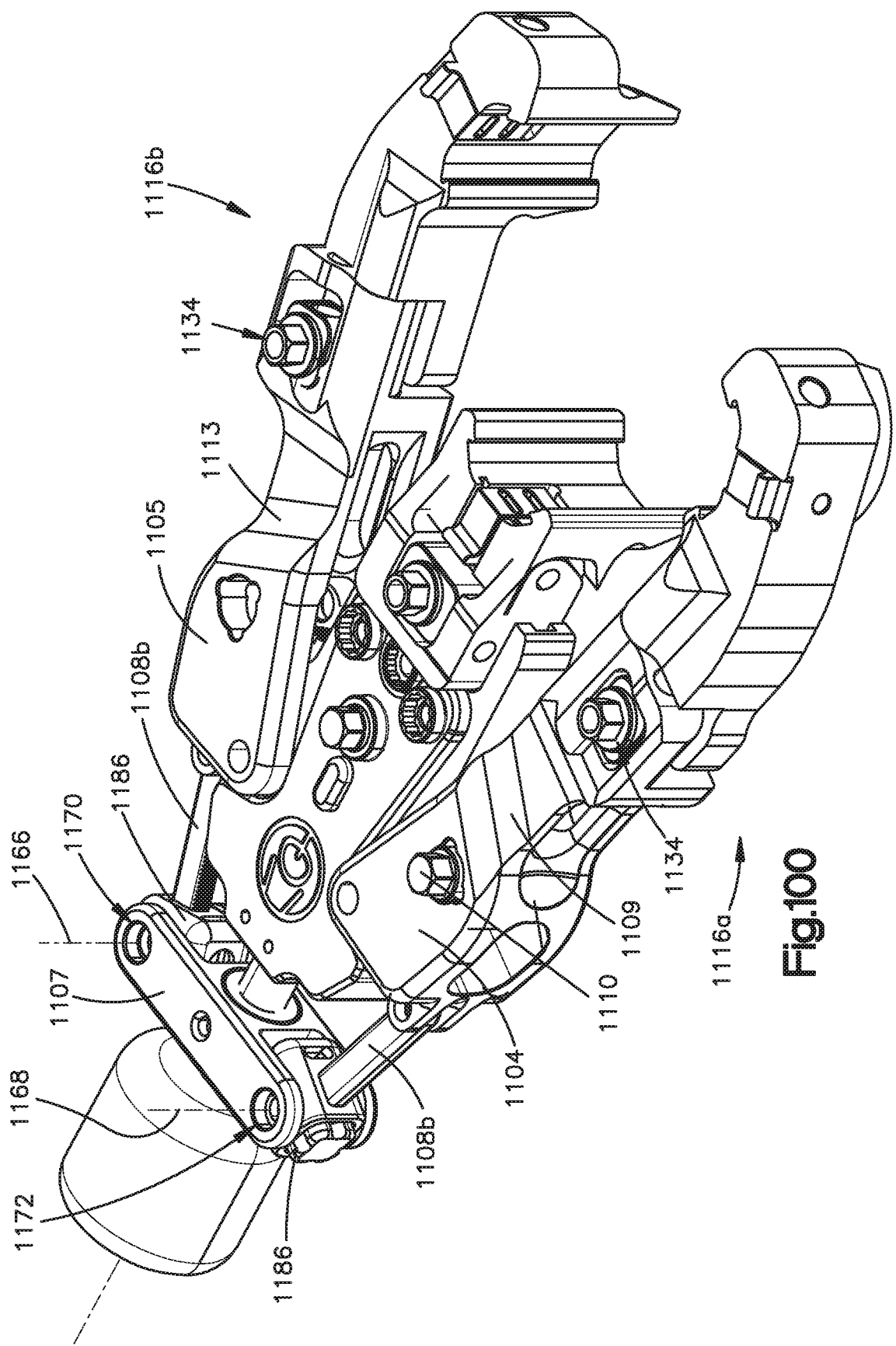
FIG. 100 is a perspective view of the surgical retractor illustrated in FIG. 99
Figure 102:
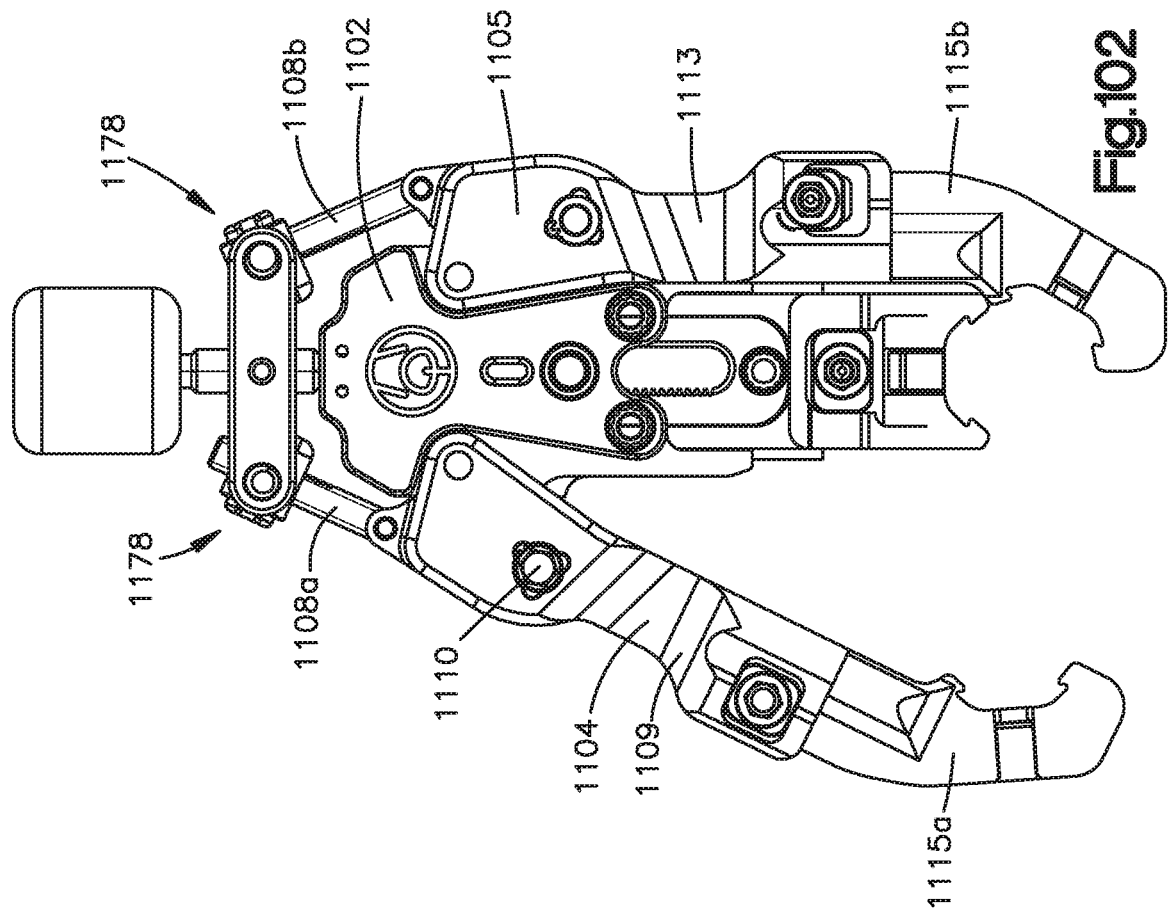
FIG. 102 is a top view of the surgical retractor illustrated in FIG. 99 with one lateral arm in the open position.
Figure 101:
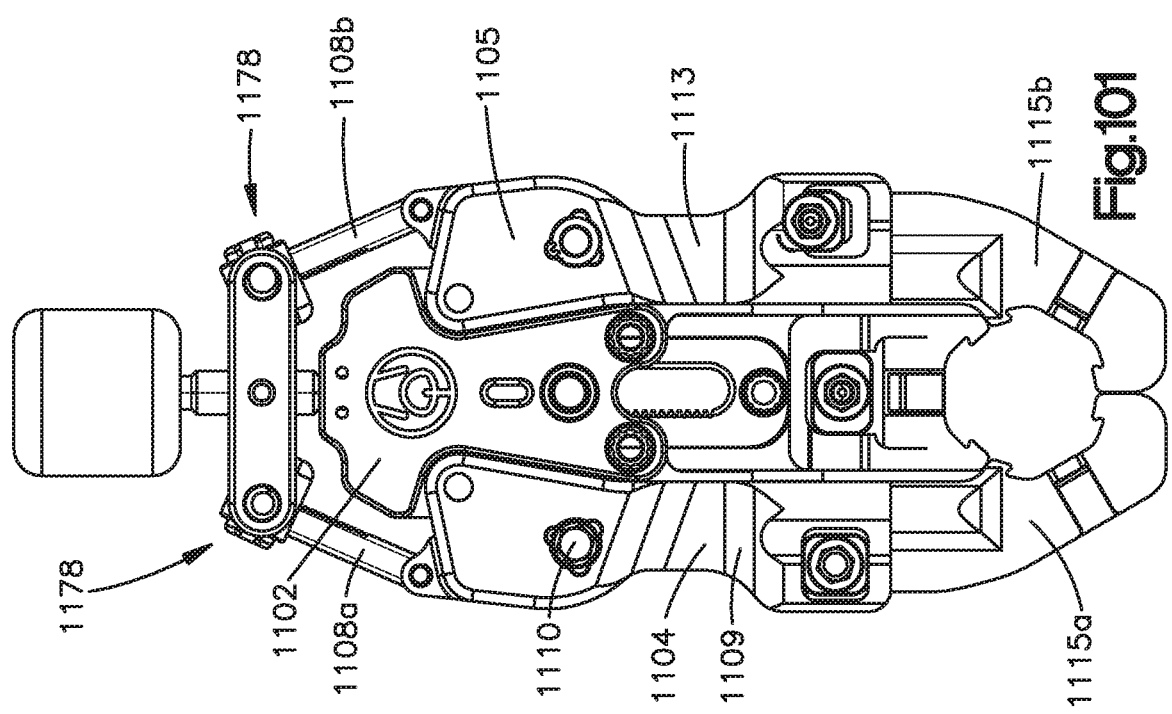
FIG. 101 is a top view of the surgical retractor illustrated in FIG. 99 with lateral arms in the closed position.
Figure 104:
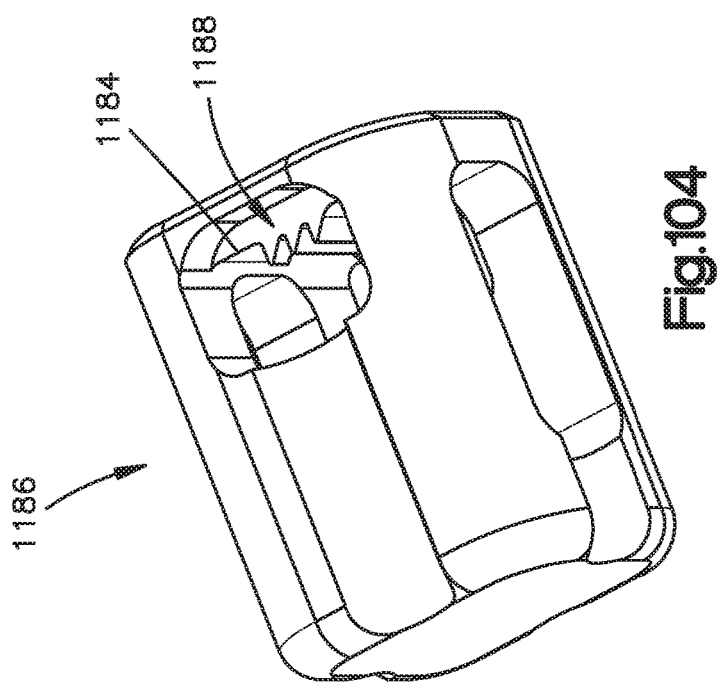
FIG. 104 is a perspective view of a connector of the surgical retractor illustrated in FIG. 99.
Figure 103:
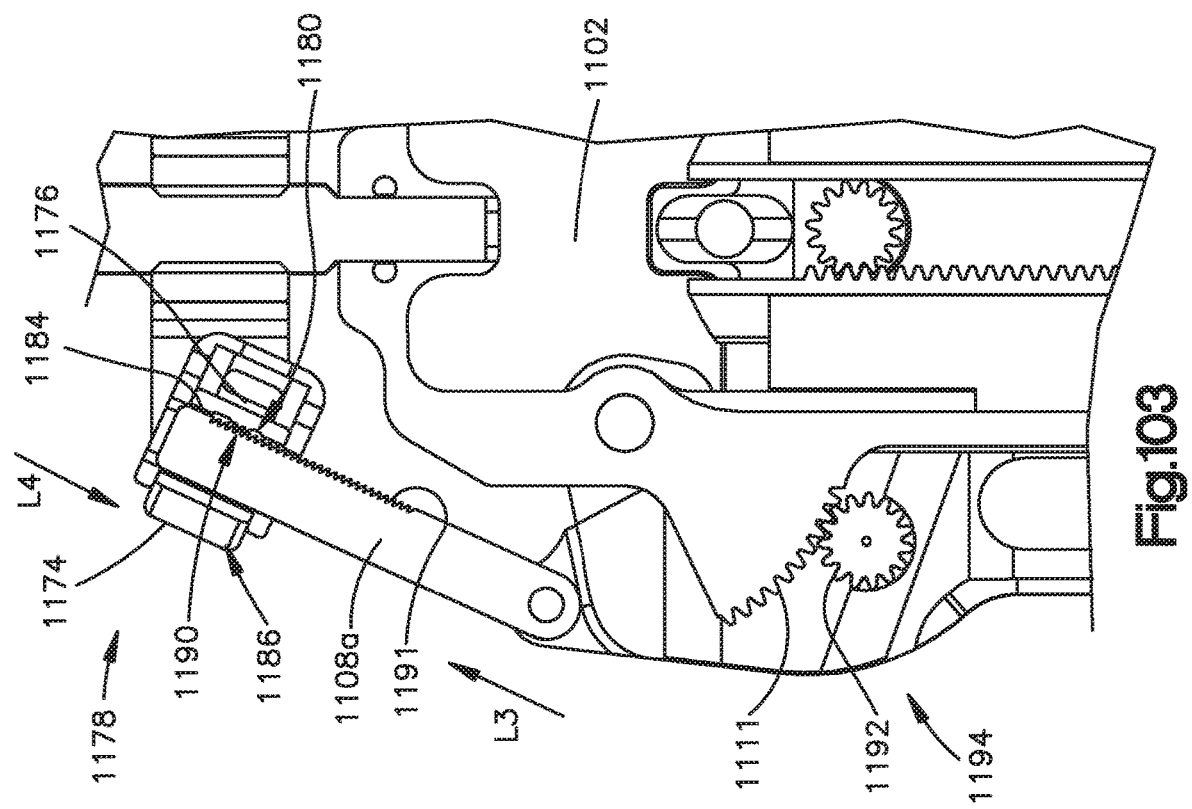
FIG. 103 is a top view of a proximal portion of the surgical retractor illustrated in FIG. 99, including cutouts showing a rack and pinion mechanism.

With reference to FIGS. 99 and 100, a retractor 1100 in according another embodiment of the present invention includes a leadscrew mechanism for bilateral tissue retraction and a pair ratcheted gear mechanisms each configured for unilateral tissue retraction. The retraction 1100 includes a leadscrew 1101, which is connected to a central body 1102. The leadscrew 1101 can rotate about axis 1103 but cannot translate along the axis 1103. First and second arms 1104 and 1105 are attached to the central body 1102. Specifically, a pivot member or pin 1198 pivotally connects the first arm 1104 to the central body 1102, and a pivot member or pin 1196 pivotally couples the second arm 1105 to the central body 1102. Accordingly, the first arm 1104 can pivot about axis 1106a relative to the central body 1102, and second arm 1105 can pivot about axis 1106b with respect to the central body 1102. A follower 1107 and a lateral connection bar 1108a and 1108b operatively connect each of the first and second arms 1104 and 1105 to the leadscrew 1101. In particular, the lateral connection bar 1108a is connected to the follower 1107 and to the first arm 1104. The lateral connection bar 1108b is connected to the follower and to the second arm 1105.

The follower 1107 has inner thread configured to mate with the outer threads of the leadscrew 1101. Thus, the leadscrew 1101 can be rotated to force the follower 1107 to translate along longitudinal axis 1103. When the follower 1107 translates in a proximal direction, it pulls the connection bars 1108a and 1108b. As the connection bars 1108a and 1108b move proximally, the first and second arms 1104 and 1105 move simultaneously away from each other from a first or closed position (FIG. 99) to a second or open position (FIG. 100). This movement of the first and second arms 1104 and 1105 allows bilateral tissue retraction by blades (not show) operatively connected to the first and second arms 1104 and 1105.

With reference to FIGS. 101-104, in addition to bilateral tissue retraction, retractor 1100 can allows for independent unilateral retraction of each of the first and second arms 1104 and 1105. This is achieved rack and pinion mechanisms 1194. Although the first and second arms 1104 and 1105 can have identical rack and pinion mechanism 1194 for unilateral retraction, the present disclosure only describes the rack and pinion mechanism 1194 operatively associated with the first arm 1104 in the interest of brevity. The rack and pinion mechanism 1194 includes rotating member or pinion 1110 and rack 1111 attached to the central body 1102. The rotating member 1110 includes a head adapted to be driven a suitable tool and a toothed shaft 1192. The rack 1111 have teeth adapted to mate with teeth of the toothed shaft 1192. When the rotating member 1110 is rotated, the toothed shaft 1192 moves along the rack 1111, urging the first arm 1104 to move toward or away from the second arm 1105. Thus, the first arm 1104 is configured to move independently of the second arm 1105, and vice versa, when the rotating member 1110 is turned. Specifically, the first arm 1104 is adapted to move away from the second arm 1105 from a first position (FIG. 101), in which it relatively close to the second arm 1105, to a second position (FIG. 102), in which it is farther away from the second arm 1105. As discussed above, the second arm 1105 can also include a rack and pinion mechanism 1194 to move independently (and in relation to) the first arm 1104.

A locking or ratchet mechanism 1178 can lock the position of the first arm 1104 relative to the second arm 1105 after. Another locking mechanism 1178 can lock the position of the second arm 1105 with respect to the first arm 1104. These two locking mechanism 1178 can be identical. Thus, in the interest of brevity, only one locking mechanism 1178 is described herein. The locking mechanism 1178 includes a first teeth 1190 arranged along an inner surface 1191 of the lateral connection bar 1108a and second teeth 1180 arranged along an inner surface 1184 of a hollow connector or housing 1186. The first and second teeth 1190 and 1180 are angled and configured so that the lateral connection bar 1108a can move relative to the connector 1186 in the direction indicated by arrow L3 but not in the direction indicated by arrow L4 when the first and second teeth 1190 and 1180 are engaged to one another. The locking mechanism 1178 further includes a biasing member 1176, such as a spring, biasing the second teeth 1180 toward the first teeth 1190. The second teeth 1180 can be disengaged from the first teeth 1190 by pushing the connector 1186 (via button 1174) against the influence of the biasing member 1176. When the second teeth 1180 disengage the first teeth 1190, the lateral connection bar 1108a can move relative to the connector 1186 in the direction indicated by arrow L3 and in the direction indicated by arrow L4. At this point, the locking mechanism 1178 is in an unlocked state. Thus, upon actuation of button 1174, the locking mechanism 1178 can change from a locked state to an unlocked state.

With reference again to FIG. 100, one connector 1186 pivotally couples the follower 1107 to the lateral connection bar 1108a, and another connector 1186 pivotally couples the follower 1107 to the lateral connection bar 1108b. In the illustrated embodiment, a pivot member or pin 1172 pivotally connects the connector 1186 to the follower 1107 and the lateral connector arm 1108. As a consequence, the connector 1186 can rotate about axis 1168. In the depicted embodiment, a pivot member or pin 1170 pivotally connects the connector 1186 to the follower 1107 and the lateral connector arm 1108. Thus, the connector 1186 can rotate about an axis 1166.

With reference again to FIG. 105, the first arm 1104 includes a proximal portion 1109 attached to a distal portion 1115a. Similarly, the second arm 1105 includes a proximal portion attached to a distal portion 1115b. A blade rotation or angulation mechanism 1116a connects the proximal portion 1109 to the distal portion 1115a. Another blade rotation or angulation mechanism 1116b connects the proximal portion 1113 to the distal portion. Each distal arm 1115a and 1115b is configured to hold a retractor member (1117a, 1117b or 1117c), such as a blade. The structure and operation of the angulation mechanism 1116a and 1116b are substantially similar (or identical) as the structure and operation of the angulation mechanism 416 shown in FIGS. 11A-12C. Retractor members 1117a and 1117b are attached to distal arms 1115a and 1115b, respectively, using the blade attachment mechanisms 1118a and 1118b. A third, central blade holder 1120 is connected to the central body 1102 onto which a third, central blade 1117c can be added in a similar way to all other blades. Thus, the central blade holder 1120 includes a blade attachment mechanism 1118c.

With reference to FIGS. 106-111, all blade attachments mechanisms 1118a, 1118b, and 1118c can be substantially similar to one another. In the interest of brevity, only blade attachment mechanism 1118a is described herein. The blade attachment mechanism 1118a includes an engagement member 1164, such as a follower, which is loosely mated to the distal arm 1115a, and can translate along axis 1119). The engagement member 1164 is movably connected to the distal arm 1115a and can therefore move relative to the distal arm 1115a along axis 1119. The distal arm 1115a includes a slot 1162 configured to receive the retractor member 1117a. The retractor member includes an engagement member or camming member 1160. The engagement member 1160 protrudes outwardly from an outer surface 1165 of the retractor member 1117a. The engagement member 1164 has a plurality of recesses or grooves 1158 adapted and sized to securely receive the engagement member or camming member 1160 of the retractor member 1117a. The recesses or grooves 1158 are arranged in a linear row along the engagement member 1164 to allow the retractor member 1117a to be fixed to the arm 1115a at different attachment positions. The engagement member 1164 is configured to move toward and away from the slot 1162 (FIG. 106) to allow the engagement member 1160 to be positioned in one of the plurality of recesses 1158 to secure the blade to the arm. Upon insertion of the retractor member 1117a into the slot 1162 (FIG. 106) of the distal arm 1115a, the engagement member or camming member 1160 pushes the engagement member 1164 so that it translates outwardly along axis 1119. As the engagement member 1164 translates outwardly, the retractor member 1117a can moved downwardly until the engagement member or camming member 1160 engages next recess or groove 1158. The retractor member 1117a can be further moved downwardly until it reaches the desired depth. The blade is them locked from backing out due to the geometry of the stops.

The retractor 1110 can include the arm 1104, which defines a slot 1162 that is configured to slidably retain a retractor member 1117a that is configured to retract tissue. The retractor 1110 can further include the first engagement member 1164 movably connected to the arm 1104. The first engagement member 1164 defines the plurality of recesses 1158. Each of the plurality of recesses 1158 is selectively configured to securely receive the complementary second engagement member 1160 of the retractor member 1117*a*. The first engagement member 1164 is configured to move toward the slot 1162 so as to engage the second engagement member 1160, thereby causing the second engagement member 1160 to be securely received in a select one of the plurality of recesses 1158, and further configured to move away from the slot so as to disengage the second engagement member 1160 and allow the second engagement member 1160 to slide along the slot 1162. The retractor 1100 can further include the first retractor member 1117*a*. The first retractor member 1117*a* defines the outer surface 1165. The second engagement member 1160 protrudes out from the outer surface 1165. The plurality of recesses 1158 are arranged in a linear row along the second engagement member 1160 to allow the first retractor member 1117*a* to be fixed to the arm at different attachment positions.

Figure 113:
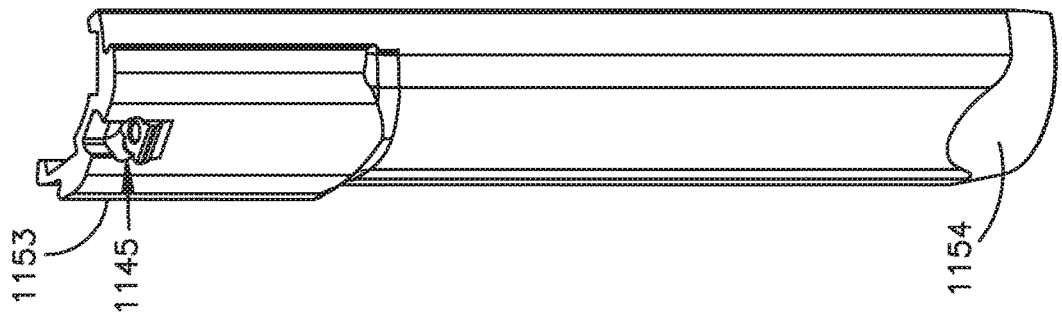
FIG. 113 is a perspective rear view of the blade shown in FIG. 112.
Figure 112:
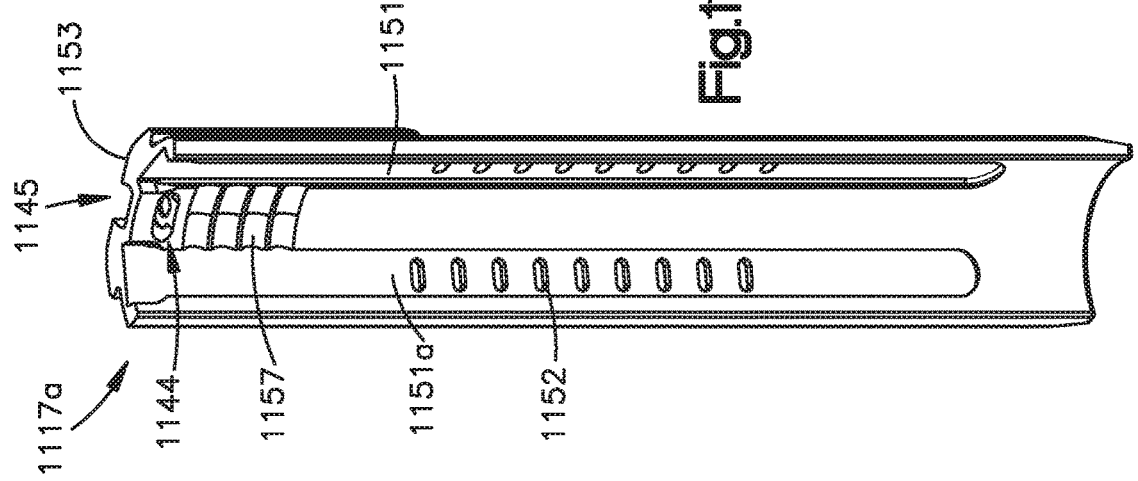
FIG. 112 is a perspective front view of a blade in accordance with an embodiment of the present invention.

With reference to FIGS. 112 and 113, the retractor member 1117*a* includes a mounting member or protrusion 1153 sized and configured to be received within a slot 1162 (FIG. 106) of the distal arm 1115*a*. The slot 1162 (FIG. 106) is adapted and sized to slidably receive the retractor member 1117*a*. All or some of the blades described herein can include the features of this embodiment. The retractor member 1117*a* can be wholly or partly made of a radiolucent material to improve visibility under fluoroscopy. In addition to this, the retractor member 1117*a* allows for the insertion of various accessories along grooves 1151*a* and 1151*b*. The grooves 1151*a* and 1151*b* are adapted to receive accessories such as a light, bone anchors, a winglet, a blade extension, etc. In order to retain the accessories within the grooves 1151*a* and 1151*b*, recesses 1152 are arranged along the grooves 1151*a* and 11151*b*. In order to minimize tissue disruption at the spine, the retractor member 1117*a* has have a distal tapered end 1154. The retractor member 1117*a* further has a proximal opening 1145 and a hole 1144 on its inner surface. The hole 1144 is in communication with the proximal opening 1145. The retractor member 1117*a* can also include grip grooves 1157 along its inner surface adapted to allow a user to grab the retractor member 1117*a*.

The first arm 1104 includes the proximal portion 1109 and the distal portion 1115*a*. The distal portion 1115*a* is configured to retain the first retractor member 1117*a*. The distal portion 1115*a* is configured to rotate relative to the proximal portion 1109 about a first axis 1125. The second arm 1105 is configured to retain the second retractor member 1117*c*, such that rotation of the distal portion 1115*b* about the first axis 1125 causes the first retractor member to pivot toward or away from the second retractor member 1115*b* when the first retractor member 1104 and the second retractor member 119 are coupled to the first arm 1104 and the second arm 1105, respectively. The rotating member 418, 830, 1134 is coupled between the proximal portion 1109 and the distal portion 1115*a*. The rotating member 1134 is configured to rotate about a second axis 1128, wherein rotation of the rotating member 1134 about the second axis 1128 causes the distal portion 1115*a* to rotate relative to the proximal portion 1109 about the first axis 1125.

FIG. 1114 shows an alternative embodiment of a retractor member 1156, such as a blade, that is similar to the retractor member 1117*a*. The retractor member 1156, however, includes a protruding distal anchor 1155 configured to penetrate an intervertebral disc. The disc anchor 1155 is monolithically formed with the retractor member 1156. In other words, the retractor member 1156 and the disc anchor 1155 is a one-piece structure. The disc anchor 1155 is located at a distal end of the retractor member 11566 and can have a substantially planar configuration. In combination with the blade attachment mechanisms 1118*a*, the blade anchor 1115 can be used as a intervertebral disc anchor to give additional stabilization to the retractor 1110 (FIG. 99). In addition, when the anchor 1155 is placed into the posterior portion of the intervertebral disc space, it can act to prevent unintentional injury to the posterior nervous structure (dura). In the case where it is placed into the intervertebral disc space, it should be placed into the blade attachment mechanism which resides over the intervertebral disc space. Placement into the disc space is achieved using the telescoping mechanism described earlier (FIG. 110-111).

Figure 116:
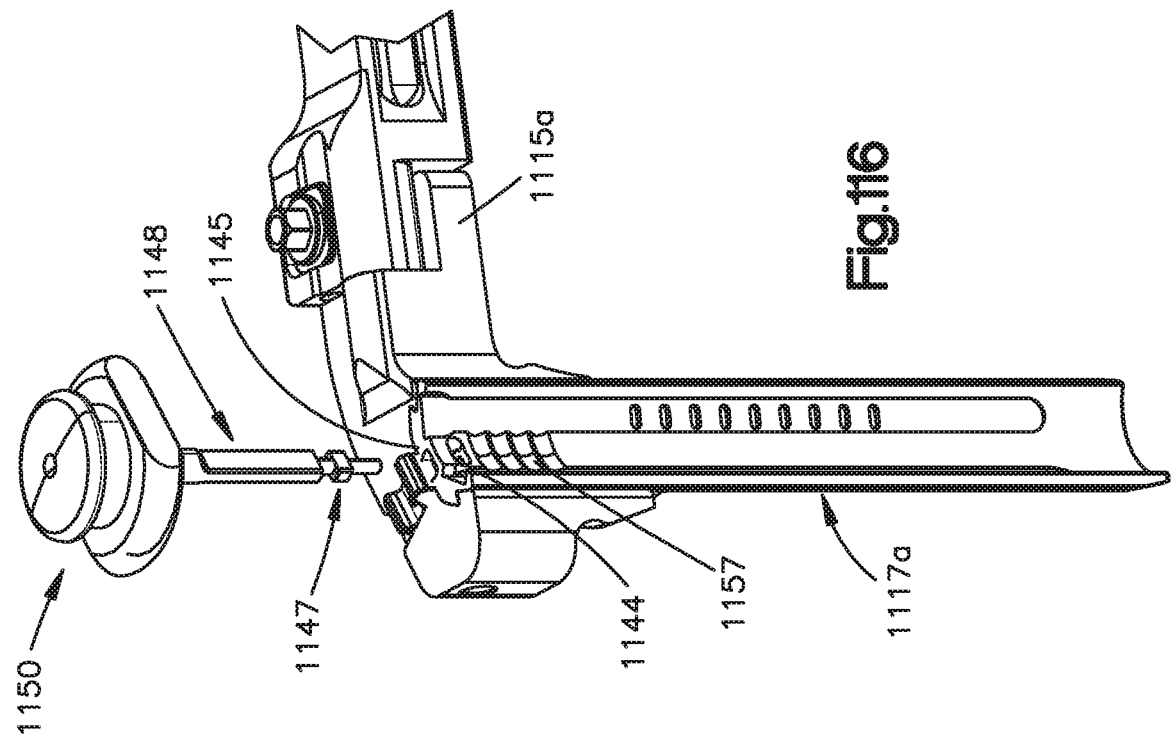
FIG. 116 is a perspective view of the blade pusher and removal tool, a blade, and the blade holder of the surgical retractor illustrated in FIG. 99.
Figure 115:
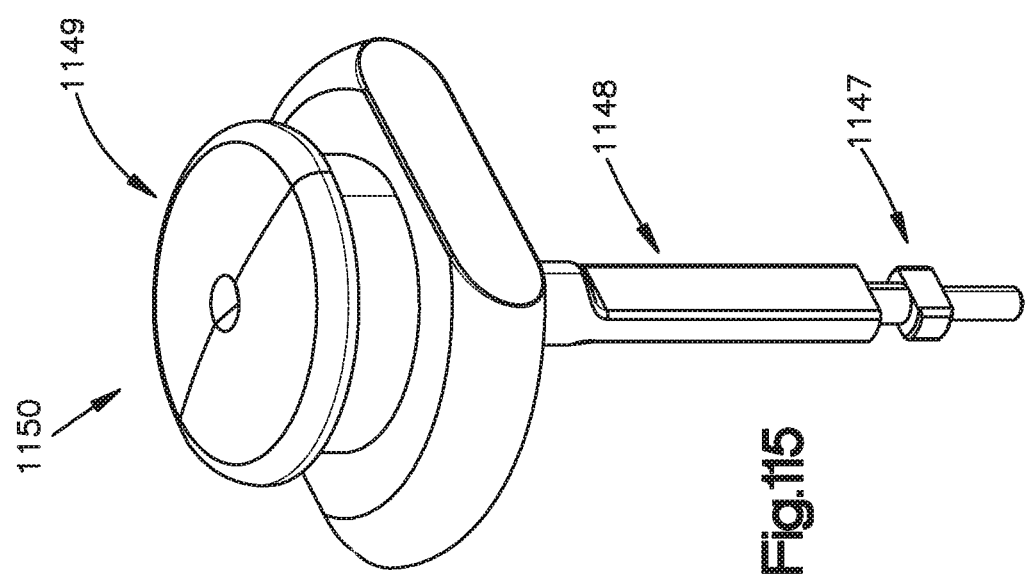
FIG. 115 is a perspective view of a blade pusher and removal tool in accordance with an embodiment of the present invention.
Figure 118:
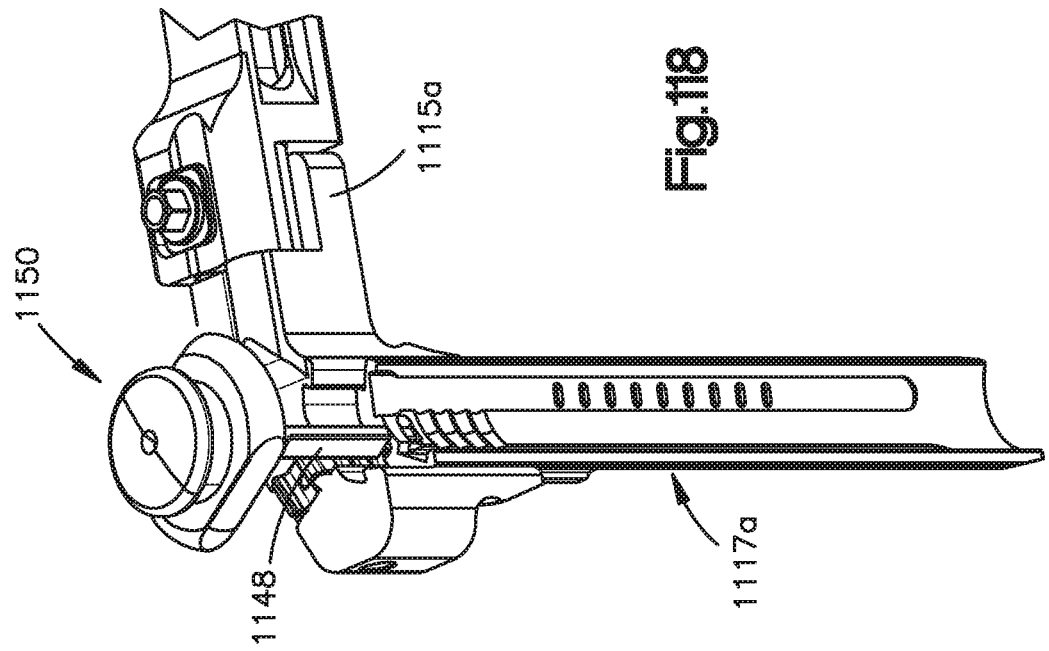
FIGS. 117 and 118 are perspective view showing an exemplary method of pushing the blade positioned in the blade holder of the surgical retractor shown in FIG. 99 using the tool shown in FIG. 116.
Figure 117:
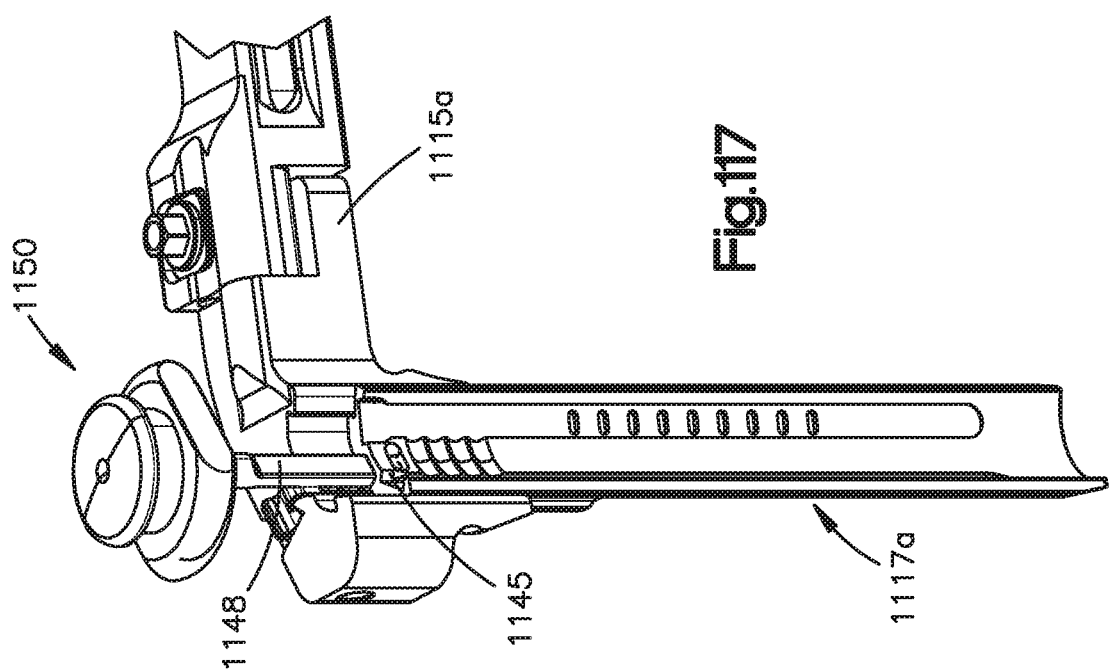
Figure 121:
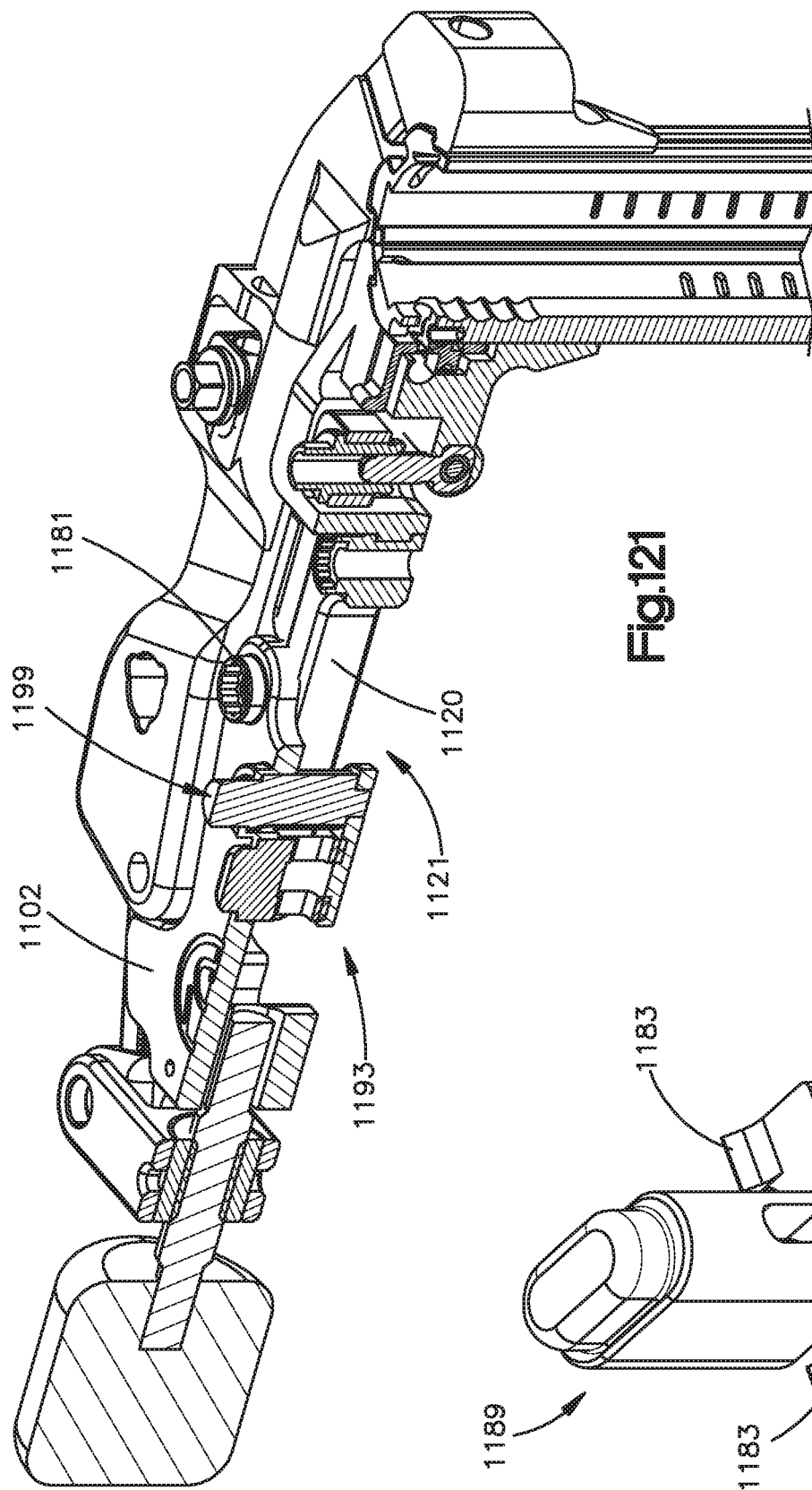
FIG. 121 is a sectional perspective view of the surgical retractor illustrated in FIG. 99.
Figure 122:
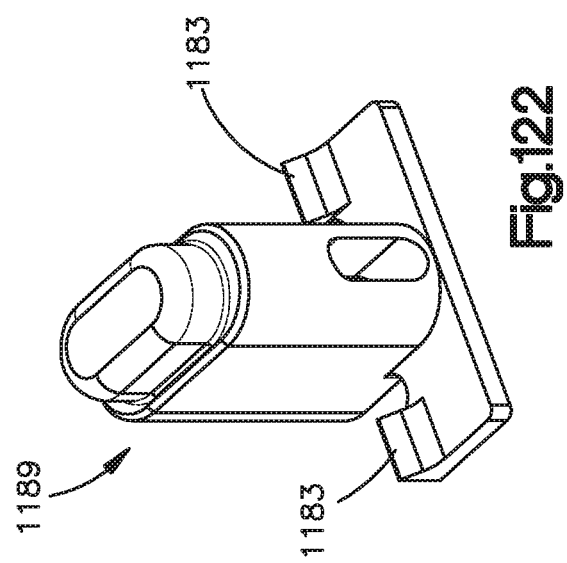
FIG. 122 is a perspective view of a locking portion of the surgical retractor illustrated in FIG. 99.
Figure 123:
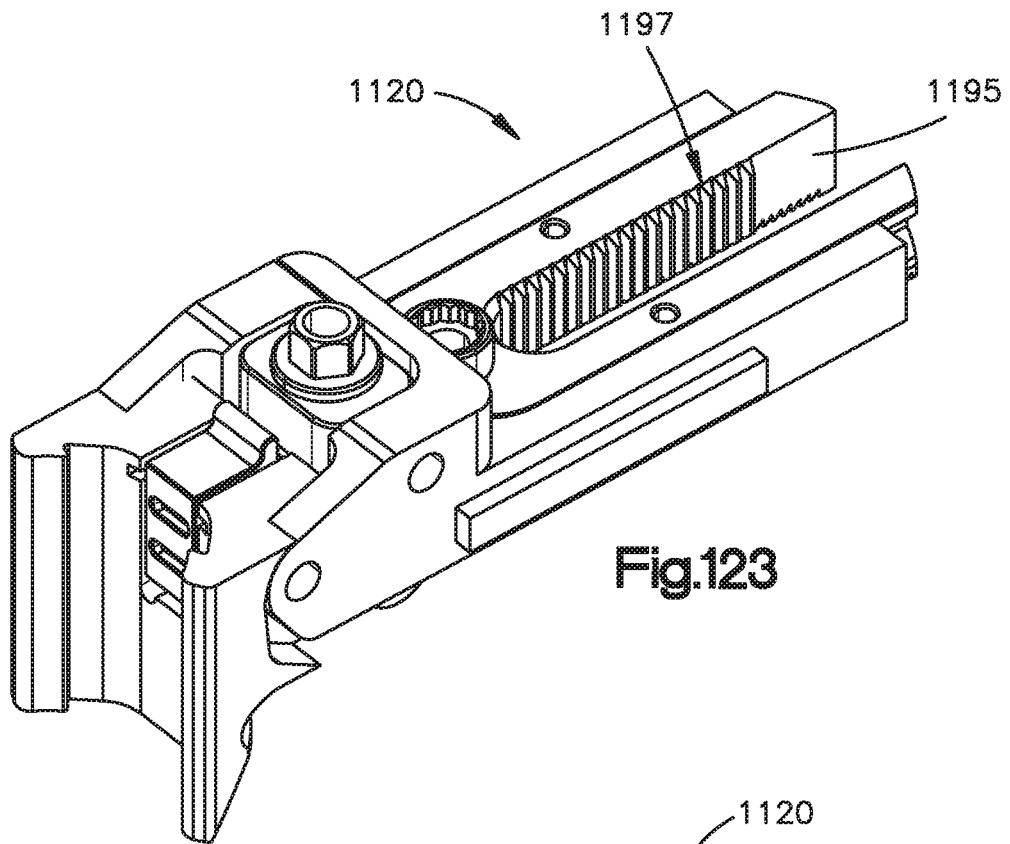
FIG. 123 is a perspective top view of a central arm of the surgical retractor illustrated in FIG. 99.
Figure 124:
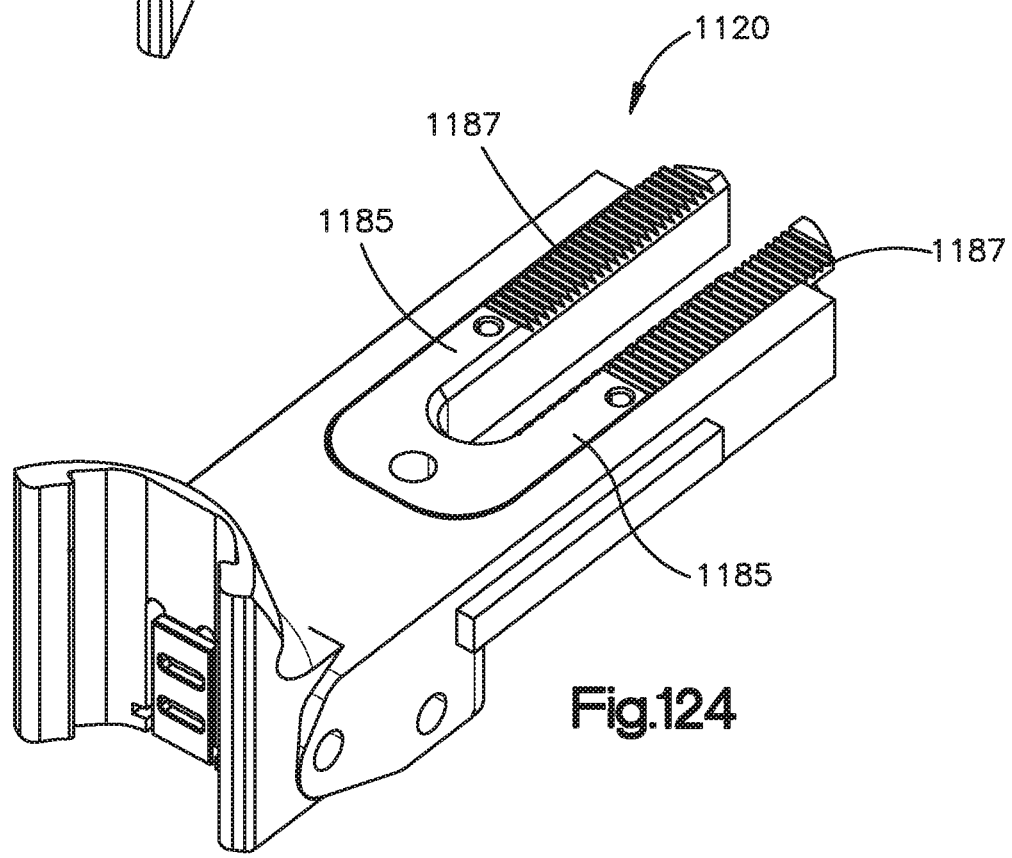
FIG. 124 is a perspective bottom view of the central arm shown in FIG. 123.

With reference to FIGS. 115-117, a blade pusher and blade removal tool 1150 can be is used to push or remove the retractor member 1117*a* (or any other blade) from the blade holder 1115*a* (or any other blade holder). The tool 1150 includes a handle 1149 and an elongated member or shaft 1148 extending from the handle 1149. The shaft 1148 is sized and adapted to be received in the proximal opening 1145 of the blade 1115*a* and includes an engagement member or male connector 1147 adapted and sized to be receive within the proximal opening 1145 and the hole 1144 of the blade 1115*a*. To push the retractor member 1117*a* farther down, the shaft 1148 of the tool 1150 is inserted through the proximal opening 1145 of the blade 1117*a*, and then the tool 1150 is pushed downwardly to move the retractor member 1117*a* downwardly relative to the distal arm 1115*a* as seen in FIG. 117. A user can also manually push the retractor member 1117*a* downwardly via the grip grooves 1157.

With reference to FIGS. 117-120, the tool 1150 can also be used to remove the retractor member 1117*a* from the distal arm 1115*a*. To do so, the shaft 1148 of the tool is inserted through the proximal opening 1145 of the retractor member 1117*a* as seen in FIG. 1117. Subsequently, the tool 1150 is turned (as seen in FIG. 1118) until the engagement member 1147 is positioned within the hole 1144 of the blade 1117*a*. As the tool 1150 is turned, the engagement member 1147 pushes the follower 1164 away from the camming member 1160 (FIG. 110) of the blade 1117*a*, disengaging the camming member 1160 from the grooves 1158. When the camming member 1160 (FIG. 110) is disengaged from the groove 1158, the tool 1150 can be pulled upwardly to remove the retractor member 1117*a* from the distal arm 1115*a*.

With reference to FIGS. 121-124, The third, central arm 1120 is loosely fitted to the central body 1102. A rack and pinion mechanism 1121 can be substantially similar to the rack and pinion mechanism 272 shown in FIG. 4 and is configured to move central arm 1120 longitudinally along axis 1103 (FIG. 99) between a distal position and a proximal position. Thus, the rack and pinion mechanism 1121 can retract the blade 1117*c* attached to the central arm 1120. The central arm 1120 is slidably connected to the central body 1102. The rack and pinion mechanism 1121 includes a geared rotating member or pinion 1199 and rack 1197 arranged on an inner surface 1195 of the central arm 1120. The rotating member 1199 has a teeth adapted to mate with the teeth of the rack 1197. When the rotation member 1199 is turned, its teeth engage the teeth of the rack 1197, causing the central arm 1120 to move longitudinally along the axis 1103 (FIG. 99) with respect to the central body 1102.

The position of the central arm 1120 relative to the central body 1102 can be locked using a locking mechanism 1193. The locking mechanism 1193 includes a locking portion 1189 and a pair of ratchets 1187 arranged along lower surfaces 1185 of the central arm 1185. The locking portion 1189 includes a pair of teeth 1183 adapted to engage the teeth of ratchets 1187. When the teeth of ratchets 1187 engage the teeth 1183 of locking portion 1189, the central arm 1120 cannot move relative to the central body 1102. The locking portion 1189 can be spring loaded such that the teeth 1183 are biased toward the ratchets 1187. To unlock the central arm 1120, the locking portion 1189 can be moved against the biased of the spring to disengage the teeth 1183 from the teeth of the ratchets 1187, thereby allowing the central arm 1120 to move with respect to the central body 1102. The retractor 1100 can further include one or more connection members 1181 substantially similar or identical to connection members 256 and 346 shown in FIG. 7. The structure and operation of connection members 181 is substantially similar or identical to the structure and operation of connection members 256 and/or 346 (FIG. 7). The connection members 1181 are configured to be attached, for example, to a table fixation device.

Figure 105:
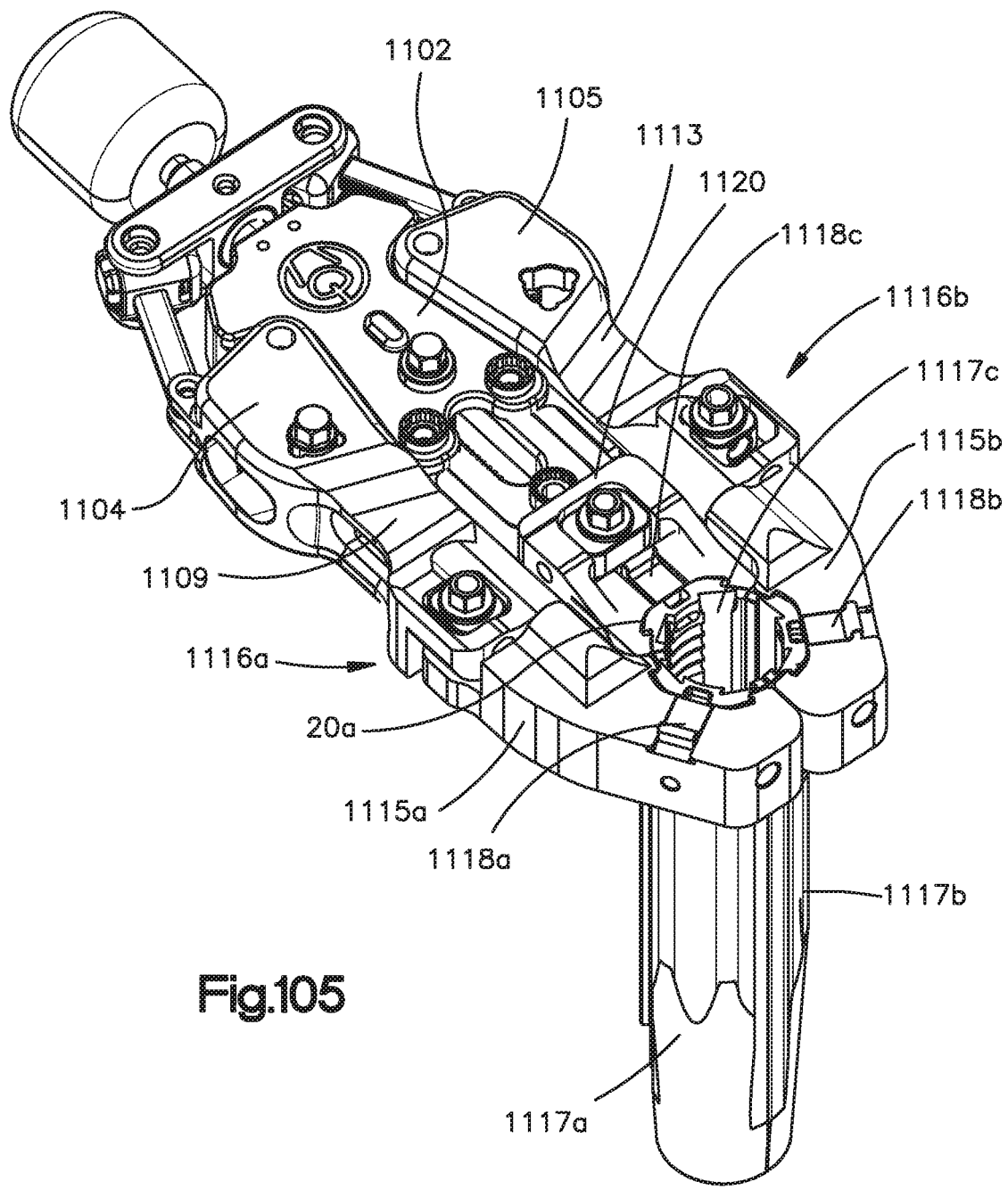
FIG. 105 is a perspective view of the surgical retractor illustrated in FIG. 99 with blades attached thereto.
Figure 106:
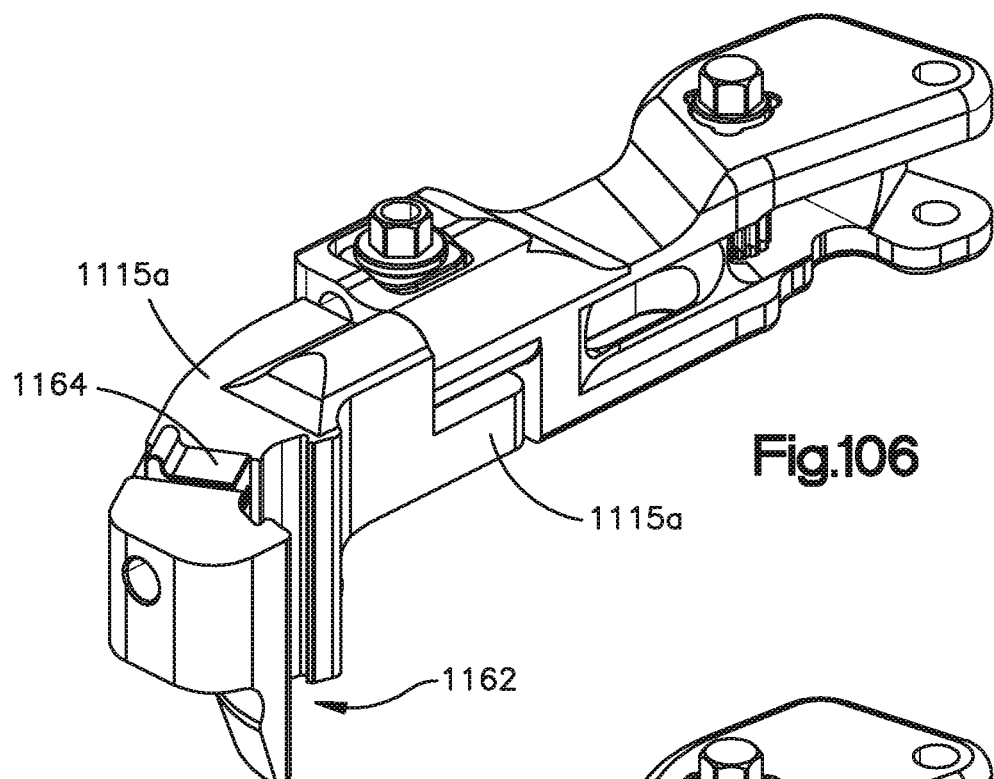
FIG. 106 is a perspective view of a blade holder of the surgical retractor illustrated in FIG. 99.
Figure 107:
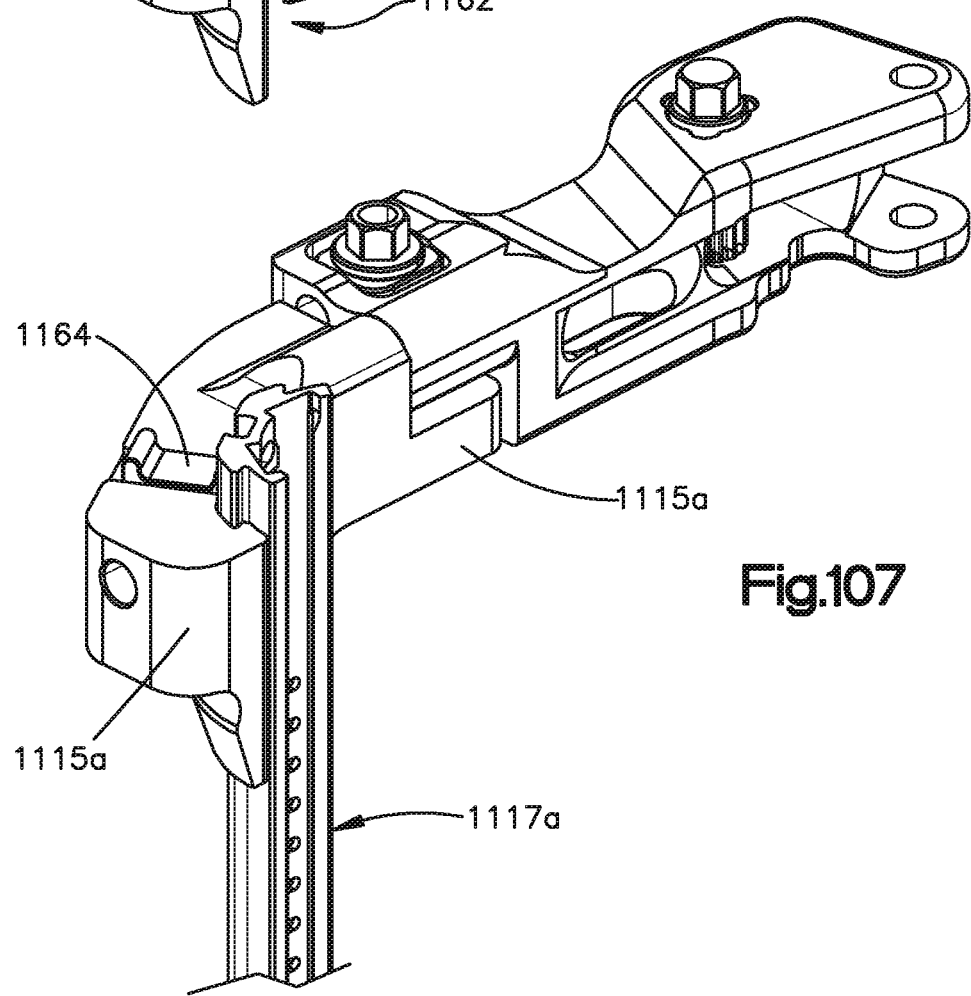
FIG. 107 is a perspective view of a blade being mounted to the blade holder shown in FIG. 106.
Figure 109:
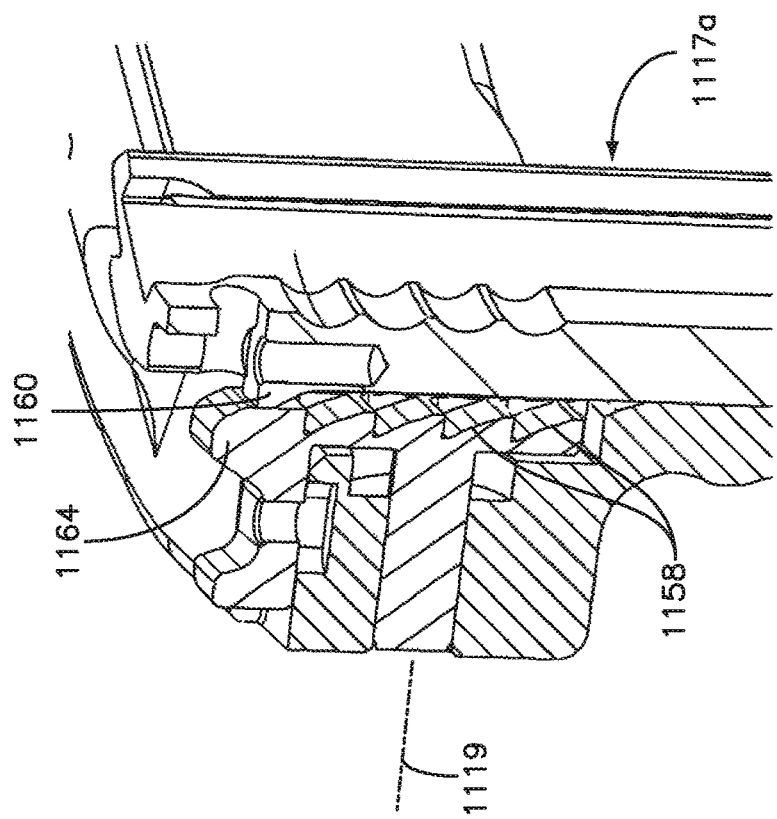
FIG. 109 is an enlarged perspective cross-sectional view of the blade shown in FIG. 107 being mounted to the blade holder shown in FIG. 106.
Figure 108:
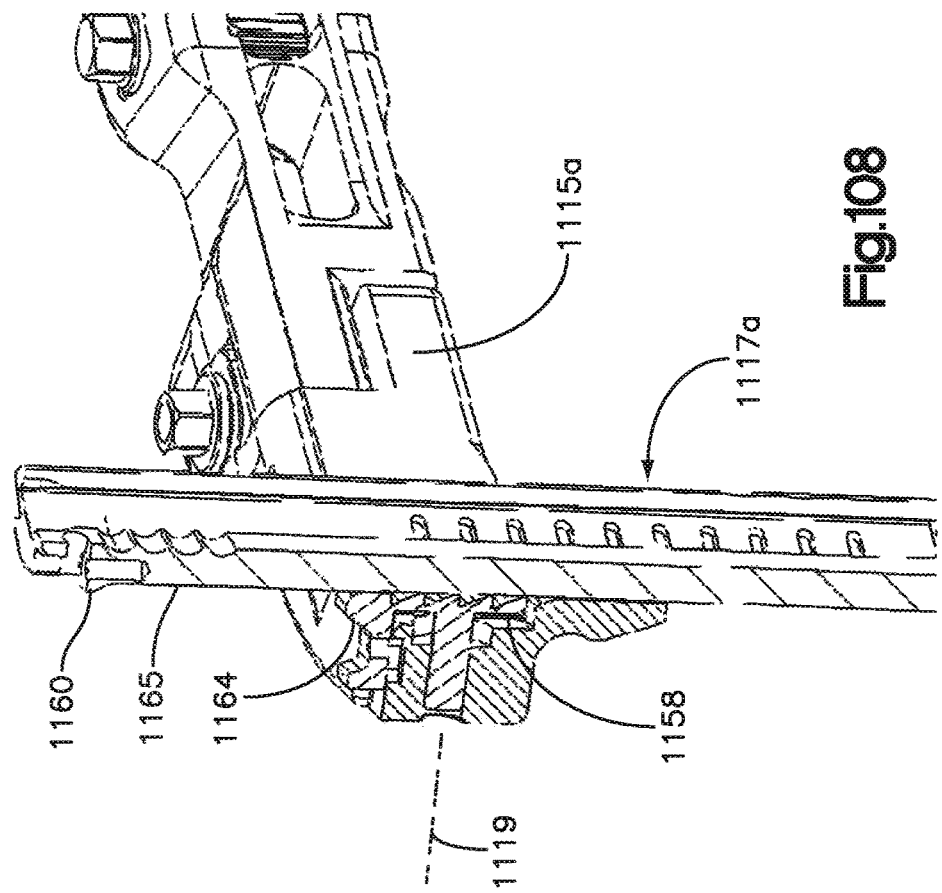
FIG. 108 is a perspective cross-sectional view of the blade shown in FIG. 107 being mounted to the blade holder shown in FIG. 106.
Figure 111:
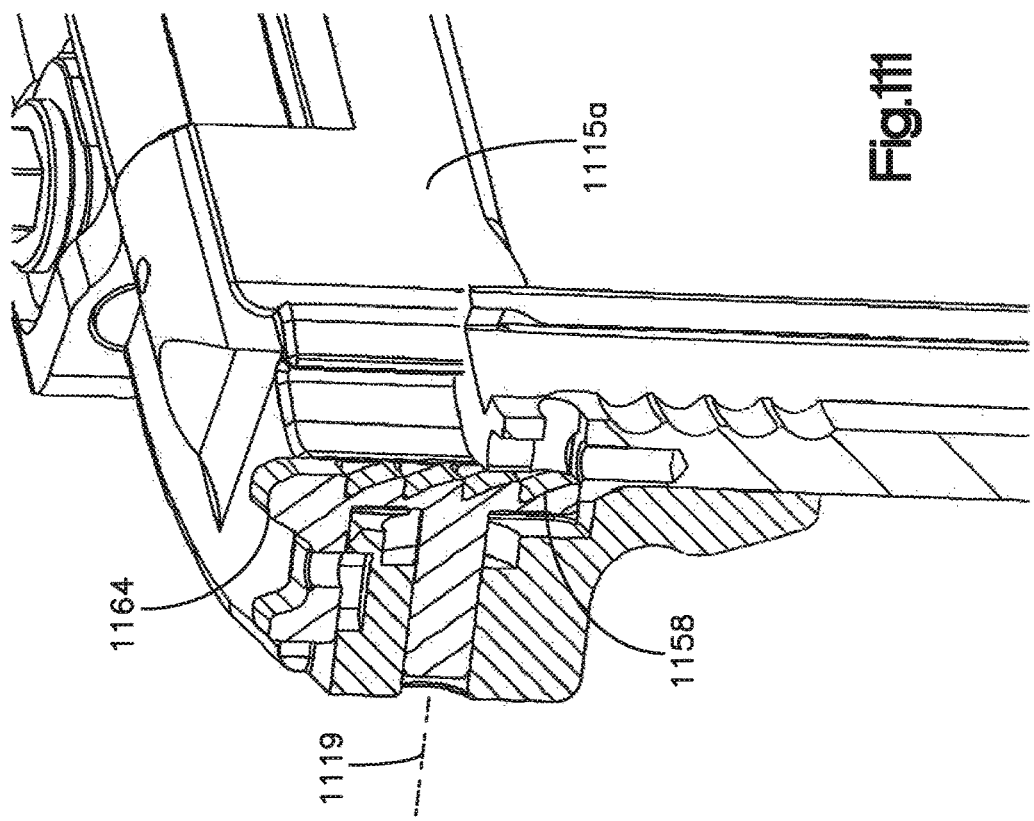
FIG. 111 is an enlarged perspective cross-sectional view of the blade shown in FIG. 107 mounted to the blade holder shown in FIG. 106 at a second position.
Figure 110:
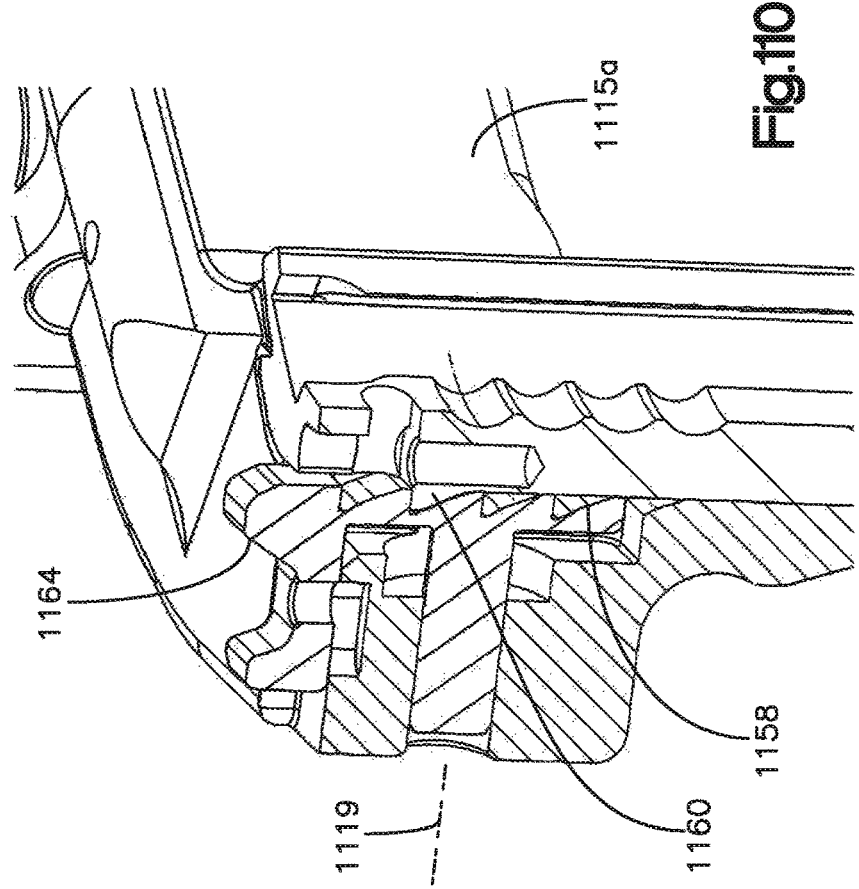
FIG. 110 is an enlarged perspective cross-sectional view of the blade shown in FIG. 107 mounted to the blade holder shown in FIG. 106 at a first position.
Figure 114:
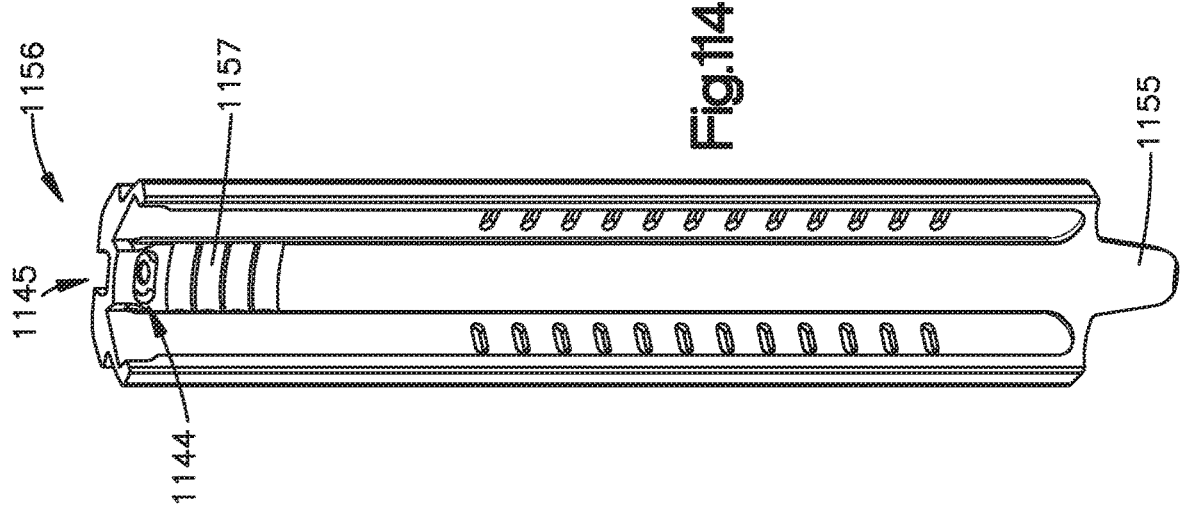
FIG. 114 is a perspective front view of a blade in accordance with another embodiment of the present invention.
Figure 127:
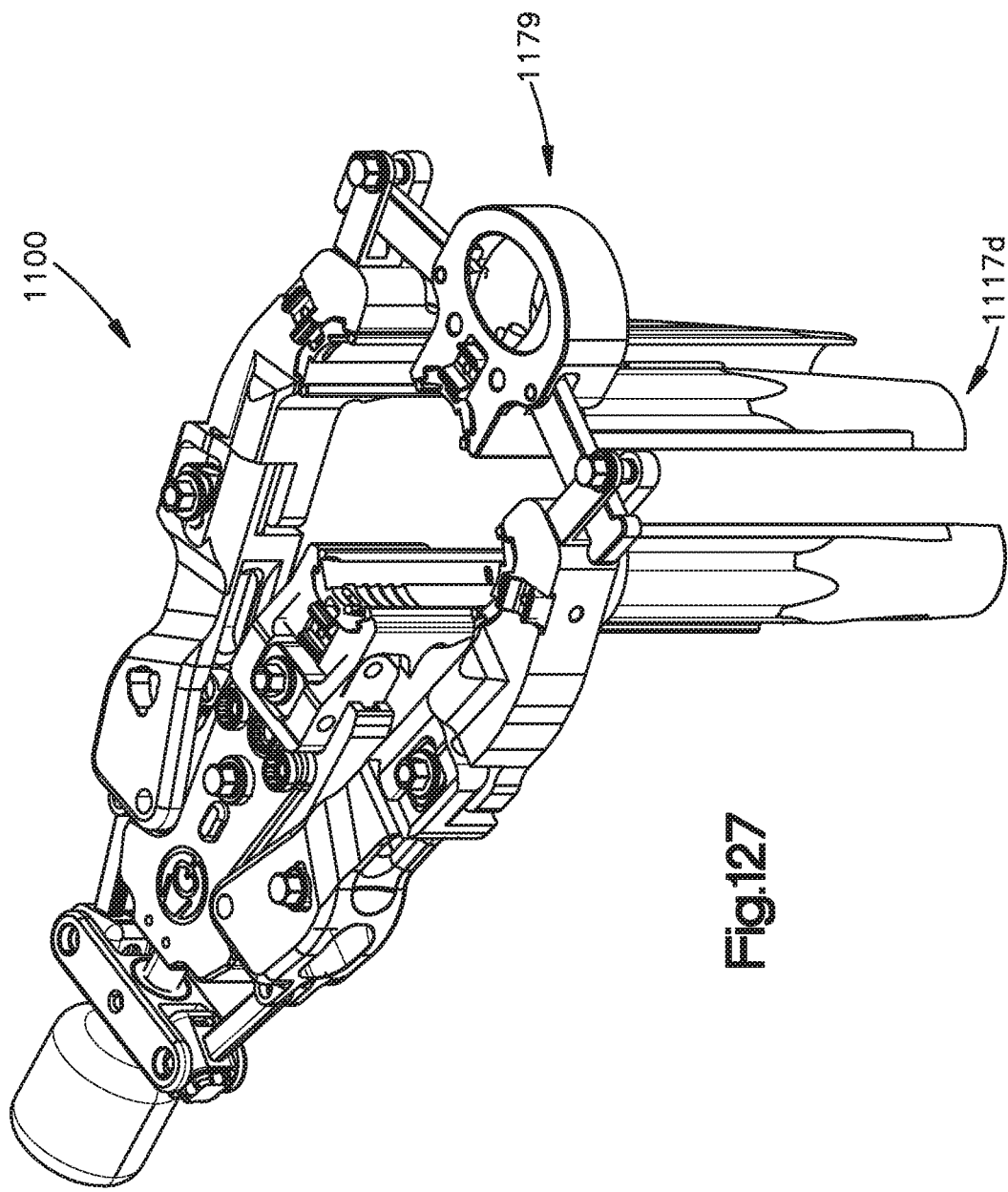
FIG. 127 is a perspective view of the blade assembly shown in FIG. 125 mounted to the surgical retractor shown in FIG. 99.

With reference to FIGS. 125-127, in addition to the three arms on the retractor 110, there is the possibility to attach a fourth blade 1117d using the fourth blade assembly 1179. The fourth blade assembly 1179 includes a blade holder 1129, which has a blade attachment mechanism 1177 substantially similar (or identical to) blade attachment mechanism 1118a, 1118b, and 1118c. (FIG. 105). The blade holder 1129 further includes a first or left arm 1130a and a right or second arm 1130b pivotally connected to the blade holder 1129. The first arm 1130a can pivot about a pivot member or pin 1175 pivotally coupling the blade holder 1129 and the first arm 1130a. The second arm 1130b can pivot about a pivot member or pin 1173 pivotally coupling the blade holder 1129 to the second arm 1130b. A first clamping assembly 1131a is attached to an end of the first arm 1130a. A second clamping assembly 1131b is attached to an end of the second arm 1130b. An engagement member 1132a, (illustrated as a boss or protrusion) extends from the first clamping assembly 1131a. The engagement member 1132a is sized and configured to be securely received in a hole 1127a at the distal end of the distal arm 115a. An engagement member 1132b (illustrated as a boss or protrusions) extends from the second clamping assembly 1132b. The engagement member 1132b is sized and configured to be securely received in a hole 1127b at the distal end of the distal arm 1115a. In order to mount the blade assembly 1179 onto the retractor 1100, the engagement members 1132a and 1132b are inserted in the holes 1127a and 1127b, respectively, of the retractor 1100.

The clamping assembly 1131a can be fixed relative to first arm 1130a via a fixation member 1171a. In the depicted embodiment, the fixation member 1171a is a nut but it can be any other suitable structure or mechanism capable of fixing the position of the clamping assembly 1131a relative to the 1130a. The clamping assembly 1131a can move along the arm 1130a when, for instance, the fixation member 1171a (in case it is a nut) is not tightened. Similarly, the clamping assembly 1131b can be fixed relative to the second arm 1130b via a fixation member 1171b, which can be a nut or any other suitable device or mechanism. The clamping assembly 1131b can move along the second arm 1130b when the fixation member 1171b is not tightened. Once the blade assembly 1179 is mounted to the retractor 1110, the fixation members 1171a and 1171b are untightened to allow the clamping assemblies 1131a and 1131b to move along the first and second arms 1130a and 1130b, respectively, thereby allowing unilateral tissue retraction with the blade 1117d attached to the blade assembly 1179. The user can manually move the blade assembly 1179 away from the distal arms 1115a and 1115b to unilaterally retract tissue with the blade 1117d. Once the appropriate retraction has been achieved, the fixation members 1171a and 1171b are tightened to fix the positions of the clamping assemblies 1131a and 1131b relative to the arms 1130a and 1130b, respectively.

Figure 128:
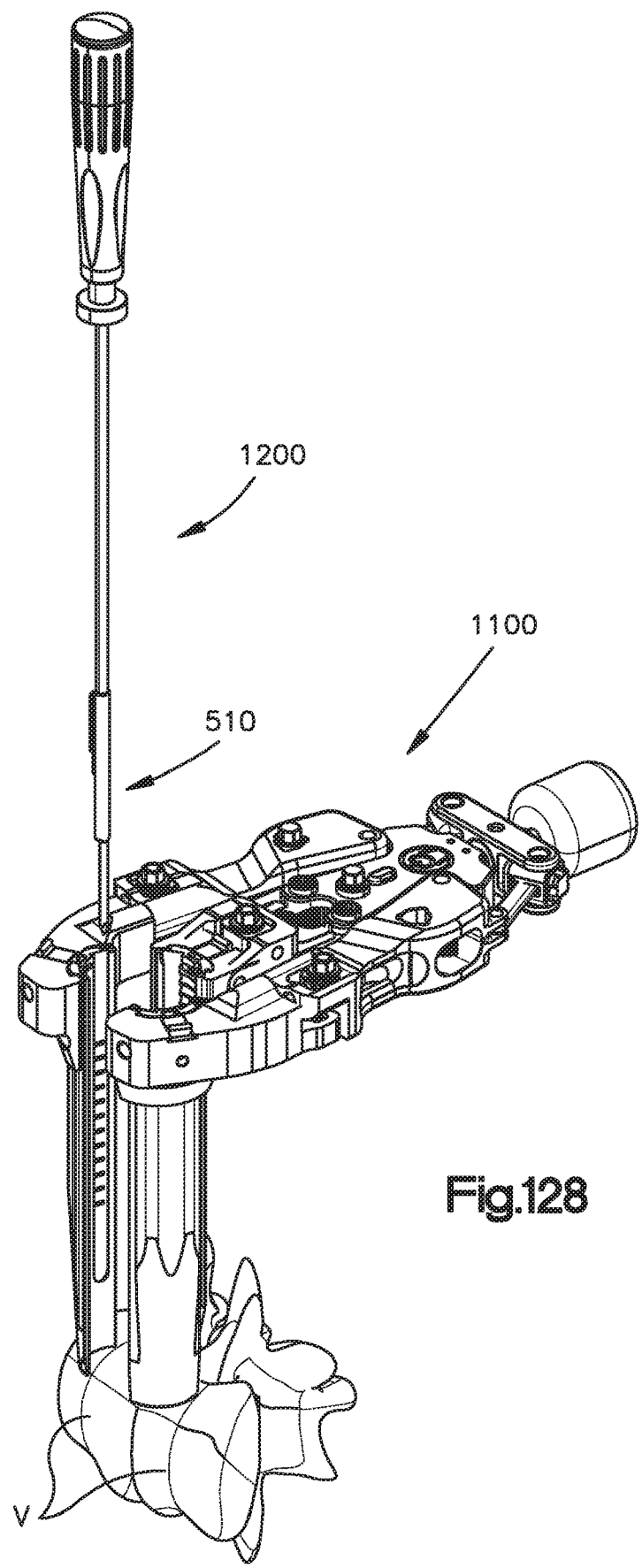
FIG. 128 is a perspective view of the bone anchor shown in FIG. 23 being inserted along the surgical retractor shown in FIG. 99 using an insertion tool.
Figures 129, 130:
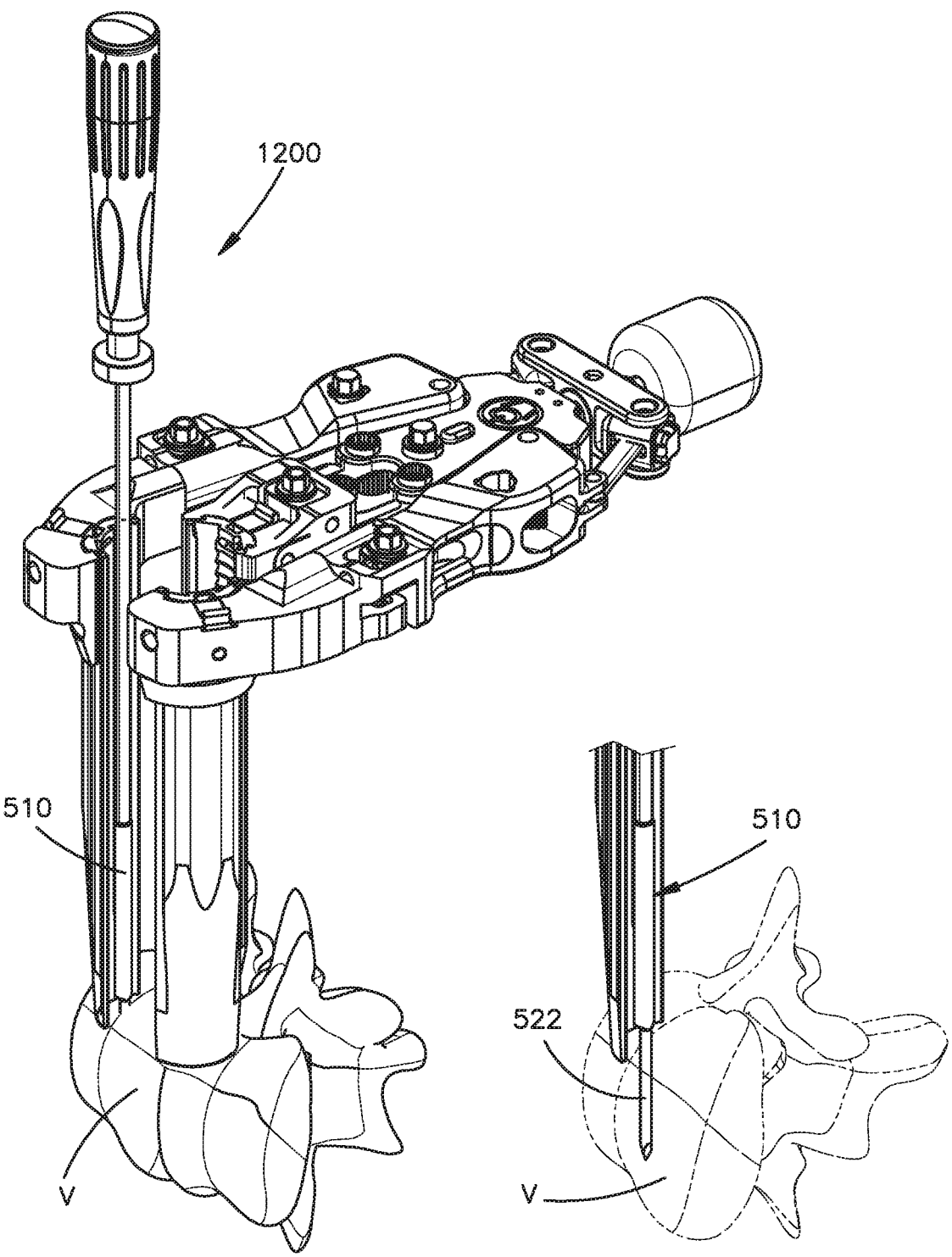
FIG. 129 is a perspective view of the bone anchor shown in FIG. 23 inserted into a vertebral body through the surgical retractor shown in FIG. 99 using the insertion tool illustrated in FIG. 129.
FIG. 130 is an enlarged perspective view of the bone anchor shown in FIG. 23 inserted into the vertebral body through the surgical retractor shown in FIG. 99 using the insertion tool illustrated in FIG. 129.

With regard to FIGS. 128-130, the bone anchor 510 shown in FIG. 23 can be inserted into a vertebral body V through the surgical retractor 1110. The bone anchor 510 can be attached to a driving tool 1200. The insertion tool 1200 includes a threaded tip (not shown) adapted to mate with threads formed around the threaded bore 518 (FIG. 23) of the bone anchor 510. After attaching the insertion tool 1200 to the bone anchor 510, the bone anchor 510 is advanced along one of the blades of the retractor 1100 as shown in FIG. 129. While advancing the bone anchor 510, the guiding member 520 (FIG. 23) slide through one of the slots 386, 388, 394 or 396 (see FIG. 7) of the blades. Then, the bone anchor 510 is further advanced until the sharp distal tip 522 penetrates a vertebral body V. The attachment of the bone anchor 510 to the vertebral body V provides additional stability to the retractor 1100.

With reference to FIG. 131, a light source or lightning device 1300 can be mounted to the retractor 1100 via one of the retractor members (1117a, 1117b or 1117c). In the illustrated embodiment, the lightning device 1300 has a curved body 1302 and a substantially planar end portion 1304 extending from the curved body 1302. The end portion 1304 is sized, shaped and configured to be received in one of the grooves 1151a and 1151b of the retractor member (1117a, 1117b or 1117c). In the depicted embodiment, the end portion 1304 is securely positioned within the groove 1151b of the blade 1117c. Once attached to the retractor members (1117a, 1117b or 1117c), the lightning device 1300 can illuminate the surgical operating site.

FIG. 132 illustrates the lateral retractor member or winglet 492 discussed above with respect to FIG. 20. The lateral retractor member 492 can also be used with the retractor 1100 (FIG. 99) to block tissue from entering the surgical operating site defined within the retractor member 1117a, 1117b or 1117c (FIG. 105) of the retractor 1100. As discussed above, the lateral retraction member 492 can be attached to one of the retractor members 1117a, 1117b or 1117c (FIG. 105) and includes body 494 adapted to displace soft tissue. The body 494 can be flat or curved and has a proximal end 496 and a distal end. In addition, the body 494 includes a connection assembly 500 at its proximal end 496. In the depicted embodiment, the connection assembly 500 includes a threaded bore 502 adapted to mate with a threaded portion of an insertion tool (not shown) and a biasing member 504 (FIG. 20) adjacent the bore 502. The biasing member 504 (FIG. 20) is adapted to bias an engagement member 506 toward an inner portion of the body 494. In the depicted embodiment, the engagement member 506 is cantilevered from the body 494. Moreover, the engagement member 506 can be a protrusion and is configured to engage an engagement portion of the insertion tool to maintain the lateral retractor member 492 attached to the insertion tool. In the depicted embodiment, the engagement member 506 is sized and configured to be inserted into one of the recesses 1152 (FIG. 112) of the retractor member (1117a, 1117b or 1117c) (FIG. 105) to attach the lateral retraction member 492 to the blade. Additionally, the lateral retractor member 492 defines an opening 505 between the engagement member 506 and the proximal end 496 of the body 494. The opening 505 is sized and adapted to receive a portion of the holding tool. The lateral retractor member 492 further includes a guiding member 508, such as a guiding protrusion, extending from an outer wall of the body 494. The guiding member 508 is shaped, sized, and adapted to be inserted through one of the grooves 1151a and 1151b (FIG. 112) of the retractor member (1117a, 1117b or 1117c) (FIG. 105), such that the lateral retractor member 492 can be slid along the retractor member (1117a, 1117b or 1117c). Once the lateral retractor member 492 is inserted in one of the grooves 1151a and 1151b (FIG. 112), the lateral retractor member 492 can block, or at least inhibit, soft tissue from entering the surgical operating field defined within the retractor member 1117a, 1117b or 1117c (FIG. 105).

The first arm 1104 defines the slot 1162 that is configured to slidably retain the first retractor member 1117a that is configured to retract tissue. The first engagement member 1164 movably connected to the first arm 1104. The first engagement member 1164 defines a plurality of recesses 1158. Each of the plurality of recesses 1158 is selectively configured to securely receive a complementary second engagement member 1160 of the first retractor member 1117a. The first engagement member 1164 is configured to move toward the slot 1162 so as to engage the second engagement member 1160, thereby causing the second engagement member 1160 to be securely received in a select one of the plurality of recesses 1158. The first engagement member 1164 is configured to move away from the slot 1162 so as to disengage the second engagement member 1160 and allow the second engagement member 1160 to slide along the slot 1162. The retractor 1100 includes the first retractor member 1117a. The first retractor member 1117a defining the outer surface 1165. The second engagement member 1160 protrudes out from the outer surface 1165. The plurality of recesses 1158 are arranged in a linear row along the second engagement member 1160 to allow the first retractor member 1117a to be fixed to the arm at different attachment positions.

With reference to FIGS. 133 and 134, a holding tool 1400 can be used to attach or remove the lateral retraction member 492 from the blade 1117a, 1117b or 1117c (FIG. 105). The holding tool 1400 includes a handle assembly 1404 at its proximal end 1406, clamping assembly 1408 at its distal end 1410, and an elongated connecting portion 1412 coupling the handle assembly and the clamping assembly 1408. The handle assembly 1404 includes a stationary handle member 1414 adapted to be grabbed by a user and a trigger 1416 movable relative to the handle member 1414 between a first position (FIG. 134) and a second or actuated position. A biasing member 1418, such as a coil spring, biases the trigger 1416 to the first position. The trigger is operatively connected to a first elongated member 1420, such as a shaft or rod, and a second elongated member 1422, such as a rod or shaft, such that the, when the trigger 1416 is moved from the first position to the actuated position, the clamping assembly 1408 moves from a closed position to an open position. The clamping assembly 1408 includes a first or male engagement member 1402 adapted and sized to be inserted in the opening 505 of the lateral retraction member 492 and a second distal engagement member 1424. The first and second engagement members 1402 and 1424 are configured to move from an open position and a closed position upon actuation of the handle assembly 1404.

Figure 135:
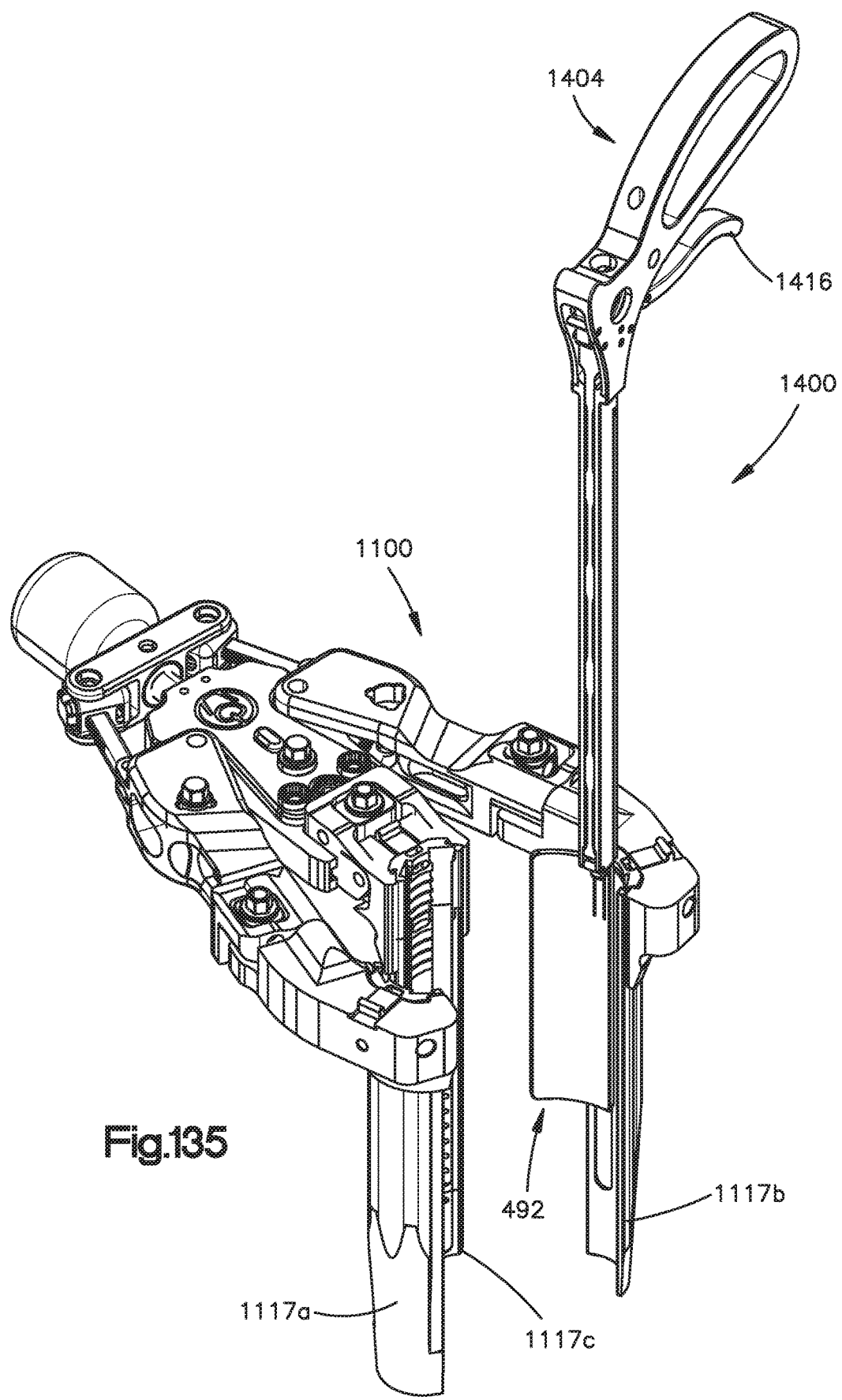
Figure 136:
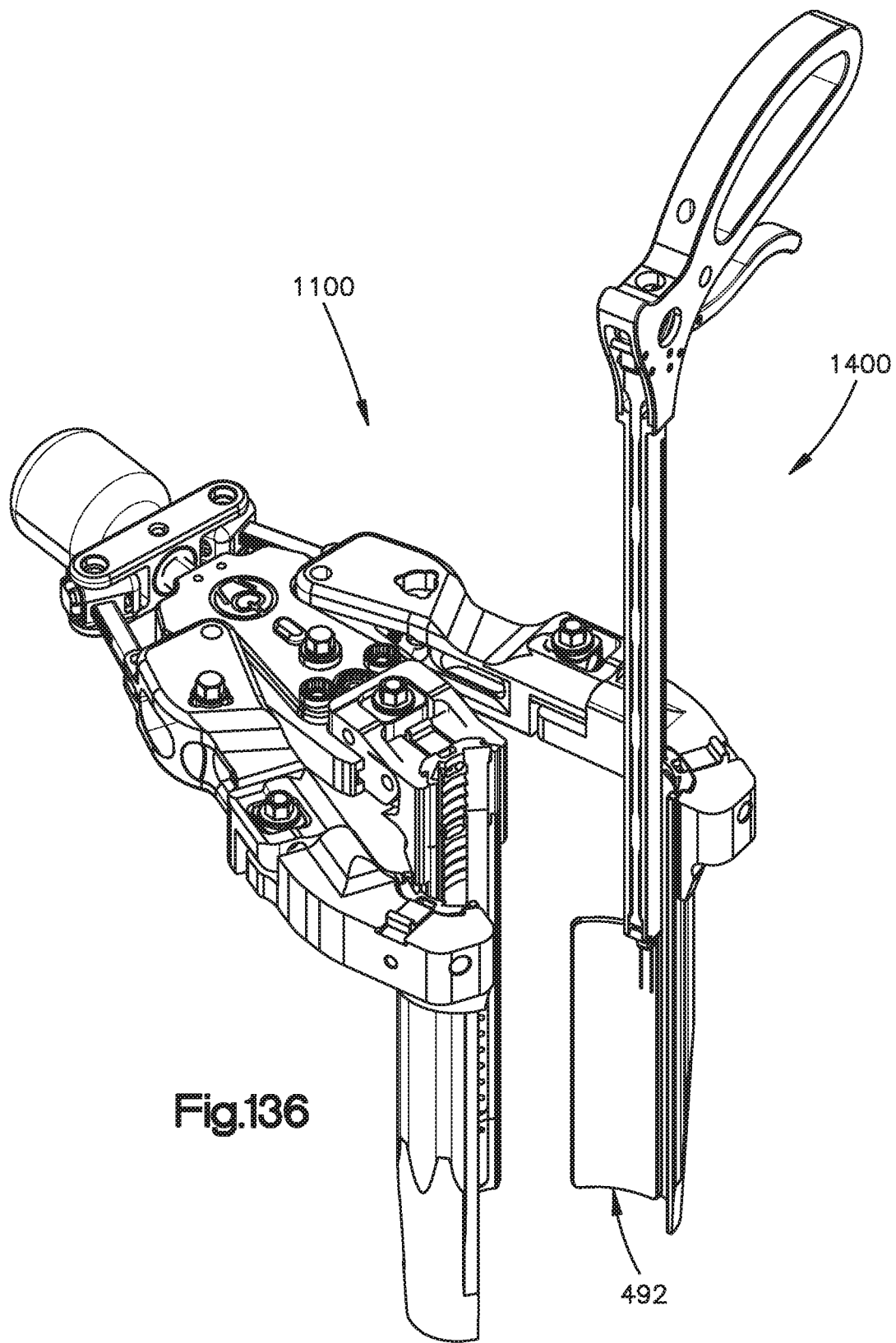
Figure 137:
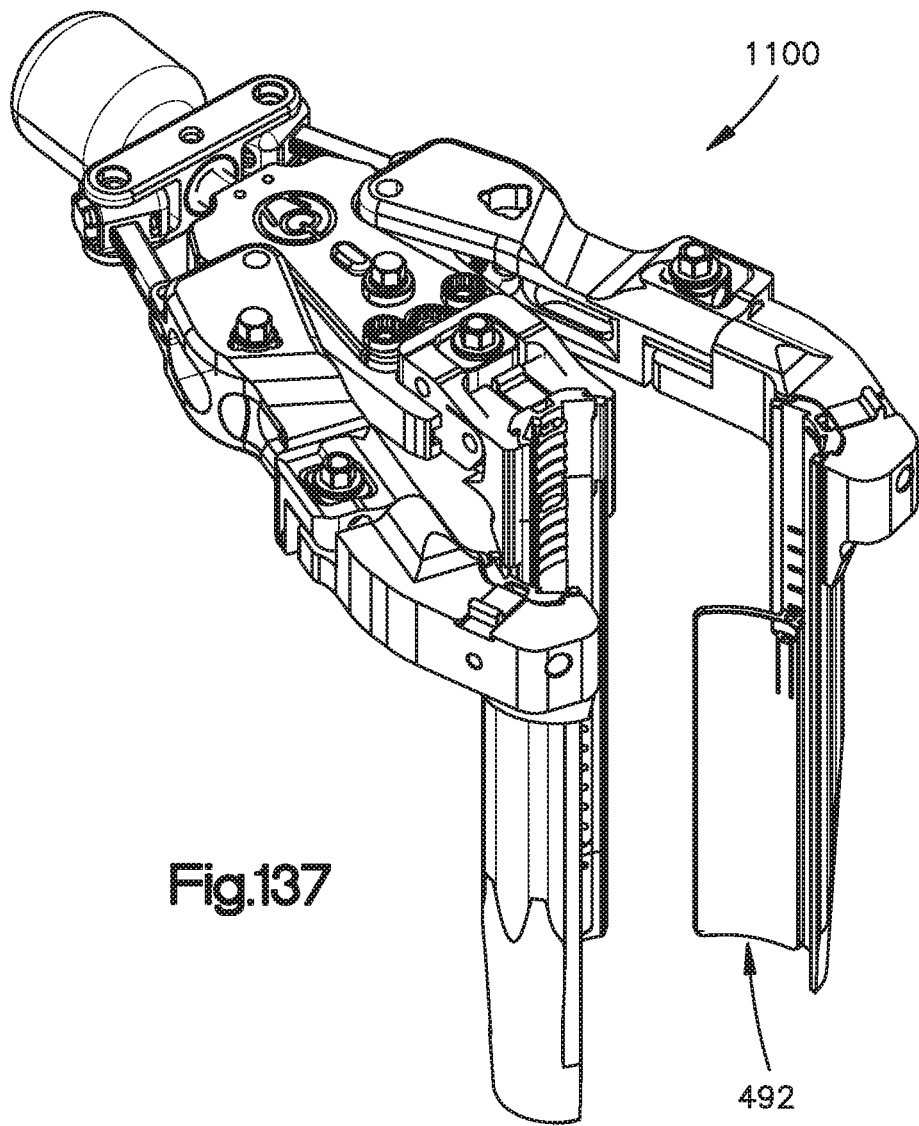

With reference to FIGS. 135-137, the holding tool 1400 can be used to attach the lateral retractor member 492 to the retractor member 1117b (or 1117a or 1117c). First, the handle assembly 114 is actuated by moving the trigger 1416 from the first position to the second or actuated position. As a result, the clamping assembly 1408 (FIG. 133) moves from the closed position to the open position. While the clamping assembly 1408 is the open position, the first male engagement member 1402 (FIG. 134) is inserted in the opening 505 (FIG. 132) such that the clamping assembly 1408 latches onto the lateral retraction member 492. The handle assembly 1404 is released so that the clamping assembly 1408 (FIG. 134) moves from the open position to the closed position, thereby securing holding tool 1400 to the lateral retraction member 492. The lateral retraction member 492 is then advanced toward the target site inserting the guiding member 508 (FIG. 132) into the groove 1151a or 1151b (FIG. 112) of the retractor member 1117b as seen in FIGS. 135 and 136. The insertion tool 1400 is then detached from the lateral retraction member 492 by releasing the clamping assembly 1408 from the lateral retraction member 492. The insertion tool 1400 can be used in a similar manner to remove the lateral retraction member 492 from the blade 1117b.

Figure 139:
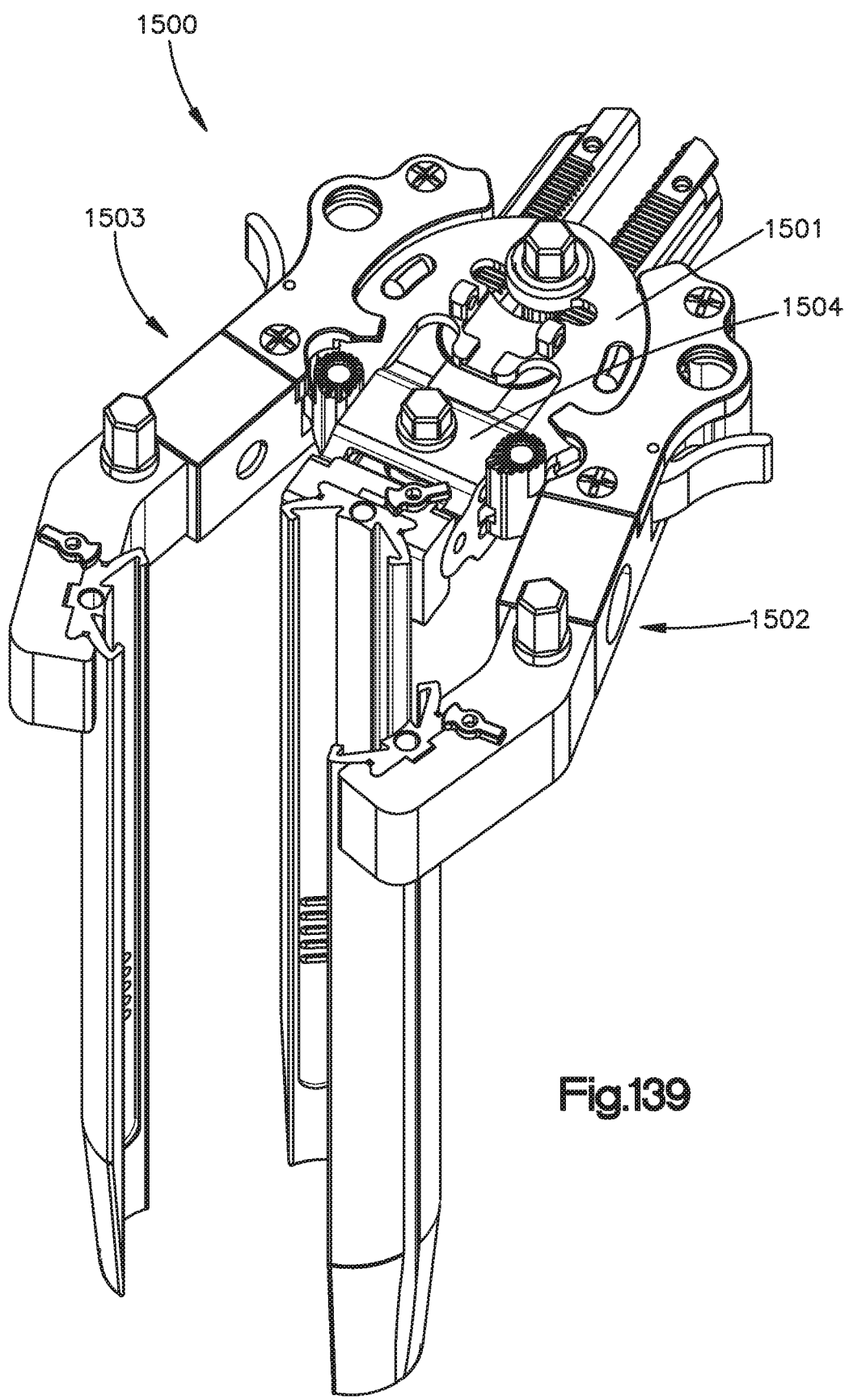
Figure 140:
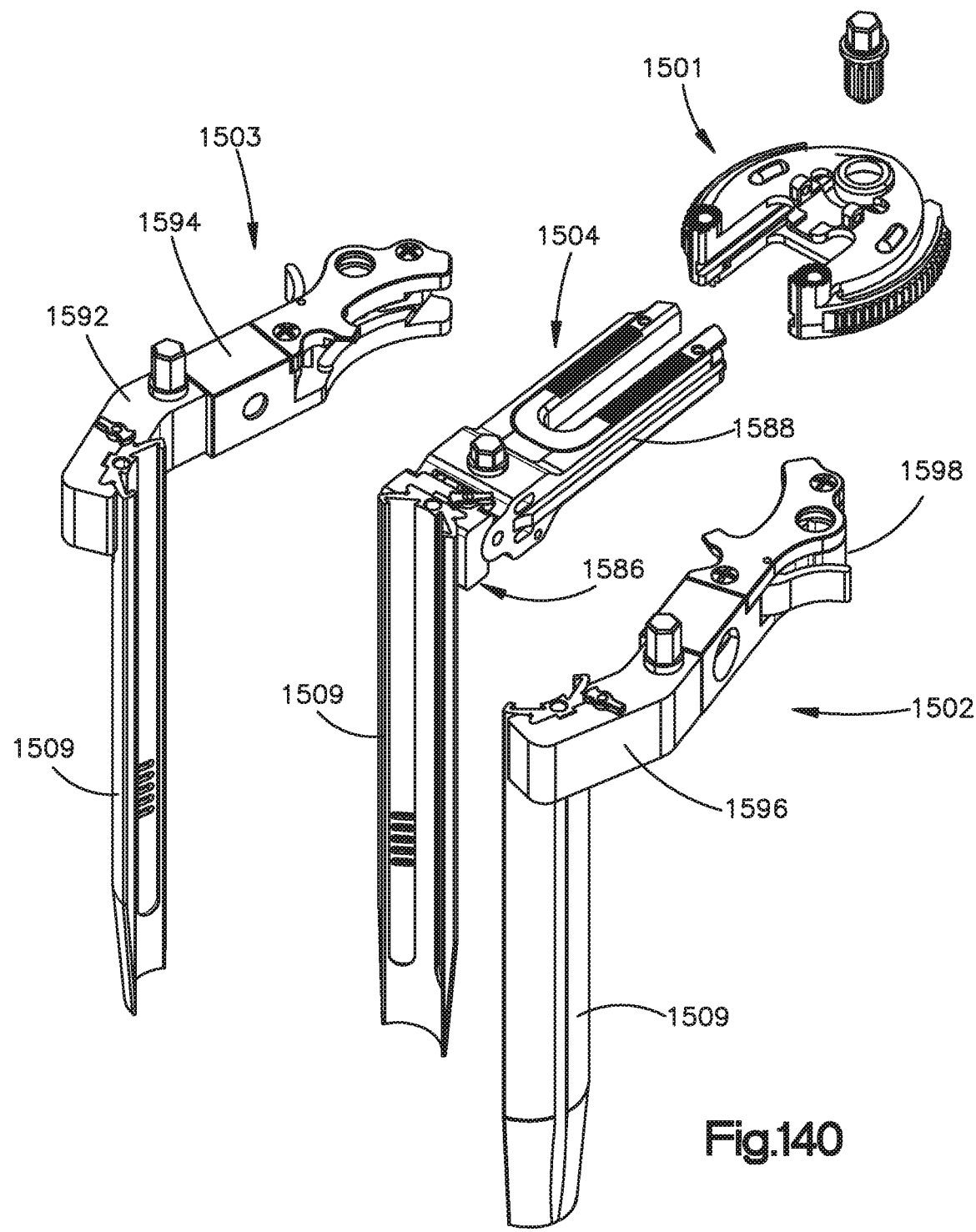
Figure 141:
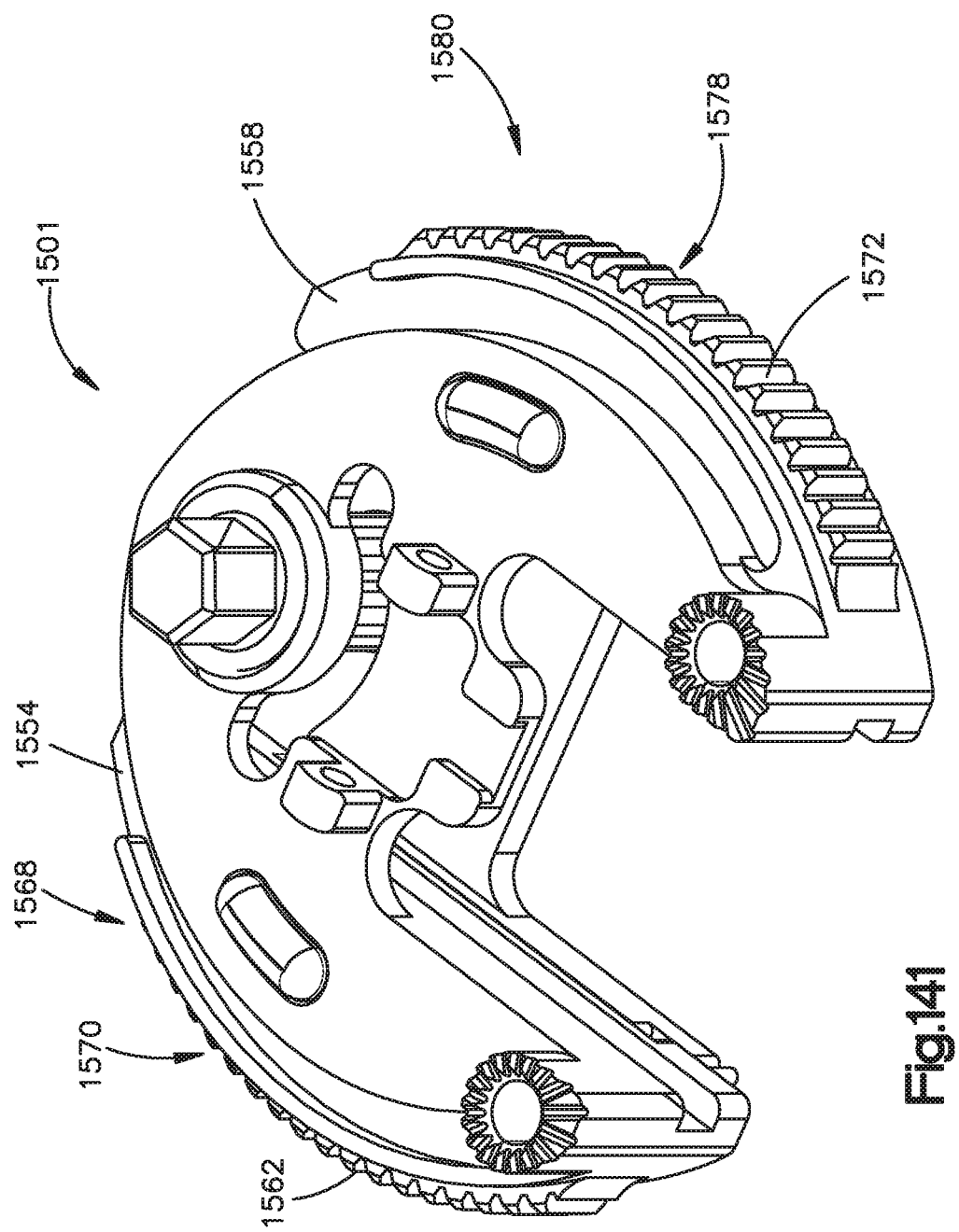
Figure 144:
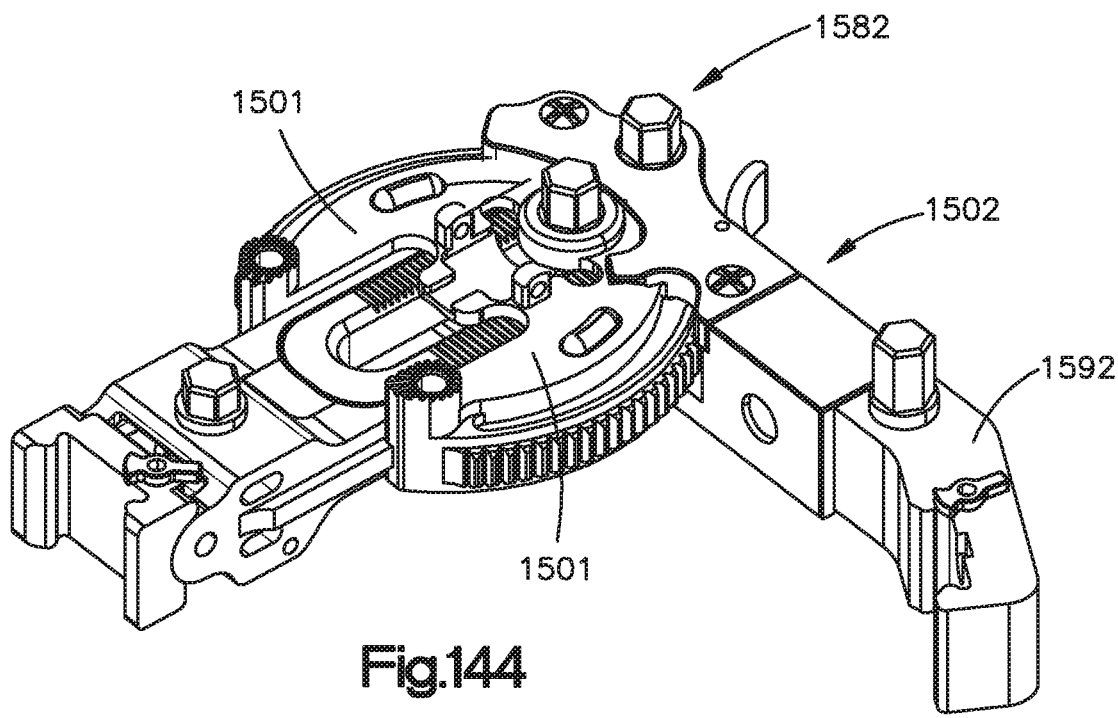

With reference to FIG. 138-140, a surgical retractor 1500 in accordance with an embodiment of the present invention includes a central body 1501, first and second lateral arms 1502 and 1503, and a central or third arm 1504. The first and second arms 1502 and 1503 are removably attached to the central body 1501 to facilitate cleaning. The lateral arms 1502 and 1503 are each configured to move between a first or closed position (FIG. 138) and a second or open position (FIG. 139) to retract tissue with the blades attached to them. The central or third arm 1504 is configured to move longitudinally between a first or distal position (FIG. 138) and a second or proximal position (FIG. 139) to retract tissue with a blade attached to it. The third arm 1504 is removably attached to the central body 1504 to facilitate cleaning.

With reference to FIG. 140, the lateral arms 1502 and 1503 are each movably connected to the central body 1501 such that each can move independently from each other between the first position (FIG. 138) and the second position (FIG. 140). In the illustrated embodiment, The lateral arm 1502 includes a proximal portion 1598 and a distal portion or blade holder 1596. The blade 1596 can be pivotally connected to the proximal portion 1598 as described in detail below. The lateral arm 1502 includes a proximal portion 1594 and a distal portion or blade holder 1592. The blade holder 1592 can be pivotally connected to the proximal portion 1594 as described in detail below. The blade holders 1596 and 1596 are each adapted to hold and support a blade 1509 as discussed above with respect to other embodiments. The blade 1509 is substantially rigid and, in some embodiments, is wholly or partly made of a radiolucent material. Regardless of the materials used, the blade 9 is configured to displace and hold soft or hard tissue. The blades 1509 can have any suitable structural features including the features discussed above with respect to other embodiments.

The central arm 1504 is movably connected to the central body 1501 in order to move between the distal position (FIG. 138) and the proximal position (FIG. 140). In the illustrated embodiment, the central arm 1504 includes a proximal portion 1588 and a distal portion 1586 or blade holder 1586. The blade holder 1586 can be pivotally connected to the proximal portion 1588 as discussed in detail below. The blade holder 1586 is adapted to hold and support a blade 1509. Additionally, the blade holder 1586 can have the same or substantially similar features as the blade holder described above with respect to other embodiments.

With reference to FIGS. 141-147, the retractor 1500 can include gear mechanisms configured to move the lateral arms 150 relative to the central body 1501. The first gear mechanism includes a rotating member or pinion 1582 rotatably mounted to the lateral arm 1502 and a curved rack or ratchet 1578 arranged along a first side 1580 of the central body 1501. The rotating member 1582 includes a head 1576 adapted to be turned by a driving tool and a geared shaft 1574 having a plurality of teeth. The rack 1578 includes a plurality of teeth 1572 adapted to mate with the teeth of the geared shaft 1574. As a result, when the rotating member 1582 is turned, it moves along the rack 1578, thereby urging the lateral arm 1502 to move relative to the central body 1501. The lateral arm 1502 additionally includes a guiding slot or rail 1560 sized and configured to receive a guide member or protrusion 1558. The guide member 1558 extends along at least a portion of the first side 1580 of the central body 1501. The guide member 1558 is positioned within the guiding slot or rail 1560 to guide the movement of the lateral arm 1502 relative to the body 1501. In operation, when the rotating member 1582 is rotated, the lateral arm 1502 moves independently of the lateral arm 1503 from a first or closed position (FIG. 145) to a second or open position (FIG. 144) to unilaterally retract tissue with a blade 1509 (FIG. 140) attached to the blade holder 1592.

The gear mechanism includes a rotating member or pinion 1584 rotatably mounted to the lateral arm 1503 and a curved rack or ratchet 1570 arranged along a second side 1568 of the central body 1501. The second side 1568 is disposed in a diametrically opposed relation to the first side 1580. The rotating member 1584 includes a head 1566 adapted to be turned by a driving tool and a geared shaft 1564 having a plurality of teeth. The rack 1570 includes a plurality of teeth 1562 adapted to mate with the teeth of the geared shaft 1564. As a consequence, when the rotating member 1584 is turned, it moves along the rack 1570, thereby urging the lateral arm 1503 to move relative to the central body 1501. The lateral arm 1503 additionally includes a guiding slot or rail 1556 sized and configured to receive a guide member or protrusion 1554. The guide member 1554 extends along at least a portion of the second side 1568 of the central body 1501. The guide member 1558 is positioned within the guiding slot or rail 1556 to guide the movement of the lateral arm 1503 relative to the body 1501. In operation, when the rotating member 1584 is rotated, the lateral arm 1503 moves independently of the lateral arm 1502 from a first or closed position (FIG. 147) to a second or open position (FIG. 146) to unilaterally retract tissue with a blade 1509 (FIG. 140) attached to the blade holder 1596.

With reference to FIG. 148, each lateral arm 1502 and 1503 is operatively associated with a locking mechanism 1512 configured to lock the position of the lateral arm 1502 or 1503 in relation to the central body 1501. In the interest of brevity, only the locking mechanism 1512 operatively associated with the lateral arm 1502 is discussed herein. However, the lateral arm 1503 is operatively associated with an identical or substantially similar locking mechanism 1512. In the illustrated embodiment, the locking mechanism 1512 is a ratchet mechanism and includes an engagement member or pawl 1530 pivotally connected to the lateral arm 1502 and the rack or ratchet 1578. The pawl 1530 includes a tooth or protrusion 1532 adapted to engage the teeth 1572 of the rack 1578 so that, when the tooth 1532 engages the teeth 1572, the lateral arm 1502 can move in a direction indicated by arrow T5 but is precluded from moving in a direction indicated by arrow T6. In addition, the pawl 1530 includes a concave extension 1534 adapted to receive a finger. A pivot member 1536, such as pin, pivotally connects the pawl 1530 to the lateral arm 1502. In operation, a user can unlock the locking mechanism 1512 by pushing the extension 1534 backwards. When the extension 1534 is pushed backwards, the pawl 1530 pivots about pivot member 1536 and the tooth 1532 disengages the rack or ratchet 1578, thereby allowing the lateral arm to freely move in either the direction indicated by arrow T5 or the direction indicated by arrow T6.

With reference to FIGS. 149 and 150, the surgical retractor 1500 includes a rack and pinion mechanism 1538 for translating the central arm 1504 with respect to the central body 1501 and therefore unilaterally retract tissue with the blade attached to the blade holder 1586. The rack and pinion mechanism 1538 can be substantially similar to the translating mechanism 272 shown in FIG. 4 and the rack and pinion mechanism 1121 illustrated in FIG. 121. In the illustrated embodiment, the mechanism 1538 includes a rack 1520 arranged along an inner surface 1540 of the central arm 1504 and a rotating member or pinion 1542 adapted to engage the rack 1520. The rack 1520 includes a plurality of teeth configured to mate with the teeth of the rotating member 1542. Accordingly, when the rotating member 1542 is rotated, the central arm 1504 moves longitudinally with respect to the central body 1501. The central arm 1504 can also include a pair of ratchets 1544 adapted to engage a locking portion (not shown) as discussed in detail above with respect to FIG. 124.

With respect to FIGS. 151-154, an angulation mechanism 1550 is configured to angulate the blade holder 1586 in relation to the central arm 1504. In the illustrated embodiment, the angulation mechanism 1550 includes a rotating member 1552, such as a screw, rotatably attached to a distal housing 1554 of the central arm 1504. One or more retaining members 1555, such as pins, preclude the rotating member 1552 from translating relative to the distal housing 1554. Consequently, the rotating member 1552 can only rotate relative to the distal housing 1554. The rotating member 1552 includes a head 1557 (e.g., hex head) adapted to be driving by a driving tool and a threaded shaft 1561. The angulation mechanism further includes a translating member or threaded ring 1563. The translating member 1563 has a threaded bore and is configured to translate along the threaded shaft 1561 upon rotation of the rotating member 1552. The translating member 1563 is pivotally coupled to the blade holder 1586. Consequently, when the rotating member 1552 is rotated, the translating member 1563 moves along the rotating member 1552, causing the blade holder 1586 to angulate relative to the central arm 1504 as shown in FIGS. 153 and 154. As the blade holder 1586 pivots relative to the central arm 1504, the blade attached to the blade holder 1586 can angularly retract tissue.

With reference to FIGS. 155 and 156, the retractor 1500 can further include an angulation mechanism 1565 for angulating the lateral arms 1503. The angulation mechanism 156 can be the same or substantially similar to any of the angulation mechanisms described above with respect to the other embodiments. Regardless of the angulation mechanism employed, the mechanism allows the retractor 1500 to angularly retract tissue with the blade 1509.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments of the process, machine, manufacture, and composition of matter, means, methods and steps described in the specification. As one of ordinary skill in the art will readily appreciate from the disclosure of the present invention, processes, machines, manufacture, composition of matter, means methods, or steps, presently existing or later to be developed that perform substantially the same function or achieve substantially the same result as the corresponding embodiments described herein may be utilized according to the present disclosure.

The present invention has been described using detailed descriptions of embodiments thereof that are provided by way of example and are not intended to necessarily limit the scope of the invention. The described embodiments comprise different features, not all of which are required in all embodiments of the invention. Some embodiments of the invention utilize only some of the features or possible combinations of the features, shown in a particular described exemplary embodiment. Alternatively or additionally, portions of the invention described/depicted as a single unit may reside is two or more separate physical entities which act in concert to perform the described/depicted function. Alternatively or additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. In particular, features described in the context of a method may be incorporated into a device or system.

What is claimed:

1. A retractor configured to retract tissue, comprising:
a first arm comprising a proximal portion and a distal portion, the distal portion configured to retain a first retractor member, the distal portion configured to rotate relative to the proximal portion about a first axis;
a second arm configured to retain a second retractor member, such that rotation of the distal portion of the first arm about the first axis causes the first retractor member to pivot toward or away from the second retractor member when the first retractor member and the second retractor member are coupled to the first arm and the second arm, respectively;
a translating member coupled between the proximal and distal portions of the first arm, the translating member configured to receive a drive force that causes the translating member to bias the distal portion to pivot relative to the proximal portion about the first axis, wherein the translating member comprises a threaded shaft,
a rotating member that is threadedly coupled to the translating member, the rotating member defining a threaded bore configured to receive at least a portion of the threaded shaft, wherein the rotating member and the translating member are configured such that rotation of the rotating member moves the threaded shaft along the threaded bore to urge the distal portion to rotate in relation to the proximal portion about the first axis; and
a rotating sleeve surrounding at least a portion of the rotating member, wherein the rotating sleeve rotatably connects the rotating member to the proximal portion, and the rotating sleeve is configured to rotate the rotating member relative to the proximal portion when the threaded shaft moves along the threaded bore.

2. The retractor of claim 1, wherein the distal portion extends from the proximal portion along the first axis.

3. The retractor of claim 1, wherein the rotating member is configured to rotate about an additional axis that is substantially perpendicular to the first axis, and the translating member is configured to translate along the additional axis with respect to the rotating member.

4. The retractor of claim 1, further comprising:
an extension protruding outwardly from the proximal portion, the extension defining an opening configured to receive the rotating member and the rotating sleeve; and
one or more pivot pins rotatably connecting the rotating member to the extension.

5. The retractor of claim 1, wherein:
the second arm comprises a proximal portion and a distal portion, wherein the distal portion of the second arm is configured to rotate relative to the proximal portion of the second arm about a second axis, and
the retractor further comprises:
a second translating member coupled between the proximal portion and the distal portion of the second arm, the second translating member configured to receive a drive force that causes the second translating member to bias the distal portion of the second arm to pivot relative to the proximal portion of the second arm about the second axis, wherein the second translating member comprises a second threaded shaft;
a second rotating member that is threadedly coupled to the second translating member, the second rotating member defining a second threaded bore configured to receive at least a portion of the second threaded shaft, wherein the second rotating member and the second translating member are configured such that rotation of the second rotating member moves the second threaded shaft along the second threaded bore to urge the distal portion of the second arm to rotate in relation to the proximal portion of the second arm about the second axis; and
a second rotating sleeve surrounding at least a portion of the second rotating member, wherein the second rotating sleeve rotatably connects the second rotating member to the proximal portion of the second arm and is configured to rotate the second rotating member relative to the proximal portion of the second arm when the second threaded shaft moves along the second threaded bore.

6. A retractor configured to retract tissue, comprising:
a first arm having a proximal portion and a distal portion spaced from the proximal portion, the distal portion of the first arm configured to carry a first retractor member;
a second arm having a proximal portion and a distal portion spaced from the proximal portion of the second arm, the distal portion of the second arm configured to carry a second retractor member, wherein the distal portions of the first and second arms are spaced from one another along a first direction, and the first and second arms are pivotably coupled to each other;
a first retraction mechanism coupled to the first and second arms, wherein the first retraction mechanism is configured to move the first and second arms in unison relative to each other so as to increase a distance between the distal portions of the first and second arms along the first direction; and
a second retraction mechanism coupled to the first arm, wherein the second retraction mechanism comprises:
a rotating member that is configured to rotate about an axis so as to pivot the distal portion of the first arm relative to the proximal portion of the first arm unilaterally so as to increase the distance between the distal portions of the first and second arms in the first direction; and a rotating sleeve surrounding at least a portion of the rotating member, wherein the rotating sleeve rotatably connects the rotating member to the proximal portion of the first arm, and the rotating sleeve is configured to rotate the rotating member relative to the proximal portion about another axis when the rotating member rotates about the axis.

7. The retractor of claim 6, wherein the distal portion of the first arm extends from the proximal portion of the first arm along a first axis, and the second retraction mechanism is configured to pivot the distal portion of the first arm relative to the proximal portion of the first arm about the first axis.

8. The retractor of claim 6, further comprising a third retraction mechanism coupled to the second arm, wherein the third retraction mechanism is configured to pivot the distal portion of the second arm relative to the proximal portion of the second arm so as to increase the distance between the distal portions of the first and second arms in the first direction.

9. The retractor of claim 8, wherein the distal portion of the second arm extends from the proximal portion of the second arm along a second axis, and the third retraction mechanism is configured to pivot the distal portion of the second arm relative to the proximal portion of the second arm about the second axis.

10. The retractor of claim 9, further comprising a handle assembly that includes a first handle portion and a second handle portion spaced from each other, wherein the proximal portion of the first arm extends from the first handle portion, the proximal portion of the second arm extends from the second handle portion, and the retractor is configured such that moving the first handle portion toward the second handle portion causes the first and second arms to move in unison relative to each other so as to increase the distance between the distal portions of the first and second arms along the first direction.

11. The retractor of claim 6, wherein the first retraction mechanism comprises a pivot member that pivotally connects the first and second arms together, whereby the first and second arms are configured to move in unison relative to each other to increase the distance between the distal portions of the first and second arms along the first direction.

12. The retractor of claim 6, further comprising a connecting mechanism that connects the first and second arms together, wherein the connecting mechanism is configured to control a relative position of the first and second arms relative to each other.

13. The retractor of claim 12, wherein the connecting mechanism comprising a connection bar and a knob, the connection bar having a threaded portion, the knob having a threaded bore configured to threadedly receive the threaded portion, wherein rotation of the knob about the threaded portion of the connection bar causes the knob to translate along the connection bar, wherein the knob is configured to move along the connection bar toward or away from the first arm, so that the knob is configured to secure a position of the first arm with respect to the second arm when the knob contacts the first arm.

14. The retractor of claim 6, further comprising:
a central body connected to the first and second arms; and
a third arm extending from the central body along a longitudinal axis, a distal portion of the third arm configured to carry a third retractor member, wherein the third arm is configured to move longitudinally with respect to the central body along the longitudinal axis.

15. The retractor of claim 14, further comprising:
a pinion connected to the central body; and
a rack defined by the third arm,
wherein the rack is operatively coupled to the pinion such that rotation of the pinion moves the third arm relative to the central body along the longitudinal axis.

16. The retractor of claim 15, wherein the third arm is configured to move along the longitudinal axis between a distal position and a proximal position responsive to rotation of the pinion independent of movement between the first and second arms along the first direction.

17. The retractor of claim 14, wherein the central body carries a pivot member that pivotally connects the first and second arms together, whereby the first and second arms are configured to move in unison relative to each other to increase the distance between the distal portion of the first and second arms along the first direction.

18. The retractor of claim 14, further comprising a disc anchor that is attached to the third retractor member, wherein the disc anchor is movably supported on an inner surface of the third retractor member such that the disc anchor is movable from a retracted position to an extended position with respect to the third retractor member, wherein the disc anchor is insertable into an intervertebral disc space when in the extended position.

19. The retractor of claim 18, wherein:
the third retractor member defines a proximal end, a distal end spaced from the proximal end of the third retractor member along a distal direction, a plurality of indentations disposed between the proximal and distal ends, and a distal wall spaced from all of the plurality of indentations in the distal direction,
the disc anchor includes an engagement member that is received in respective ones of the plurality of indentations when in the retracted and extended positions, and
the disc anchor is further movable in the distal direction from the extended position to a cleaning position at which the engagement member of the disc anchor is out of engagement with all of the plurality of indentations and is disposed along the inner surface at a location that is spaced in the distal direction from all of the plurality of indentations to facilitate cleaning of the disc anchor.

20. A retractor configured to retract tissue, comprising:
a first arm comprising a proximal portion and a distal portion, the distal portion configured to retain a first retractor member, the distal portion configured to rotate relative to the proximal portion about a first axis;
a second arm configured to retain a second retractor member, such that rotation of the distal portion of the first arm about the first axis causes the first retractor member to pivot toward or away from the second retractor member when the first retractor member and the second retractor member are coupled to the first arm and the second arm, respectively;
a translating member coupled between the proximal and distal portions of the first arm;
a rotating member coupled to the translating member, wherein the rotating member and the translating member are configured such that rotation of the rotating member about a second axis offset from the first axis moves the translating member along the second axis to urge the distal portion to rotate in relation to the proximal portion about the first axis; and
a rotating sleeve surrounding at least a portion of the rotating member, wherein the rotating sleeve rotatably connects the rotating member to the proximal portion and is configured to rotate the rotating member relative to the proximal portion about a third axis offset from the second axis when the translating member moves along the second axis.

* * * * *